(12) United States Patent
Badorc et al.

(10) Patent No.: US 8,623,862 B2
(45) Date of Patent: Jan. 7, 2014

(54) DERIVATIVES OF N-[(1H-PYRAZOL-1-YL)ARYL]-1H-INDOLE OR 1H-INDAZOLE-3-CARBOXAMIDE, PREPARATION THEREOF AND APPLICATIONS THEREOF IN THERAPEUTICS

(75) Inventors: Alain Badorc, Paris (FR); Christophe Boldron, Paris (FR); Nathalie Delesque, Paris (FR); Valérie Fossey, Paris (FR); Gilbert Lassalle, Paris (FR); Xavier Yvon, Paris (FR)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/231,376

(22) Filed: Sep. 13, 2011

(65) Prior Publication Data

US 2012/0277205 A1    Nov. 1, 2012

(30) Foreign Application Priority Data

Apr. 29, 2011    (FR) ..................... 11 53659

(51) Int. Cl.
| | |
|---|---|
| A61K 31/4155 | (2006.01) |
| C07D 403/14 | (2006.01) |
| A61K 31/501 | (2006.01) |
| C07D 241/20 | (2006.01) |
| A61K 31/497 | (2006.01) |
| C07D 413/14 | (2006.01) |
| A61K 31/5355 | (2006.01) |
| C07D 243/08 | (2006.01) |
| A61K 31/551 | (2006.01) |
| C07D 471/04 | (2006.01) |
| C07D 487/08 | (2006.01) |
| A61K 31/55 | (2006.01) |
| A61P 7/02 | (2006.01) |

(52) U.S. Cl.
USPC ........... 514/214.02; 514/406; 514/252.06; 514/252.11; 514/235.2; 514/218; 540/575; 540/580; 544/238; 544/357; 544/114; 544/350; 544/254.05; 546/364.7

(58) Field of Classification Search
USPC ............ 544/238, 357, 114, 350, 254.05; 514/252.02, 406, 252.06, 252.11, 514/235.2, 218, 214.02; 540/575, 580; 546/364.7
See application file for complete search history.

(56) References Cited

U.S. PATENT DOCUMENTS 8,124,641 B2 * 2/2012 Chen et al. ............ 514/406
2012/0277255 A1 * 11/2012 Honigberg et al. ..... 514/262.1

FOREIGN PATENT DOCUMENTS

| WO | WO2005/070920 A1 | 8/2005 |
| WO | WO2007/002635 A2 | 1/2007 |
| WO | WO2009/080226 A2 | 7/2009 |

OTHER PUBLICATIONS

International Search Report dated Nov. 3, 2011 issued PCT/EP2011/065885.

* cited by examiner

*Primary Examiner* — James O Wilson
*Assistant Examiner* — Cecilia M Jaisle
(74) *Attorney, Agent, or Firm* — Scully, Scott, Murphy & Presser, P.C.

(57) ABSTRACT

The present invention relates to compounds corresponding to formula (I):

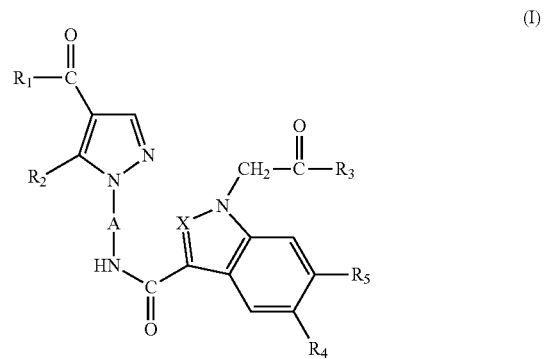

X represents a —CH— group or a nitrogen atom;
$R_1$ represents a ($C_1$-$C_4$)alkyl or a ($C_1$-$C_4$)alkoxy;
$R_2$ represents a group Alk;
$R_5$ represents a hydrogen atom, a halogen atom or a group Alk;
$R_6$ represents a hydrogen atom, a halogen atom, a cyano, a group —COOAlk or a —$CONH_2$ group.

8 Claims, No Drawings

DERIVATIVES OF N-[(1H-PYRAZOL-1-YL)ARYL]-1H-INDOLE OR 1H-INDAZOLE-3-CARBOXAMIDE, PREPARATION THEREOF AND APPLICATIONS THEREOF IN THERAPEUTICS

The present invention relates to novel derivatives of N-[(1H-pyrazol-1-yl)aryl]-1H-indole or 1H-indazole-3-carboxamide, preparation thereof and application thereof in therapeutics.

The compounds according to the present invention are reversible antagonists of the P2Y12 purinergic receptor. These compounds are antiplatelet drugs, exerting a powerful antithrombotic effect. They can be used for treating and preventing cardiovascular disorders such as thromboembolic diseases or restenoses.

In the industrialized world, medical complications associated with occurrence of a thrombosis represent one of the main causes of mortality. Some examples of pathologies associated with the development of a thrombosis include acute myocardial infarction, unstable angina and chronic stable angina, transient ischemic attacks, cerebrovascular accidents, peripheral vascular disease, pre-eclampsia and eclampsia, deep vein thrombosis, embolisms (cerebral, pulmonary, coronary, renal etc.), disseminated intravascular coagulation, or thrombotic thrombocytopenic purpura. There are also risks of thrombotic and restenotic complications during and following invasive surgery, such as angioplasty, carotid endarterectomy, aortocoronary bypass graft, or placement of stents or of endovascular prostheses.

Arterial thromboses can occur following a lesion of a vessel wall or rupture of an atherosclerotic plaque. Platelets play an essential role in the formation of these thromboses. Platelets can be activated either by mediators released in the bloodstream by circulating cells or by damaged endothelial cells present along the vessel wall, or by thrombogenic molecules of the subendothelial matrix—such as collagen—exposed during vascular lesions. Moreover, platelets can also be activated in conditions of blood flow with high shear stress as is observed in stenotic vessels. After activation, the circulating platelets adhere and accumulate at the vascular lesion, forming a thrombus. During this process, the thrombi generated can be sufficiently voluminous for the blood flow in the vessel to be blocked partially or completely.

In the veins, thrombi can also form where there is stasis or slow blood flow. Owing to their nature, these venous thrombi can produce emboli which move through the vascular system. These emboli can then block the blood flow in vessels that are more remote, such as pulmonary or coronary arteries.

Numerous studies have demonstrated that adenosine 5'-diphosphate (ADP) is a major mediator of platelet activation and aggregation, playing a crucial role in initiation and progression of thrombus formation (Maffrand et al., Thromb. Haemostas. (1988) 59, 225-230; Herbert et al., Arterioscl. Thromb. (1993) 13, 1171-1179).

ADP is released into the circulation by damaged red blood cells and the endothelial cells of the atherosclerotic wall, and more specifically is secreted by the activated platelets where ADP is stored in the dense granules at very high concentration. ADP-induced platelet aggregation is triggered by its binding to two specific purinergic receptors, expressed on the cell membrane of human platelets: P2Y1 and P2Y12. The P2Y1 receptor, coupled with stimulation of PLCβ via Gαq, is responsible for mobilization of the internal stores of calcium, the change in shape of the platelets, and transient aggregation on ADP. The P2Y12 receptor, coupled with inhibition of adenylcyclase via Gαi2 and with activation of PI-3 kinase, is responsible for amplification of the responses and stabilization of aggregation (Gachet, Thromb. Haemost. (2001) 86, 222-232; Andre et al., J. Clin. Invest. (2003) 112, 398-406). The use of P2Y1-/- transgenic mice (Gachet et al., J Clin Invest (1999) 104, 1731-1737; Gachet et al., Circulation (2001) 103, 718-723; Gachet et al., Haematology (2002) 87, 23) and P2Y12-/- (Conley et al., Nature (2001) 409, 202-207) demonstrated the importance of these two receptors in the development of thromboses in vivo. In humans, genetic defects for P2Y12 have been described as being associated with a hemorrhagic phenotype and with pronounced deterioration of ADP-induced platelet aggregation (Kanakura et al., J Thromb Haemost. (2005) 3, 2315-2323).

The use of clopidogrel in human clinical practice has supplied proof that blocking of the P2Y12 receptor by an antagonist represents a key therapeutic strategy in the treatment of cardiovascular diseases. Clopidogrel is a prodrug of the thienopyridine family, whose active metabolite binds covalently to the P2Y12 receptor, leading to irreversible inhibition of platelet activity in vivo. (Savi et al., Biochem Biophys Res Commun (2001) 283, 379-383; Savi et al., Proc Natl Acad Sci (2006) 103, 11069-11074). This molecule had initially shown its efficacy in several clinical trials, reducing the risk of cardiovascular accidents in patients at risk ("A randomised, blinded, trial of clopidogrel versus aspirin in patients at risk of ischaemic events (CAPRIE)" CAPRIE steering committee Lancet (1996) 348, 1329-1339; "The Clopidogrel in Unstable Angina to Prevent Recurrent Events (CURE). Effects of Clopidogrel in Addition to Aspirin in Patients with Acute Coronary Syndromes without ST-Segment Elevation" CURE steering committee N Engl J Med (2001) 345, 7, 494-502).

Synthetic antagonists of the P2Y12 receptor that display antiplatelet and antithrombotic activity have been described. Nevertheless, there is still a need for new antagonists possessing better properties, notably the need for reversible antagonists with a better benefit/risk ratio.

The present invention relates to compounds corresponding to formula (I):

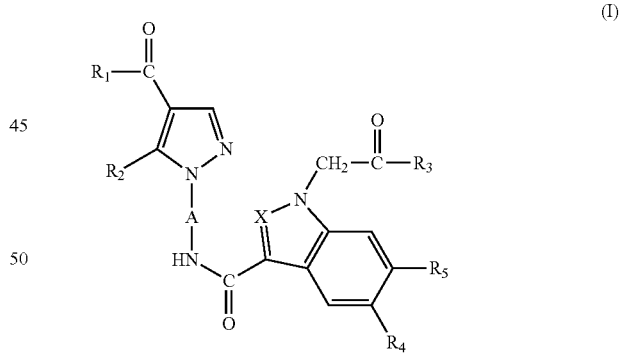

in which:
A represents a divalent aromatic radical selected from:

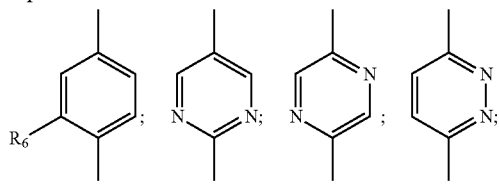

X represents a —CH— group or a nitrogen atom;
$R_1$ represents a $(C_1-C_4)$alkyl or a $(C_1-C_4)$alkoxy;

$R_2$ represents a group Alk;
$R_3$ represents a hydroxyl or a group —$NR_7R_8$;
$R_4$ represents a hydrogen atom, a halogen atom, a cyano, a phenyl, a group Alk, a group OAlk or a group —$NR_9R_{10}$;
$R_5$ represents a hydrogen atom, a halogen atom or a group Alk;
$R_6$ represents a hydrogen atom, a halogen atom, a cyano, a group —COOAlk or a —$CONH_2$ group;
$R_7$ represents a hydrogen atom or a $(C_1$-$C_4)$alkyl;
$R_8$ represents;
a) a hydrogen atom;
b) a $(C_1$-$C_4)$alkyl, unsubstituted or substituted with:
  (i) a hydroxyl;
  (ii) a group OAlk;
  (iii) a group —$NR_9R_{10}$;
  (iv) a $(C_3$-$C_6)$heterocycloalkyl, unsubstituted or substituted with a $(C_1$-$C_4)$alkyl or with a group —COOAlk;
  (v) a heteroaryl, unsubstituted or substituted with a $(C_1$-$C_4)$alkyl;
c) a $(C_3$-$C_7)$cycloalkyl;
d) a $(C_3$-$C_6)$heterocycloalkyl, unsubstituted or substituted with a $(C_1$-$C_4)$alkyl, a group —COOAlk or with one or two oxo groups;
e) a group —$SO_2$Alk;
or else $R_7$ and $R_8$, together with the nitrogen atom to which they are attached, constitute a heterocycle, saturated or unsaturated, mono- or polycyclic, condensed or bridged, comprising 4 to 10 ring members and which can contain one, two or three other nitrogen atoms or another heteroatom selected from an oxygen atom or a sulfur atom; said heterocycle being unsubstituted or substituted once, twice or three times with substituents selected independently from:
a) a halogen atom;
b) a hydroxyl;
c) a group —$OR_{11}$;
d) an oxo;
e) a group —$NR_9R_{10}$;
f) a group —$NR_{12}COR_{13}$;
g) a group —$NR_{12}COOR_{13}$;
h) a group —$COR_{13}$;
i) a group —$COOR_{13}$;
j) a group —$CONR_{14}R_{15}$;
k) a $(C_3$-$C_7)$cycloalkyl, unsubstituted or substituted with a hydroxyl or with a $(C_1$-$C_4)$alkyl;
l) a $(C_3$-$C_6)$heterocycloalkyl, unsubstituted or substituted with one or two oxo groups;
m) a phenyl, unsubstituted or substituted one or more times with substituents selected independently from a halogen atom, a group Alk or a group OAlk;
n) a pyridinyl;
o) a $(C_1$-$C_4)$alkyl, unsubstituted or substituted one or more times with substituents selected independently from:
  (i) a halogen atom;
  (ii) a hydroxyl;
  (iii) a group —$OR_{11}$;
  (iv) a group —$NR_9R_{10}$;
  (v) a group —$NR_{12}COR_{13}$;
  (vi) a group —$COOR_{13}$;
  (vii) a group —$CONR_{14}R_{15}$;
  (viii) a group —$SO_2$Alk;
  (ix) a $(C_3$-$C_7)$cycloalkyl;
  (x) a $(C_3$-$C_6)$heterocycloalkyl;
  (xi) a phenyl, unsubstituted or substituted one or more times with substituents selected independently from a halogen atom, a group Alk or a group OAlk;
  (xii) a heteroaryl, unsubstituted or substituted with a $(C_1$-$C_4)$alkyl;
$R_9$ and $R_{10}$ represent, each independently, a hydrogen atom or a $(C_1$-$C_4)$alkyl;
$R_{11}$ represents a group Alk, a $(C_1$-$C_4)$alkylene-OH or a $(C_1$-$C_4)$alkylene-OAlk;
$R_{12}$ represents a hydrogen atom or a $(C_1$-$C_4)$alkyl;
$R_{13}$ represents a $(C_1$-$C_4)$alkyl;
$R_{14}$ and $R_{15}$ represent, each independently, a hydrogen atom, a $(C_1$-$C_4)$alkyl or a $(C_3$-$C_7)$cycloalkyl;
or else $R_{14}$ and $R_{15}$, together with the nitrogen atom to which they are attached, constitute a heterocyclic radical selected from: azetidin-1-yl, pyrrolidin-1-yl, piperidin-1-yl, morpholin-4-yl or piperazin-1-yl;
Alk represents a $(C_1$-$C_4)$alkyl, unsubstituted or substituted one or more times with a fluorine atom.

The compounds of formula (I) can have one or more asymmetric carbon atoms. They can therefore exist in the form of enantiomers or diastereoisomers. These enantiomers, diastereoisomers as well as mixtures thereof, including the racemic mixtures, form part of the invention.

The compounds of formula (I) can exist in the form of bases or salified by acids or by bases, notably pharmaceutically acceptable acids or bases. Said salts of addition form part of the invention.

These salts are advantageously prepared with pharmaceutically acceptable acids or bases, but salts of other acids or bases that can be used, for example, for purification or isolation of the compounds of formula (I), also form part of the invention.

Halogen atom means a bromine, chlorine, fluorine or iodine atom.

$(C_1$-$C_4)$alkyl means a linear or branched alkyl radical with one to four carbon atoms, such as the methyl, ethyl, propyl, isopropyl, butyl, isobutyl, sec-butyl, tert-butyl radical.

$(C_1$-$C_4)$alkylene means a divalent radical with one to four carbon atoms such as the methylene, ethylene, trimethylene or tetramethylene radical.

$(C_1$-$C_4)$alkoxy means a linear or branched alkoxy radical with one to four carbon atoms, such as the methoxy, ethoxy, propoxy, isopropoxy, butoxy, isobutoxy, sec-butoxy, tert-butoxy radical.

$(C_3$-$C_7)$cycloalkyl means a cyclopropyl, cyclobutyl, cyclopentyl, cyclohexyl or cycloheptyl carbon-containing radical.

$(C_3$-$C_6)$heterocycloalkyl means a saturated monocyclic ring, comprising 3 to 6 ring members and one or more heteroatoms such as nitrogen, oxygen or sulfur atoms. As examples, a heterocycloalkyl can be an aziridine, an azetidine, a pyrrolidine, a morpholine, a piperazine, a piperidine, an imidazolidine, a pyrazolidine, a thiomorpholine, an oxetane, a tetrahydrofuran, a tetrahydro-2H-pyran, a tetrahydrothiophene.

Heteroaryl means an aromatic monocyclic system comprising 5 to 6 ring members, and comprising one or more heteroatoms such as nitrogen, oxygen or sulfur atoms. The nitrogen atoms can be in the form of N-oxides. As examples of monocyclic heteroaryls we may mention thiazole, thiadiazole, thiophene, imidazole, triazole, tetrazole, pyridine, furan, oxazole, isoxazole, oxadiazole, pyrrole, pyrazole, pyrimidine, pyridazine and pyrazine.

Saturated or unsaturated, mono- or polycyclic, condensed or bridged heterocycle, comprising 4 to 10 ring members, means a heterocycloalkyl such as for example an aziridine, an azetidine, a pyrrolidine, a piperidine, a piperazine, a morpholine, a thiomorpholine, as well as, for example, the following heterocycles: an octahydro-2H-pyrido[1,2-a]pyrazine, a 5,6,7,8-tetrahydro[1,2,4]triazolo[4,3-a]pyrazine, a 2,3-dihydro-1H-pyrrolo[3,4-c]pyridine, an octahydropyrrolo[1,2-a]pyrazine, a 1,4-diazepane, a 5,6,7,8-tetrahydroimidazo[1,2-a]pyrazine, a 4,5,6,7-tetrahydro-1H-pyrazolo[4,3-c]pyridine, a 1,4,5,6-tetrahydropyrrolo[3,4-c]pyrazole, a 6,7-dihydro-5H-pyrrolo[3,4-b]pyridine, a 3,8-diazabicyclo[3.2.1]octane, a 4,5,6,7-tetrahydro-1H-imidazo[4,5-c]pyridine, a 4,5,6,7-tetrahydro-1H-pyrazolo[3,4-c]pyridine, a 2,5-diazabicyclo[2.2.2]octane, a 2,5-diazabicyclo[2.2.1]heptane, an octahydropyrrolo[3,4-b]pyrrole, an octahydropyrrolo[3,4-c]pyrrole, an octahydro-2H-pyrazino[1,2-a]pyrazine.

According to the present invention, a distinction is made between:
the compounds of formula (I) in which $R_3$ represents a hydroxyl (reference IA) and the other substituents A, X, $R_1$, $R_2$, $R_4$ and $R_5$ are as defined for a compound of formula (I);
the compounds of formula (I) in which $R_3$ represents a group —$NR_7R_8$ (reference IB) and the other substituents A, X, $R_1$, $R_2$, $R_4$, $R_5$, $R_7$ and $R_8$ are as defined for a compound of formula (I);
in the form of a base or of salts of addition with acids or bases.

According to the present invention, we may mention the compounds of formula (I) in which:

A represents a divalent aromatic radical selected from:

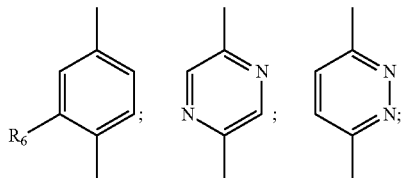

X represents a —CH— group or a nitrogen atom;
$R_1$ represents a methyl, ethyl, n-propyl radical or an ethoxy radical;
$R_2$ represents a methyl radical;
$R_3$ represents a hydroxyl or a group —$NR_7R_8$;
$R_4$ represents a hydrogen atom, a bromine, chlorine or fluorine atom, a cyano, a phenyl, a methyl radical, a trifluoromethyl radical, a methoxy radical or a dimethylamino group;
$R_5$ represents a hydrogen atom, a bromine, chlorine or fluorine atom or a methyl radical;
$R_6$ represents a hydrogen atom, a bromine atom, a cyano, a methoxycarbonyl group or a —$CONH_2$ group;
$R_7$ represents a hydrogen atom or a methyl radical;
$R_8$ represents:
a) a hydrogen atom;
b) a methyl radical, a 2-hydroxyethyl, a 3-hydroxypropyl, a 2-methoxyethyl, a 2-(methylamino)ethyl, a 2-(dimethylamino)ethyl, a 2-(dimethylamino)propyl, a 2-(dimethylamino)-1-methylethyl, a 2-(dimethylamino)-2-methylpropyl, a 3-(dimethylamino)propyl, a (1-methylpiperidin-3-yl)methyl, a tetrahydrofuran-3-ylmethyl, a tetrahydro-2H-pyran-4-ylmethyl, a 2-furylmethyl, a (3-methyl-1H-1,2,4-triazol-5-yl)methyl, 1-(1H-tetrazol-5-yl)ethyl, a 2-(1H-pyrrol-1-yl)ethyl, a 2-(1H-imidazol-1-yl)ethyl;
c) a cyclopropyl;
d) a 1,1-dioxidotetrahydro-3-thienyl, a pyrrolidin-3-yl, a 1-methylpyrrolidin-3-yl, a 1-(tert-butoxycarbonyl)pyrrolidin-3-yl, a piperidin-3-yl, a 1-methylpiperidin-3-yl, a 1-(tert-butoxycarbonyl)piperidin-3-yl, a 1-methylpiperidin-4-yl;
e) a methylsulfonyl group;
or else $R_7$ and $R_8$, together with the nitrogen atom to which they are attached, constitute a heterocycle selected from: an azetidine, a pyrrolidine, a piperidine, a piperazine, a morpholine, a thiomorpholine, an octahydro-2H-pyrido[1,2-a]pyrazine, a 5,6,7,8-tetrahydro[1,2,4]triazolo[4,3-a]pyrazine, a 2,3-dihydro-1H-pyrrolo[3,4-c]pyridine, an octahydropyrrolo[1,2-a]pyrazine, a 1,4-diazepane, a 5,6,7,8-tetrahydroimidazo[1,2-a]pyrazine, a 4,5,6,7-tetrahydro-1H-pyrazolo[4,3-c]pyridine, a 1,4,5,6-tetrahydropyrrolo[3,4-c]pyrazole, a 6,7-dihydro-5H-pyrrolo[3,4-b]pyridine, a 3,8-diazabicyclo[3.2.1]octane, a 4,5,6,7-tetrahydro-1H-imidazo[4,5-c]pyridine, a 4,5,6,7-tetrahydro-1H-pyrazolo[3,4-c]pyridine, a 2,5-diazabicyclo[2.2.2]octane, a 2,5-diazabicyclo[2.2.1]heptane, an octahydropyrrolo[3,4-b]pyrrole, an octahydropyrrolo[3,4-c]pyrrole, an octahydro-2H-pyrazino[1,2-a]pyrazine; said heterocycle being unsubstituted or substituted once, twice or three times with substituents selected independently from:
a) a fluorine atom;
b) a hydroxyl;
c) a methoxy radical, a 2-hydroxyethoxy, a 2-methoxyethoxy;
d) an oxo;
e) an amino group, a methylamino, a dimethylamino;
f) an acetamido group;
g) a (tert-butoxycarbonyl)amino group, a (tert-butoxycarbonyl)(methyl)amino;
h) an acetyl group;
i) a methoxycarbonyl group, a tert-butoxycarbonyl;
j) a dimethylcarbamoyl group, a cyclopropylcarbamoyl, a cyclobutylcarbamoyl;
k) a cyclopropyl, a cyclobutyl, a 2-hydroxycyclopentyl radical;
l) an oxetan-3-yl, a 1,1-dioxidotetrahydro-3-thienyl, a piperidin-1-yl, a morpholin-4-yl radical;
m) a 4-fluorophenyl;
n) a pyridin-2-yl;
o) a methyl radical, an ethyl, an n-propyl, an isopropyl, an n-butyl, a trifluoromethyl, a 2-fluoroethyl, a 2,2-difluoroethyl, a 2,2,2-trifluoroethyl, a 3,3,3-trifluoropropyl, a 3,3,3-trifluoro-2-hydroxypropyl, a hydroxymethyl, a 2-hydroxyethyl, a 2-hydroxy-1,1-dimethylethyl, a methoxymethyl, a 2-methoxyethyl, a 2-methoxy-1-methylethyl, a 2-methoxy-1,1-dimethylethyl, a 2-ethoxyethyl, a 2-(trifluoromethoxy)ethyl, a 2-(2-hydroxyethoxy)ethyl, a 2-(2-methoxyethoxy)ethyl, a 2-(dimethylamino)ethyl, a 2-acetamidoethyl, a 2-[acetyl(methyl)amino]ethyl, a 2-methoxy-2-oxoethyl, a 2-ethoxy-2-oxoethyl, a 3-ethoxy-3-oxopropyl, a 2-amino-2-oxoethyl, a 2-(methylamino)-2-oxoethyl, a 2-(isopropylamino)-2-oxoethyl, a 2-(dimethylamino)-2-oxoethyl, a 2-(cyclopropylamino)-2-oxoethyl, a 2-oxo-2-pyrrolidin-1-ylethyl, a 2-(methylsulfonyl)ethyl, a cyclopropylmethyl, a pyrrolidin-1-ylmethyl, tetrahydrofuran-2-ylmethyl, a 2-thienylmethyl, a 4-chlorobenzyl, a 4-fluorobenzyl, a 2-methoxybenzyl, a 3-fluoro-4-methoxybenzyl, a pyridin-4-ylmethyl, a (5-methyl-1,2,4-oxadiazol-3-yl)methyl, a (5-methylisoxazol-3-yl)methyl;

in the form of a base or of salts of addition with acids or bases.

According to the present invention, we may mention compounds of formula (I) in which:

A represents a divalent aromatic radical selected from:

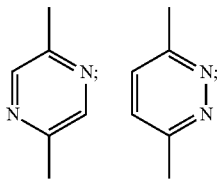

X represents a —CH— group;
R₁ represents an n-propyl radical;
R₂ represents a methyl radical;
R₃ represents a hydroxyl or a group —NR₇R₈;
R₄ represents a chlorine atom;
R₅ represents a hydrogen atom;
R₇ represents a hydrogen atom or a methyl radical;
R₈ represents:
b) a methyl radical, a 2-hydroxyethyl, a 3-hydroxypropyl, a 2-methoxyethyl, a 2-(dimethylamino)ethyl, a 2-(dimethylamino)propyl, a 2-(dimethylamino)-2-methylpropyl, a 3-(dimethylamino)propyl, a tetrahydrofuran-3-ylmethyl, a tetrahydro-2H-pyran-4-ylmethyl, a 2-furylmethyl, a (3-methyl-1H-1,2,4-triazol-5-yl)methyl, 1-(1H-tetrazol-5-yl)ethyl, a 2-(1H-pyrrol-1-yl) ethyl;
c) a cyclopropyl;
d) a 1-methylpyrrolidin-3-yl, a 1-(tert-butoxycarbonyl)piperidin-3-yl, a 1-methylpiperidin-4-yl;
or else R₇ and R₈, together with the nitrogen atom to which they are attached, constitute a heterocycle selected from: an azetidine, a pyrrolidine, a piperidine, a piperazine, a morpholine, a thiomorpholine, an octahydro-2H-pyrido[1,2-a]pyrazine, a 5,6,7,8-tetrahydro[1,2,4]triazolo[4,3-a]pyrazine, a 2,3-dihydro-1H-pyrrolo[3,4-c]pyridine, an octahydropyrrolo[1,2-a]pyrazine, a 1,4-diazepane; said heterocycle being unsubstituted or substituted once, twice or three times with substituents selected independently from:
b) a hydroxyl;
c) a methoxy radical;
d) an oxo;
h) an acetyl group;
i) a methoxycarbonyl group;
j) a dimethylcarbamoyl group;
k) a cyclobutyl radical;
l) a 1,1-dioxidotetrahydro-3-thienyl, a piperidin-1-yl, a morpholin-4-yl;
m) a 4-fluorophenyl;
o) a methyl radical, an ethyl, an n-propyl, an isopropyl, an n-butyl, a trifluoromethyl, a 3,3,3-trifluoropropyl, a hydroxymethyl, a 2-hydroxyethyl, a methoxymethyl, a 2-methoxyethyl, a 2-ethoxyethyl, a 2-(trifluoromethoxy)ethyl, a 2-(dimethylamino)ethyl, a 2-methoxy-2-oxoethyl, a 2-ethoxy-2-oxoethyl, a 2-(isopropylamino)-2-oxoethyl, a 2-(dimethylamino)-2-oxoethyl, a 2-(cyclopropylamino)-2-oxoethyl, a 2-oxo-2-pyrrolidin-1-ylethyl, a tetrahydrofuran-2-ylmethyl, a 4-fluorobenzyl, a 3-fluoro-4-methoxybenzyl, a pyridin-4-ylmethyl, a (5-methyl-1,2,4-oxadiazol-3-yl)methyl;
in the form of a base or of salts of addition with acids or bases.
According to the present invention, we may mention compounds of formula (I) in which:

A represents a divalent aromatic radical:

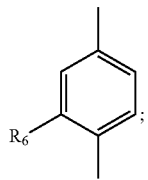

X represents a —CH— group or a nitrogen atom;
R₁ represents a methyl, ethyl, n-propyl radical or an ethoxy radical;
R₂ represents a methyl radical;
R₃ represents a hydroxyl or a group —NR₇R₈;
R₄ represents a hydrogen atom, a bromine, chlorine or fluorine atom, a cyano, a phenyl, a methyl radical, a trifluoromethyl radical, a methoxy radical or a dimethylamino group;
R₅ represents a hydrogen atom, a bromine, chlorine or fluorine atom or a methyl radical;
R₆ represents a hydrogen atom, a bromine atom, a cyano, a methoxycarbonyl group or a —CONH₂ group;
R₇ represents a hydrogen atom or a methyl radical;
R₈ represents:
b) a methyl radical, a 2-hydroxyethyl, a 2-methoxyethyl, a 2-(methylamino)ethyl, a 2-(dimethylamino)ethyl, a 2-(dimethylamino)-1-methylethyl, a (1-methylpiperidin-3-yl)methyl, a 2-(1H-imidazol-1-yl)ethyl;
d) a 1,1-dioxidotetrahydro-3-thienyl, a pyrrolidin-3-yl, a 1-methylpyrrolidin-3-yl, a 1-(tert-butoxycarbonyl)pyrrolidin-3-yl, a piperidin-3-yl, a 1-methylpiperidin-3-yl, a 1-(tert-butoxycarbonyl)piperidin-3-yl;
e) a methylsulfonyl group;
or else R₇ and R₈, together with the nitrogen atom to which they are attached, constitute a heterocycle selected from: an azetidine, a pyrrolidine, a piperidine, a piperazine, a morpholine, a 5,6,7,8-tetrahydro[1,2,4]triazolo[4,3-a]pyrazine, an octahydropyrrolo[1,2-a]pyrazine, a 1,4-diazepane, a 5,6,7,8-tetrahydroimidazo[1,2-a]pyrazine, a 4,5,6,7-tetrahydro-1H-pyrazolo[4,3-c]pyridine, a 1,4,5,6-tetrahydropyrrolo[3,4-c]pyrazole, a 6,7-dihydro-5H-pyrrolo[3,4-b]pyridine, a 3,8-diazabicyclo[3.2.1]octane, a 4,5,6,7-tetrahydro-1H-imidazo[4,5-c]pyridine, a 4,5,6,7-tetrahydro-1H-pyrazolo[3,4-c]pyridine, a 2,5-diazabicyclo[2.2.2]octane, a 2,5-diazabicyclo[2.2.1]heptane, an octahydropyrrolo[3,4-b]pyrrole, an octahydropyrrolo[3,4-c]pyrrole, an octahydro-2H-pyrazino[1,2-a]pyrazine; said heterocycle being unsubstituted or substituted once, twice or three times with substituents selected independently from:
a) a fluorine atom;
b) a hydroxyl;
c) a 2-hydroxyethoxy, a 2-methoxyethoxy;
d) an oxo;
e) an amino group, a methylamino, a dimethylamino;
f) an acetamido group;
g) a (tert-butoxycarbonyl)amino group, a (tert-butoxycarbonyl)(methyl)amino group;
i) a methoxycarbonyl group, a tert-butoxycarbonyl;
j) a cyclopropylcarbamoyl group, a cyclobutylcarbamoyl;
k) a cyclopropyl, a cyclobutyl, a 2-hydroxycyclopentyl radical;
l) an oxetan-3-yl, a morpholin-4-yl;
n) a pyridin-2-yl;
o) a methyl radical, an ethyl, an n-propyl, an isopropyl, an n-butyl, a trifluoromethyl, a 2-fluoroethyl, a 2,2-difluoroethyl, a 2,2,2-trifluoroethyl, a 3,3,3-trifluoro-2-hydroxypropyl, a hydroxymethyl, a 2-hydroxyethyl, a 2-hydroxy-1,1-dimethylethyl, a methoxymethyl, a 2-methoxyethyl, a 2-methoxy-1-methylethyl, a 2-methoxy-1,1-dimethylethyl, a 2-ethoxyethyl, a 2-(trifluoromethoxy)ethyl, a 2-(2-hydroxyethoxy)ethyl, a 2-(2-methoxyethoxy)ethyl, a 2-(dimethylamino)ethyl, a 2-acetamidoethyl, a 2-[acetyl(methyl)amino]ethyl, a 2-ethoxy-2-oxoethyl, a 3-ethoxy-3-oxopropyl, a 2-amino-2-oxoethyl, a 2-(methylamino)-2-oxoethyl, a 2-(dimethylamino)-2-oxoethyl, a 2-oxo-2-pyrrolidin-1-ylethyl, a 2-(methylsulfonyl)ethyl, a cyclopropylmethyl, a pyrrolidin-1-ylmethyl, a 2-thienylmethyl, a 4-chlorobenzyl, a 4-fluorobenzyl, a 2-methoxybenzyl, a (5-methylisoxazol-3-yl)methyl;

in the form of a base or of salts of addition with acids or bases.

According to the present invention, we may mention compounds of formula (I) in which:

A represents a divalent aromatic radical selected from:

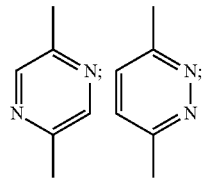

X represents a —CH— group;

$R_1$ represents an n-propyl radical;

$R_2$ represents a methyl radical;

$R_3$ represents a hydroxyl or a group —$NR_7R_8$ selected from:

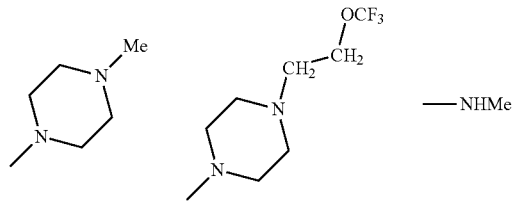

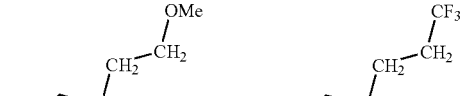

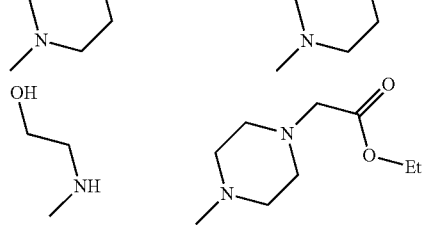

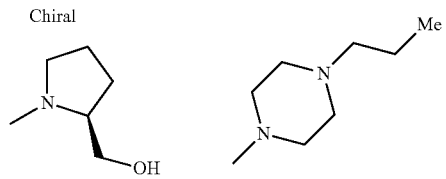

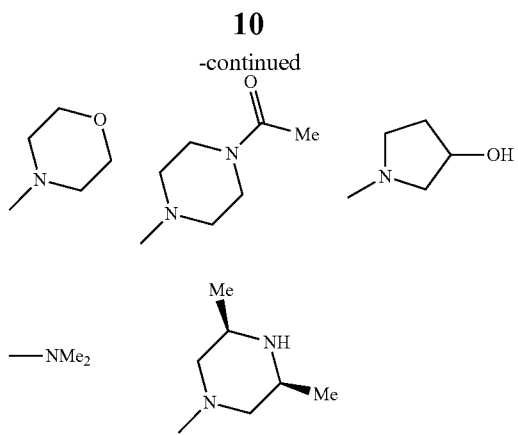

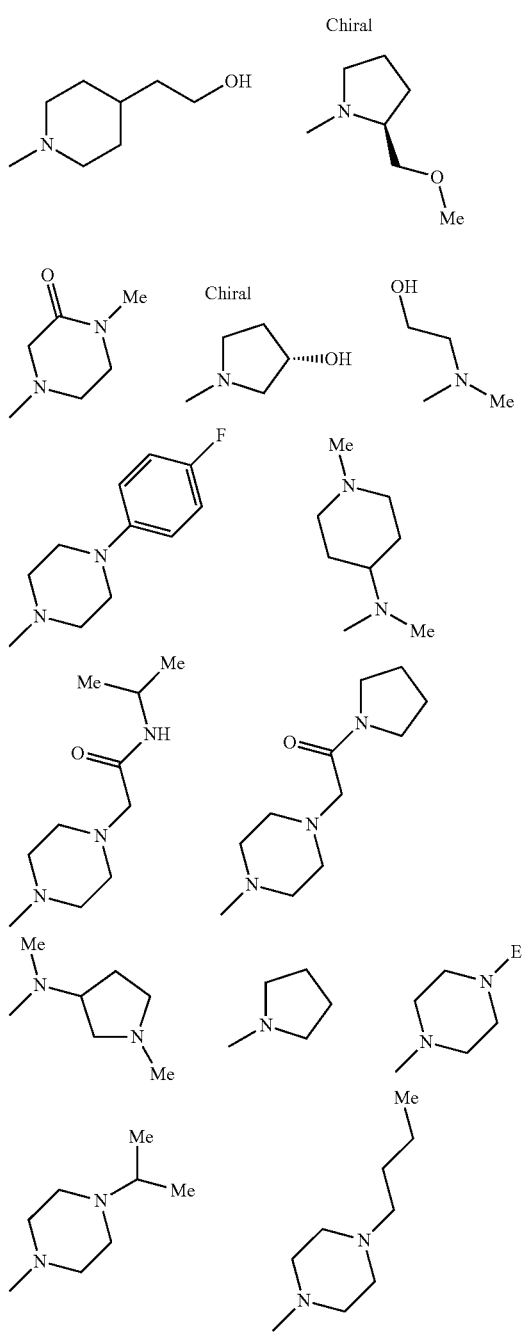

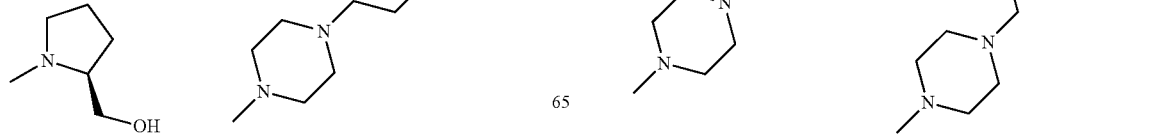

11
-continued
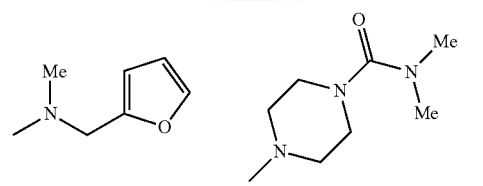
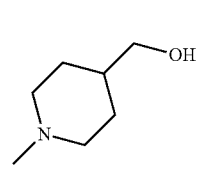
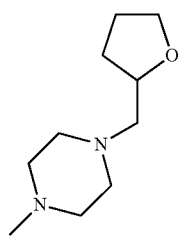
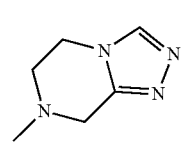
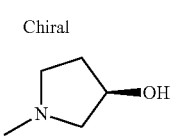
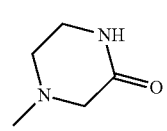
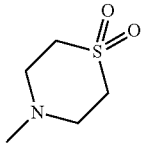
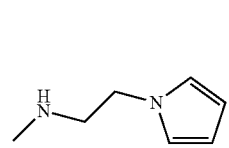
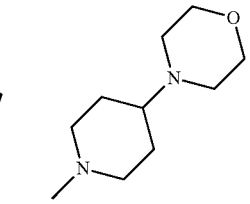
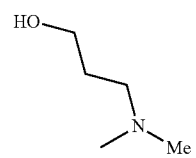
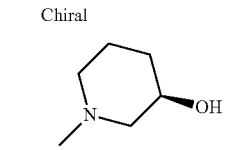
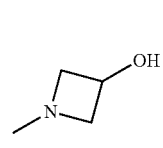
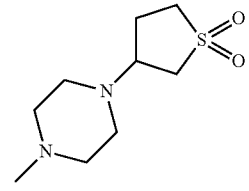
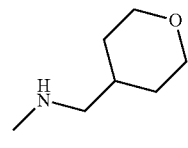
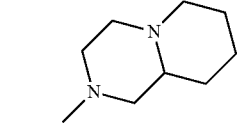
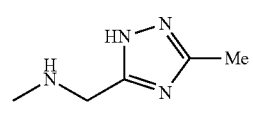
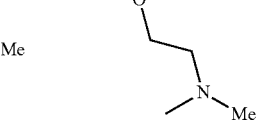
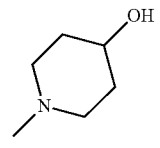
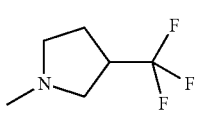
12
-continued
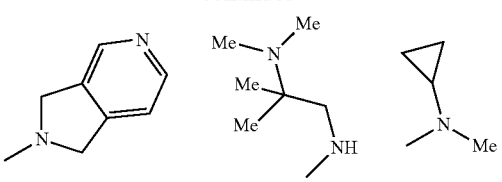
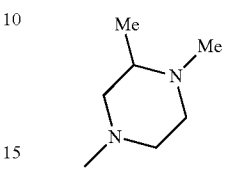
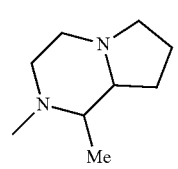
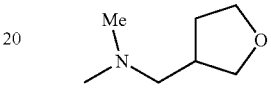
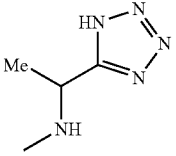
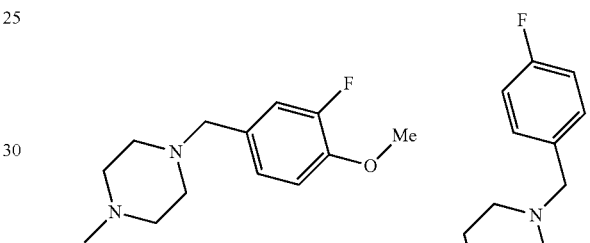
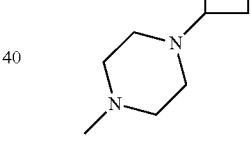
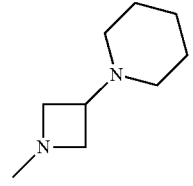
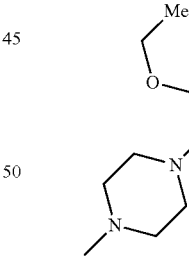
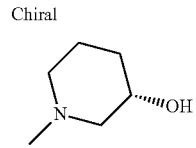
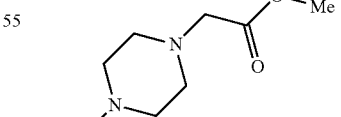
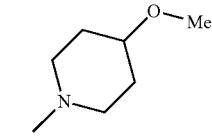
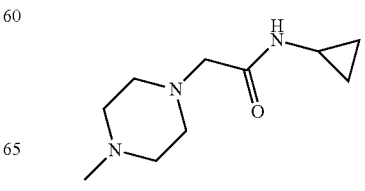
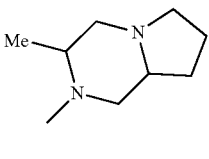

-continued

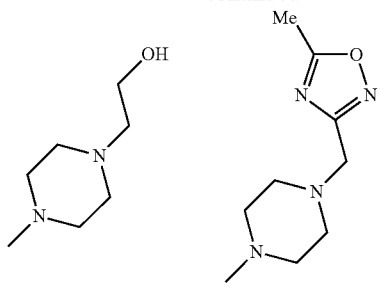
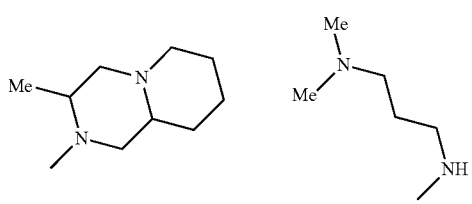
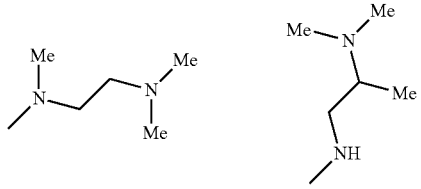
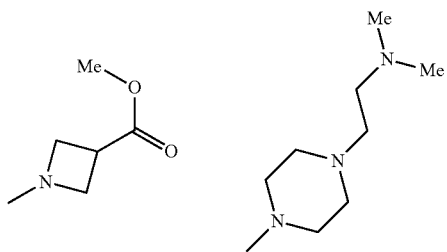
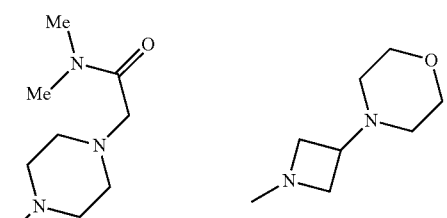
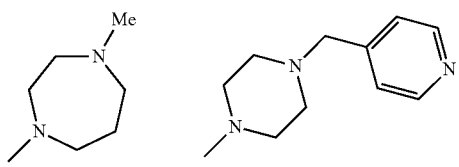

$R_4$ represents a chlorine atom;

$R_5$ represents a hydrogen atom; in the form of a base or of salts of addition with acids or bases.

According to the present invention, we may mention compounds of formula (I) in which:

A represents a divalent aromatic radical:

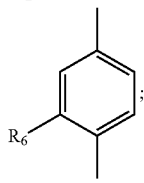

X represents a —CH— group or a nitrogen atom;

$R_1$ represents a methyl, ethyl, n-propyl radical or an ethoxy radical;

$R_2$ represents a methyl radical;

$R_3$ represents a hydroxyl or a group —NR$_7$R$_8$ selected from:

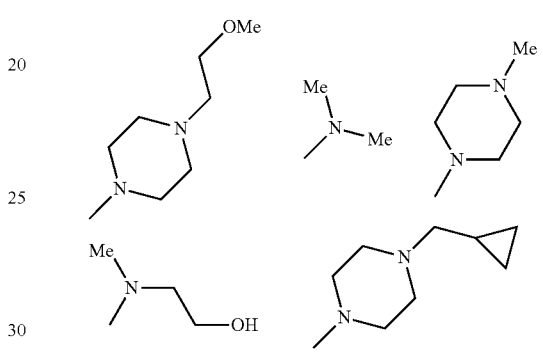
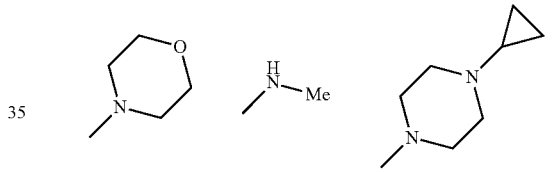
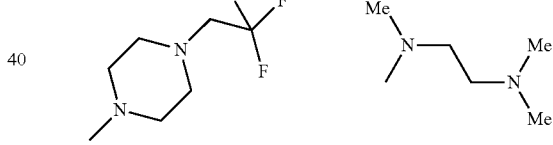
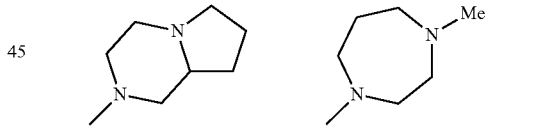
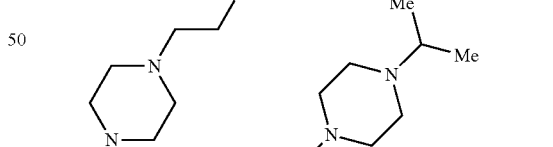
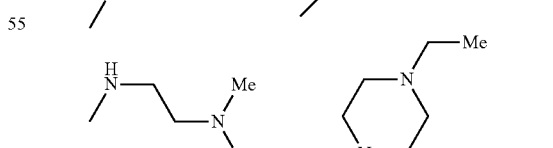
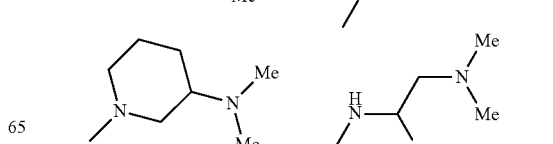

-continued
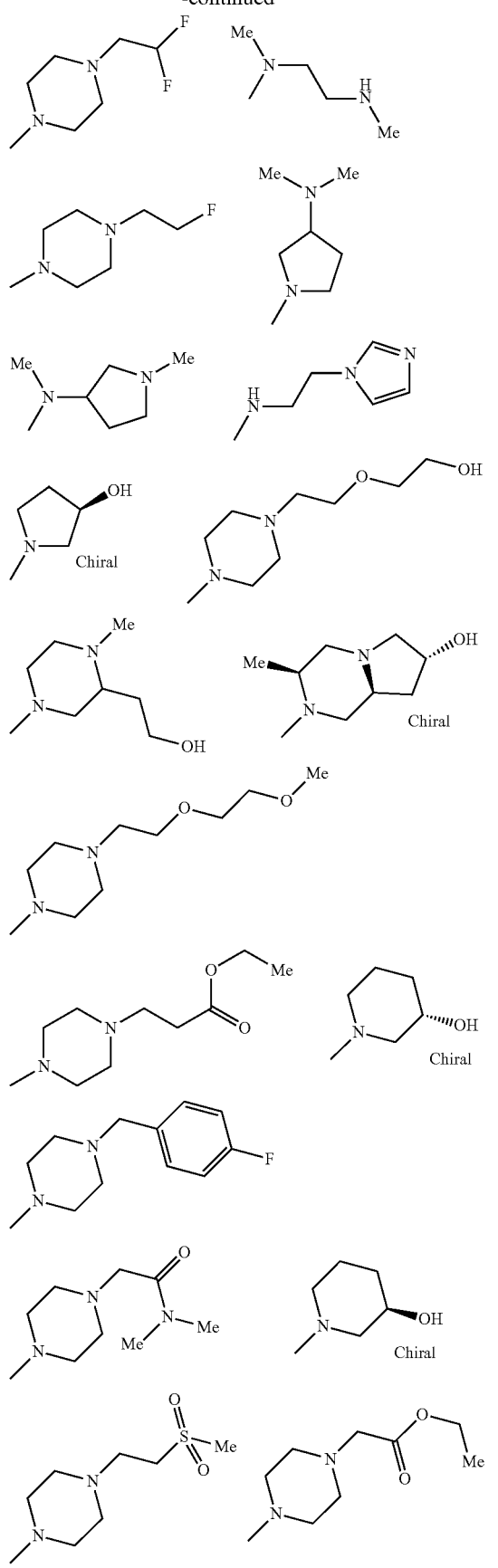
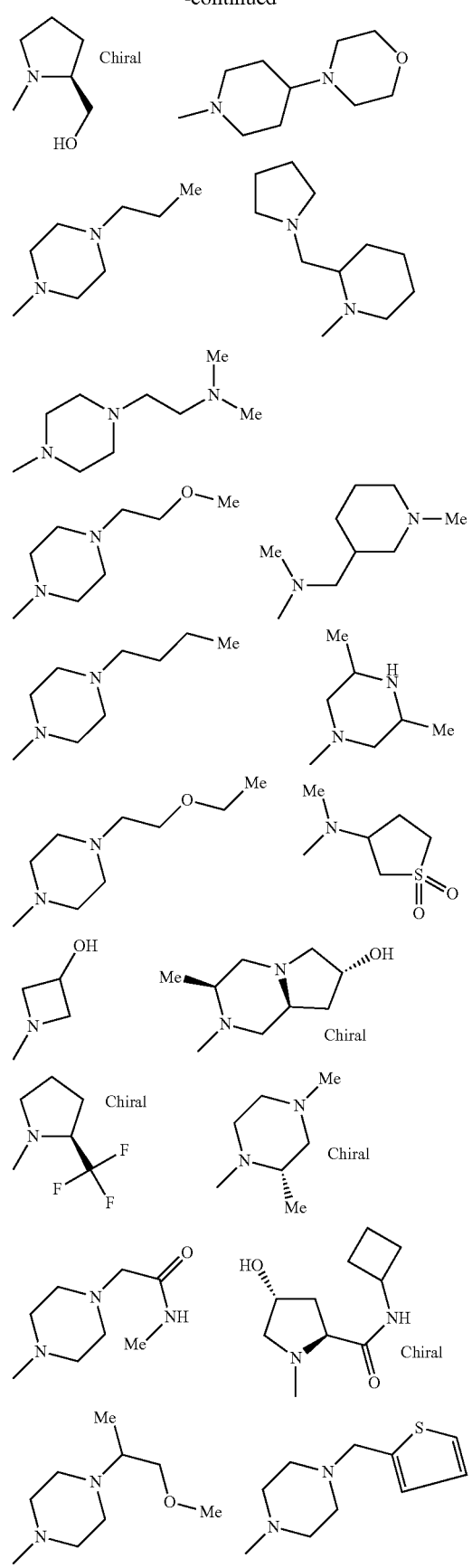

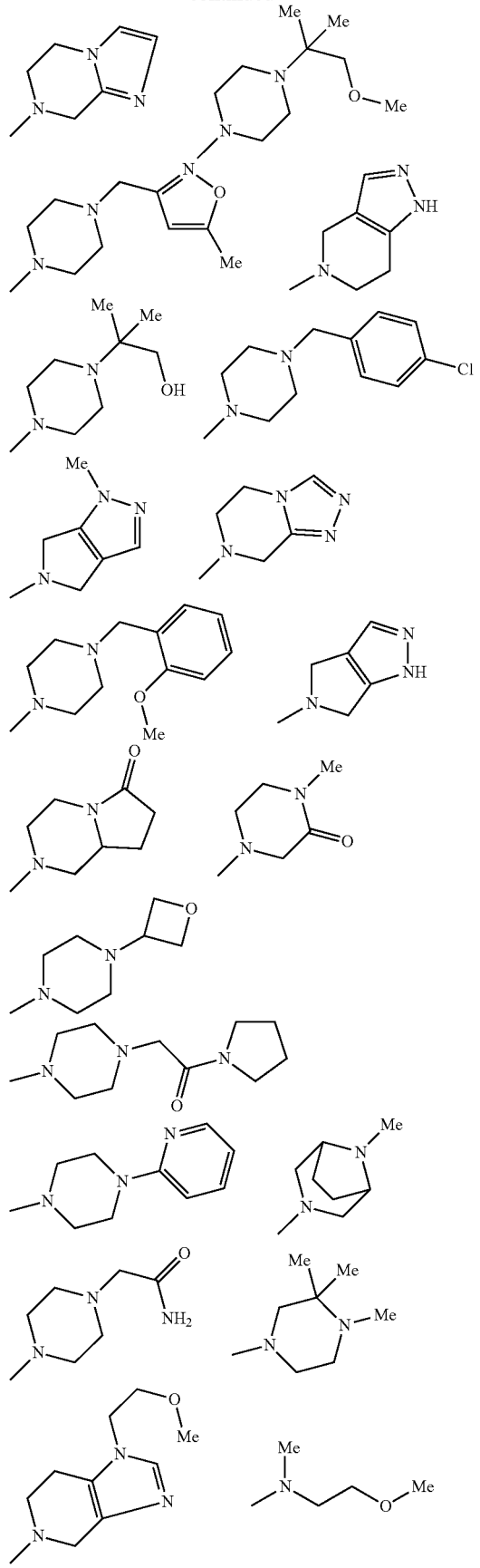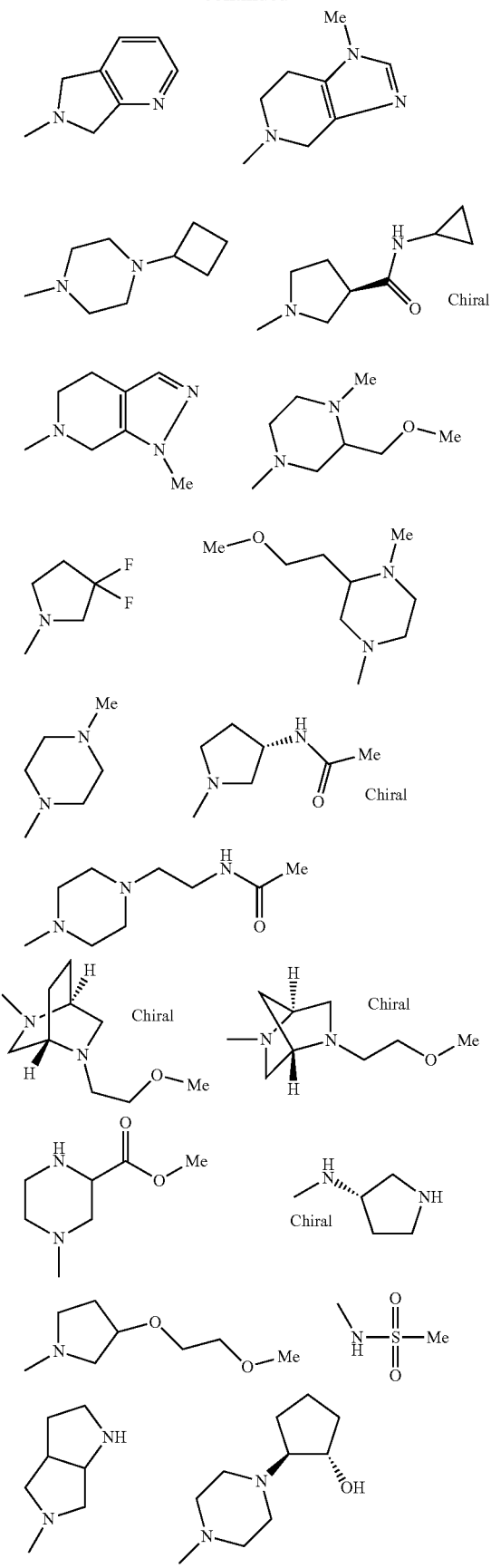

-continued

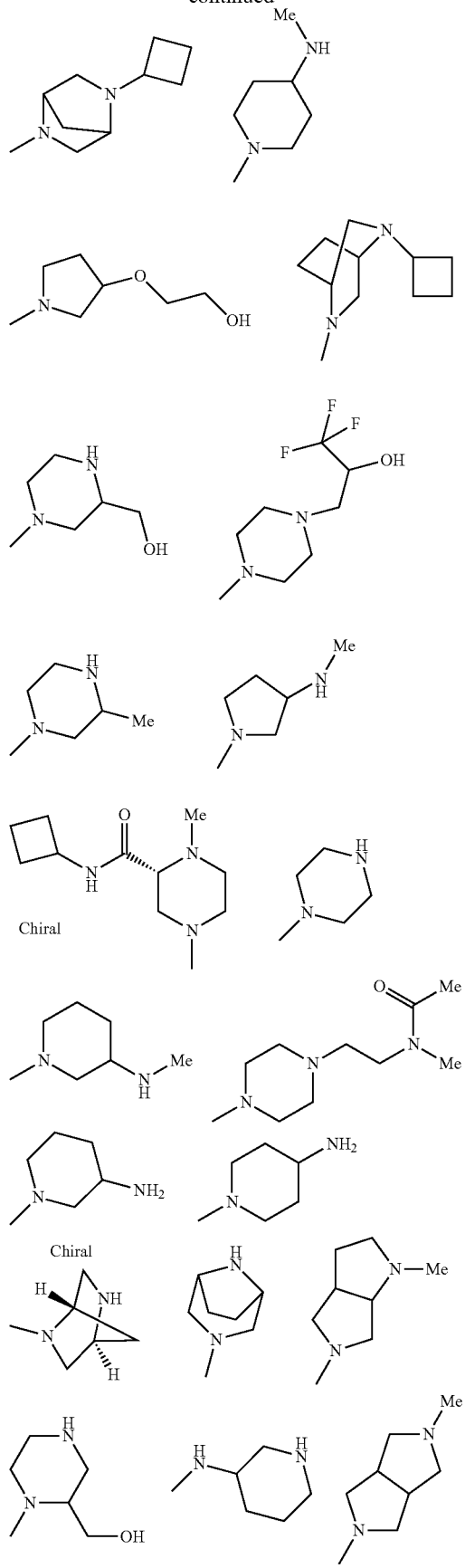

-continued

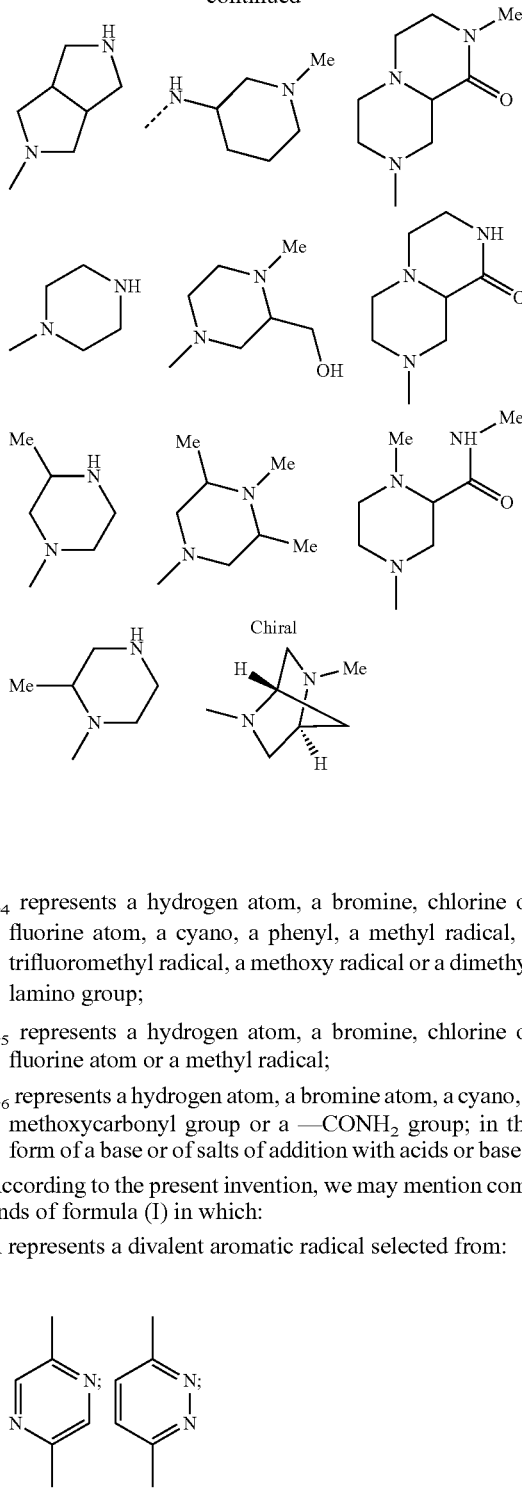

R₄ represents a hydrogen atom, a bromine, chlorine or fluorine atom, a cyano, a phenyl, a methyl radical, a trifluoromethyl radical, a methoxy radical or a dimethylamino group;

R₅ represents a hydrogen atom, a bromine, chlorine or fluorine atom or a methyl radical;

R₆ represents a hydrogen atom, a bromine atom, a cyano, a methoxycarbonyl group or a —CONH₂ group; in the form of a base or of salts of addition with acids or bases.

According to the present invention, we may mention compounds of formula (I) in which:

A represents a divalent aromatic radical selected from:

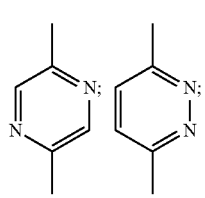

X represents a —CH— group;

R₁ represents an n-propyl radical;

R₂ represents a methyl radical;

R₃ represents a hydroxyl or a group —NR₇R₈ selected from:

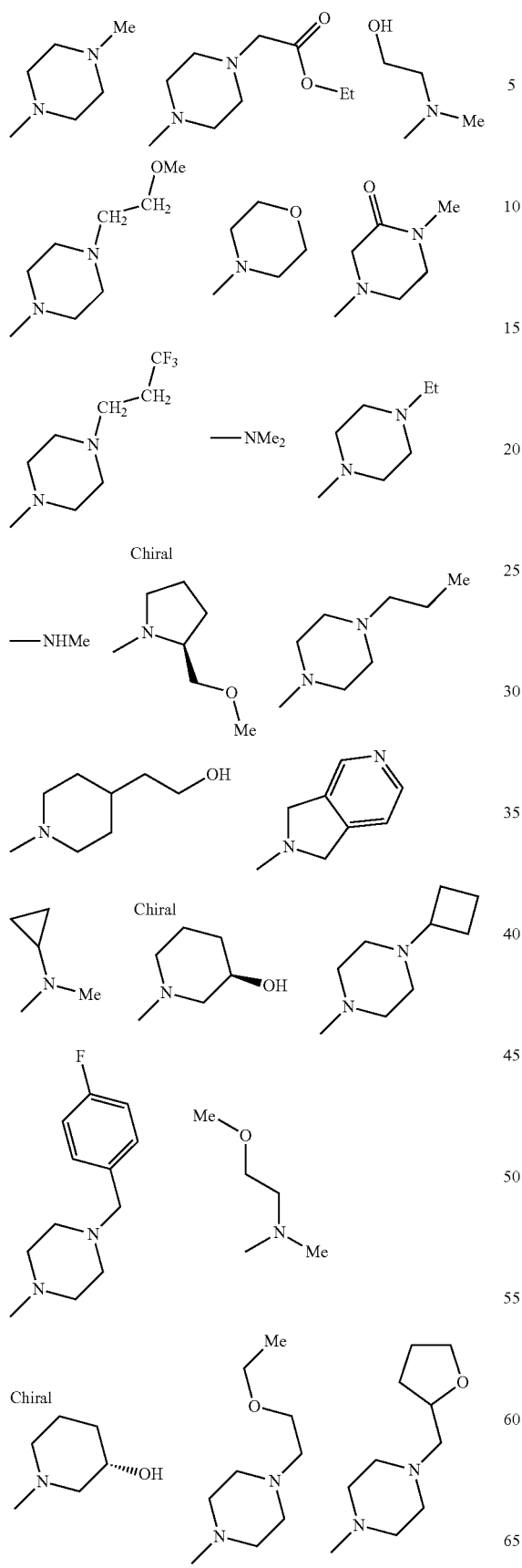

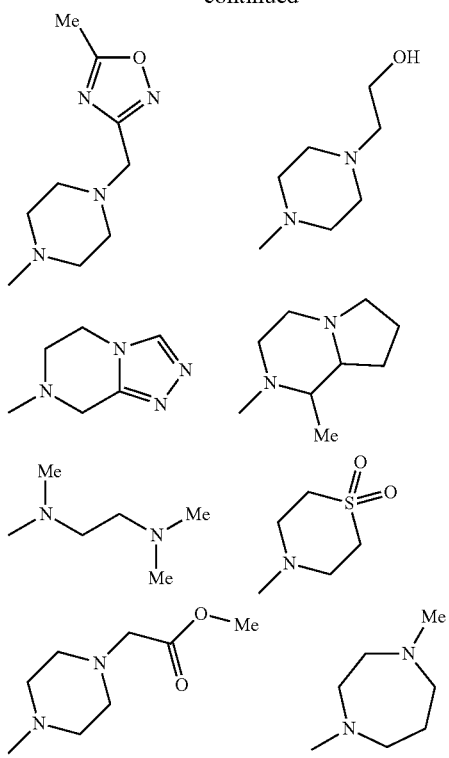

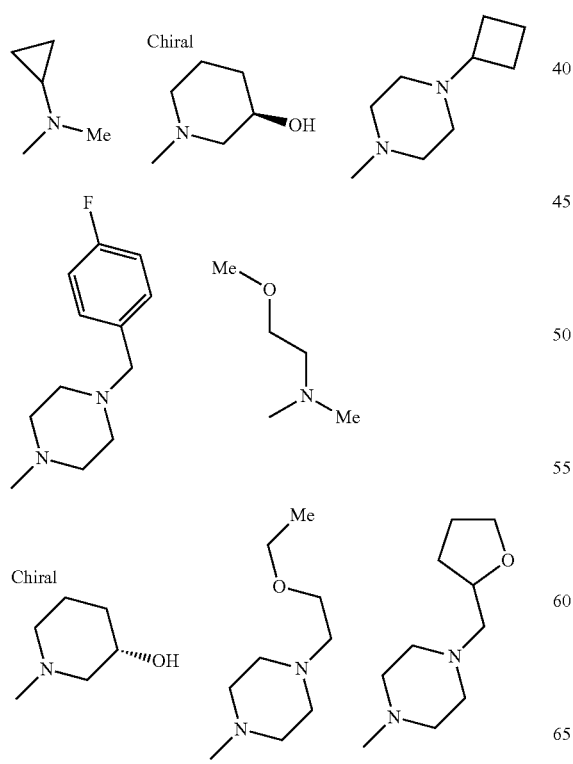

-continued

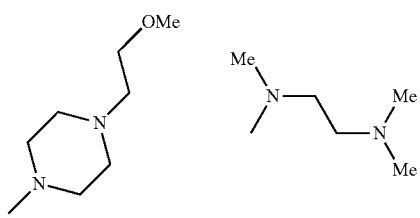

$R_4$ represents a chlorine atom;

$R_5$ represents a hydrogen atom;

in the form of a base or of salts of addition with acids or bases.

According to the present invention, we may mention compounds of formula (I) in which:

A represents a divalent aromatic radical:

X represents a —CH— group or a nitrogen atom;

$R_1$ represents a methyl, ethyl, n-propyl radical or an ethoxy radical;

$R_2$ represents a methyl radical;

$R_3$ represents a hydroxyl or a group —$NR_7R_8$ selected from:

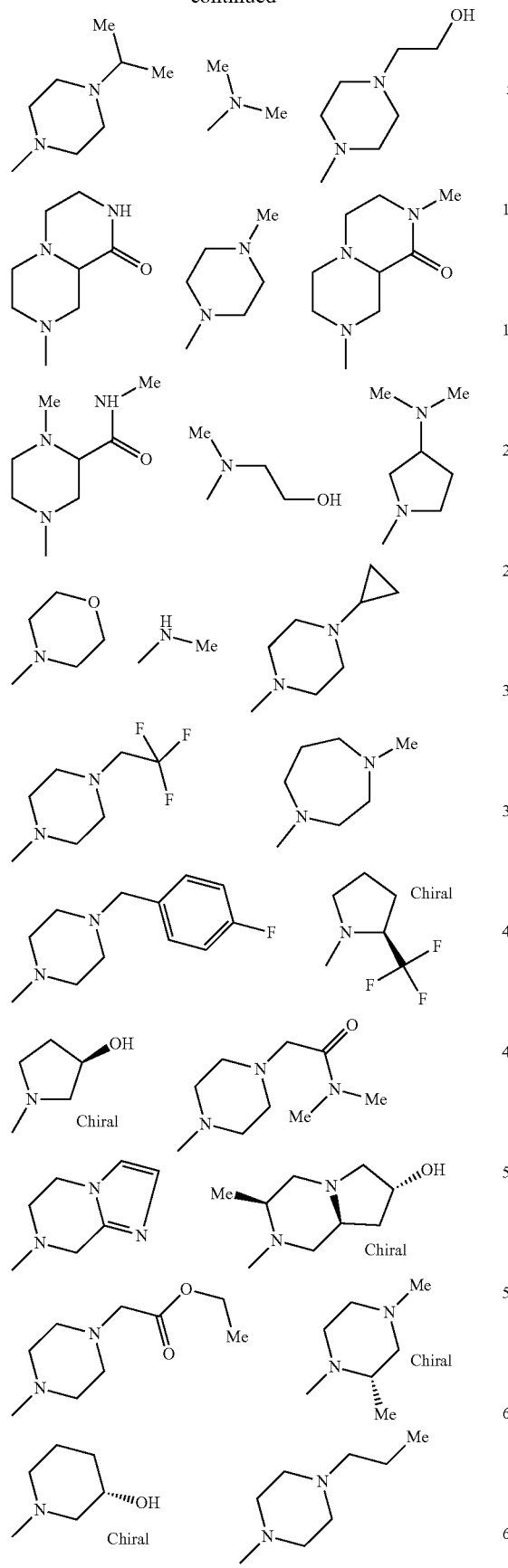
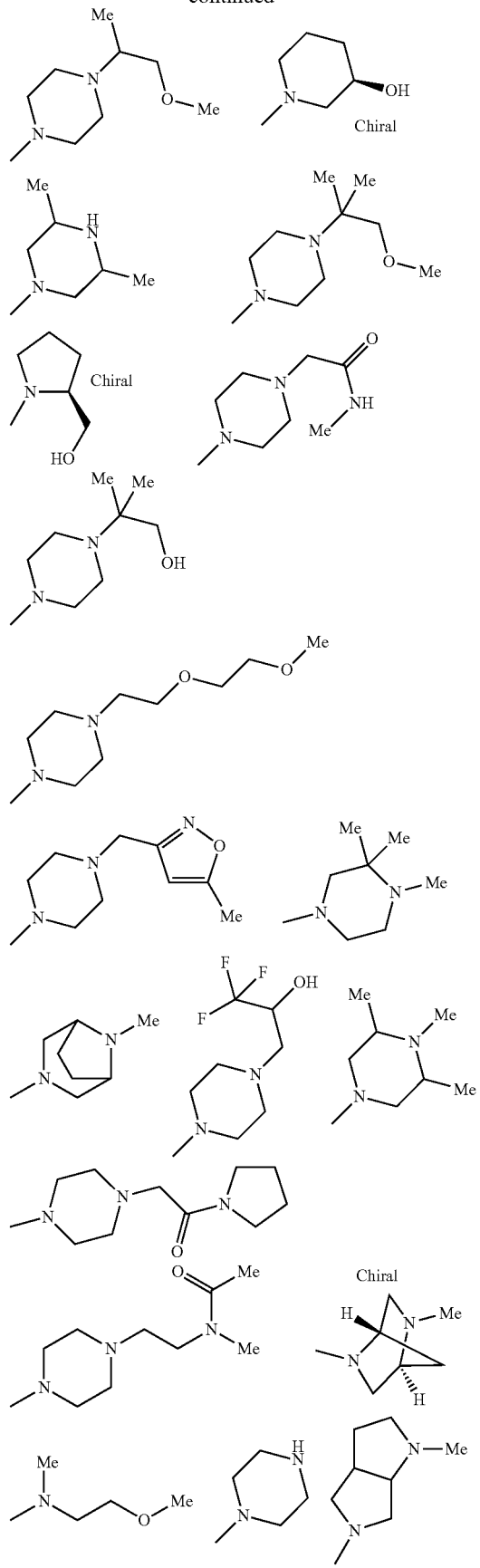

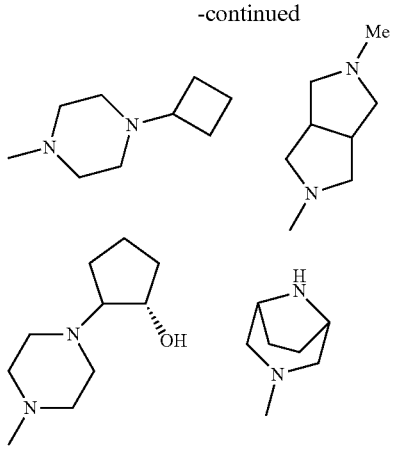

R₄ represents a hydrogen atom, a bromine, chlorine or fluorine atom, a cyano, a phenyl, a methyl radical, a trifluoromethyl radical, a methoxy radical or a dimethylamino group;

R₅ represents a hydrogen atom, a bromine, chlorine or fluorine atom or a methyl radical;

R₆ represents a hydrogen atom, a bromine atom, a cyano, a methoxycarbonyl group or a —CONH₂ group;

in the form of a base or of salts of addition with acids or bases.

Among the compounds of formula (I) according to the invention, we may notably mention the following compounds:

(3-{[4-(4-butyryl-5-methyl-1H-pyrazol-1-yl)phenyl]carbamoyl}-5-methyl-1H-indol-1-yl)acetic acid;

(3-{[4-(4-butyryl-5-methyl-1H-pyrazol-1-yl)phenyl]carbamoyl}-5,6-dimethyl-1H-indol-1-yl)acetic acid;

(3-{[6-(4-butyryl-5-methyl-1H-pyrazol-1-yl)pyridazin-3-yl]carbamoyl}-5-chloro-1H-indol-1-yl)acetic acid;

N-[5-(4-butyryl-5-methyl-1H-pyrazol-1-yl)pyrazin-2-yl]-5-chloro-1-[2-(4-methylpiperazin-1-yl)-2-oxoethyl]-1H-indole-3-carboxamide;

N-[6-(4-butyryl-5-methyl-1H-pyrazol-1-yl)pyridazin-3-yl]-5-chloro-1-[2-(4-methyl piperazin-1-yl)-2-oxoethyl]-1H-indole-3-carboxamide;

N-[6-(4-butyryl-5-methyl-1H-pyrazol-1-yl)pyridazin-3-yl]-5-chloro-1-{2-[4-(2-methoxyethyl)piperazin-1-yl]-2-oxoethyl}-1H-indole-3-carboxamide;

N-[6-(4-butyryl-5-methyl-1H-pyrazol-1-yl)pyridazin-3-yl]-5-chloro-1-{2-oxo-2-[4-(3,3,3-trifluoropropyl)piperazin-1-yl]ethyl}-1H-indole-3-carboxamide;

N-[6-(4-butyryl-5-methyl-1H-pyrazol-1-yl)pyridazin-3-yl]-5-chloro-1-[2-(methylamino)-2-oxoethyl]-1H-indole-3-carboxamide;

N-[6-(4-butyryl-5-methyl-1H-pyrazol-1-yl)pyridazin-3-yl]-5-chloro-1-(2-morpholin-4-yl-2-oxoethyl)-1H-indole-3-carboxamide;

N-[6-(4-butyryl-5-methyl-1H-pyrazol-1-yl)pyridazin-3-yl]-5-chloro-1-[2-(dimethylamino)-2-oxoethyl]-1H-indole-3-carboxamide;

N-[6-(4-butyryl-5-methyl-1H-pyrazol-1-yl)pyridazin-3-yl]-5-chloro-1-{2-[(2S)-2-(methoxymethyl)pyrrolidin-1-yl]-2-oxoethyl}-1H-indole-3-carboxamide;

N-[6-(4-butyryl-5-methyl-1H-pyrazol-1-yl)pyridazin-3-yl]-5-chloro-1-[2-(4-ethylpiperazin-1-yl)-2-oxoethyl]-1H-indole-3-carboxamide;

N-[6-(4-butyryl-5-methyl-1H-pyrazol-1-yl)pyridazin-3-yl]-5-chloro-1-[2-(4-propylpiperazin-1-yl)-2-oxoethyl]-1H-indole-3-carboxamide;

N-[6-(4-butyryl-5-methyl-1H-pyrazol-1-yl)pyridazin-3-yl]-5-chloro-1-{2-[(2-methoxyethyl)(methyl)amino]-2-oxoethyl}-1H-indole-3-carboxamide;

N-[6-(4-butyryl-5-methyl-1H-pyrazol-1-yl)pyridazin-3-yl]-5-chloro-1-{2-oxo-2-[4-(tetrahydrofuran-2-ylmethyl)piperazin-1-yl]ethyl}-1H-indole-3-carboxamide;

N-[6-(4-butyryl-5-methyl-1H-pyrazol-1-yl)pyridazin-3-yl]-5-chloro-1-[2-(5,6-dihydro[1,2,4]triazolo[4,3-a]pyrazin-7(8H)-yl)-2-oxoethyl]-1H-indole-3-carboxamide;

N-[6-(4-butyryl-5-methyl-1H-pyrazol-1-yl)pyridazin-3-yl]-5-chloro-1-[2-(4-cyclobutyl piperazin-1-yl)-2-oxoethyl]-1H-indole-3-carboxamide;

N-[6-(4-butyryl-5-methyl-1H-pyrazol-1-yl)pyridazin-3-yl]-5-chloro-1-(2-[(4-[(5-methyl-1,2,4-oxadiazol-3-yl)methyl]piperazin-1-yl]-2-oxoethyl)-1H-indole-3-carboxamide;

{4-[(3-{[6-(4-butyryl-5-methyl-1H-pyrazol-1-yl)pyridazin-3-yl]carbamoyl}-5-chloro-1H-indol-1-yl)acetyl]piperazin-1-yl}methyl acetate;

N-[6-(4-butyryl-5-methyl-1H-pyrazol-1-yl)pyridazin-3-yl]-5-chloro-1-{2-[cyclopropyl(methyl)amino]-2-oxoethyl}-1H-indole-3-carboxamide;

N-[6-(4-butyryl-5-methyl-1H-pyrazol-1-yl)pyridazin-3-yl]-5-chloro-1-{2-[4-(4-fluorobenzyl)piperazin-1-yl]-2-oxoethyl}-1H-indole-3-carboxamide;

N-[6-(4-butyryl-5-methyl-1H-pyrazol-1-yl)pyridazin-3-yl]-5-chloro-1-{2-[4-(2-ethoxyethyl)piperazin-1-yl]-2-oxoethyl}-1H-indole-3-carboxamide;

N-[6-(4-butyryl-5-methyl-1H-pyrazol-1-yl)pyridazin-3-yl]-5-chloro-1-{2-[4-(2-hydroxyethyl)piperazin-1-yl]-2-oxoethyl}-1H-indole-3-carboxamide;

N-[6-(4-butyryl-5-methyl-1H-pyrazol-1-yl)pyridazin-3-yl]-5-chloro-1-(2-{[2-(dimethylamino)ethyl](methyl)amino}-2-oxoethyl)-1H-indole-3-carboxamide;

N-[6-(4-butyryl-5-methyl-1H-pyrazol-1-yl)pyridazin-3-yl]-5-chloro-1-[2-(4-methyl-1,4-diazepan-1-yl)-2-oxoethyl]-1H-indole-3-carboxamide;

N-[4-(4-butyryl-5-methyl-1H-pyrazol-1-yl)phenyl]-5-chloro-1-[2-(8-methyl-9-oxooctahydro-2H-pyrazino[1,2-a]pyrazin-2-yl)-2-oxoethyl]-1H-indole-3-carboxamide;

N-[4-(4-butyryl-5-methyl-1H-pyrazol-1-yl)-2-cyanophenyl]-5-chloro-1-[2-(4-methylpiperazin-1-yl)-2-oxoethyl]-1H-indole-3-carboxamide;

N-[4-(4-butyryl-5-methyl-1H-pyrazol-1-yl)phenyl]-5-chloro-1-{2-[4-(4-fluorobenzyl)piperazin-1-yl]-2-oxoethyl}-1H-indole-3-carboxamide;

N-[4-(4-butyryl-5-methyl-1H-pyrazol-1-yl)phenyl]-5-chloro-1-{2-[4-(2-methoxyethyl)piperazin-1-yl]-2-oxoethyl}-1H-indole-3-carboxamide;

N-[4-(4-butyryl-5-methyl-1H-pyrazol-1-yl)phenyl]-1-{2-[4-(2-methoxyethyl)piperazin-1-yl]-2-oxoethyl}-5-methyl-1H-indole-3-carboxamide;

N-[4-(4-butyryl-5-methyl-1H-pyrazol-1-yl)phenyl]-5-chloro-1-[2-(4-methylpiperazin-1-yl)-2-oxoethyl]-1H-indole-3-carboxamide;

N-[4-(4-butyryl-5-methyl-1H-pyrazol-1-yl)phenyl]-5-chloro-1-{2-[4-(2-methoxy-1-methylethyl)piperazin-1-yl]-2-oxoethyl}-1H-indole-3-carboxamide;

N-[4-(4-butyryl-5-methyl-1H-pyrazol-1-yl)phenyl]-5-methyl-1-[2-(4-methylpiperazin-1-yl)-2-oxoethyl]-1H-indole-3-carboxamide;

N-[4-(4-butyryl-5-methyl-1H-pyrazol-1-yl)phenyl]-5-chloro-6-fluoro-1-{2-[4-(2-methoxyethyl)piperazin-1-yl]-2-oxoethyl}-1H-indole-3-carboxamide;

N-[4-(4-butyryl-5-methyl-1H-pyrazol-1-yl)phenyl]-5-methoxy-1-[2-(4-methylpiperazin-1-yl)-2-oxoethyl]-1H-indole-3-carboxamide;

N-[4-(4-butyryl-5-methyl-1H-pyrazol-1-yl)phenyl]-5-chloro-1-{2-[4-methyl-3-(methylcarbamoyl)piperazin-1-yl]-2-oxoethyl}-1H-indole-3-carboxamide;

N-[4-(4-butyryl-5-methyl-1H-pyrazol-1-yl)phenyl]-5,6-dimethyl-1-[2-(4-methylpiperazin-1-yl)-2-oxoethyl]-1H-indole-3-carboxamide;

N-[4-(4-butyryl-5-methyl-1H-pyrazol-1-yl)phenyl]-5-methyl-1-[2-(4-methylpiperazin-1-yl)-2-oxoethyl]-1H-indazole-3-carboxamide;

N-[4-(4-butyryl-5-methyl-1H-pyrazol-1-yl)phenyl]-5-methyl-1-(2-oxo-2-piperazin-1-ylethyl)-1H-indole-3-carboxamide;

N-[4-(4-butyryl-5-methyl-1H-pyrazol-1-yl)phenyl]-5-chloro-6-fluoro-1-[2-(4-methylpiperazin-1-yl)-2-oxoethyl]-1H-indole-3-carboxamide;

N-[4-(4-butyryl-5-methyl-1H-pyrazol-1-yl)phenyl]-5-chloro-1-(2-{4-[(5-methylisoxazol-3-yl)methyl]piperazin-1-yl}-2-oxoethyl)-1H-indole-3-carboxamide;

N-[4-(4-butyryl-5-methyl-1H-pyrazol-1-yl)phenyl]-5-methyl-1-(2-morpholin-4-yl-2-oxoethyl)-1H-indole-3-carboxamide;

N-[4-(4-butyryl-5-methyl-1H-pyrazol-1-yl)phenyl]-5-chloro-1-(2-oxo-2-piperazin-1-ylethyl)-1H-indole-3-carboxamide;

N-[4-(4-butyryl-5-methyl-1H-pyrazol-1-yl)phenyl]-5-chloro-1-{2-[4-(2-methoxy-1,1-dimethylethyl)piperazin-1-yl]-2-oxoethyl}-1H-indole-3-carboxamide;

N-[4-(4-butyryl-5-methyl-1H-pyrazol-1-yl)phenyl]-5-chloro-1-{2-[4-(2-hydroxy-1,1-dimethylethyl)piperazin-1-yl]-2-oxoethyl}-1H-indole-3-carboxamide;

N-[4-(4-butyryl-5-methyl-1H-pyrazol-1-yl)phenyl]-5-chloro-1-[2-(8-methyl-3,8-diazabicyclo[3.2.1]oct-3-yl)-2-oxoethyl]-1H-indole-3-carboxamide;

N-[4-(4-butyryl-5-methyl-1H-pyrazol-1-yl)phenyl]-1-[2-(4-methylpiperazin-1-yl)-2-oxoethyl]-5-(trifluoromethyl)-1H-indole-3-carboxamide;

N-[4-(4-butyryl-5-methyl-1H-pyrazol-1-yl)phenyl]-5-chloro-1-[2-oxo-2-(9-oxooctahydro-2H-pyrazino[1,2-a]pyrazin-2-yl)ethyl]-1H-indole-3-carboxamide;

in the form of a base or salt of addition with an acid or a base.

Hereinafter, protective group Pg means a group that makes it possible, on the one hand, to protect a reactive function such as a hydroxyl or an amine during a synthesis and, on the other hand, to regenerate the reactive function intact at the end of synthesis. Examples of protective groups as well as of methods of protection and of deprotection are given in "Protective Groups in Organic Synthesis", Greene et al., 4th Edition, John Wiley & Sons, Inc., New York, 2007.

Leaving group means, hereinafter, a group that can be easily cleaved from a molecule by rupture of a heterolytic bond, with departure of an electron pair. This group can thus easily be replaced with another group during a substitution reaction, for example. Said leaving groups are, for example, the halogens or an activated hydroxyl group such as a methanesulfonate, benzenesulfonate, p-toluenesulfonate, triflate, acetate, etc. Examples of leaving groups as well as references for their preparation are given in "Advanced Organic Chemistry", M. B. Smith and J. March, 6th Edition, Wiley Interscience, 2007, p. 496-501.

According to the invention, the compounds of formula (I) in which $R_3$=—OH (compound IA) can be prepared by a method that is characterized in that:

a compound of formula (II):

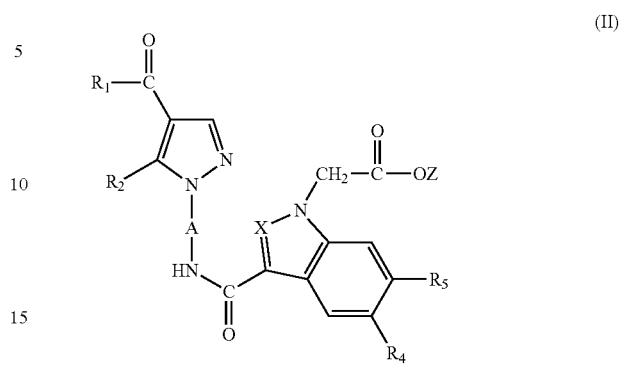

in which A, X, $R_1$, $R_2$, $R_4$ and $R_5$ are as defined for a compound of formula (I) and Z represents a $(C_1-C_4)$ alkyl, are hydrolyzed, in an acid or basic medium.

Optionally, the compound of formula (I) is transformed to one of its salts with mineral or organic bases.

The reaction is carried out in an acid medium by the action of a strong acid, for example hydrochloric acid or sulfuric acid, in a solvent such as for example dioxane or water and at a temperature between −10° C. and 110° C.

The reaction is carried out in a basic medium by the action of an alkaline base, for example potassium hydroxide, lithium hydroxide or sodium hydroxide, in a solvent such as for example dioxane, tetrahydrofuran, water, methanol, ethanol or a mixture of these solvents and at a temperature between −10° C. and the reflux temperature of the solvent.

According to the invention, the compounds of formula (I) in which $R_3$=—$NR_7R_8$ (compound IB) can be prepared by a method that is characterized in that:

a compound of formula (IA):

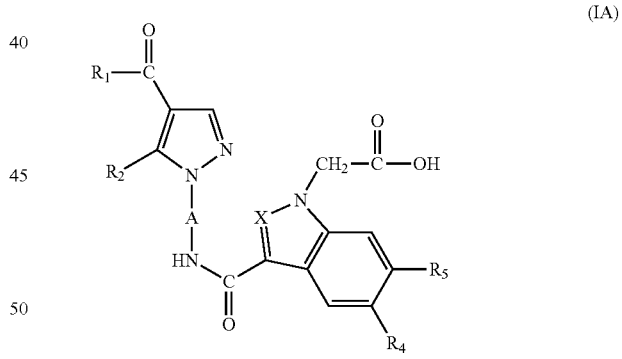

in which A, X, $R_1$, $R_2$, $R_4$ and $R_5$ are as defined for a compound of formula (I), is reacted with an amine of formula (III):

in which $R_7$ and $R_8$ are as defined for a compound of formula (I).

Optionally, the compound of formula (I) is transformed into one of its salts with mineral or organic acids.

The reaction is carried out in the presence of a base, for example triethylamine, 4-dimethylaminopyridine, N-methylmorpholine, N-ethylmorpholine or pyridine and in the presence of a coupling agent, for example bis(2-oxo-1,3-oxazolidin-3-yl)phosphinic chloride, isobutyl chloroformate, 1,1'-carbonyldiimidazole, 1-(3-dimethylaminopropyl)-3- ethylcarbodiimide hydrochloride, 2-cyano-2-(hydroxyimino)ethyl acetate. The solvent used is, for example, dichloromethane, 1,2-dichloroethane or N,N-dimethylformamide. The reaction temperature is between −10° C. and the reflux temperature of the solvent.

In particular, certain compounds of formula (I) can be prepared from other compounds of formula (I).

The compounds of formula (I) thus obtained can be separated subsequently from the reaction mixture and purified by classical methods, for example by crystallization or silica gel column chromatography.

The compounds of formula (I) thus obtained are isolated in the form of free base or of salt, by classical techniques.

The compounds of formula (II) can be prepared by reaction of an acid or of an activated functional derivative of said acid of formula:

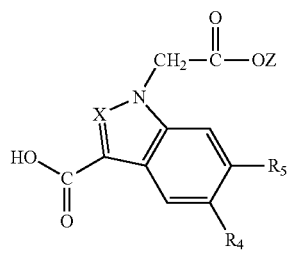

(IV)

in which X, $R_4$ and $R_5$ are as defined for a compound of formula (I) and Z represents a $(C_1-C_4)$alkyl, with a compound of formula:

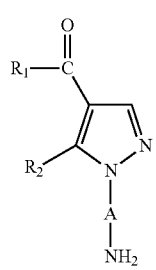

(V)

in which A, $R_1$ and $R_2$ are as defined for a compound of formula (I).

When a compound of formula (V) is treated with the acid of formula (IV) itself, this is carried out in the presence of a coupling agent used in peptide chemistry such as 1,3-dicyclohexylcarbodiimide or benzotriazol-1-yl-oxytris(dimethylamino)phosphonium hexafluorophosphate or benzotriazol-1-yl-oxytris(pyrrolidino)phosphonium hexafluorophosphate or 2-(1H-benzotriazol-1-yl)-1,1,3,3-tetramethyluronium tetrafluoroborate or 1-(3-dimethylaminopropyl)-3-ethylcarbodiimide hydrochloride, in the presence of a base such as triethylamine. N,N-diisopropylethylamine or 4-dimethylaminopyridine, in a solvent such as dichloromethane, 1,2-dichloroethane, N—N-dimethylformamide or tetrahydrofuran at a temperature between −10° C. and the reflux temperature of the solvent.

As the activated functional derivative of acid (IV), it is possible to use the acid chloride, the anhydride, a mixed anhydride, a $C_1-C_4$ alkyl ester in which the alkyl is linear or branched, an activated ester, for example the p-nitrophenyl ester.

Thus, for example, the chloride of the acid obtained by reaction of thionyl chloride or of oxalyl chloride on the acid of formula (IV) can be reacted with the compound of formula (V), in a solvent, such as a chlorinated solvent (dichloromethane, 1,2-dichloroethane, chloroform for example), an ether (tetrahydrofuran, dioxane for example), an amide (N,N-dimethylformamide for example) or pyridine, under an inert atmosphere, at a temperature between 0° C. and the reflux temperature of the solvent, in the presence of a tertiary amine such as triethylamine, N-methylmorpholine, pyridine, 4-dimethylaminopyridine or 1,8-diazabicyclo[5.4.0]undec-7-ene.

The compounds of formula (II) can also be prepared by reacting a compound of formula:

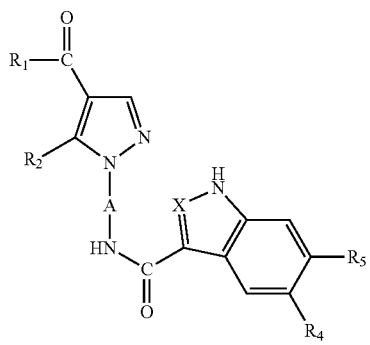

(VI)

in which A, X, $R_1$, $R_2$, $R_4$ and $R_5$ are as defined for a compound of formula (I), with a compound of formula:

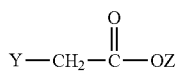

(VII)

in which Y represents a leaving group such as a halogen atom, a methanesulfonate, a benzenesulfonate, a p-toluene sulfonate or a triflate and Z represents a $(C_1-C_4)$alkyl.

The reaction is carried out in the presence of a base such as for example sodium carbonate or potassium carbonate, in a solvent such as for example N,N-dimethylformamide and at a temperature between −20° C. and the reflux temperature of the solvent, In particular, certain compounds of formula (II) can be prepared from other compounds of formula (II).

Thus, for example, starting from the compounds of formula (II) in which $R_4$=Br, it is possible to prepare the compounds of formula (II):

- in which $R_4$=phenyl, by reaction with phenylboronic acid in the presence of a palladium catalyst such as tetrakis(triphenylphosphine)palladium(0);
- in which $R_4$=—$NR_9R_{10}$, by reaction with an amine $HNR_9R_{10}$ in the presence of a copper(I) catalyst such as copper(I) iodide;
- in which $R_4$=CN, by reaction with zinc(II) cyanide and in the presence of a catalyst such as tetrakis(triphenylphosphine)palladium(0).

Starting from the compounds of formula (II) in which:
A=

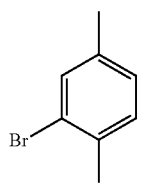

it is possible to prepare the compounds of formula (II) in which:

A=

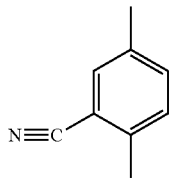

by the action of zinc(II) cyanide in the presence of Tetrakis (triphenylphosphine)palladium(0).

The compounds of formula (III) are known, are commercially available or are prepared by methods known by a person skilled in the art, for example those described in WO 95/18105.

The compounds of formula (IV) are prepared by reacting a compound of formula:

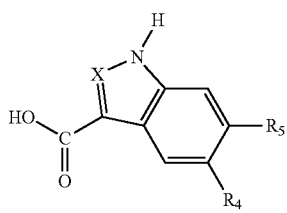
(VIII)

in which X, $R_4$ and $R_5$ are as defined for a compound of formula (I), with a compound of formula (VII):

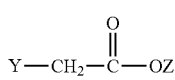
(VII)

in which Y represents a leaving group such as a halogen atom, a methanesulfonate, a benzenesulfonate, a p-toluenesulfonate or a triflate and Z represents a $(C_1$-$C_4)$alkyl.

The reaction is carried out in the presence of two equivalents of a strong base, for example sodium hydride, in a solvent, for example N,N-dimethylformamide and at a temperature between −30° C. and the reflux temperature of the solvent.

The compounds of formula (V) are prepared by reacting a compound of formula:

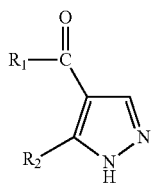
(IX)

in which $R_1$ and $R_2$ are as defined for a compound of formula (I), with a compound of formula:

Y-A-NH$_2$ (X)

in which A is as defined for a compound of formula (I) and Y represents a leaving group such as a halogen atom, a methanesulfonate, a benzene sulfonate, a p-toluenesulfonate, a triflate or an acetate.

The reaction is carried out in the presence of a base, for example potassium carbonate or cesium carbonate, mixed with proline. The reaction is carried out in the presence of a metallic agent, for example copper iodide, in a solvent such as dimethylsulfoxide, dioxane or tetrahydrofuran for example, and at a temperature between 0° C. and 150° C.

The compounds of formula (V) can also be prepared by reduction of a

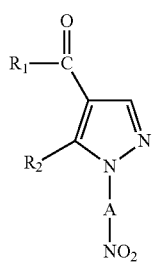
(XI)

in which $R_1$ and $R_2$ are as defined for a compound of formula (I).

The reduction reaction can be carried out, for example, in the presence of a metal such as iron(0), zinc or tin with an acid such as acetic acid for example, in a solvent, for example methanol, ethanol, water or a mixture of these solvents and at a temperature between 0° C. and the reflux temperature of the solvent. A reduction can also be carried out under hydrogen pressure in the presence of a catalyst such as palladium for example.

The compounds of formula (V) in which $R_1$ represents a $(C_1$-$C_4)$alkyl can also be prepared by acid hydrolysis of a compound of formula:

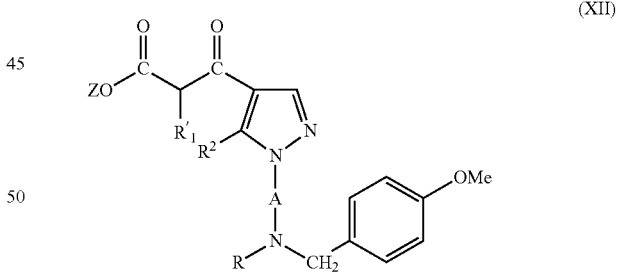
(XII)

in which A and $R_2$ are as defined for a compound of formula (I), Z represents a $(C_1$-$C_4)$ alkyl, $R'_1$ represents a hydrogen atom or a $(C_1$-$C_3)$ alkyl and R represents a tert-butoxycarbonyl or a hydrogen atom.

The reaction is effected by the action of a strong acid, for example hydrochloric acid in a solvent such as water and at a temperature between room temperature and the reflux temperature of the reaction mixture.

In particular, certain compounds of formula (V) can be prepared from other compounds of formula (V).

Thus, for example, starting from the compounds of formula (V) in which A represents an unsubstituted phenyl, the compounds of formula (V) can be prepared in which:

A=

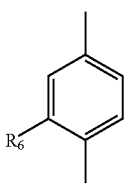

with $R_6$=Br, by reaction with N-bromosuccinimide;

Starting from these compounds of formula (V, $R_6$=Br) thus obtained, the compounds of formula (V) are prepared in which:

A=

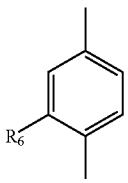

with $R_6$=CN, by reaction with zinc cyanide;

Starting from these compounds of formula (V, $R_6$=CN) thus obtained, by basic hydrolysis, the compounds of formula (V) are prepared in which:

A=

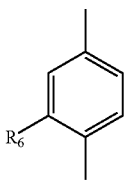

with $R_6$=COOH or $CONH_2$

Starting from these compounds of formula (V, R6=COOH) thus obtained, the compounds of formula (V) are prepared, by alkylation, in which:

A=

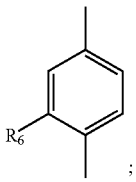

with $R_6$=COOAlk

The compounds of formula (VI) can be prepared according to SCHEME below, in which A, X, $R_1$, $R_2$, $R_4$ and $R_5$ are as defined for a compound of formula (I), and Pg represents an N-protective group, preferably an acetyl group.

SCHEME I

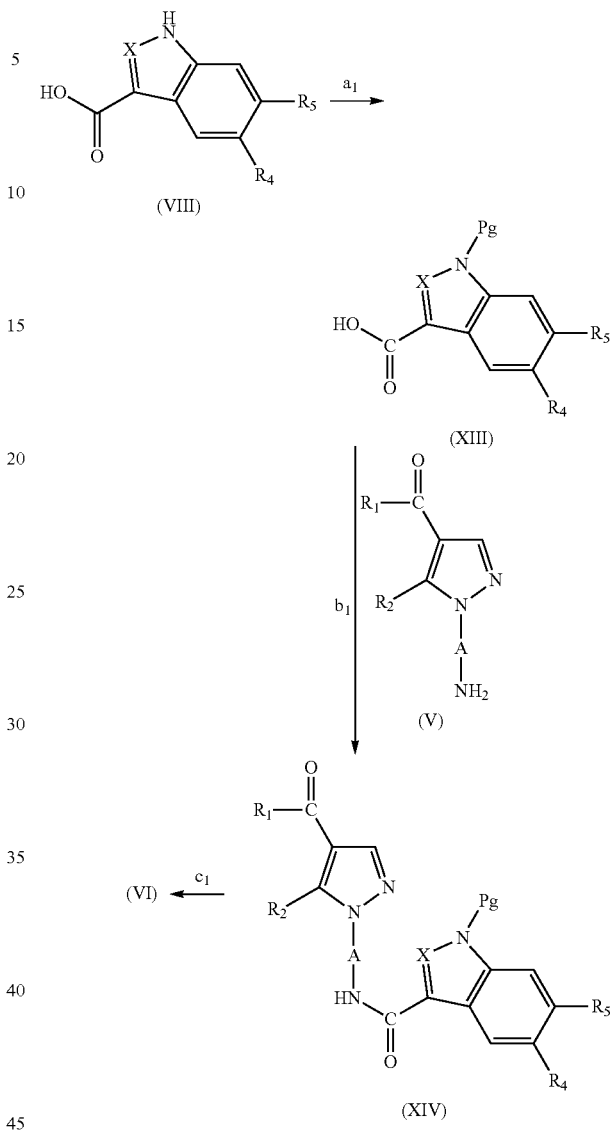

In step $a_1$ of SCHEME I, the nitrogen atom of the compounds of formula (VIII) is protected selectively by means of an acylating agent.

In step $b_1$, the acid or a functional derivative of said acid of formula (XIII) is reacted with a compound of formula (V) to obtain the compound of formula (XIV). The reaction is carried out according to the methods described above, by reaction of a compound of formula (IV) with the compound of formula (V).

In step $c_1$, the compound of formula (XIV) thus obtained is deprotected by the classical methods.

In particular, certain compounds of formula (VI) can be prepared from other compounds of formula (VI). Thus, for example, starting from compounds of formula (VI) in which $R_4$=Br, the compounds of formula (VI) can be prepared in which $R_4$=Cl by reaction with nickel(II) chloride by the classical methods.

The compounds of formula (VII) are known, are commercially available or can be prepared by known methods.

The compounds of formula (VIII) in which X=—CH— can be prepared according to an adaptation of the method described in *Journal of Fluorine Chemistry* (1977) 10, 437-445 and illustrated in SCHEME II below in which $R_4$ and $R_5$ are as defined for a compound of formula (I).

SCHEME II

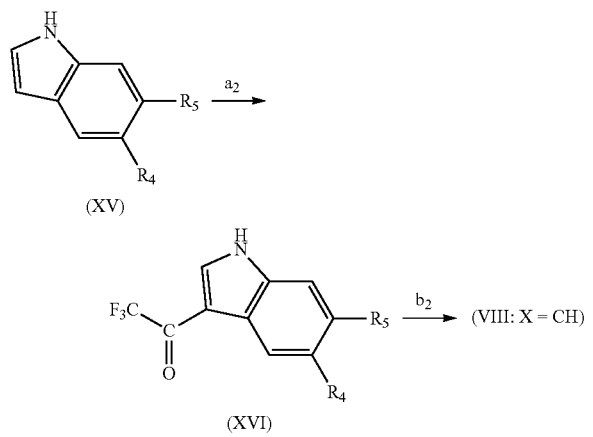

In step $a_2$ of SCHEME II, a compound of formula (XV) is reacted with trifluoroacetic anhydride, in a solvent such as for example diethyl ether and at a temperature less than or equal to 0° C.

In step $b_2$, the compound of formula (XVI) thus obtained is hydrolyzed by the action of a strong base such as for example sodium hydroxide or potassium hydroxide. The reaction is carried out in a solvent, for example water or ethanol and at a temperature between room temperature and the reflux temperature of the solvent.

The compounds of formula (VIII) in which X=—CH— can also be prepared according to an adaptation of the method described in *Synthesis* (1990) 215-218 and illustrated in SCHEME III below in which $R_4$ and $R_5$ are as defined for a compound of formula (I) and Hal represents a halogen atom, preferably bromine or iodine.

SCHEME III

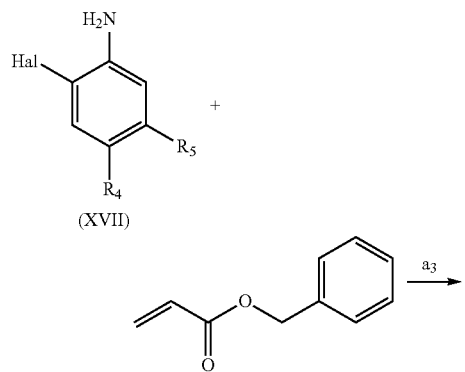

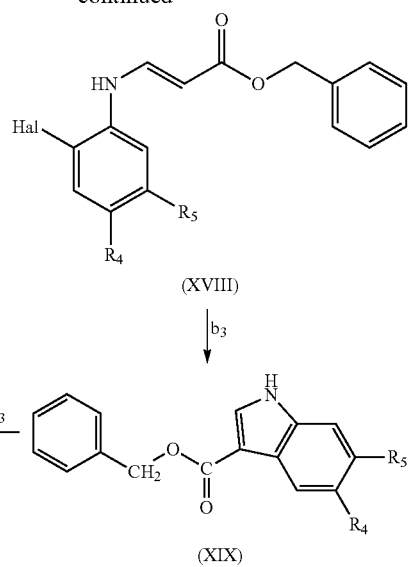

In step $a_3$ of SCHEME III, a compound of formula (XVII) is reacted with benzyl acrylate, in the presence of 1,4-benzoquinone, lithium chloride and palladium acetate. The reaction is carried out in a solvent, for example tetrahydrofuran and at a temperature between 0° C. and the reflux temperature of the solvent.

In step $b_3$, the compound of formula (XVIII) thus obtained is cyclized in the presence of a base such as for example triethylamine or 1,4-diazabicyclo[2.2.2]octane and in the presence of a palladium complex such as for example palladium acetate. The reaction is carried out in a solvent, for example N,N-dimethylformamide and at a temperature between room temperature and 130° C.

In step $c_3$, the compound of formula (XIX) thus obtained is debenzylated according to known methods (Protective Groups in Organic Synthesis, Greene et al., 4th Edition, John Wiley & Sons, Inc., New York, 2007) to give the expected acid of formula (VIII).

The compounds of formula (VIII) in which X=N can be prepared by the method described in *Synthetic Communications* (2005) 35 (20), 2681-2684 and illustrated in SCHEME IV below in which $R_4$ and $R_5$ are as defined for a compound of formula (I).

SCHEME IV

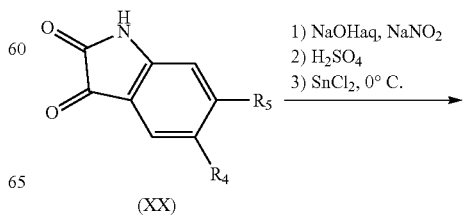

-continued

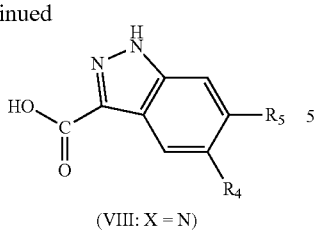

(VIII: X = N)

The compounds of formula (IX) in which $R_1=(C_1-C_4)$ alkyl can be prepared according to SCHEME V below in which $R_2$ is as defined for a compound of formula (I). Pg represents a protective group, preferably a trityl group.

SCHEME V

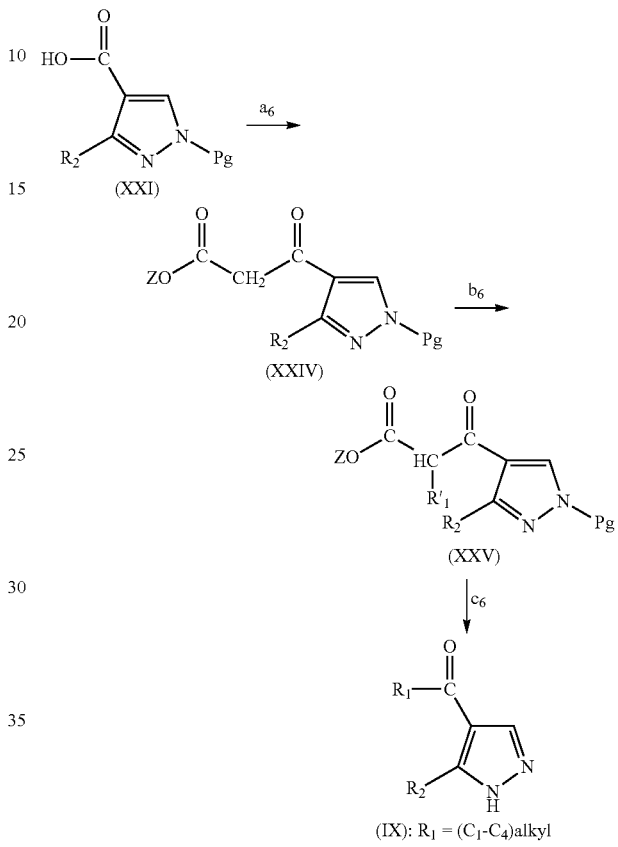

In step $a_5$ of SCHEME V, the nitrogen atom of the compound of formula
(IX) is protected, in particular by a trityl group, than the intermediate obtained is hydrolyzed in a basic medium.

In step $b_5$, the compound of formula (XXI) thus obtained is reacted with N-methoxymethanamine, in the presence of a coupling agent such as for example bis(2-oxo-1,3-oxazolidin-3-yl)phosphinic chloride and in the presence of a base such as for example 4-dimethylaminopyridine. The reaction is carried out in a solvent, for example dichloromethane and at a temperature between 0° C. and room temperature.

The compound of formula (XXII) thus obtained is reacted in step $c_5$ with an organometallic compound such as a $(C_1-C_4)$alkylmagnesium halide, in a solvent such as diethyl ether or tetrahydrofuran and at a temperature between −70° C. and room temperature.

The compound of formula (XXIII) thus obtained is deprotected in step $d_5$ by the classical methods (Protective Groups in Organic Synthesis, Greene et al., 4th Edition, John Wiley & Sons, Inc., New York, 2007).

The compounds of formula (IX) in which $R_1=(C_1-C_4)$ alkyl can also be prepared according to SCHEME VI below in which $R_2$ is as defined for a compound of formula (I). Pg represents a protective group, preferably a trityl group, Z represents a $(C_1-C_4)$alkyl and $R'_1$ represents a hydrogen atom or a $(C_1-C_3)$alkyl.

SCHEME VI

In step $a_6$ of SCHEME VI, the compound of formula (XXI) is reacted with 1,1'-carbonyldiimidazole then, without isolating, the intermediate thus obtained is treated with a magnesium salt of a hemi-ester of malonic acid according to the method described in *Angew. Chem. Int. Ed. Engl* (1979) 18 (1), 72-74.

In step $b_6$, the compound of formula (XXIV) thus obtained is alkylated by reaction of a $(C_1-C_3)$alkyl halide, mesylate or tosylate, in the presence of a strong base such as for example sodium hydride, in a solvent, for example tetrahydrofuran and at a temperature between 0° C. and room temperature.

In step $c_6$, the compound of formula (XXV) thus obtained is hydrolyzed in an acid medium. The reaction is effected by the action of a strong acid such as for example hydrochloric acid, in a solvent such as water and at a temperature between room temperature and 105° C. The spontaneous decarboxylation that ensues is able to generate the compound of formula (IX), The compounds of formula (IX) in which $R_1=(C_1-C_4)$ alkoxy are known, are commercially available or are prepared according to known methods (*Synlett* (2004) 4, 703-707).

The compounds of formula (X) are known, are commercially available or are prepared according to known methods (*Tetrahedron* (1988) 44 (10), 2977-2983; *J. Org. Chem.* (2008) 73 (23), 9326-9333).

The compounds of formula (XI) in which $R_1=(C_1-C_4)$ alkyl are prepared according to SCHEME VII below in which A and $R_2$ are as defined for a compound of formula (I). Z represents a $(C_1-C_4)$alkyl and $R'_1$ represents a hydrogen atom or a $(C_1-C_3)$alkyl.

SCHEME VII

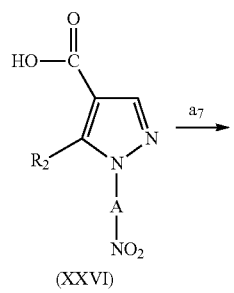
(XXVI)

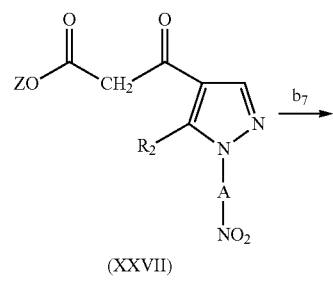
(XXVII)

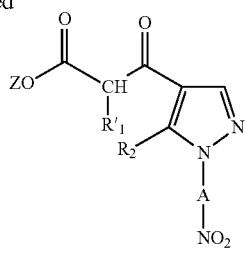
(XXVIII)

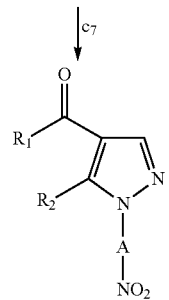
(XI): $R_1 = (C_1-C_4)$alkyl

Steps $a_7$, $b_7$ and $c_7$ of SCHEME VII are carried out according to the same protocols as those described for steps $a_6$, $b_6$ and $c_6$ of SCHEME VI.

The compounds of formula (XII) can also be prepared according to SCHEME VIII below in which A and $R_2$ are as defined for a compound of formula (I), Z represents a $(C_1-C_4)$alkyl, $R'_1$ represents a hydrogen atom or a $(C_1-C_3)$alkyl, Y represents a leaving group as defined previously and Boc represents a tert-butoxycarbonyl.

SCHEME VIII

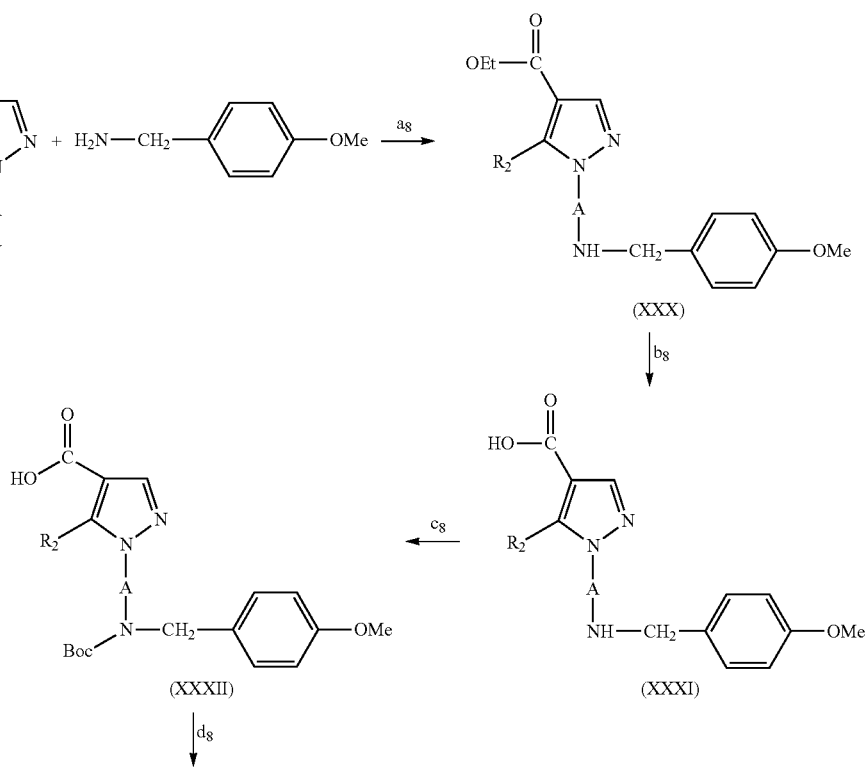

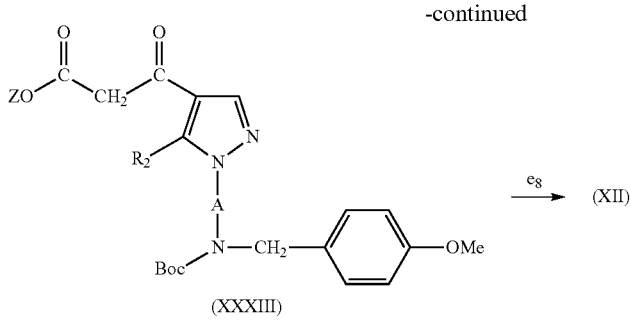

(XXXIII)

In step $a_8$ of SCHEME VIII, the compound of formula (XXIX) is reacted with 4-methoxybenzylamine in a solvent such as dioxane and at the reflux temperature of the solvent.

In step $b_8$, the compound of formula (XXX) thus obtained is hydrolyzed in a basic medium, with a base such as potassium hydroxide to give the acid of formula (XXXI).

In step $c_8$, the compound of formula (XXXI) is protected by a group Boc, in the presence of bases such as triethylamine or 4-dimethylaminopyridine in a solvent such as DMF.

Steps $d_8$ and $e_8$ are carried out according to the same protocols as those described for steps $a_6$ and $b_6$ of SCHEME VI.

The compounds of formula (XV), (VIII), (XX) are known, are commercially available or can be prepared by known methods.

The compounds of formula (XXVI) are known, are commercially available or are prepared according to methods described in EP 1 176 140.

The compounds of formula (XXIX) in which A represents a pyridazinyl radical are prepared according to the method described in J. Heterocyclic Chem. (2009) 46, 584-590.

According to another of its aspects, the invention also relates to novel compounds of formula (II). These compounds are useful as synthesis intermediate for the compounds of formula (I).

Thus, the invention relates to compounds of formula:

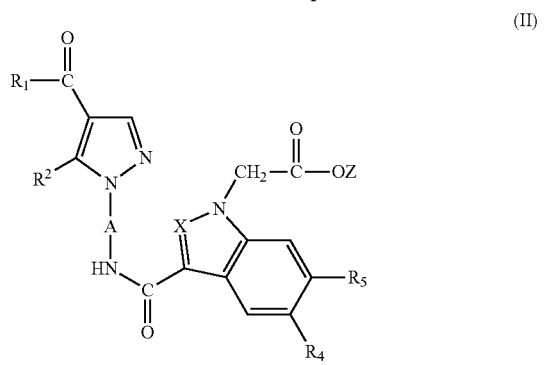

(II)

in which:

A represents a divalent aromatic radical selected from:

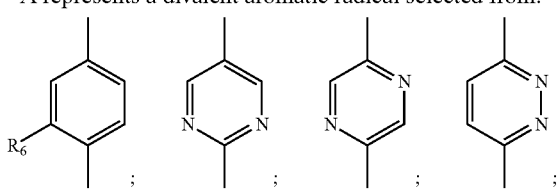

X represents a —CH— group or a nitrogen atom;
$R_1$ represents a $(C_1\text{-}C_4)$alkyl or a $(C_1\text{-}C_4)$alkoxy;
$R_2$ represents a group Alk;
$R_4$ represents a hydrogen atom, a halogen atom, a cyano, a phenyl, a group Alk, a group OAlk or a group —$NR_9R_{10}$;
$R_5$ represents a hydrogen atom, a halogen atom or a group Alk;
$R_6$ represents a hydrogen atom, a halogen atom, a cyano, a group —COOAlk or a —$CONH_2$ group;
$R_9$ and $R_{10}$ represent, each independently, a hydrogen atom or a $(C_1C_4)$alkyl;
Z represents a $(C_1\text{-}C_4)$alkyl;
Alk represents a $(C_1\text{-}C_4)$alkyl, unsubstituted or substituted one or more times with a fluorine atom.

According to another of its aspects, the invention also relates to the use of compounds of formula (I), as they are or in radiolabeled form as pharmacological tools in humans or in animals, for the detection and labeling of the P2Y12 purinergic receptor.

The following examples describe the preparation of some compounds according to the invention. These examples are not limiting and are only intended to illustrate the present invention. The numbers of compounds in the examples refer to those given in TABLES X to XV below, which illustrate the chemical structures and physical properties of some compounds according to the invention.

The following abbreviations are used in the preparations and in the examples:

Me: methyl
Et: ethyl
n-Pr: n-propyl
Ph: phenyl
ether: diethyl ether
iso ether: diisopropyl ether
DMSO: dimethylsulfoxide
DMF: N,N-dimethylformamide
THF: tetrahydrofuran
DCM: dichloromethane
EtOAc: ethyl acetate
DMAP: 4-dimethylaminopyridine
DIPEA: diisopropylethylamine
HOAT: 1-hydroxy-7-azabenzotriazole
HOBT: 1-hydroxybenzotriazole
TFA: trifluoroacetic acid
BOP: benzotriazol-1-yloxytris(dimethylamino)phosphonium hexafluorophosphate
BOP-Cl: bis(2-oxo-1,3-oxazolidin-3-yl)phosphinic chloride
EDC: 1-(3-dimethylaminopropyl)-3-ethylcarbodiimide hydrochloride
NaOH: sodium hydroxide
KOH: potassium hydroxide
HCl: hydrochloric acid NaBH$_4$: sodium borohydride
NaHCO$_3$: sodium hydrogen carbonate
NaH: sodium hydride
Na$_2$SO$_4$: sodium sulfate
1N or 2N hydrochloric ether: 1N or 2N solution of hydrochloric acid in diethyl ether
1N (or 2N)HCl in ether: IN (or 2N) solution of hydrochloric acid in diethyl ether
4N HCl in dioxane: 4N solution of hydrochloric acid in dioxane
m.p.: melting point
RT: room temperature
b.p.: boiling point
HPLC: high-performance liquid chromatography
Brine: saturated solution of sodium chloride in water.

The proton nuclear magnetic resonance spectra ($^1$H NMR) are recorded on Bruker spectrometers (250 and 400 MHz) in DMSO-d$_6$. The chemical shifts δ are expressed in parts per million (ppm). The following abbreviations are used for interpreting the spectra: s: singlet, d: doublet, t: triplet, q: quadruplet: m: massive, mt: multiplet, bs: broad singlet, dd: doublet of doublets, br: broad peak.

The compounds according to the invention are analyzed by coupled HPLC-UV-MS (liquid chromatography/UV detection/mass spectroscopy).

The equipment used is composed of a chromatographic chain equipped with a diode array detector and a quadrupole mass spectrometer. The molecular peak (MH$^+$) and the retention time (t$_R$) in minutes are measured.

Method A: WatersXBridge C18, 4.6×50 mm, 2.5 μm
Solvent A: water+0.05% TFA
Solvent B: MeCN+0.05% TFA
1.3 ml/min; 40° C.; Waters LCT classic TOF-MS

| Gradient (minutes) | A | B |
| --- | --- | --- |
| 0 | 95 | 5 |
| 0.3 | 95 | 5 |
| 3.5 | 5 | 95 |
| 4 | 5 | 95 |

Method B: Waters XBridge C18 4.6×50 mm, 2.5 μm,
Solvent A: water+0.1% of formic acid
Solvent B: MeCN+0.08% of formic acid
1.3 ml/min; 20° C.; Waters Ultima Triple Quad MS

| Gradient (minutes) | A | B |
| --- | --- | --- |
| 0 | 97 | 3 |
| 3.5 | 40 | 60 |
| 4 | 2 | 98 |
| 5 | 2 | 98 |
| 5.2 | 97 | 3 |
| 6.5 | 97 | 3 |

Method C: YMC-Pack Jsphere H80 33×2.1 mm, 4.0 μm
Solvent A: water+0.05% TFA
Solvent B: methanol+0.05% TFA
1.0 ml/min; 20° C.; Waters LCT classic TOF-MS, 8-channel Mux

| Gradient (minutes) | A | B |
| --- | --- | --- |
| 0 | 98 | 2 |
| 1 | 98 | 2 |
| 5 | 5 | 95 |
| 6.25 | 5 | 95 |

Method D: WatersXBridge C18, 4.6×50 mm, 2.5 μm
Solvent A: water+0.05% TFA
Solvent B: MeCN+0.05% TFA
1.7 ml/min, 40° C.; Waters LCT classic TOF-MS

| Gradient (minutes) | A | B |
| --- | --- | --- |
| 0 | 95 | 5 |
| 0.2 | 95 | 5 |
| 2.4 | 5 | 95 |
| 3.2 | 5 | 95 |
| 3.3 | 95 | 5 |
| 4 | 95 | 5 |

Method E: Waters XBridge C18 4.6×50 mm; 2.5 μm
Solvent A: water+0.1% of formic acid
Solvent B: MeCN+0.1% of formic acid
1.3 ml/min, 45° C.; Waters ZQ Single Quadrupole

| Gradient (minutes) | A | B |
| --- | --- | --- |
| 0 | 97 | 3 |
| 3.5 | 40 | 60 |
| 4 | 2 | 98 |
| 5 | 2 | 98 |
| 5.2 | 97 | 3 |
| 6.5 | 97 | 3 |

Method m.p.: Merck Chromolith FastGrad. RP-18e, 50×2 mm
Solvent A: water+0.05% TFA
Solvent B: MeCN+0.05% TFA
2.4 ml/min, 50° C.; Waters LOT classic TOF-MS

| Gradient (minutes) | A | B |
| --- | --- | --- |
| 0 | 98 | 2 |
| 0.2 | 98 | 2 |
| 2.4 | 2 | 98 |
| 3.2 | 2 | 98 |
| 3.3 | 98 | 2 |
| 4 | 98 | 2 |

Method G: Agilent 1100 series. Symmetry C18 3.5 μm (2.1×50 mm, Waters)
Solvent A: water+0.005% TFA
Solvent B: MeCN+0.005% TFA
0.4 ml/min, 25° C.; MSD SL (Agilent) ESI$^+$.

| Gradient (minutes) | A | B |
| --- | --- | --- |
| 0 | 100 | 0 |
| 10 | 0 | 100 |
| 15 | 0 | 100 |

Method H: Agilent 1100 series. Symmetry C18 3.5 μm (2.1×50 mm, Waters)
Solvent A: water+0.005% TFA
Solvent B: MeCN+0.005% TFA
0.4 ml/min, 25° C.; MSD SL (Agilent) ESI⁺.

| Gradient (minutes) | A | B |
|---|---|---|
| 0 | 100 | 0 |
| 30 | 0 | 100 |
| 35 | 0 | 100 |

Method I: Agilent 1100 series. X Terra C18 3.5 μm (2.1×50 mm, Waters)
Solvent A: ammonium acetate buffer 10 mM pH 7
Solvent B: MeCN
0.4 ml/min, 30° C.; MSD SL (Agilent) ESI⁺.

| Gradient (minutes) | A | B |
|---|---|---|
| 0 | 100 | 0 |
| 10 | 10 | 90 |
| 15 | 10 | 90 |

Method J. Waters UPLC BEH, C18 2.1×50 mm; 1.7 um
Solvent A: water+0.05% of formic acid
Solvent B: MeCN+0.035% of formic acid
0.9 ml/min; 55° C.

| Gradient (minutes) | A | B |
|---|---|---|
| 0 | 95 | 5 |
| 1.1 | 5 | 95 |
| 1.7 | 5 | 95 |
| 1.8 | 95 | 5 |
| 2 | 95 | 5 |

The mass spectra are recorded in positive electrospray mode (ESI), in order to observe the ions resulting from protonation of analyzed compounds (MH⁺), or from the formation of adducts with other cations such as Na⁺, K⁺, etc.

PREPARATIONS

1. Preparations of the compounds of formula (XVI).

Preparation 1.1

1-(5-Bromo-1H-indol-3-yl)-2,2,2-trifluoroethanone (XVI): $R_4$=Br; $R_5$=H.
A solution of 21.3 ml of trifluoroacetic anhydride in 70 ml of ether is added dropwise to a solution of 20 g of 5-bromoindole in 250 ml of ether cooled to −5° C. It is stirred for 2 hours at −5° C. The precipitate formed is drained and is washed with ether. 24.5 g of the expected compound is obtained in the form of a white powder.
m.p.=254° C.
¹H NMR: DMSO-$d_6$ (250 MHz): δ (ppm): 7.50 (1H, d); 7.58 (1H, d); 8.31 (1H, s); 8.55 (1H, s); 12.85 (1H, br).
Following the procedure described in preparation 1.1, the 3-trifluoroacetylindoles of formula (XVI) presented in TABLE I below are prepared:

TABLE I

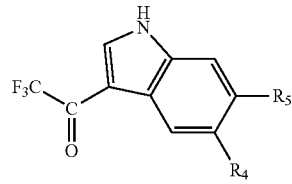

(XVI)

| $R_4$ | $R_5$ | ¹H NMR: DMSO-$d_6$ (250 MHz): δ (ppm) |
|---|---|---|
| Preparation 1.2 | Me | Br | 2.47 (3H, s); 7.81 (1H, s); 8.14 (1H, s); 8.47 (1H, s); 12.70 (1H, br) |
| Preparation 1.3 | Br | Me | 2.47 (3H, s); 7.58 (1H, s); 8.33 (1H, s); 8.48 (1H, s); 12.70 (1H, br) |
| Preparation 1.4 | Cl | F | 7.63 (1H, d); 8.23 (1H, d); 8.58 (1H, s); 12.90 (1H, br) |

2. Preparations of the compounds of formula (VIII: X=CH).

Preparation 2.1

5-Bromo-1H-indole-3-carboxylic acid (VIII): X=CH; $R_4$=Br; $R_5$=H.
24 g of the compound obtained in Preparation 1.1 is added to a solution of 46.1 g of potassium hydroxide in 25 ml of water, and is heated for 4 hours under reflux. The reaction mixture is cooled and is washed with ether. The aqueous phase is cooled to 5° C. and is then neutralized with a solution of phosphate buffer preloaded with 35% hydrochloric acid. The precipitate formed is drained and is washed with water. 15.6 g of the expected compound is obtained in the form of a white powder.
m.p.=234° C.
¹H NMR: DMSO-$d_6$ (250 MHz): δ (ppm): 7.32 (1H, d); 7.46 (1H, d); 8.06 (1H, s); 8.14 (1H, s); 12.00/7H, br).
Following the procedure described in preparation 2.1, the 3-carboxyindoles of formula (VIII: X=CH) presented in TABLE II below are prepared:

TABLE II

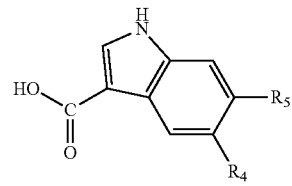

(VIII)

| $R_4$ | $R_5$ | ¹H NMR: DMSO-$d_6$ (250 MHz): δ (ppm) |
|---|---|---|
| Preparation 2.2 | Me | Br | 2.44 (3H, s); 7.68 (1H, s); 7.95 (1H, s); 7.98 (1H, s); 11.70 (1H, br); 12.00 (1H, br) |
| Preparation 2.3 | Br | Me | 2.44 (3H, s); 7.45 (1H, s); 7.98 (1H, s); 8.15 (1H, s); 11.90 (1H, br); 12.10 (1H, br) |
| Preparation 2.4 | Cl | Cl | 7.73 (1H, s); 8.10 (1H, s); 8.13 (1H, s); 12.00 (2H, br) |
| Preparation 2.5 | Cl | F | 7.49 (1H, d); 8.00-8.08 (2H, m); 12.00 (1H, br); 12.20 (1H, br) |

Preparation 2.6

5,6-Dimethyl-1H-indole-3-carboxylic acid (VIII): X=CH; $R_4$=Me; $R_5$=Me.
Step 1: 3-[(2-Iodo-4,5-dimethylphenyl)amino]benzyl acrylate (XVIII).

60.8 g of lithium chloride is added to a solution of 15.5 g of [1,4]-benzoquinone in 350 ml of THF, and it is degassed with nitrogen. 3.2 g of palladium acetate and 23.7 g of benzyl acrylate are added and it is degassed with nitrogen for about 30 minutes. Than a solution of 35.1 g of 2-iodo-4,5-dimethylaniline (prepared according to J. Med. Chem 2001, 44, 3856-3871) in 150 ml of THF is added and it is stirred overnight. It is filtered and the filtrate is evaporated. The solid residue thus obtained is triturated with ether. It is filtered, the filtrate is washed with a solution of NaOH 0.5N and then with water and with brine. It is evaporated and then the solid residue is purified by silica gel chromatography, eluting with a cyclohexane/EtOAc mixture (8/2; v/v). 57.6 g of the expected compound is obtained in the form of a white powder.

$^1$H NMR: DMSO-$d_6$ (250 MHz): δ (ppm): 2.14 (3H, s); 2.19 (3H, s); 4.93 (1H, d); 5.18 (2H, s); 7.23 (1H, s); 7.30-7.45 (5H, m); 7.59 (1H, s); 7.72 (1H, dd); 10.05 (1H, d).

Following the same procedure, the compound of formula (XVIII) shown below is prepared:

| $R_4$ | $R_5$ | $^1$H NMR: DMSO-$d_6$ (250 MHz): δ (ppm): |
|---|---|---|
| $CF_3$ | H | 5.15 (1H, d); 5.21 (2H, s); 7.30-7.50 (5H, m); 7.70 (2H, m); 7.88 (1H, dd); 8.02 (1H, s); 10.50 (1H, d). |

Step 2: Benzyl 5,6-dimethyl-1H-indole-3-carboxylate (XIX).

8.60 g of 1,4-diazabicyclo[2.2.2]octane is added to a solution of 25.5 g of the compound obtained in step 1 in 120 ml of DMF. It is degassed with nitrogen, then 0.703 g of palladium acetate is added and the reaction mixture is heated at 120° C. for 7 hours. EtOAc is added, then it is washed with water and with brine, dried over $Na_2SO_4$ and evaporated. After trituration of the solid residue with iso ether, 12.3 g of the expected compound is obtained in the form of a beige powder.

$^1$H NMR: DMSO-$d_6$ (250 MHz): δ (ppm): 2.29 (3H, s); 2.30 (3H, s); 5.32 (2H, s); 7.24 (1H, s); 7.30-7.50 (5H, m); 7.76 (1H, s); 7.98 (1H, d); 11.70 (1H, br).

Following the same procedure, the compound of formula (XIX) presented below is prepared:

| $R_4$ | $R_5$ | $^1$H NMR: DMSO-$d_6$ (250 MHz): δ (ppm): |
|---|---|---|
| $CF_3$ | H | 5.38 (2H, s); 7.35-7.55 (6H, m); 7.71 (1H, d); 8.33 (1H, s); 8.35 (1H, s); 12.35 (1H, br). |

Step 3: 5,6-Dimethyl-1H-indole-3-carboxylic acid.

0.54 g of Pd/C 10% and 16.9 g of ammonium formate are added to a solution of 5 g of the compound obtained in step 2 in 120 ml of MeOH. It is heated under reflux for 2 hours. It is filtered on talc and the filtrate is evaporated.

The solid residue is extracted with EtOAc. It is washed with 0.1N HCl solution, dried over $Na_2SO_4$ and evaporated to dryness. 2.87 g of the expected compound is obtained in the form of a white powder.

$^1$H NMR: DMSO-$d_6$ (250 MHz): δ (ppm): 2.31 (6H, s); 7.23 (1H, s); 7.77 (1H,

Following the same procedure, the compound of formula (VIII: X=CH) presented below is obtained:

| $R_4$ | $R_5$ | $^1$H NMR: DMSO-$d_6$ (250 MHz): δ (ppm): |
|---|---|---|
| Preparation 2.7 | $CF_3$ | H | 7.48 (1H, d); 7.79 (1H, d); 8.06 (1H, s); 8.69 (1H, s); 12.05 (2H, br). |

The 3-carboxylndazoles (compounds of formula VIII, X=N) are synthesized from commercial isatine according to the method described in *Synthetic Communications* (2005), 2681-2684.

3. Preparations of the compounds of formula (IV).

Preparation 3.1

5-Chloro-1-(2-methoxy-2-oxoethyl)-1H-indole-3-carboxylic acid (IV): X=CH; $R_4$=Cl; $R_5$=H; Z=Me.

110 ml of a solution containing 10 g of 5-chloro-1H-indole-3-carboxylic acid (commercial) in DMF is added dropwise to a mixture of 4.50 g of NaH (60% in oil) in 400 ml of DMF at −10° C. After it returns to RT, it is stirred for 1 hour. The reaction mixture is cooled to −20° C. 4.86 ml of methyl bromoacetate is added dropwise, it is returned to RT for a period of 5 hours and is stirred for 15 hours. The reaction mixture is added to 1 L of EtOAc/1N HCl mixture, the organic phase is collected and the aqueous phase is extracted with EtOAc. The organic phases are combined, washed with water and with brine, then dried over $Na_2SO_4$ and evaporated to dryness. 8.9 g of the expected compound is obtained in the form of a white powder.

$^1$H NMR: DMSO-$d_6$ (250 MHz): δ (ppm): 3.70 (3H, s); 7.26 (1H, d); 7.57 (1H, d); 7.98 (1H, s); 8.12 (1H, s); 12.3 (1H, br).

Following the procedure described in preparation 3.1, the compounds of formula (IV) in which X=CH and Z=Me, presented in TABLE III below, are prepared:

TABLE III

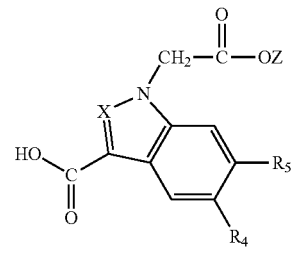

(IV)

(X = CH; Z = Me)

| | $R_4$ | $R_5$ | $^1$H NMR: DMSO-$d_6$ (250 MHz): δ (ppm) |
|---|---|---|---|
| Preparation 3.2 | Me | H | 2.42 (3H, s); 3.70 (3H, s); 5.21 (2H, s); 7.06 (1H, d); 7.37 (1H, d); 7.83 (1H, s); 8.00 (1H, s); 12.00 (1H, br). |
| Preparation 3.3 | OMe | H | 3.69 (3H, s); 3.79 (3H, s); 5.20 (2H, s); 6.86 (1H, d); 7.39 (1H, d); 7.50 (1H, s); 7.99 (1H, s); 12.05 (1H, br). |
| Preparation 3.4 | $CF_3$ | H | 3.72 (3H, s); 5.35 (2H, s); 7.55 (1H, d); 7.78 (1H, d); 8.26 (1H, s); 8.36 (1H, s); 12.50 (1H, br). |
| Preparation 3.5 | Br | H | 3.71 (3H, s); 5.27 (2H, s); 7.37 (1H, d); 7.53 (1H, d); 8.14 (2H, m); 12.25 (1H, br). |
| Preparation 3.6 | Me | Me | 2.32 (6H, s); 3.70 (3H, s); 5.18 (2H, s); 7.26 (1H, s); 7.79 (1H, s); 7.92 (1H, s); 11.90 (1H, br). |

TABLE III-continued (IV)

(X = CH; Z = Me)

| | R$_4$ | R$_5$ | $^1$H NMR: DMSO-d$_6$ (250 MHz): δ (ppm) |
|---|---|---|---|
| Preparation 3.7 | Cl | Cl | 3.71 (3H, s); 5.27 (2H, s); 8.00 (1H, s); 8.14 (1H, s); 8.16 (1H, s); 12.45 (1H, br). |

4. Preparations of the compounds of formula (XIII).

Preparation 4.1

1-Acetyl-5-chloro-6-fluoro-1H-indole-3-carboxylic acid (XIII): X=CH; R$_4$=Cl; R$_5$=F; Pg=—COMe.

A solution of 4.4 g of the compound from Preparation 2.5 in 100 ml of DCM is cooled to 0° C., 6.28 ml of triethylamine and 0.51 g of DMAP are added and then, dropwise, 1.47 ml of acetyl chloride and it is stirred for 3 hours. The reaction mixture is washed with 1N HCl solution and then with water, with saturated NaCl solution, the organic phase is dried over Na$_2$SO$_4$ and the solvent is evaporated under vacuum. 4.82 g of the expected compound is obtained in the form of white powder.

$^1$H NMR: DMSO-d$_6$ (250 MHz): δ (ppm): 2.74: s: 3H, 8.13: d: 1H, 8.25: d: 1H, 8.52: s: 1H, 13.10: br: 1H.

Following the procedure described in preparation 4.1, the compounds of formula (XIII) in which Pg=—COMe, presented in TABLE IV below, are prepared;

TABLE IV (XIII)

Pg = —COMe

| | R$_4$ | R$_5$ | X | $^1$H NMR: DMSO-d$_6$ (250 MHz): δ (ppm) |
|---|---|---|---|---|
| Preparation 4.2 | H | Me | CH | 2.49 (3H, s); 2.73 (3H, s); 7.21 (1H, d); 7.96 (1H, d); 8.20 (1H, s); 8.81 (1H, s); 12.75 (1H, br) |
| Preparation 4.3 | F | H | CH | 2.75 (3H, s); 7.27 (1H, dd); 7.76 (1H, d); 8.38 (1H, dd); 8.52 (1H, s); 12.90 (1H, br) |
| Preparation 4.4 | Me | Br | CH | 2.46 (3H, s); 2.72 (3H, s); 8.01 (1H, s); 8.42 (1H, s); 8.53 (1H, s); 12.85 (1H, br) |
| Preparation 4.5 | Br | Me | CH | 2.48 (3H, s); 2.73 (3H, s); 8.22 (1H, s); 8.35 (1H, s); 8.42 (1H, s); 12.95 (1H, br) |
| Preparation 4.6 | Me | H | N | 2.50 (3H, s); 2.76 (3H, s); 7.52 (1H, d); 7.98 (1H, s); 8.25 (1H, d); 13.85 (1H, br) |

5. Preparations of the compounds of formula (IX).

Preparation 5.1

1-(5-Methyl-1H-pyrazol-4-yl)butan-1-one (IX): R$_1$=n-Pr; R$_2$=Me.

Step 1: 3-methyl-1-trityl-1H-pyrazole-4-carboxylic acid (XXI).

8.46 g of potassium carbonate and 15.8 g of chloride trityl are added to a solution of 6.60 g of methyl 5-methyl-1H-pyrazole-4-carboxylate in 50 ml of DMF. After 5 days at RT. EtOAc is added, it is washed with water, with brine, dried over Na$_2$SO$_4$ and evaporated to dryness. The oily residue thus obtained is dissolved in 100 ml of EtOH/water mixture (50/50; v/v), 9.95 g of potassium hydroxide is added and it is heated under reflux for 6 hours. The reaction mixture is filtered while hot, the filtrate is concentrated and acidified with 1N HCl solution. The precipitate that formed is drained, dried under vacuum and then washed with EtOAc/iso ether mixture (50/50; v/v) and dried under vacuum. 9.70 g of the expected compound is obtained in the form of a white powder.

$^1$H NMR: DMSO-d$_6$ (250 MHz): δ (ppm): 2.33 (3H, s); 7.03-7.09 (6H, m); 7.34-7.43 (9H, m); 7.61 (1H, s).

Step 2: N-methoxy-N,3-dimethyl-1-trityl-1H-pyrazole-4-carboxamide (XXII).

10.3 g of DMAP and 10.3 g of BOP-Clare added to a solution of 9.70 g of the compound obtained in the preceding step, in 100 ml of DCM. Then 3.85 g of N-methoxymethanamine hydrochloride is added in portions and stirred for 1 hour at RT. The reaction mixture is concentrated under vacuum, the residue is extracted with EtOAc, it is washed with water, with brine, dried over Na$_2$SO$_4$ and then evaporated to dryness. It is triturated with iso ether, filtered and dried in a vacuum stove. 10.4 g of the expected compound is obtained in the form of a white powder.

$^1$H NMR: DMSO-d$_6$ (250 MHz): δ (ppm): 2.34 (3H, s); 3.13 (3H, s); 3.39 (3H, s); 7.05-715/8H, m); 7.33-7.44/9H, m); 7.71 (1H, s).

Step 3: 1-(3-methyl-1-trityl-1H-pyrazol-4-yl)butan-1-one (XXIII).

32.7 ml of a 2M solution of n-propylmagnesium chloride in ether is added dropwise to a solution of 10.4 g of the compound obtained in the preceding step, in 130 ml of THF at −30° C. It is returned to RT and then stirred for 4 hours. The reaction mixture is cooled to −30° C. and then 50 ml of water is added (dropwise at first). It is returned to RT, 250 ml of 1N HCl solution is added and then it is extracted with EtOAc. It is washed with water, with brine, dried over Na$_2$SO$_4$ and then evaporated to dryness. It is triturated in iso ether, filtered and dried in a vacuum stove. 8.4 g of the expected compound is obtained in the form of a white powder.

$^1$H NMR: DMSO-d$_6$ (400 MHz): δ (ppm): 0.84 (3H, t); 1.52 (2H, sext); 2.34 (3H, s); 2.62 (2H, t); 7.04-7.12 (6H, m); 7.33-7.45 (9H, m); 7.93 (1H, s).

Step 4: 1-(5-methyl-1H-pyrazol-4-yl)butan-1-one.

A suspension of 8.4 g of the compound obtained in the preceding step, in 50 ml of 4N HCl in dioxane is stirred for 6 hours. It is evaporated to dryness, triturated with iso ether, filtered and dried in a vacuum stove. 3.1 g of the expected compound is obtained in the form of a colorless gum.

$^1$H NMR: DMSO-d$_6$ (250 MHz): δ (ppm): 0.90 (3H, t); 1.58 (2H, sext); 2.39 (3H, s); 2.71 (2H, t); 8.15 (1H, s).

6. Preparations of the compounds of formula (V).

Preparation 6.1

1-[1-(5-Aminopyrazin-2-yl)-5-methyl-1H-pyrazol-4-yl]butan-1-one (V): R₁=n-Pr; R₂=Me; A=

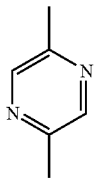

A mixture of 0.60 g of the compound from Preparation 5.1, 1.37 g of 5-bromo-pyrazin-2-ylamine (X), 1.30 g of potassium carbonate, 0.38 g of proline and 0.23 g of copper(I) iodide in 15 ml of DMSO is heated at 130° C. for 20 hours. 100 ml of water is added and it is extracted with DCM. The organic phase is washed with a saturated solution of sodium bicarbonate and then with brine, dried over Na₂SO₄ and evaporated to dryness. It is purified by silica gel chromatography, eluting with a gradient of DCM/EtOAc mixture from (80/20; v/v) to (40/60; v/v). 0.17 g of the expected compound is obtained in the form of powder.

¹H NMR: DMSO-d₆ (250 MHz): 5/ppm): 0.93 (3H, t); 1.62 (2H, sext); 2.55 (3H, s); 2.80 (2H, t); 6.86 (2H, br); 7.80 (1H, s); 8.19-8.22 (2H, m).

Preparation 6.2

1-[1-(6-Aminopyridazin-3-yl)-5-methyl-1H-pyrazol-4-yl]butan-1-one

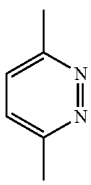

(V): R₁=n-Pr; R₂=Me; A=
Step 1: 1-[6-(4-methoxybenzylamino)-pyridazin-3-yl]-5-methyl-1H-pyrazole-4-ethyl carboxylate (XXX).

0.31 ml of 4-methoxybenzylamine is added to a solution of 0.30 g of ethyl 1-(6-chloropyridazin-3-yl)-5-methyl-1H-pyrazole-4-carboxylate (synthesized by the method described in J. Heterocyclic Chem. 2009, 46, 584-590) in 2 ml of dioxane, then it is heated at 130° C. for 2 hours. It is evaporated to dryness, triturated with water, the precipitate is drained and dried under vacuum. The precipitate is taken up in iso ether, drained and dried under vacuum. 0.30 g of the expected product is obtained in the form of powder.

¹H NMR: DMSO-d₆ (250 MHz): δ (ppm): 1.30 (3H, t); 2.69 (3H, s); 3.74 (3H, s); 4.26 (2H, q); 4.55 (2H, d); 6.91 (2H, d); 7.09 (1H, d); 7.32 (2H, d); 7.62 (1H, d); 7.67 (1H, t); 8.03 (1H, s).

Step 2: 1-[6-(4-Methoxybenzylamino)-pyridazin-3-yl]-5-methyl-1H-pyrazole-4-carboxylic acid (XXXI).

A solution of 5 g of the compound obtained in the preceding step in 50 ml of EtOH is added to a solution of 3.82 g of KOH in 50 ml of water. It is heated at 80° C. for 2 hours. It is evaporated to dryness and then the residue is taken up in 100 ml of water. 68 ml of 1N HCl solution is added dropwise, with stirring. The precipitate that formed is drained, it is washed with water and then dried in a vacuum stove. 4.5 g of the expected compound is obtained in the form of a white powder.

¹H NMR: DMSO-d₆ (250 MHz): δ (ppm): 2.71 (3H, s); 3.75 (3H, s); 4.57 (2H, s); 6.93 (2H, d); 7.30-737 (3H, m); 7.81 (1H, d); 8.04 (1H, s); 8.42 (1H, br).

Step 3: 1-{6-[(tert-Butoxycarbonyl)-(4-methoxybenzyl)-amino]-pyridazin-3-yl}-5-methyl-1H-pyrazole-4-carboxylic acid (XXXII).

0.17 g of DMAP, 2.32 ml of triethylamine and 3 g of di-tert-butyl bicarbonate are added to a solution of 1.87 g of the compound from the preceding step in 22 ml of DMF, then it is stirred for 20 hours at RT. 0.47 g of potassium hydroxide in solution in 10 ml of water is added, then it is stirred for 20 hours. 500 ml of water is added and it is washed with ether. The aqueous phase is buffered with phosphate buffer pre-loaded with 1N hydrochloric acid. The precipitate that formed is drained, it is washed with water and dried in a vacuum stove at 50° C. 1.35 g of the expected compound is obtained in the form of powder.

¹H NMR: DMSO-d₆ (250 MHz): δ (ppm): 1.43 (9H, s); 2.83 (3H, s); 3.71 (3H, s); 5.19 (2H, br); 6.88 (1H, d); 7.25 (1H, d); 8.05-8.21 (3H, m); 12.7 (1H, br).

Step 4: Ethyl 3-(1-{6-[(tert-butoxycarbonyl)-(4-methoxybenzy)amino]pyridazin-3-yl}-5-methyl-1H-pyrazol-4-yl)-3-oxo-propanoate (XXXIII).

0.53 g of 1,1'-carbonyldiimidazole is added to a solution of 1.1 g of the compound obtained in the preceding step in 17 ml of THF, and it is stirred for 20 hours at RT. 0.82 g of magnesium bis(3-ethoxy-3-oxopropanoate) is added and it is stirred at 55° C. for 20 hours. 50 ml of EtOAc is added, it is washed with 0.1 N soda, with brine, dried over Na₂SO₄ and evaporated to dryness. It is purified by silica gel chromatography, eluting with DCM and then eluting with DCM/MeOH mixture (95/5; v/v). 1.18 g of the expected compound is obtained in the form of a white powder.

¹H NMR: DMSO-d₆ (250 MHz): δ (ppm): 1.21 (3H, t); 1.43 (9H, s); 2.82 (3H, s); 3.72 (3H, s); 4.04 (2H, s); 4.13 (2H, q); 5.19 (2H, s); 6.88 (2H, d); 7.25 (2H, d); 8.09 (1H, d); 8.22 (1H, d); 8.41 (1H, s).

Step 5: Ethyl 2-{1-[6-(4-methoxybenzylamino)-pyridazin-3-yl]-5-methyl-1H-pyrazole-4-carbonyl}butanoate (XII).

1.25 g of potassium carbonate, 0.98 g of tetrabutylammonium bromide and 0.44 ml of iodoethane are added to a solution of 1.15 g of the compound obtained in the preceding step in 23 ml of THF, then it is stirred at 55° C. for 20 hours. After it returns to RT, 150 ml of EtOAc is added, it is washed with water, with brine, dried over Na₂SO₄ and evaporated to dryness. It is purified by silica gel chromatography, eluting with DCM/MeOH mixture (97/3; v/v). 1.18 g of the expected compound is obtained in the form of a white powder.

¹H NMR: DMSO-d₆ (250 MHz): δ (ppm): 0.92 (3H, t); 1.15 (3H, t); 1.43 (9H, s); 1.88 (2H, quint); 2.82 (3H, s); 3.72 (3H, s); 4.10 (2H, q); 4.28 (1H, t); 5.19 (2H, s); 6.88 (2H, d); 7.25 (2H, d); 8.09 (1H, d); 8.22 (1H, d); 8.49 (1H, s).

Step 6: 1-[1-(6-Amino-pyridazin-3-yl)-5-methyl-1H-pyrazol-4-yl]butan-1-one.

1.18 g of the compound from the preceding step in 5 ml of 6NHCl is heated under reflux for 6 hours. After it returns to RT, 50 ml of water is added, it is washed with EtOAc, and then the aqueous phase is evaporated to dryness. 50 ml of 0.2N NaOH solution is added and it is extracted with EtOAc. The organic phase is washed with brine, dried over $Na_2SO_4$ and evaporated to dryness. 0.42 g of the expected compound is obtained in the form of a white powder.

$^1$H NMR: DMSO-$d_6$ (250 MHz): δ (ppm): 0.93 (3H, t); 1.62 (2H, sext); 2.65 (3H, s); 2.82 (2H, t); 6.76 (2H, br); 7.00 (1H, d); 7.59 (1H, d); 8.27 (1H, s).

Preparation 6.3

1-[1-(4-Aminophenyl)-5-methyl-1H-pyrazol-4-yl]butan-1-one (V): $R_1$=n-Pr; $R_2$=Me; A=

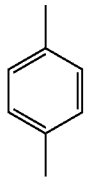

Step 1: Ethyl 3-[5-Methyl-1-(4-nitrophenyl)-1H-pyrazol-4-yl]-3-oxopropanoate (XXVII).

2.95 g of 1,1'-carbonyldiimidazole is added to a solution of 3 g of 5-methyl-1-(4-nitrophenyl)-1H-pyrazole-4-carboxylc acid (XXVI) in 120 ml of THF, and stirred for 20 hours at RT. 5.2 g of magnesium bis(3-ethoxy-3-oxopropanoate) (synthesized according to the method described in Angew. Chem. Int, Ed. Engl., 1979, 18, 72-74) is added and it is heated at 45° C. for 16 hours. The reaction mixture is concentrated under vacuum, the residue is extracted with EtOAc, the organic phase is washed with a saturated solution of $Na_2CO_3$, with water, dried over $MgSO_4$ and the solvent is evaporated under vacuum. The residue is chromatographed on silica gel, eluting with DCM and then with DCM/EtOH mixture (99.5/0.5; v/v). 2.82 g of the expected compound is obtained.

$^1$H NMR: $CDCl_3$ (250 MHz): δ (ppm): 1.28 (3H, t); 270/3H, s); 3.88 (2H, s); 4.26 (2H, q); 7.70 (2H, d); 8.09 (1H, s); 8.42 (2H, d).

Step 2: Ethyl 2-{[5-Methyl-1-(4-nitrophenyl)-1H-pyrazol-4-yl]carbonyl}butanoate (XXVIII).

A solution of 2.44 g of the compound from the preceding step in 25 ml of THF is cooled to 0° C., 0.34 g of NaH (60% in oil) is added in portions and stirred for 30 minutes. Then 0.92 ml of iodoethane is added and stirred for 24 hours at RT. Water is added slowly, then the reaction mixture is concentrated under vacuum. The residue is extracted with DCM, the organic phase is washed with water, dried over $MgSO_4$ and the solvent is evaporated under vacuum. The residue is chromatographed on silica gel, eluting with EtOAc/cyclohexane mixture (gradient from 10 to 20% of EtOAc). 2.10 g of the expected compound is obtained.

$^1$H NMR: $CDCl_3$ (250 MHz): δ (ppm): 1.02 (3H, t); 1.28 (3H, t); 2.06 (3H, m); 2.72 (3H, s); 3.97 (1H, t); 4.23 (2H, q); 7.70 (2H, d); 8.18 (1H, s); 8.42 (2H, d).

Step 3: 1-[5-Methyl-1-(4-nitrophenyl)-1H-pyrazol-4-yl]butan-1-one (XI).

2.4 g of the compound from the preceding step in 58 ml of an aqueous solution of HCl at 37% is heated at 105° C. for 2 hours. The reaction mixture is cooled to 0° C., 60 ml of 35% NaOH is added slowly, it is extracted with EtOAc, the organic phase is washed with water, dried over $MgSO_4$ and the solvent is evaporated under vacuum. 1.8 g of the expected compound is obtained.

$^1$H NMR: $CDCl_3$ (250 MHz): δ (ppm): 1.02 (3H, t); 1.78 (2H, m); 2.75 (3H, s); 2.85 (2H, t); 7.70 (2H, d); 8.10 (1H, s); 8.42 (2H, d).

Step 4: 1-[1-(4-Aminophenyl)-5-methyl-1H-pyrazol-4-yl]butan-1-one.

450 ml of EtOH is poured onto 5 g of palladium/charcoal under a controlled argon stream. Then a suspension of 48.7 g of the compound from the preceding step in 50 ml of EtOH is added, and then 181 ml of cyclohexene and it is heated under reflux for 4 hours. After cooling to RT, the reaction mixture is filtered on Celite®, it is washed with EtOAc and the filtrate is concentrated under vacuum. The residue is taken up in petroleum ether, the precipitate that formed is drained, it is washed with petroleum ether and dried under vacuum at 50° C. 41.3 g of the expected compound is obtained.

$^1$H NMR: DMSO-$d_6$ (250 MHz); δ (ppm): 0.93 (3H, t); 1.60 (2H, m); 2.41 (3H, s); 2.77 (2H, t); 5.6 (2H, br); 6.66 (2H, d); 7.10 (2H, d); 8.14 (1H, s).

Preparation 6.4

1-[1-(4-Aminophenyl)-5-methyl-1H-pyrazol-4-yl]propane-1-one (V): $R_1$=Et; $R_2$=Me; A=

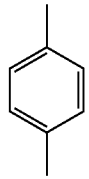

Step 1: Ethyl 2-methyl-3-[5-methyl-1-(4-nitrophenyl)-1H-pyrazol-4-yl]-3-oxo-propanoate.

0.07 g of NaH (60% in oil) is added slowly in small portions to 0.50 g of the compound obtained in step 1 of Preparation 6.3 in 5 ml of THF at 0° C. It is stirred for 30 minutes and then 0.15 ml of iodomethane is added. After 24 h at RT, water is added slowly and the THF is evaporated. The residue is extracted with DCM and the organic phase is washed with water, dried over $Na_2SO_4$ and evaporated to dryness. The residue is recrystallized from cyclohexane, obtaining 0.5 g of a yellow solid.

$^1$H NMR: DMSO-$d_6$ (250 MHz): δ (ppm): 1.16 (3H, t); 1.32 (1H, d); 2.61 (3H, s); 4.09 (2H, q); 4.44 (1H, q); 7.90 (2H, d); 8.38-8.44 (3H, m).

Step 2: 1-[5-Methyl-1-(4-nitrophenyl)-1H-pyrazol-4-yl]propane-1-one.

0.5 g of the compound obtained in the preceding step in 13 ml of 35% HCl is heated at 105° C. for 2 hours. It is cooled to 0° C. and 14 ml of 35% NaOH is added slowly. It is extracted with EtOAc, washed with water, with brine, dried over $Na_2SO_4$ and evaporated to dryness. The residue is chromatographed on silica gel, eluting with EtOAc/cyclohexane mixture (gradient from 0 to 20% of EtOAc). 0.39 g of a beige solid is obtained.

$^1$H NMR: DMSO-$d_6$ (250 MHz): δ (ppm): 1.08 (3H, t); 2.62 (3H, s); 2.89 (2H, q); 7.88 (2H, d); 8.36-8.43 (3H, m).

Step 3: 1-[1-(4-Aminophenyl)-5-methyl-1H-pyrazol-4-yl]propane-1-one.

0.5 g of the compound from the preceding step is dissolved in 20 ml of EtOAc/MeOH mixture (50/50; v/v). It is reduced using the H-Cube continuous hydrogenation apparatus (Cartridge Pd 10%, Mode Full H2, 50° C., flow 1 ml/min). It is concentrated to dryness, the solid residue is taken up in iso ether, the precipitate that formed is drained and 0.25 g of a white powder is obtained.

¹H NMR: DMSO-d₆ (250 MHz): δ (ppm): 1.07 (3H, t); 2.42 (3H, s); 2.82 (2H, q); 5.44 (2H, br); 6.64 (2H, d); 7.07 (2H, d); 8.12 (1H, s).

Preparation 6.5

1-[1-(4-Aminophenyl)-5-methyl-1H-pyrazol-4-yl]ethanone (V): R₁=Me; R₂=Me; A=

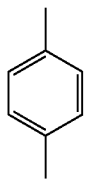

2 ml of acetic acid and 0.64 g of iron(0) are added to 0.94 g of 1-[5-methyl-1-(4-nitrophenyl)-1H-pyrazol-4-yl]ethanone (Journal of Chemical Research, Synopses (1986), (5), 166-7) in 60 ml of EtOH/water mixture (65/35; v/v). It is heated at 75° C. for 2 hours. It is concentrated, filtered on Celite®, the filtrate is neutralized with saturated Na₂CO₃ and it is extracted with DCM. The organic phase is washed with water, with brine, it is dried over Na₂SO₄ and evaporated. 0.70 g of yellow powder is obtained.

¹H NMR: DMSO-d₆ (250 MHz): δ (ppm): 2.41 (3H, s); 5.47 (2H, br); 6.65 (2H, d); 7.08 (2H, d); 8.12 (1H, s).

Preparation 6.6

1-(4-Aminophenyl)-5-methyl-1H-pyrazole-4-ethyl carboxylate (V): R₁F=OEt; R₂=Me; A=

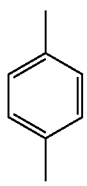

0.1 g of ethyl 5-methyl-1-(4-nitrophenyl)-1H-pyrazole-4-carboxylate (*Russian Journal of Organic Chemistry English* (2000) 36, 2, 191-194) is dissolved in 20 ml of EtOAc/MeOH mixture (50/50; v/v). It is reduced using the continuous hydrogenation apparatus (Cartridge Pd 10%, Mode Full H2, 50° C., flow 1 ml/min). It is concentrated to dryness, the solid residue is taken up in iso ether and the precipitate that formed is drained. 0.08 g of a white powder is obtained.

¹H NMR: DMSO-d₆ (250 MHz): δ (ppm): 1.41 (3H, t); 4.35 (2H, q); 6.74 (2H, d); 7.20 (2H, d); 8.03 (1H, s).

Preparation 6.7

1-[1-(4-Amino-3-bromophenyl)-5-methyl-1H-pyrazol-4-yl]butan-1-one (V): R₁=n-Pr; R₂=Me; A=

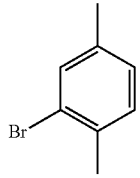

2.2 g of N-bromosuccinimide is added to 3 g of the compound from Preparation 6.3 in 50 ml of acetonitrile, then heated under reflux for 1 hour. After it returns to RT, 1N NaHCO₃ solution is added, it is extracted with EtOAc, washed with water, with brine, dried over Na₂SO₄ and evaporated to dryness. The residue is taken up in petroleum ether, and the precipitate that formed is drained, obtaining 3.5 g of a beige powder.

¹H NMR: DMSO-d₆ (250 MHz): δ (ppm): 0.92 (3H, t); 1.62 (2H, sext); 2.44 (3H, s); 2.78 (2H, t); 5.69 (2H, br); 6.89 (1H, d); 7.19 (1H, d); 7.49 (1H, s); 8.17 (1H, s).

Preparation 6.8

2-Amino-5-(4-butyryl-5-methyl-1H-pyrazol-1-yl)benzonitrile (V): R₁=n-Pr; R₂=Me; A=

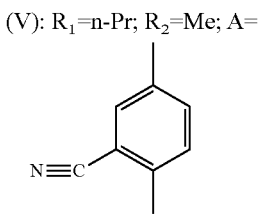

0.44 g of zinc cyanide and 0.18 g of Tetrakis(triphenylphosphine)palladium are added to 1 g of the compound from Preparation 6.7 in 20 ml of DMF in a sealed tube, and it is heated at 100° C. for 7 hours. The reaction mixture is poured into saturated solution of NaHCO₃ and extracted with EtOAc. It is washed with water, with brine, dried over Na₂SO₄ and evaporated to dryness. The residue is taken up in iso ether and the precipitate that formed is drained, obtaining 0.71 g of a white powder.

¹H NMR: DMSO-d₆ (250 MHz): δ (ppm): 0.92 (3H, t); 1.61 (2H, sext); 2.44 (3H, s); 2.78 (2H, t); 6.45 (2H, br); 6.90 (1H, d); 7.42 (1H, d); 7.58 (1H, s); 8.19 (1H, s).

Preparation 6.9

Methyl 2-amino-5-(4-butyryl-5-methyl-1H-pyrazol-1-yl)benzoate (V) R₁=n-Pr; R₂=Me; A=

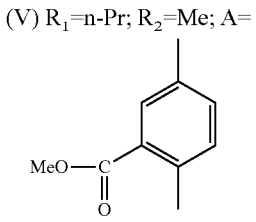

Step 1: 2-Amino-5-(4-butyryl-5-methyl-1H-pyrazol-1-yl)benzoic acid.

17 ml of 2N NaOH is added to 1.5 g of the compound from Preparation 6.8 and it is heated at 100° C. for 8 hours. Water is added, it is washed with DCM and then acidified with 2N HCl. The precipitate is drained, it is washed with water and dried in a vacuum stove. 1.4 g of the expected compound is obtained in the form of a white powder.

¹H NMR: DMSO-d₆ (250 MHz): δ (ppm): 0.93 (3H, t); 1.62 (2H, sext); 2.44

Step 2: Methyl 2-amino-5-(4-butyryl-5-methyl-pyrazol-1-yl)-benzoate.

0.38 g of potassium bicarbonate and then 0.24 ml of methyl iodide are added to 1 g of the compound from the preceding step in 20 ml of DMF. After 3 hours at RT, water is added and it is extracted with EtOAc. The organic phase is washed with water, with brine, dried over Na$_2$SO$_4$ and evaporated to dryness, obtaining 0.89 g of a beige powder.

$^1$H NMR: DMSO-d$_6$ (250 MHz): δ (ppm): 0.93 (3H, t); 1.62 (2H, sext); 2.44 (3H, s); 2.78 (2H, t); 3.80 (3H, s); 6.91 (1H, d); 6.97 (2H, br); 7.38 (1H, d); 7.72 (1H, s); 8.17 (1H, s).

Preparation 6.10

2-Amino-5-(4-butyryl-5-methyl-1H-pyrazol-1-yl)benzamide (V): R$_1$=n-Pr; R$_2$=Me; A=

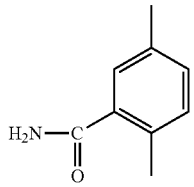

2.2 ml of 2N NaOH is added to 0.2 g of the compound from Preparation 6.8 in 5 ml of dioxane, then it is heated at 100° C. for 20 h. After it returns to RT, water is added and it is extracted with DCM. It is dried over Na$_2$SO$_4$ and evaporated to dryness. It is purified by silica gel chromatography, eluting with DCM/MeOH mixture (up to 95/5; v/v). 0.14 g of a white powder is obtained.

$^1$H NMR: DMSO-d$_6$ (250 MHz): δ (ppm): 0.93 (3H, t); 1.62 (2H, sext); 2.44 (3H, s); 2.78 (2H, t); 6.81 (1H, d); 6.98 (2H, br); 7.18 (1H, br); 7.24 (1H, d); 7.65 (1H, s); 7.81 (1H, br); 8.16 (1H, s).

7. Preparations of the compounds of formula (III).

Preparation 7.1

1-(1-Methoxypropan-2-yl)piperazine dihydrochloride (III): HNR$_7$R$_8$=

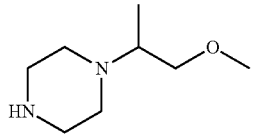

Step 1: tert-Butyl 4-(1-methoxy-1-oxopropan-2-yl)piperazine-1-carboxylate.

2.97 g of potassium carbonate and 1.97 g of methyl 2-bromopropanoate are added to a solution of 2 g of tert-butyl piperazine-1-carboxylate in 36 ml of DMF, and then it is heated at 60° C. for 1 hour. After it returns to RT, 150 ml of EtOAc is added, it is washed with water, with brine, dried over Na$_2$SO$_4$ and then evaporated to dryness. 2.8 g of the expected compound is obtained in the form of a colorless oil.

$^1$H NMR: DMSO-d$_6$ (250 MHz): δ (ppm): 1.18 (3H, d); 1.39 (9H, s); 2.49 (4H, m); 3.26 (4H, m); 3.37 (1H, q); 3.62 (3H, s).

Step 2: 2-[4-(tert-Butoxycarbonyl)piperazin-1-yl]propanoic acid.

6.33 ml of a solution of 2N NaOH is added to a solution of 2.3 g of the compound obtained in the preceding step in 30 ml of MeOH, and it is stirred for 20 hours. The reaction mixture is added to a solution of ammonium chloride and then evaporated to dryness. The solid residue is taken up in DCM/MeOH mixture (9/1; v/v), filtered and the filtrate evaporated. The residue is taken up in ether and drained. 1.2 g of the expected compound is obtained in the form of a white powder.

$^1$H NMR: DMSO-d$_6$ (250 MHz): δ (ppm): 1.17 (3H, d); 1.39 (9H, s); 2.50 (m, 4H); 3.22-3.32 (m, 5H); 7.25 (1H, br).

Step 3: tert-Butyl 4-(1-hydroxypropan-2-yl)piperazine-1-carboxylate.

1.10 g of 1,1'-carbonyldimidazole is added to a solution of 1.35 g of the compound obtained in the preceding step, in 15 ml of THF, and it is stirred for 30 minutes. In addition, a solution of 0.33 g of NaBH$_4$ in 6 ml of water is prepared at 0° C. and is added dropwise to the initial solution of activated ester, previously cooled to −5° C. 30 ml of water is added and it is extracted with EtOAc. It is washed with brine, dried over Na$_2$SO$_4$ and evaporated to dryness. It is purified by silica gel chromatography, eluting with DCM/MeOH mixture (gradient from 2 to 5% of MeOH). 1 g of the expected compound is obtained in the form of a colorless oil.

$^1$H NMR: DMSO-d$_6$ (250 MHz): δ (ppm): 0.90 (3H, d); 1.39 (9H, s); 2.42 (m, 4H); 2.57 (1H, q); 3.22-3.45 (m, 6H); 4.24 (1H, t), Step 4: tert-Butyl 4-(1-methoxypropan-2-yl)piperazine-1-carboxylate.

A solution of 0.49 g of the compound obtained in the preceding step in 5 ml of THF is added to a suspension of 0.17 g of NaH (60% in oil) in 5 ml of THF at 0° C., and it is stirred for 30 minutes. 0.27 ml of iodomethane is added at 0° C., and stirred for 20 hours. 10 ml of EtOAc is added, it is washed with water, with brine, dried over Na$_2$SO$_4$ and evaporated to dryness. It is purified by silica gel chromatography, eluting with DCM/MeOH mixture (97/3; v/v). 0.41 g of the expected compound is obtained in the form of a colorless oil.

$^1$H NMR: DMSO-d$_6$(250 MHz): δ (ppm): 0.93 (3H, d); 1.39 (9H, s); 2.42 (m, 4H); 2.70 (1H, q); 3.17-3.48 (m, 11H).

Step 5: 1-(1-Methoxypropan-2-yl)piperazine dihydrochloride.

3.88 ml of a solution of 4N hydrochloric acid in dioxane is added to a solution of 0.40 g of the compound obtained in the preceding step in 7 ml of DCM. After 2 hours at RT, it is evaporated to dryness, taken up in acetone and filtered. 0.34 g of the expected compound is obtained in the form of a white powder.

$^1$H NMR: DMSO-d$_6$ (250 MHz): δ (ppm): 1.30 (3H, d); 3.31 (3H, s); 3.40-4.00 (m, 11H); 9.75 (2H, br); 11.75 (1H, br).

Preparation 7.2

Oxetan-3-ylpiperazine 2.6 g of 3-oxetanone, 1.0 g of sodium cyanoborohydride and 0.16 ml of acetic acid are added to a solution of 2.0 g of benzyl piperazine-1-carboxylate in 20 ml of acetonitrile and then stirred for 16 hours at RT. The reaction mixture is diluted with water and filtered through a Chem Elut® cartridge, eluting with DCM. The combined organic phases are dried over MgSO$_4$ and the solvent is evaporated under vacuum. The residue is purified by preparative HPLC and 1.7 g of a white solid is obtained. 0.5 g of this solid is dissolved in 20 ml of EtOH, 0.2 g of Pd/C at 10% is added and the mixture is stirred under a hydrogen atmosphere (4 bar) for 3 hours. The reaction mixture is filtered on Celite® and the filtrate is concentrated under vacuum. The expected compound is obtained.

Preparation 7.3

N-Methyl-N[2-(piperazin-1-yl)ethyl]acetamide ditrifluoroacetate 0.341 g of 60% NaH in oil is added to a solution of 0.748 g of N-methylacetamide in 80 ml of THF and stirred for 10 minutes at RT. Then 2 g of tert-butyl 4-(2-bromoethyl)piperazinecarboxylate is added and stirred for 16 hours at RT. Water is added to the reaction mixture, it is decanted and the organic solvent is evaporated under vacuum. The residue is dissolved in DCM, filtered through a Chem Elut® cartridge, eluting with DCM and the solvents are evaporated under vacuum. The residue is purified by preparative HPLC and a white solid is obtained. The solid is dissolved in 5 ml of DCM, 1.2 ml of TFA is added and it is stirred for 16 hours at RT. The reaction mixture is diluted by adding 100 ml of toluene and the solvents are concentrated under vacuum. 1.5 g of the expected compound is obtained.

Preparation 7.4

(1S,4S)-2-(2-Methoxyethyl)-2,5-diazabicyclo[2.2.1]heptane ditrifluoroacetate 2 ml of DIPEA and 0.52 ml of 1-bromo-2-methoxyethane are added to a solution of 1.0 g of tert-butyl (1S,4S)-2,5-diazabicyclo[2.2.1]heptane-2-carboxylate hydrochloride in 10 ml of EtOH and heated under reflux for 16 hours. After cooling to RT, the reaction mixture is diluted by adding water and filtered through a Chem Elut® cartridge, eluting with DCM. The combined organic phases are dried over $MgSO_4$ and the solvent is evaporated under vacuum. The residue is dissolved in 10 ml of DCM, 15 ml of TFA is added and stirred for 2 hours at RT. 100 ml of toluene is added and the solvents are concentrated under vacuum. 1.45 g of the expected compound is obtained.

Preparation 7.5

(2R)-2-(Cyclobutylcarbamoyl)-1-methylpiperazine ditrifluoroacetate 0.39 ml of a solution of formaldehyde at 37% in water, 0.32 g of sodium cyanoborohydride and 0.994 ml of acetic acid are added to a solution of 1 g of tert-butyl (3R)-piperazine-1,3-dicarboxylate in 26 ml of MeOH and stirred for 3 hours at RT. The reaction mixture is diluted by adding a saturated solution of $K_2CO_3$, extracted with DCM, the organic phase is dried over $MgSO_4$ and the solvent is evaporated under vacuum. The residue is dissolved in 4 ml of DMF, 0.19 g of HOAT, 0.267 g of EDC and 0.1 g of cyclobutylamine are added and it is stirred for 16 hours at RT. The reaction mixture is diluted by adding a saturated solution of $NaHCO_3$, extracted with DCM, the organic phase is dried over $MgSO_4$ and the solvent is evaporated under vacuum. The residue is purified by preparative HPLC, the fractions containing the product are concentrated under vacuum and lyophilized, obtaining 031 g of a white solid. The solid is dissolved in 2 ml of DCM, 2.5 ml of TFA is added and stirred for 4 hours at RT. It is diluted by adding 100 ml of toluene and the solvents are concentrated under vacuum. 0.94 g of the expected compound is obtained.

Preparation 7.6

1,1,1-Trifluoro-3-(piperazin-1-yl)propan-2-ol

Step 1: Benzyl 4-(3,3,3-trifluoro-2-hydroxypropyl)piperazine-1-carboxylate.

0.47 ml of 1,1,1-trifluoro-2,3-epoxypropane is added to a solution of 1 g of benzyl piperazine-1-carboxylate in 100 ml of N-methylpyrrolidine and it is heated at 80° C. for 12 hours. 0.05 ml of 1,1,1-trifluoro-2,3-epoxypropane is added and it is heated at 80° C. for 48 hours, The reaction mixture is extracted with DCM, the organic phase is washed with a 4% solution of LiCl in water, it is dried over $MgSO_4$ and the solvent is evaporated under vacuum. The residue is purified by preparative HPLC and 1.7 g of the expected compound is obtained.

Step 2: 1,1,1-Trifluoro-3-(piperazin-1-yl)propan-2-Ol.

0.15 g of Pd/C at 10% is added, under an argon atmosphere, to a solution of 1.7 g of the compound from the preceding step in 50 ml of EtOH and it is stirred for 16 hours under a hydrogen atmosphere (3 bar). The reaction mixture is filtered on Celite®, it is washed with EtOH and the filtrate is concentrated under vacuum. 1.2 g of the expected compound is obtained.

Preparation 7.7

1-(2-Methoxyethyl)-4,5,6,7-tetrahydro-1H-imidazo[4,5-c]pyridine

Step 1: Benzyl 1,4,6,7-tetrahydro-5H-imidazo[4,5-c]pyridine-5-carboxylate.

A mixture of 2.0 g of 4,5,6,7-tetrahydro-1H-imidazo[4,5-c]pyridine dihydrochloride, 2.36 g of $NaHCO_3$ and 2.45 g of N-(benzyloxycarbonyloxy)succinimide in 80 ml of dioxane/water mixture (50/50; v/v) is stirred for 16 hours at RT. The reaction mixture is extracted with EtOAc, the organic phase is washed with a saturated solution of $NaHCO_3$, with 0.1M HCl solution, with saturated NaCl solution, it is dried and the solvent is evaporated under vacuum. The residue is chromatographed on silica gel, eluting with DCM/MeOH mixture. 1.9 g of the expected compound is obtained.

Step 2: Benzyl 1-(2-methoxyethyl)-1,4,6,7-tetrahydro-5H-imidazo[4,5-c]pyridine-5-carboxylate.

3.6 ml of 6N NaOH, 0.051 g of tetrabutylammonium bromide and 0.308 g of 1-bromo-2-methoxyethane are added to a solution of 0.475 g of the compound from the preceding step in 20 ml of toluene and 5 ml of DCM and it is stirred for 12 hours at RT. 0.308 g of 1-bromo-2-methoxyethane and 0.05 g of tetrabutylammonium iodide are added and stirred for 36 hours at RT. The reaction mixture is concentrated under vacuum, the residue is extracted with DCM, the organic phase is washed with water, it is dried and the solvent is evaporated under vacuum. The product thus obtained is purified by preparative HPLC and 0.24 g of the expected compound is obtained.

Step 3: 1-(2-Methoxyethyl)-4,5,6,7-tetrahydro-1H-imidazo[4,5-c]pyridine.

0.025 g of Pd/C at 10% is added under argon to a solution of 0.25 g of the compound from the preceding step in 50 ml of EtOH and stirred for 16 hours under a hydrogen atmosphere (1 bar). It is filtered on Celite®, washed with EtOH and the filtrate is concentrated under vacuum. 0.115 g of the expected compound is obtained.

Preparation 7.8

Trans-2-(piperazin-1-yl)cyclopentanol

Step 1: Benzyl 4-(trans-2-hydroxycyclopentyl)piperazine-1-carboxylate.

A solution of 0.524 g of benzyl piperazine-1-carboxylate is cooled to 0° C., 0.2 g of 1,2-epoxycyclopentane is added and it is heated at 80° C. for four days. The reaction mixture is concentrated under vacuum and the residue is purified by silica gel chromatography, eluting with EtOAc/MeOH mixture. 0.32 g of the expected compound is obtained.

Step 2: Trans-2-(piperazin-1-yl)cyclopentanol.

0.025 g of Pd/C at 10% is added under argon to a solution of 0.32 g of the compound from the preceding step in 50 ml of EtOH and it is stirred for 16 hours under a hydrogen atmosphere (3 bar). The reaction mixture is filtered on Celite, it is washed with EtOH and the filtrate is concentrated under vacuum. 0.19 g of the expected compound is obtained.

Preparation 7.9

2-(Pyrrolidin-3-yloxy)ethanol

Step 1: Benzyl 3-(2-benzyloxyethoxy)pyrrolidine-1-carboxylate.

A solution of 1.29 g of benzyl 3-hydroxypyrrolidine-1-carboxylate in 80 ml of THF is cooled to 0° C., 0.245 g of 60% NaH in oil is added and then 1.26 g of [(2-bromoethoxy)methyl]benzene and 0.108 g of tetrabutylammonium iodide and it is heated at 80° C. for 3 hours. 0.28 g of NaH and 0.40 g of [(2-bromoethoxy)methyl]benzene are added and it is heated at 80° C. for 2 hours. The reaction mixture is concentrated under vacuum, the residue is extracted with DCM, the organic phase is washed with 0.1M HCl solution, with a saturated solution of NaHCO₃, it is dried and the solvent is evaporated under vacuum. The product thus obtained is purified by preparative HPLC and 0.46 g of the expected compound is obtained.

Step 2: 2-(Pyrrolidin-3-yloxy)ethanol.

0.05 g of Pd/C at 10% is added, under argon, to a solution of 0.459 g of the compound from the preceding step in 35 ml of EtOH and it is stirred for 16 hours under a hydrogen atmosphere (3 bar). The reaction mixture is filtered on Celite, it is washed with EtOH and the filtrate is concentrated under vacuum. 0.205 g of the expected compound is obtained.

Preparation 7.10

(2S,4R)-2-(Cyclobutylcarbamoyl)-4-hydroxypyrrolidine trifluoroacetate

Step 1: tert-Butyl (2S,4R)-2-(cyclobutylcarbamoyl)-4-hydroxypyrrolidine-1-carboxylate.

1.17 g of HOAT, 1.60 g of 1-(3-dimethylaminopropyl)-3-ethylcarbodiimide hydrochloride and 0.615 g of cyclobutylamine are added to a solution of 2.0 g of (4R)-1-(tert-butoxycarbonyl)-4-hydroxy-L-proline in 20 ml of DMF. 1.5 ml of a saturated solution of NaHCO₃ is added and the reaction mixture is filtered on a Chem Elut® cartridge, eluting with DCM. The solvents are concentrated under vacuum and the residue is purified by filtration on silica gel, eluting with EtOAc. 1.22 g of the expected compound is obtained.

Step 2: (2S,4R)-2-(cyclobutylcarbamoyl)-4-hydroxypyrrolidine trifluoroacetate.

3.2 ml of TFA is added to a solution of 1.22 g of the compound from the preceding step in 31 ml of DCM and it is stirred for 12 hours at RT. It is concentrated under vacuum, the residue is taken up in toluene and the solvent is evaporated under vacuum. 1.51 g of the expected compound is obtained, Preparation 7.11

2-(Methoxymethyl)-1-methyl piperazine ditrifluoroacetate

Step 1: tert-Butyl 3-(hydroxymethyl)-4-methylpiperazine-1-carboxylate.

0.303 g of sodium acetate, 0.375 g of formaldehyde and 0.218 g of sodium cyanoborohydride are added to a solution of 0.5 g of tert-butyl 3-(hydroxymethyl)piperazine-1-carboxylate in 50 ml of MeOH and stirred for 1 hour at RT. A saturated solution of NaHCO₃ is added, it is extracted with DCM, the organic phase is dried over Na₂SO₄ and the solvent is evaporated under vacuum. The residue is chromatographed on silica gel, eluting with DCM/MeOH mixture. 0.31 g of the expected compound is obtained.

Step 2: tert-Butyl 3-(methoxymethyl)-4-methylpiperazine-1-carboxylate.

A solution of 0.125 g of the compound from the preceding step in 12 ml of DMF is cooled to 0° C., 0.024 g of NaH (60% in oil) and 0.092 g of iodomethane are added and it is stirred for 16 hours at RT. Water is added to the reaction mixture, it is extracted with DCM, the organic phase is dried over Na₂SO₄ and the solvent is evaporated under vacuum. 0.122 g of the expected compound is obtained.

Step 3: 2-(Methoxymethyl)-1-methylpiperazine ditrifluoroacetate.

0.4 ml of TFA is added to a solution of 0.122 g of the compound from the preceding step in 5 ml of DCM and stirred for 12 hours at RT. It is concentrated under vacuum, the residue is taken up in toluene and the solvent is evaporated under vacuum. 0.14 g of the expected compound is obtained.

Preparation 7.12

3-Methyl-4,5,6,7-tetrahydro-3H-imidazo[4,5-c]pyridine

Step 1: Benzyl 3,4,6,7-tetrahydro-5H-imidazo[4,5-c]pyridine-5-carboxylate.

A mixture of 2.0 g of 4,5,6,7-tetrahydro-3H-imidazo[4,5-c]pyridine dihydrochloride, 2.36 g of NaHCO₃ and 2.45 g of N-(benzyloxycarbonyloxy)succinimide in 80 ml of dioxane/water mixture (50/50; v/v) is stirred for 16 hours at RT. The reaction mixture is extracted with EtOAc, the organic phase is washed with a saturated solution of NaHCO₃, with a 0.1 M solution of HCl, with saturated NaCl solution, it is dried over Na$_2$SO$_4$ and the solvent is evaporated under vacuum. The residue is purified by silica gel chromatography, eluting with DCM/MeOH mixture. 1.9 g of the expected compound is obtained.

Step 2: Benzyl 3-methyl-3,4,6,7-tetrahydro-5H-imidazo[4,5-c]pyridine-5-carboxylate.

3.6 ml of 6N NaOH, 0.051 g of tetrabutylammonium bromide and 0.313 g of iodomethane are added to a solution of 0.475 g of the compound from the preceding step in 20 ml of toluene and 5 ml of DCM and stirred for 12 hours at RT. The reaction mixture is concentrated under vacuum, the residue is extracted with DCM, the organic phase is washed with water, it is dried and the solvent is evaporated under vacuum. The residue is purified by preparative HPLC. 0.32 g of the expected compound is obtained.

Step 3: 3-Methyl-4,5,6,7-tetrahydro-3H-imidazo[4,5-c]pyridine.

0.025 g of Pd/C at 10% is added, under argon, to a solution of 0.3 g of the compound from the preceding step in 50 ml of EtOH and stirred for 16 hours under a hydrogen atmosphere (1 bar). The reaction mixture is filtered on Celite®, it is washed with EtOH and the filtrate is concentrated under vacuum. 0.166 g of the expected compound is obtained in the form of oil.

8. Preparations of the compounds of formula (VI).

Preparation 8.1

N-[4-(4-Butyryl-5-methyl-1H-pyrazol-1-yl)phenyl]-6-methyl-1H-indole-3-carboxamide (VI): R$_1$=n-Pr; R$_2$=Me; R$_4$=H; R$_5$=Me; A=

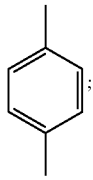

X=CH

Step 1: 1-acetyl-N-[4-(4-butyryl-5-methyl-1H-pyrazol-1-yl)phenyl]-6-methyl-1H-indole-3-carboxamide (XIV).

A mixture of 1.03 g of the compound from Preparation 4.2 in 20 ml of DCM is cooled to 0° C., 0.81 g of the compound from Preparation 6.3, 0.62 g of DMAP and then 0.97 g of 1-(3-dimethylaminopropyl)-3-ethylcarbodiimide hydrochloride are added and stirred for 2 hours, allowing the temperature to return to RT. 100 ml of EtOAc is added, the organic phase is washed with 1N HCl solution, with a solution of 1N NaOH, with water, with saturated NaCl solution, dried over Na$_2$SO$_4$ and the solvent is evaporated under vacuum. The residue is taken up in iso ether, the precipitate that formed is drained and dried under vacuum. 1.39 g of the expected compound is obtained.

$^1$H NMR: DMSO-d$_6$ (250 MHz): δ (ppm): 0.95 (3H, t); 1.65 (2H, m); 2.47-2.52 (6H); 2.77 (3H, s); 2.83 (2H, t); 7.24 (1H, d); 7.55 (2H, d); 7.95 (2H, d); 8.13 (1H, d); 8.24 (2H, d); 8.75 (1H, s); 10.30 (1H, s).

Following the procedure described in step 1, the compounds of formula (XIV) presented in TABLE V below are prepared:

TABLE V

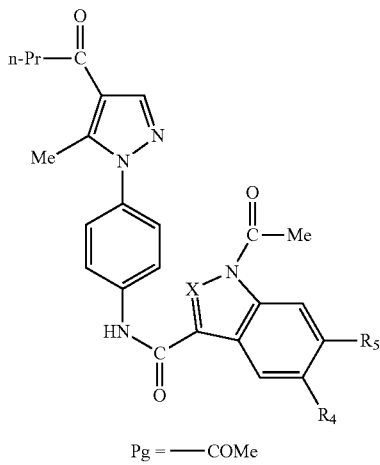

Pg = —COMe

| X | R$_4$ | R$_5$ | $^1$H NMR: DMSO-d$_6$ (250 MHz): δ (ppm) |
|---|---|---|---|
| CH | F | H | 0.94 (3H, t); 1.64 (2H, m); 2.53 (3H, s); 2.77 (3H, s); 2.82 (2H, t); 7.29 (1H, t); 7.56 (2H, d); 7.95 (3H, m); 8.25 (1H, s); 8.39 (1H, dd); 8.92 (1H, s); 10.35 (1H, s). |
| CH | Me | Br | 0.94 (3H, t); 1.64 (2H, m); 2.48-2.52 (6H); 2.76 (3H, s); 2.82 (2H, t); 7.55 (2H, d); 7.94 (2H, d); 8.22 (1H, s); 8.25 (1H, s); 8.58 (1H, s); 8.82 (1H, s); 10.30 (1H, s). |
| CH | Br | Me | 0.94 (3H, t); 1.64 (2H, m); 2.52 (3H, s); 2.76 (3H, s); 2.82 (2H, t); 7.55 (2H, d); 7.95 (2H, d); 8.27 (1H, s); 8.38 (1H, s); 8.45 (1H, s); 8.86 (1H, s); 10.35 (1H, s). |
| CH | Cl | F | 0.94 (3H, t); 1.64 (2H, m); 2.52 (3H, s); 2.76 (3H, s); 2.82 (2H, t); 7.55 (2H, d); 7.93 (2H, d); 8.20-8.40 (3H, m); 8.92 (1H, s); 10.35 (1H, s). |
| N | Me | H | 0.95 (3H, t); 1.64 (2H, m); 2.48-2.52 (6H); 2.83 (2H, t); 2.90 (3H, s); 7.54-7.62 (3H, m); 8.03-8.10 (3H, m); 8.27-8.30 (2H, m); 10.75 (1H, s). |

Step 2: N-[4-(4-Butyryl-5-methyl-1H-pyrazol-1-yl)phenyl]-6-methyl-1H-indole-3-carboxamide 1.5 g of K$_2$CO$_3$ is added to a solution of 1.15 g of the compound from step 1 in 40 ml of MeOH/THF mixture (50/50; v/v) and stirred for 4 hours at RT. The reaction mixture is concentrated under vacuum, the residue is taken up in EtOAc/water mixture, the organic phase is washed with water, with saturated NaCl solution, dried over Na$_2$SO$_4$ and the solvent is evaporated under vacuum. The residue is taken up in iso ether and the precipitate that formed is drained. 0.9 g of the expected compound is obtained.

$^1$H NMR: DMSO-d$_6$ (250 MHz): δ (ppm): 0.95: t 3H; 1.65: m: 2H, 2.42: s: 3H, 2.50: s: 3H, 2.82: t: 2H; 7.00: d: 1H, 7.27: s: 1H, 7.47: d: 2H, 7.95: d: 2H, 8.07: d: 1H, 8.24: s: 1H, 8.25: s: 1H, 9.90: s: 1H, 11.60 s: 1H.

Following the procedure described in step 2, the compounds of formula (VI) presented in TABLE VI below are prepared:

TABLE VI

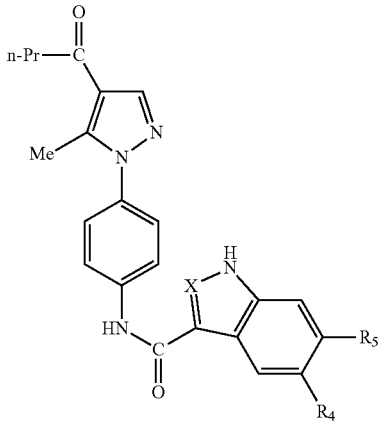

| | X | R₄ | R₅ | ¹H NMR: DMSO-d₆ (250 MHz): δ (ppm) |
|---|---|---|---|---|
| Preparation 8.2 | CH | F | H | 0.95 (3H, t); 1.63 (2H, m); 2.52 (3H, s); 2.83 (2H, t); 7.07 (1H, t); 7.47-7.55 (3H, m); 7.90 (1H, d); 7.96 (2H, d); 8.26 (1H, s); 8.43 (1H, dd); 10.03 (1H, s); 11.95 (1H, br). |
| Preparation 8.3 | CH | Me | Br | 0.94 (3H, t); 1.64 (2H, m); 2.46 (3H, s); 2.50 (3H, s); 2.81 (2H, t); 7.48 (2H, d); 7.73 (1H, s); 7.94 (2H, d); 8.17 (1H, s); 8.24 (1H, s); 8.32 (1H, s); 8.98 (1H, s); 11.75 (1H, s). |
| Preparation 8.4 | CH | Br | Me | 0.95 (3H, t); 1.65 (2H, m); 2.46 (3H, s); 2.50 (3H, s); 2.82 (2H, t); 7.47-7.52 (3H, m); 7.95 (2H, d); 8.24 (1H, s); 8.34 (1H, s); 8.39 (1H, s); 10.00 (1H, s); 11.85 (1H, s). |
| Preparation 8.5 | CH | Cl | F | 0.94 (3H, t); 1.64 (2H, m); 2.50 (3H, s); 2.81 (2H, t); 7.46-7.57 (3H, m); 7.94 (2H, d); 8.24 (1H, s); 8.29 (1H, d); 8.41 (1H, s); 10.10 (1H, s); 12.00 (1H, br). |
| Preparation 8.6 | N | Me | H | 0.95 (3H, t); 1.64 (2H, m); 2.48 (3H, s); 2.50 (3H, s); 2.83 (2H, t); 7.31 (1H, d); 7.51 (2H, d); 8.04 (1H, d); 8.10 (2H, d); 8.25 (1H, s); 10.55 (1H, s); 13.75 (1H, s). |

Preparation 8.7

N-[4-(4-Butyryl-5-methyl-1H-pyrazol-1-yl)phenyl]-5-chloro-6-methyl-1H-indole-3-carboxamide (VI): R₁=n-Pr; R₂=Me; R₄=Cl; R₅=Me; A=

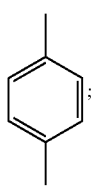

X=CH 0.5 g of nickel(II) chloride is added to a solution of 1 g of the compound from Preparation 8.4 in 6 ml of DMF and it is heated in a microwave for 30 minutes at 200° C. After cooling to RT, 60 ml of water is added, it is extracted with EtOAc, the organic phase is washed with saturated NaCl solution, dried over Na₂SO₄ and the solvent is evaporated under vacuum. The residue is taken up in acetone/iso ether mixture (50/50; v/v) and the precipitate that formed is drained. 0.66 g of the expected compound is obtained.

¹H NMR: DMSO-d₆ (250 MHz): δ (ppm): 0.94 (3H, t); 1.64 (2H, m); 2.47 (3H, s); 2.52 (3H, s); 2.82 (2H, t); 7.46-7.51 (3H, m); 7.94 (2H, d); 8.19 (1H, s); 8.24 (1H, s); 8.34 (1H, s); 9.95 (1H, s); 11.80 (1H, br).

9. Preparations of the compounds of formula (II).

Preparation 9.1

Methyl (3-{[5-(4-butyryl-5-methyl-1H-pyrazol-1-yl)pyrazin-2-yl]carbamoyl}-5-chloro-1H-indol-1-yl)acetate (II): R₁=n-Pr; R₂=Me; R₄=Cl; R₅=H; A=

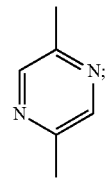

X=CH; Z=Me

Step 1: Methyl [5-chloro-3-(chlorocarbonyl)-1H-indol-1-yl]acetate.

6.6 ml of thionyl chloride and a few drops of DMF are added to a solution of 6.00 g of the compound from Preparation 3.1 in 200 ml of DCM. After 3 h under reflux, it is evaporated to dryness and the solid residue is triturated with 80 ml of DCM. The precipitate formed is filtered, and washed with DCM, obtaining 4.5 g of a white powder.

Step 2: Methyl (3-{[5-(4-butyryl-5-methyl-1H-pyrazol-1-yl)pyrazin-2-yl]carbamoyl}-5-chloro-1H-indol-1-yl)acetate.

0.18 ml of 1,8-diazabicyclo[5.4.0]undec-7-ene and 0.26 g of the compound from step 1 are added to 0.17 g of the compound from Preparation 6.1 in 10 ml of 1,2-dichloroethane, then it is heated at 80° C. for 2 hours. After it returns to RT, the reaction mixture is washed with water and then with brine and dried over Na₂SO₄. It is evaporated and then the solid residue is purified by silica gel chromatography, eluting with DCM/MeOH mixture (gradient from 1 to 2% of MeOH). The solid residue is triturated with iso ether and then filtered, obtaining 0.14 g of a yellow powder.

¹H NMR: DMSO-d₆ (250 MHz): δ (ppm): 0.94 (3H, t); 1.63 (2H, m); 2.78 (3H, s); 2.86 (2H, t); 3.73 (3H, s); 5.32 (2H, s); 7.31 (1H, d); 7.61 (1H, d); 8.25 (1H, s); 8.36 (1H, s); 8.62 (1H, s); 8.86 (1H, s); 9.42 (1H, s); 11.15 (1H, s).

Preparation 9.2

Methyl (3-{[6-(4-butyryl-5-methyl-1H-pyrazol-1-yl)pyridazin-3-yl]carbamoyl}-5-chloro-1H-indol-1-yl)acetate (II): R₁=n-Pr; R₂=Me; R₄=Cl; R₅=H; A=

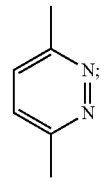

X=CH; Z=Me

A solution of 0.35 g of the compound from Preparation 6.2 and 0.59 g of DMAP is stirred for 30 minutes in the presence of 1 g of molecular sieve 4A in 20 ml of 1,2-dichloroethane. 0.92 g of the compound obtained in step 1 of Preparation 9.1 is added, then it is heated at 80° C. for 6 hours. After it returns to RT, the molecular sieve is removed by filtration, the reaction mixture is washed with water and then with brine and dried over $Na_2SO_4$. It is evaporated and then the solid residue is purified by silica gel chromatography, eluting with DCM/MeOH mixture (gradient from 0 to 5% of MeOH), obtaining 0.51 g of a white powder.

$^1$H NMR: DMSO-$d_6$ (250 MHz): δ (ppm): 0.94 (3H, t); 1.64 (2H, m); 2.82 (3H, s); 2.87 (2H, t); 3.73 (3H, s); 5.33 (2H, s); 7.32 (1H, d); 7.62 (1H, d); 8.13 (1H, d); 8.23 (1H, s); 8.41 (1H, s); 8.65 (1H, s); 8.71 (1H, d); 11.42 (1H, s).

Preparation 9.3

Methyl (3-{[4-(4-butyryl-5-methyl-1H-pyrazol-1-yl)phenyl]carbamoyl}-5-chloro-6-fluoro-1H-indol-1-yl)acetate (II): $R_1$=n-Pr; $R_2$=Me; $R_4$=Cl; $R_5$=F; A=

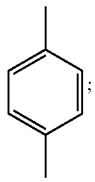

X=CH; Z=Me

A solution of 1.25 g of the compound from Preparation 8.5 in 15 ml of DMF is cooled to 0° C., 0.47 g of $K_2CO_3$ and then 0.49 g of methyl bromoacetate are added and it is stirred for 3 hours at RT. 50 ml of EtOAc and 100 ml of water are added, it is decanted, the organic phase is washed with water and with saturated NaCl solution, dried over $Na_2SO_4$ and the solvent is evaporated under vacuum. 1.38 g of a white powder is obtained.

$^1$H NMR: DMSO-$d_6$ (250 MHz): δ (ppm): 0.94 (3H, t); 1.64 (2H, m); 2.51 (3H, s); 2.81 (2H, t); 3.73 (3H, s); 5.32 (2H, s); 7.50 (2H, d); 7.78 (1H, d); 7.94 (2H, d); 8.24 (1H, d); 8.30 (1H, d); 8.35 (1H, s); 10.20 (1H, s).

Following the procedure described in Preparation 9.3, the compounds of formula (II) presented in TABLE VII below are prepared:

TABLE VII (II)

[Structure of formula (II)]

| | X | $R_4$ | $R_5$ | Z | $^1$H NMR: DMSO-$d_6$ (250 MHz): δ (ppm) |
|---|---|---|---|---|---|
| Preparation 9.4 | CH | F | H | Me | 0.94 (3H, t); 1.64 (2H, m); 2.51 (3H, s); 2.82 (2H, t); 3.73 (3H, s); 5.33 (2H, s); 7.13 (1H, t); 7.49 (2H, d); 7.56 (1H, dd); 7.87-7.97 (3H, m); 8.24 (1H, s); 8.35 (1H, s); 10.10 (1H, s). |
| Preparation 9.5 | CH | H | Me | Me | 0.94 (3H, t); 1.64 (2H, m); 2.44 (3H, s); 2.50 (3H, s); 2.81 (2H, t); 3.73 (3H, s); 5.26 (2H, s); 7.06 (1H, d); 7.32 (1H, s); 7.49 (2H, d); 7.95 (2H, d); 8.09 (1H, d); 8.20 (1H, s); 8.24 (1H, s); 10.05 (1H, s). |
| Preparation 9.6 | CH | Me | Br | Me | 0.94 (3H, t); 1.64 (2H, m); 2.47 (3H, s); 2.52 (3H, s); 2.82 (2H, t); 3.73 (3H, s); 5.31 (2H, s); 7.49 (2H, d); 7.89 (1H, s); 7.94 (2H, d); 8.17 (1H, s); 8.24 (1H, s); 8.25 (1H, s); 10.10 (1H, s). |
| Preparation 9.7 | CH | Br | Me | Me | 0.95 (3H, t); 1.64 (2H, m); 2.44 (3H, s); 2.51 (3H, s); 2.83 (2H, t); 3.74 (3H, s); 5.30 (2H, s); 7.50 (2H, d); 7.60 (1H, s); 7.94 (2H, d); 8.26 (1H, s); 8.28 (1H, s); 8.41 (1H, s); 10.15 (1H, s). |
| Preparation 9.8 | CH | Cl | Me | Me | 0.95 (3H, t); 1.65 (2H, m); 2.45 (3H, s); 2.51 (3H, s); 2.83 (2H, t); 3.74 (3H, s); 5.31 (2H, s); 7.50 (2H, d); 7.59 (1H, s); 7.95 (2H, d); 8.21 (1H, s); 8.26 (1H, s); 8.29 (1H, s); 10.15 (1H, s). |
| Preparation 9.9 | N | Me | H | Me | 0.94 (3H, t); 1.64 (2H, m); 2.50 (3H, s); 2.53 (3H, s); 2.82 (2H, t); 3.72 (3H, s); 5.55 (2H, s); 7.37 (1H, d); 7.51 (2H, d); 7.71 (1H, d); 8.06-8.10 (3H, m); 8.25 (1H, s); 10.60 (1H, s). |

Preparation 9.10

Methyl (3-{[4-(4-butyryl-5-methyl-1H-pyrazol-1-yl)phenyl]carbamoyl}-5

(II): $R_1$=n-Pr; $R_2$=Me; $R_4$=Cl; $R_5$=H; A=

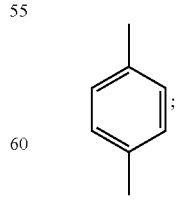

X=CH; Z=Me 2.17 g of 1-(3-dimethylaminopropyl)-3-ethylcarbodiimide hydrochloride, 2.61 g of DMAP and 2.67 g of the compound from Preparation 6.3 are added to a solution of 2.70 g of the compound from Preparation 3.1 in 50 ml of 1,2-dichloroethane and it is stirred for 20 hours at RT. The reaction mixture is washed with 1N HCl solution, with a saturated NaHCO₃ solution, and with water, the organic phase is dried over Na₂SO₄ and the solvent is evaporated under vacuum. The residue is taken up in acetone and the precipitate that formed is drained. 3.35 g of the expected compound is obtained.

$^1$H NMR: DMSO-d$_6$ (250 MHz): δ (ppm): 0.94 (3H, t); 1.62 (2H, m); 2.50 (3H, s); 2.82 (2H, t); 3.73 (3H, s); 5.34 (2H, s); 7.29 (1H, d); 7.50 (2H, d); 7.60 (1H, d); 7.94 (2H, d); 8.21 (1H, s); 8.34 (1H, s); 8.35 (1H, s); 10.20 (1H, s).

Following the procedure described in Preparation 9.10, the compounds of formula (H) presented in TABLE VIII below are prepared:

TABLE VIII (II)

| | R₁ | R₄ | R₅ | $^1$H NMR: DMSO-d$_6$ (250 MHz): δ (ppm) |
|---|---|---|---|---|
| Preparation 9.11 | OEt | Cl | H | / |
| Preparation 9.12 | Me | Cl | H | 2.45 (3H, s); 2.50 (3H, s); 3.73 (3H, s); 5.34 (2H, s); 7.29 (1H, d); 7.49 (2H, d); 7.60 (1H, d); 7.95 (2H, d); 8.21 (1H, s); 8.23 (1H, s); 8.35 (1H, s); 10.15 (1H, s) |
| Preparation 9.13 | Et | Cl | H | 1.06 (3H, t); 2.50 (3H, s); 2.85 (2H, q); 3.73 (3H, s); 5.26 (2H, s); 7.29 (1H, d); 7.49 (2H, d); 7.60 (1H, d); 7.95 (2H, d); 8.21 (1H, s); 8.23 (1H, s); 8.35 (1H, s); 10.15 (1H, s) |
| Preparation 9.14 | nPr | Me | H | 0.94 (3H, t); 1.64 (2H, m); 2.43 (3H, s); 2.50 (3H, s); 2.82 (2H, t); 3.72 (3H, s); 5.27 (2H, s); 7.08 (1H, d); 7.40 (1H, d); 7.48 (2H, d); 7.95 (2H, d); 8.02 (1H, s); 8.22 (1H, s); 8.24 (1H, s); 10.05 (1H, s) |
| Preparation 9.15 | nPr | OMe | H | 0.94 (3H, t); 1.64 (2H, m); 2.50 (3H, s); 2.81 (2H, t); 3.72 (3H, s); 3.81 (3H, s); 5.27 (2H, s); 6.89 (1H, d); 7.42 (1H, d); 7.48 (2H, d); 7.73 (1H, d); 7.95 (2H, d); 8.23 (2H, s); 10.05 (1H, s) |
| Preparation 9.16 | nPr | CF₃ | H | 0.94 (3H, t); 1.64 (2H, m); 2.50 (3H, s); 2.82 (2H, t); 3.74 (3H, s); 5.42 (2H, s); 7.50 (2H, d); 7.59 (1H, d); 7.80 (1H, d); 7.96 (2H, d); 8.24 (1H, s); 8.46 (1H, s); 8.58 (1H, s); 10.30 (1H, s) |
| Preparation 9.17 | nPr | Br | H | 0.94 (3H, t); 1.64 (2H, m); 2.50 (3H, s); 2.82 (2H, t); 3.72 (3H, s); 5.35 (2H, s); 7.40 (1H, d); 7.50 (2H, d); 7.54 (1H, d); 7.94 (2H, d); 8.26 (1H, s); 8.33 (1H, s); 8.37 (1H, s); 10.20 (1H, s) |
| Preparation 9.18 | nPr | Me | Me | 0.95 (3H, t); 1.63 (2H, m); 2.34 (6H, s); 2.51 (3H, s); 2.83 (2H, t); 3.72 (3H, s); 5.24 (2H, s); 7.30 (1H, d); 7.49 (2H, d); 7.93-7.99 (3H, m); 8.15 (1H, s); 8.25 (1H, s); 10.05 (1H, s) |

TABLE VIII-continued

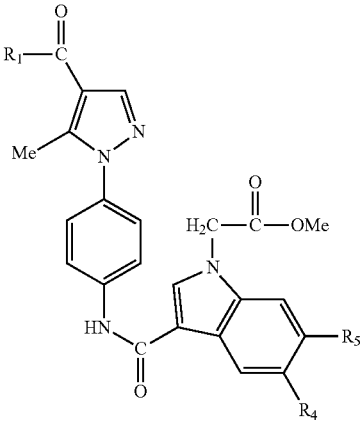

(II)

| | R₁ | R₄ | R₅ | $^1$H NMR: DMSO-d$_6$ (250 MHz): δ (ppm) |
|---|---|---|---|---|
| Preparation 9.19 | nPr | Cl | Cl | 0.95 (3H, t); 1.65 (2H, m); 2.34 (6H, s); 2.54 (3H, s); 2.83 (2H, t); 3.75 (3H, s); 5.37 (2H, s); 7.51 (2H, d); 7.95 (2H, d); 8.04 (1H, s); 8.26 (1H, s); 8.38 (1H, s); 8.39 (1H, s); 10.25 (1H, s) |

Preparation 9.20

Methyl (3-[[2-bromo-4-(4-butyryl-5-methyl-1H-pyrazol-1-yl)-phenyl]carbamoyl]-5-chloro-1H-indol-1-yl)acetate (II): R₁=n-Pr; R₂=Me; R₄=Cl; R₅=H; A=

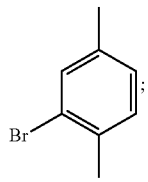

X=CH; Z=Me 0.63 ml of pyridine and then 1 g of the compound from Preparation 6.7 are added to 1.33 g of the compound from step 1 of Preparation 9.1 in 25 ml of 1,2-dichloroethane. The reaction mixture is placed in a microwave apparatus at 80° C. for 30 min (300 W). After it returns to RT, 50 ml of water is added and it is extracted with DCM. The combined organic phases are washed with saturated sodium bicarbonate, with water and with brine, dried over sodium sulfate and evaporated to dryness. The product is triturated in acetone and then filtered, obtaining 0.89 g of a white powder.

$^1$H NMR: DMSO-d$_6$ (250 MHz): δ (ppm): 0.94 (3H, t); 1.04 (2H, m); 2.58 (3H, s); 2.83 (2H, t); 3.73 (3H, s); 5.34 (2H, s); 7.29 (1H, d); 7.57-7.63 (2H, m); 7.86 (1H, d); 7.93 (1H, d); 8.18 (1H, s); 8.30 (1H, s); 8.34 (1H, s); 9.69 (1H, s).

Following the procedure described in Preparation 9.20, the compounds of formula (II) presented in TABLE IX below are prepared:

TABLE IX

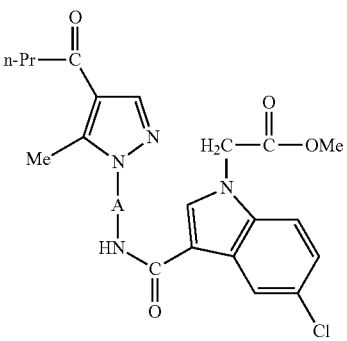

| A | $^1$H NMR: DMSO-d$_6$ (250 MHz): δ (ppm) |
|---|---|
| Preparation 9.21 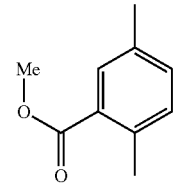 | 0.94 (3H, t); 1.64 (2H, m); 2.55 (3H, s); 2.83 (2H, t); 3.73 (3H, s); 3.93 (3H, s); 5.39 (2H, s); 7.33 (1H, d); 7.61 (1H, d); 7.86 (1H, d); 8.08 (1H, s); 8.20-8.25 (2H, m); 8.38 (1H, s); 8.74 (1H, d); 11.30 (1H, s). |
| Preparation 9.22 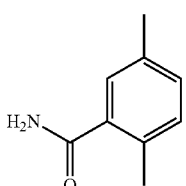 | 0.94 (3H, t); 1.64 (2H, m); 2.55 (3H, s); 2.83 (2H, t); 3.72 (3H, s); 5.37 (2H, s); 7.31 (1H, d); 7.62 (1H, d); 7.73 (1H, d); 7.94 (1H, br); 8.04 (1H, s); 8.14 (1H, s); 8.26 (1H, s); 8.29 (1H, s); 8.47 (1H, br); 8.86 (1H, d); 12.70 (1H, s). |

Preparation 9.23

Methyl 3-{[4-(4-butyryl-5-methyl-1H-pyrazol-1-yl)phenyl]carbamoyl}-5-phenyl-1H-indol-1-yl)acetate (II): $R_1$=n-Pr; $R_2$=Me; $R_4$=

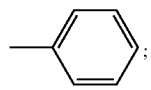

$R_5$=H; A=

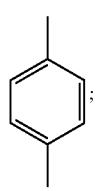

X=CH; Z=Me 0.18 g of phenylboronic acid, and 0.36 g of K$_3$PO$_4$.2H$_2$O are added to 0.60 of the compound from Preparation 9.17 in 10 ml of dioxane. The reaction mixture is degassed with argon, then 0.06 g of tetrakis(triphenylphosphine)palladium (0) is added and it is heated under reflux for 5 hours. 50 ml of EtOAc and 50 ml of water are added, the organic phase is recovered, and then the aqueous phase is extracted two more times. The organic phases are combined, washed with water and then with brine and dried over Na$_2$SO$_4$. After evaporation, the solid residue is purified by silica gel chromatography, eluting with DCM/MeOH mixture up to (98/2; v/v). 0.39 g of a white powder is obtained.

$^1$H NMR: DMSO-d$_6$ (250 MHz): δ (ppm): 0.96 (3H, t); 1.65 (2H, m); 2.54 (3H, s); 2.83 (2H, t); 3.75 (3H, s); 5.37 (2H, s); 7.33-7.75 (9H, m); 7.99 (2H, d); 8.25 (1H, s); 8.33 (1H, s); 8.48 (1H, s); 10.20 (1H, s).

Preparation 9.24

Methyl [3-{[4-(4-butyryl-5-methyl-1H-pyrazol-1-yl)-phenyl]carbamoyl}-5-(dimethylamino)-1H-indol-1-yl]acetate (II): $R_1$=n-Pr; $R_2$=Me; $R_4$=N(Me)$_2$; $R_5$=H; A=

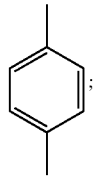

X=CH; Z=Me 0.26 g of proline and 0.21 g of copper(I) iodide are added to 1 g of the compound from Preparation 9.17 in 7 ml of DMSO in a screw-top tube. The reaction mixture is degassed with nitrogen, then 7 ml of a 2M solution of dimethylamine in THF is added. The tube is closed and it is heated at 120° C. for 7 hours. The reaction mixture is poured into water and is extracted with EtOAc, the organic phase is dried over Na$_2$SO$_4$ and evaporated. The solid residue is purified by silica gel chromatography, eluting with DCM/MeOH mixture up to (95/5; v/v). 0.11 g of powder is obtained.

$^1$H NMR: DMSO-d$_6$ (250 MHz): δ (ppm): 0.94 (3H, t); 1.64 (2H, m); 2.52 (3H, s); 2.83 (2H, t); 2.91 (6H, s); 3.71 (3H, s); 5.22 (2H, s); 6.88 (1H, d); 7.34 (1H, d); 7.47 (2H, d); 7.56 (1H, s); 7.95 (2H, d); 8.16 (1H, s); 8.24 (1H, s); 9.95 (1H, s).

Preparation 9.25

Methyl (3-{[4-(4-butyryl-5-methyl-1H-pyrazol-1-yl)-phenyl]carbamoyl}-5-cyano-1H-indol-1-yl)acetate (II): $R_1$=n-Pr; $R_2$=Me; $R_4$=CN; $R_5$=H; A=

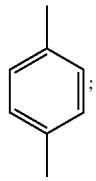

X=CH; Z=Me

In a screw-top tube, 3 g of the compound from Preparation 9.17 is dissolved in 40 ml of DMF. The reaction mixture is degassed with argon, then 0.79 g of zinc(II) cyanide and 0.32 g of tetrakis(triphenylphosphine)palladium(0) are added. The tube is closed and then it is heated at 100° C. for 7 hours. The reaction mixture is poured into a dilute solution of sodium bicarbonate, ensuring that at the end of addition the pH of the solution is basic. It is extracted with EtOAc, the organic phase is dried over $Na_2SO_4$ and evaporated. The solid residue is triturated in MeOH and then filtered, obtaining 2.2 g of white powder.

$^1$H NMR: DMSO-$d_6$ (250 MHz): δ (ppm): 0.94 (3H, t); 1.64 (2H, m); 2.52 (3H, s); 2.82 (2H, t); 3.73 (3H, s); 5.42 (2H, s); 7.52 (2H, d); 7.66 (1H, d); 7.80 (1H, d); 7.95 (2H, d); 8.25 (1H, s); 8.46 (1H, s); 8.61 (1H, s); 10.25 (1H, s).

Preparation 9.26

Methyl (3-{[4-(4-butyryl-5-methyl-1H-pyrazol-1-yl)-2-cyano-phenyl]carbamoyl}-5-chloro-1H-indol-1-yl)acetate (II): $R_1$=n-Pr; $R_2$=Me; $R_4$=Cl; $R_5$=H; A=

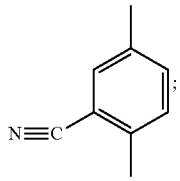

X=CH; Z=Me

In a screw-top tube, 0.78 g of the compound from Preparation 9.21 is dissolved in 15 ml of DMF. The reaction mixture is degassed with argon, then 0.21 g of zinc(11) cyanide and 0.08 g of tetrakis(triphenylphosphine)palladium(0) are added. The tube is closed and then it is heated at 100° C. for 6 hours, The reaction mixture is poured into a dilute solution of sodium bicarbonate, ensuring that at the end of addition the pH of the solution is basic. It is extracted with EtOAc, washed with water, with brine, dried over $Na_2SO_4$ and evaporated. The solid residue is triturated in iso ether and then filtered. The solid residue is purified by silica gel chromatography, eluting with DCM/MeOH mixture up to (95/5; v/v). 0.59 g of white powder is obtained.

$^1$H NMR: DMSO-$d_6$ (250 MHz): δ (ppm): 0.94 (3H, t); 1.64 (2H, m); 2.59 (3H, s); 2.83 (2H, t); 3.73 (3H, s); 5.37 (2H, s); 7.32 (1H, d); 7.64 (1H, d); 7.80 (1H, d); 7.91 (1H, d); 8.11 (1H, s); 8.17 (1H, s); 8.33 (2H, d); 10.40 (1H, s).

EXAMPLES

Example 1

Compound No. 1

Sodium (3-{[5-(4-butyryl-5-methyl-1H-pyrazol-1-yl)pyrazin-2-yl]carbamoyl}-5-chloro-1H-indol-1-yl)acetate 0.80 ml of an aqueous solution of 1N NaOH is added to 0.14 g of the compound from Preparation 9.1 in 6 ml of MeOH/dioxane mixture (50/50; v/v), and it is stirred for 3 h. The reaction mixture is evaporated to dryness. The solid residue is triturated with water and then drained, obtaining 0.10 g of a white powder.

Example 2

Compound No. 2

(3-{[5-(4-Butyryl-5-methyl-1H-pyrazol-1-yl)pyridazin-3-yl]carbamoyl}-5-chloro-1H-indol-1-yl) acetic acid 5.30 ml of an aqueous solution of 1N NaOH is added to 2.20 g of the compound from Preparation 9.2 in 42 ml of dioxane, and it is stirred for 2 h. The reaction mixture is evaporated to dryness, The solid residue is redissolved in 30 ml of water and then acidified with 7 ml of 1N HCl solution. The precipitate that formed is drained, it is washed with water, obtaining 2.07 g of a beige powder.

Example 3

Compound No. 3, (3-{[4-(4-butyryl-5-methyl-1H-pyrazol-1-yl)phenyl]carbamoyl}-5-chloro-1H-indol-1-yl)acetic acid 32.9 ml of an aqueous solution of 2N NaOH is added to 16.2 g of the compound from Preparation 9.11 in 60 ml of MeOH/dioxane mixture (50/50; v/v), and it is stirred for 2 hours. The reaction mixture is acidified with 1N HCl solution and then it is extracted with EtOAc. The combined organic phases are washed with brine, dried over $Na_2SO_4$ and then evaporated. The solid residue is triturated with acetone/iso ether mixture (50/50; v/v) and then filtered, obtaining 11 g of a white powder. The precipitate formed during concentration of the filtrate gives an additional 2.95 g, i.e. 13.95 g in total.

Example 4

Compound No. 4

Sodium (3-{[4-(4-butyryl-5-methyl-1H-pyrazol-1-yl)phenyl]carbamoyl}-5-chloro-6-methyl-1H-indol-1-yl)acetate 0.22 ml of an aqueous solution of 1N NaOH is added to 0.11 g of Preparation 9.8 in 5 ml of MeOH/dioxane mixture (50/50; v/v), and then evaporated to dryness. The solid residue is redissolved in a minimum of acetone (about 1 ml) and it is added dropwise to 10 ml of pentane. The precipitate formed is filtered, and dried in a vacuum stove, obtaining 0.082 g of a white powder.

Following the procedures described in Examples 1 to 4, the compounds of Formula (I) presented in TABLE X below are prepared:

In this table:

Me represents a methyl radical;

Et represents an ethyl radical;

nPr represents an n-propyl radical;

Ph represents a phenyl radical;

Na represents a compound in the form of sodium salt.

TABLE X

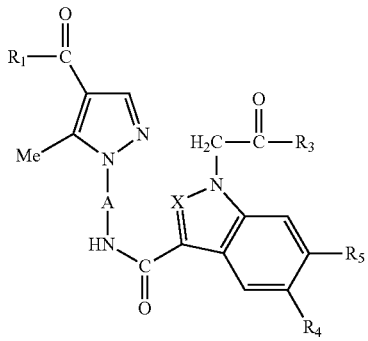
(I)

| Compounds N° | R₁ | A | X | R₃ | R₄ | R₅ | $^1$H NMR: DMSO-$d_6$ (250 MHz): δ (ppm): | Inhibition of platelet aggregation in vitro (rat blood) in μM |
|---|---|---|---|---|---|---|---|---|
| 1 | nPr | 2,5-pyrazinyl | CH | OH | Cl | H | 0.93 (3H, t); 1.63 (2H, m); 2.77 (3H, s); 2.85 (2H, t); 4.48 (2H, s); 7.20 (1H, d); 7.43 (1H, d); 8.22 (1H, s); 8.35 (1H, s); 8.63 (1H, s); 8.83 (1H, s); 9.43 (1H, s); 10.95 (1H, s). | / |
| 2 | nPr | 3,6-pyridazinyl | CH | OH | Cl | H | 0.93 (3H, t); 1.65 (2H, m); 2.82 (3H, s); 2.86 (2H, t); 5.17 (2H, s); 7.30 (1H, d); 7.61 (1H, d); 8.13 (1H, d); 8.23 (1H, s); 8.40 (1H, s); 8.66 (1H, s); 8.68 (1H, d); 11.35 (1H, s); 13.25 (1H, br). | / |
| 3 | nPr | 1,4-phenylene | CH | OH | Cl | H | 0.94 (3H, t); 1.63 (2H, m); 2.52 (3H, s); 2.81 (2H, t); 5.20 (2H, s); 7.28 (1H, d); 7.50 (2H, d); 7.59 (1H, d); 7.94 (2H, d); 8.21 (1H, s); 8.23 (1H, s); 8.36 (1H, s); 10.15 (1H, s); 13.30 (1H, br). | 2.8 |
| 4 | nPr | 1,4-phenylene | CH | ONa | Cl | Me | 0.94 (3H, t); 1.64 (2H, m); 2.42 (3H, s); 2.52 (3H, s); 2.81 (2H, t); 4.48 (2H, s); 7.39 (1H, s); 7.46 (2H, d); 7.96 (2H, d); 8.18 (1H, s); 8.23 (1H, s); 8.31 (1H, s); 10.05 (1H, s). | 3.3 |
| 5 | OEt | 1,4-phenylene | CH | OH | Cl | H | 1.30 (3H, t); 2.52 (3H, s); 4.26 (2H, q); 5.21 (2H, s); 7.28 (1H, d); 7.51 (2H, d); 7.58 (1H, d); 7.95 (2H, d); 7.98 (1H, s); 8.21 (1H, s); 8.35 (1H, s); 10.15 (1H, s); 13.25 (1H, br). | / |

TABLE X-continued (I)

[Structure: pyrazole-indazole scaffold with R₁-C(O)- at pyrazole 4-position, Me at pyrazole 5-position, linker A-NH-C(O)- to indazole 3-position, H₂C-C(O)-R₃ on indazole N1, X at indazole 2-position, R₄ and R₅ on indazole benzene ring]

| Compounds N° | R₁ | A | X | R₃ | R₄ | R₅ | ¹H NMR: DMSO-d₆ (250 MHz): δ (ppm): | Inhibition of platelet aggregation in vitro (rat blood) in μM |
|---|---|---|---|---|---|---|---|---|
| 6 | Me | 1,4-phenylene | CH | OH | Cl | H | 2.45 (3H, s); 2.52 (3H, s); 5.20 (2H, s); 7.27 (1H, d); 7.49 (2H, d); 7.59 (1H, d); 7.95 (2H, d); 8.21 (1H, s); 8.23 (1H, s); 8.36 (1H, s); 10.15 (1H, s); 13.25 (1H, br). | / |
| 7 | Et | 1,4-phenylene | CH | OH | Cl | H | 1.08 (3H, t); 2.51 (3H, s); 2.84 (2H, q); 5.19 (2H, s); 7.27 (1H, d); 7.49 (2H, d); 7.58 (1H, d); 7.95 (2H, d); 8.21 (1H, s); 8.23 (1H, s); 8.36 (1H, s); 10.15 (1H, s); 13.25 (1H, br). | / |
| 8 | nPr | 1,4-phenylene | CH | OH | H | Me | 0.94 (3H, t); 1.64 (2H, m); 2.43 (3H, s); 2.52 (3H, s); 2.81 (2H, t); 5.10 (2H, s); 7.04 (1H, d); 7.30 (1H, s); 7.47 (2H, d); 7.95 (2H, d); 8.08 (1H, d); 8.20 (1H, s); 8.23 (1H, s); 10.01 (1H, s). | 63 |
| 9 | nPr | 3-bromo-4-methylpyridinyl (Br, Me-substituted pyridine) | CH | OH | Cl | H | MH⁺ = 557; t_R = 9.17 min (Method G) | / |
| 10 | nPr | 3-carbamoyl-6-methylphenyl (H₂N-C(O)- and Me substituted phenylene) | CH | OH | Cl | H | 0.94 (3H, t); 1.64 (2H, m); 2.55 (3H, s); 2.83 (2H, t); 5.18 (2H, s); 7.29 (1H, d); 7.59 (1H, d); 7.72 (1H, d); 7.95 (1H, s); 8.04 (1H, s); 8.11 (1H, s); 8.25 (1H, s); 8.29 (1H, s); 8.47 (1H, s); 8.86 (1H, d); 12.6) (1H, s); 13.20 (1H, br). | / |

TABLE X-continued (I)

[Structure: pyrazole-indazole compound with R1-C(O)- on pyrazole (5-Me-N-N), N-A-NH-C(O)- linker to indazole position 3, indazole N1 bears -CH2-C(O)-R3, with R4, R5 substituents and X in indazole ring]

| Compounds N° | R₁ | A | X | R₃ | R₄ | R₅ | ¹H NMR: DMSO-d₆ (250 MHz): δ (ppm): | Inhibition of platelet aggregation in vitro (rat blood) in μM |
|---|---|---|---|---|---|---|---|---|
| 11 | nPr | para-phenylene | CH | OH | Me | H | 0.94 (3H, t); 1.64 (2H, m); 2.43 (3H, s); 2.52 (3H, s); 2.81 (2H, t); 5.12 (2H, s); 7.07 (1H, d); 7.39 (1H, d); 7.48 (2H, d); 7.95 (2H, d); 8.02 (1H, s); 8.23 (1H, s); 8.24 (1H, s); 10.02 (1H, s); 13.19 (1H, br). | 9.6 |
| 12 | nPr | para-phenylene | CH | ONa | OMe | H | 0.94 (3H, t); 1.63 (2H, m); 2.52 (3H, s); 2.81 (2H, t); 3.79 (3H, s); 4.41 (2H, s); 7.27 (1H, d); 7.45 (2H, d); 7.73 (1H, d); 7.98 (2H, d); 8.24 (1H, s); 8.29 (1H, s); 9.97 (1H, s). | 17 |
| 13 | nPr | para-phenylene | CH | ONa | CF₃ | H | 0.95 (3H, t); 1.64 (2H, m); 2.52 (3H, s); 2.81 (2H, t); 4.57 (2H, s); 7.45-7.49 (3H, m); 7.62 (1H, d); 7.98 (2H, d); 8.24 (1H, s); 8.56 (1H, s); 8.57 (1H, s); 10.30 (1H, s). | 4.6 |
| 14 | nPr | para-pyridinylene | CH | ONa | Br | H | 0.94 (3H, t); 1.63 (2H, m); 2.52 (3H, s); 2.82 (2H, t); 4.51 (2H, s); 7.28 (1H, d); 7.39 (1H, d); 7.46 (2H, d); 7.97 (2H, d); 8.25 (1H, s); 8.35 (1H, s); 8.42 (1H, s); 10.23 (1H, s). | 1.9 |
| 15 | nPr | para-phenylene | CH | OH | Ph | H | 0.94 (3H, t); 1.65 (2H, m); 2.52 (3H, s); 2.82 (2H, t); 5.22 (2H, s); 7.35 (1H, t); 7.47-7.52 (4H, m); 7.56 (1H, d); 7.63 (1H, d); 7.70 (2H, d); 7.97 (2H, d); 8.25 (1H, s); 8.33 (1H, s); 8.48 (1H, s); 10.15 (1H, s); 13.30 (1H, br). | 25 |

TABLE X-continued

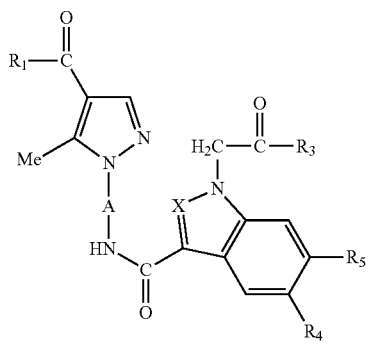

(I)

| Compounds N° | R₁ | A | X | R₃ | R₄ | R₅ | ¹H NMR: DMSO-d₆ (250 MHz): δ (ppm): | Inhibition of platelet aggregation in vitro (rat blood) in μM |
|---|---|---|---|---|---|---|---|---|
| 16 | nPr | para-phenylene | CH | OH | Me | Me | 0.94 (3H, t); 1.63 (2H, m); 2.36 (6H, s); 2.52 (3H, s); 2.82 (2H, t); 5.07 (2H, s); 7.28 (1H, s); 7.48 (2H, d); 7.94-7.98 (3H, m); 8.15 (1H, s); 8.24 (1H, s); 9.97 (1H, s); 13.20 (1H, br). | 4.6 |
| 17 | nPr | para-phenylene | CH | ONa | Cl | Cl | 0.96 (3H, t); 1.65 (2H, m); 2.54 (3H, s); 2.83 (2H, t); 4.51 (2H, s); 7.49 (2H, d); 7.74 (1H, s); 7.97 (2H, d); 8.25 (1H, s); 8.36 (1H, s); 8.44 (1H, s); 10.19 (1H, s). | 7.3 |
| 18 | nPr | para-phenylene | CH | ONa | F | H | 0.94 (3H, t); 1.63 (2H, m); 2.52 (3H, s); 2.81 (2H, t); 4.49 (2H, s); 7.01 (1H, t); 7.37-7.49 (3H, m); 7.87 (1H, d); 7.98 (2H, d); 8.24 (1H, s); 8.43 (1H, s); 10.15 (1H, s). | 36 |
| 19 | nPr | pyridinylene | CH | ONa | Me | Br | 0.94 (3H, t); 1.63 (2H, m); 2.48 (3H, s); 2.52 (3H, s); 2.81 (2H, t); 4.46 (2H, s); 7.45 (2H, d); 7.63 (1H, s); 7.96 (2H, d); 8.15 (1H, s); 8.23 (1H, s); 8.30 (1H, s); 10.10 (1H, s). | 42 |
| 20 | nPr | para-phenylene | CH | ONa | Br | Me | 0.94 (3H, t); 1.64 (2H, m); 2.43 (3H, s); 2.52 (3H, s); 2.81 (2H, t); 4.45 (2H, s); 7.40 (1H, s); 7.45 (2H, d); 7.96 (2H, d); 8.23 (1H, s); 8.32 (1H, s); 8.37 (1H, s); 10.09 (1H, s). | 3.9 |

TABLE X-continued (I)

| Compounds N° | R₁ | A | X | R₃ | R₄ | R₅ | ¹H NMR: DMSO-d₆ (250 MHz): δ (ppm): | Inhibition of platelet aggregation in vitro (rat blood) in μM |
|---|---|---|---|---|---|---|---|---|
| 21 | nPr | 1,4-phenylene | CH | OH | Cl | F | 0.94 (3H, t); 1.63 (2H, m); 2.52 (3H, s); 2.82 (2H, t); 5.19 (2H, s); 7.50 (2H, d); 7.77 (1H, d); 7.95 (2H, d); 8.24 (1H, s); 8.30 (1H, d); 8.38 (1H, s); 10.20 (1H, s); 13.33 (1H, br). | 2.8 |
| 22 | nPr | 1,4-phenylene | CH | OH | NMe₂ | H | 0.94 (3H, t); 1.63 (2H, m); 2.52 (3H, s); 2.82 (2H, t); 3.23 (6H, s); 5.26 (2H, s); 7.50 (2H, d); 7.70 (1H, d); 7.79 (1H, d); 7.99 (2H, d); 8.25 (1H, s); 8.52 (1H, s); 8.57 (1H, s); 10.31 (1H, s); 12.72 (1H, br). | 1.2 |
| 23 | nPr | 1,4-phenylene | CH | ONa | CN | H | 0.94 (3H, t); 1.64 (2H, m); 2.53 (3H, s); 2.81 (2H, t); 4.61 (2H, s); 7.44 (2H, d); 7.49 (1H, d); 7.61 (1H, d); 7.96 (2H, d); 8.24 (1H, s); 8.58 (1H, s); 8.60 (1H, s); 10.49 (1H, s). | 4.1 |
| 24 | nPr | 1,4-phenylene | N | ONa | Me | H | 0.95 (3H, t); 1.64 (2H, m); 2.46 (3H, s); 2.53 (3H, s); 2.82 (2H, t); 4.80 (2H, s); 7.25 (1H, d); 7.44-7.51 (3H, m); 8.00 (1H, s); 8.11 (2H, d); 8.24 (1H, s); 10.45 (1H, s). | 37 |

Example 5

Compound No. 25

(3-{[4-(4-Butyryl-5-methyl-1H-pyrazol-1-yl)-2-(methoxycarbonyl)phenyl]carbamoyl}-5-chloro-1H-indol-1-yl)acetic acid 0.03 g of lithium hydroxide is added to 0.71 g of the compound from Preparation 9.22 in 20 ml of THF, and it is stirred for 2 hours. It is evaporated to dryness, the solid residue is triturated with DCM and then drained. The precipitate is taken up in water, acidified with 0.175 mg of $KHSO_4$, the precipitate that formed is drained, it is washed with water and dried under vacuum, obtaining 0.47 g of a beige powder.

Following the procedure described in Example 5, the compounds of formula (I) represented in TABLE XI below are prepared:

Example 6

Compound No. 27

N-[5-(4-Butyryl-5-methyl-1H-pyrazol-1-yl)pyrazin-2-yl]-5-chloro-1-[2-(4-methylpiperazin-1-yl)-2-oxo-ethyl]-1H-indole-3-carboxamide hydrochloride 0.055 g of 1-methylpiperazine (commercial) and 0.086 g of BOP-Clare added successively to 0.10 g of the compound from Example 1 in 5 ml of DCM, The medium is heterogeneous. 2 ml of DMF is added and the homogeneous reaction mixture is stirred overnight, It is evaporated to dryness, 1M $NaHCO_3$ solution is added and it is extracted with DCM. The combined organic phases are washed with water, with brine, dried over $Na_2SO_4$ and then evaporated under vacuum. The oily residue thus obtained is purified by silica gel chromatography, eluting with DCM/MeOH mixture (gradient from 1 to

TABLE XI (I)

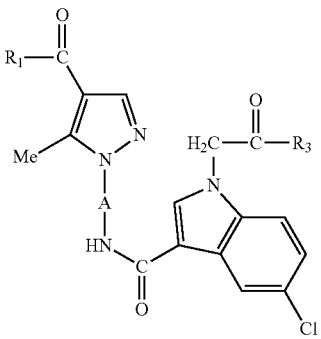

X = CH

| Compound N° | $R_1$ | A | $R_3$ | $^1$H NMR: DMSO-$d_6$ (250 MHz): δ (ppm): | Inhibition of platelet aggregation in vitro (without rat) in μM |
|---|---|---|---|---|---|
| 25 | nPr | ![MeO-C(=O)- phenyl with two methyl groups] | OH | 0.94 (3H, t); 1.64 (2H, m); 2.55 (3H, s); 2.83 (2H, t); 3.93 (3H, s); 5.26 (2H, s); 7.30 (1H, d); 7.61 (1H, d); 7.86 (1H, d); 8.08 (1H, s); 8.20-8.25 (2H, m); 8.29 (1H, s); 8.73 (1H, d); 11.30 (1H, s); 13.35 (1H, br). | / |
| 26 | nPr | ![N≡C- phenyl with two methyl groups] | OH | 0.95 (3H, t); 1.64 (2H, m); 2.59 (3H, s); 2.83 (2H, t); 5.17 (2H, s); 7.29 (1H, d); 7.60 (1H, d); 7.80 (1H, d); 7.91 (1H, d); 8.11 (1H, s); 8.17 (1H, s); 8.32 (1H, s); 8.36 (1H, s); 10.40 (1H, s). | / |

Example 7

Compound No. 28

N-[6-(4-Butyryl-5-methyl-1H-pyrazol-1-yl)pyridazin-3-yl]-5-chloro-1-[2-(4-methylpiperazin-1-yl)-2-oxoethyl]-1H-indole-3-carboxamide hydrochloride 1.66 g of 1-methylpiperazine (commercial), 2.18 g of pyridine and 4.30 g of BOP-Clare added successively to 2.65 g of the compound from Example 2 in 80 ml of DMF. It is stirred for 48 h, then the reaction mixture is poured into a mixture of EtOAc and saturated $NaHCO_3$ solution. The precipitate formed is filtered and washed with iso ether. The filtrate is transferred to a separating funnel and the organic phase is washed with water, with brine and then dried over $Na_2SO_4$. The organic phase is concentrated partially and the precipitate formed is filtered. The two precipitates are combined, and dried in a vacuum stove, obtaining 2.68 g of a white powder. It is suspended in 200 ml of MeOH, then 6.6 ml of 1N HCl solution in ether is added and it is stirred for 1 h. The precipitate that formed is drained, it is washed with iso ether and then dried in a vacuum stove at 40° C., obtaining 2.29 g of a light yellow powder.

Example 8

Compound No. 29

N-[6-(4-Butyryl-5-methyl-1H-pyrazol-1-yl)pyridazin-3-yl]-5-chloro-1-{2-[4-(2-methoxyethyl)piperazin-1-yl]-2-oxoethyl}-1H-indole-3-carboxamide hydrochloride 0.14 g of DMAP, 0.10 g of 1-(2-methoxyethyl)piperazine, and 0.17 g of BOP-Clare added successively to 0.11 g of the compound from Example 2 in 10 ml of DMF. It is stirred overnight, then the reaction mixture is poured into a mixture of EtOAc and saturated $NaHCO_3$ solution. The organic phase is washed with water, with brine, dried over $Na_2SO_4$ and then evaporated to dryness. The solid residue thus obtained is purified by silica gel chromatography, eluting with DCM/MeOH mixture (gradient from 2 to 5% of MeOH). The purified product is redissolved in 5 ml of DCM/acetone mixture (50/50; v/v) and then 0.12 ml of 2N ethyl chloride solution is added. It is concentrated partially. A precipitate slowly forms. It is drained, washed with acetone and then with pentane and dried in a vacuum stove at 60° C., obtaining 0.11 g of a light yellow powder.

10% of MeOH), obtaining 0.08 g of a white powder. It is redissolved in 6 ml of DCM/acetone mixture (50/50; v/v) and then 0.09 ml of 2N ethyl chloride solution is added. It is evaporated to dryness, triturated with acetone, drained and then dried in a vacuum stove at 60° C., obtaining 0.06 g of a white powder.

Example 9

Compound No. 30

N-[6-(4-Butyryl-5-methyl-1H-pyrazol-1-yl)pyridazin-3-yl]-5-chloro-1-(2-oxo-2-{4-[2-(trifluoromethoxy)ethyl]piperazin-1-yl}ethyl)-1H-indole-3-carboxamide hydrochloride 0.11 g of DMAP, 0.08 g of 1[2-(trifluoromethoxy)ethyl]piperazine, 0.13 ml of pyridine and 0.24 g of BOP-Clare added successively to 0.15 g of the compound from Example 2 in 20 ml of DMF, and it is stirred at RT overnight, EtOAc is added, it is washed with water, with brine, dried over $Na_2SO_4$ and then evaporated to dryness. The solid residue thus obtained is purified by silica gel column chromatography, eluting with a mixture of DCM and methanol (gradient from 1 to 10% of methanol), obtaining 0.08 g of powder. The purified product is redissolved in 4 ml of a mixture (1:1) of methanol and acetone, then 0.15 ml of 2N ethyl chloride solution is added. It is poured into 30 ml of iso ether, the precipitate that formed is drained and dried in a vacuum stove at 60° C., obtaining 0.06 g of a white powder.

Example 10

Compound No. 31

N-[6-(4-Butyryl-5-methyl-1H-pyrazol-1-yl)pyridazin-3-yl]-5-chloro-1-{2-oxo-2-[4-(3,3,3-trifluoropropyl)piperazin-1-yl]ethyl}-1H-indole-3-carboxamide hydrochloride 0.13 g of 1-(3,3,3-trifluoropropyl)piperazine, 0.04 g of DMAP and 0.13 g of BOP-Clare added successively to 0.16 g of the compound from Example 2 in 5 ml of DCM, and it is stirred at RT for 48 h. The reaction mixture is evaporated to dryness, and the solid residue is triturated with a 1M solution of $NaHCO_3$. The precipitate is filtered and is washed with water, obtaining 0.085 g of a white powder. It is redissolved in 4 ml of a mixture (1:1) of DCM and acetone and then 0.28 ml of 1N HCl solution in ether is added. The precipitate that formed is drained, and dried in a vacuum stove at 60° C., obtaining 008 g of a white powder.

Following the procedure described in Examples 6 to 10, the compounds of formula (I) presented in TABLE XII below are prepared:

In this table:

in the column "Salt", "-" represents a compound in the form of free base, whereas "HCl" represents a compound in the form of hydrochloride, "TFA" represents a compound in the form of trifluoroacetate;

Me represents a methyl radical;

Et represents an ethyl radical;

nPr represents an n-propyl radical.

TABLE XII (I)

[Structure: compound with n-Pr-C(=O)- attached to pyrazole bearing Me group, linked via N-A-NH-C(=O)- to indole; indole substituted with 5-Cl, 6-H, and N-CH₂-C(=O)-R₃]

X = —CH—
R₁ = n-Pr
R₂ = Me
R₄ = 5-Cl
R₅ = H

| Compounds No. | R₃ | A | Salt m.p. °C. MH⁺; t_R (Conditions) NMR | Inhibition of platelet aggregation in vitro (rat blood) in μM |
|---|---|---|---|---|
| 27 | [N-methylpiperazinyl-CH₂- via N, with Me on distal N] | pyrazine (2,5-linked) | HCl 282 563; 6.69 (MG) NMR | 0.30 |
| 28 | [N-methylpiperazinyl-CH₂-] | pyridazine (3,6-linked) | HCl 287 563; 6.59 (MG) NMR | 0.06 |
| 29 | [N-methylpiperazinyl-CH₂-CH(OMe)-] | pyridazine (3,6-linked) | HCl 258 607; 6.61 (MG) NMR | 0.08 |
| 30 | [N-methylpiperazinyl-CH₂-CH(OCF₃)-] | pyridazine (3,6-linked) | 2 HCl 165 661; 9.75 (MI) NMR | 0.10 |
| 31 | [N-methylpiperazinyl-CH₂-CH₂(CF₃)-] | pyridazine (3,6-linked) | HCl 230 645; 7.50 (MG) NMR | / |

TABLE XII-continued (I)

[Structure shown with:
X = —CH—
R₁ = n-Pr
R₂ = Me
R₄ = 5-Cl
R₅ = H]

| Compounds No. | R₃ | A | Salt m.p. ° C. MH⁺; $t_R$ (Conditions) NMR | Inhibition of platelet aggregation in vitro (rat blood) in μM |
|---|---|---|---|---|
| 32 | —NHMe | pyridazine | — / 494.17; 1.14 (MJ) / — | 0.19 |
| 33 | HOCH₂CH₂N(Me)— | pyridazine | — / 523.18; 1.1 (MJ) / — | 0.08 |
| 34 | 4-methylpiperazinyl-CH₂-C(O)-O-Et | pyridazine | TFA / 635.25; 1.11 (MJ) / — | 0.09 |
| 35 | morpholinyl | pyridazine | 550.2; 1.15 / — / (MJ) / — | 0.19 |
| 36 | —NMe₂ | pyridazine | — / 508.19; 1.16 (MJ) / — | 0.11 |
| 37 | Chiral (S)-1-methyl-2-(methoxymethyl)pyrrolidinyl | pyridazine | — / 578.23; 1.2 (MJ) / — | 0.09 |

TABLE XII-continued
(I)
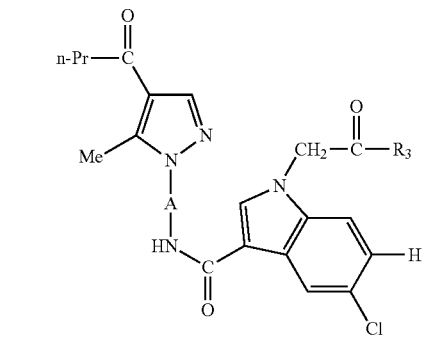
X = —CH—
R₁ = n-Pr
R₂ = Me
R₄ = 5-Cl
R₅ = H
| Compounds No. | R₃ | A | Salt m.p. ° C. MH⁺; $t_R$ (Conditions) NMR | Inhibition of platelet aggregation in vitro (rat blood) in μM |
|---|---|---|---|---|
| 38 | 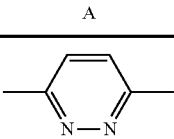 | 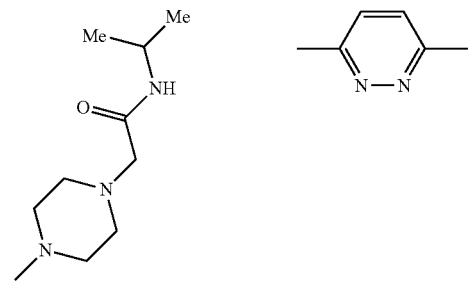 | — <br> 538.2; 1.12 <br> (MJ) <br> — | 0.07 |
| 39 | 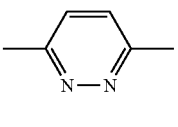 |  | TFA <br> — <br> 648.28; 1.05 <br> (MJ) <br> — | 0.04 |
| 40 | 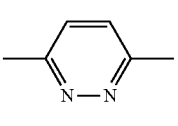 | 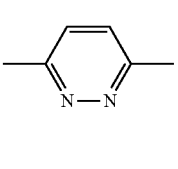 | — <br> 534.2; 1.18 <br> (MJ) <br> — | 0.10 |
| 41 | Chiral <br> 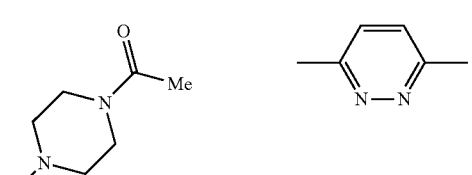 | | — <br> 564.21; 1.14 <br> (MJ) <br> — | 0.11 |
| 42 | 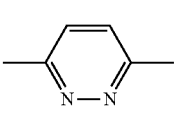 | | — <br> 591.22; 1.12 <br> (MJ) <br> — | 0.15 |

TABLE XII-continued (I)

X = —CH—
R₁ = n-Pr
R₂ = Me
R₄ = 5-Cl
R₅ = H

| Compounds No. | R₃ | A | Salt m.p. °C. MH⁺; $t_R$ (Conditions) NMR | Inhibition of platelet aggregation in vitro (rat blood) in μM |
|---|---|---|---|---|
| 43 | (2S,5R)-1,5-dimethylpiperazin-2-yl (Me, NH, Me) | pyridazine-3,6-diyl | TFA — 577.24; 1 (MJ) — | 0.12 |
| 44 | 4-methyl-3-oxopiperazin-1-yl (O, Me) | pyridazine-3,6-diyl | — — 577.21; 1.12 (MJ) — | 0.16 |
| 45 | 4-(4-fluorophenyl)piperazin-1-yl | pyridazine-3,6-diyl | — — 643.23; 1.24 (MJ) — | 0.42 |
| 46 | 2-(4-methylpiperazin-1-yl)-1-(pyrrolidin-1-yl)ethanone | pyridazine-3,6-diyl | TFA — 660.28; 1.01 (MJ) — | 0.04 |
| 47 | 4-ethyl-4'-methyl-[1,1'-bipiperazin] (Et) | pyridazine-3,6-diyl | TFA — 577.24; 0.99 (MJ) — | 0.06 |

TABLE XII-continued (I)

X = —CH—
R₁ = n-Pr
R₂ = Me
R₄ = 5-Cl
R₅ = H

| Compounds No. | R₃ | A | Salt m.p. °C. MH⁺; $t_R$ (Conditions) NMR | Inhibition of platelet aggregation in vitro (rat blood) in μM |
|---|---|---|---|---|
| 48 | *N-ethyl-4-methylpiperazine* | pyridazinyl | TFA — 591.26; 1 (MJ) — | 0.14 |
| 49 | *1-methyl-3-hydroxypyrrolidine* | pyridazinyl | — — 550.2; 1.11 (MJ) — | 0.22 |
| 50 | *1-methyl-4-(2-hydroxyethyl)piperidine* | pyridazinyl | — — 592.24; 1.15 (MJ) — | 0.05 |
| 51 | Chiral *(3R)-1-methyl-3-hydroxypyrrolidine* | pyridazinyl | — — 550.2; 1.11 (MJ) — | 0.18 |
| 52 | *1-methyl-4-(dimethylamino)piperidine* | pyridazinyl | TFA — 591.26; 0.99 (MJ) — | 0.06 |
| 53 | *3-(dimethylamino)-1-methylpyrrolidine* | pyridazinyl | TFA — 577.24; 0.99 (MJ) — | 0.09 |

TABLE XII-continued (I)

X = —CH—
R₁ = n-Pr
R₂ = Me
R₄ = 5-Cl
R₅ = H

| Compounds No. | R₃ | A | Salt m.p. °C. MH⁺; t$_R$ (Conditions) NMR | Inhibition of platelet aggregation in vitro (rat blood) in μM |
|---|---|---|---|---|
| 54 | 1-methyl-4-(1-methylethyl)piperazine (Me, Me on CH attached to piperazine N) | pyridazine-3,6-diyl | TFA — 591.26; 1 (MJ) — | 0.11 |
| 55 | 1-methyl-4-(3-methylpropyl)piperazine (Me on propyl chain) | pyridazine-3,6-diyl | TFA — 605.28; 1.01 (MJ) — | 0.16 |
| 56 | (1-methylpiperidin-4-yl)methanol | pyridazine-3,6-diyl | — — 578.23; 1.14 (MJ) — | 0.30 |
| 57 | Chiral (3S)-1-methylpyrrolidin-3-ol | pyridazine-3,6-diyl | — — 550.2; 1.11 (MJ) — | 0.06 |
| 58 | N-methyl-2-(1H-pyrrol-1-yl)ethanamine | pyridazine-3,6-diyl | — — 573.21; 1.19 (MJ) — | 0.45 |
| 59 | Chiral (3R)-1-methylpiperidin-3-ol | pyridazine-3,6-diyl | — — 564.21; 1.13 (MJ) — | 0.09 |

TABLE XII-continued

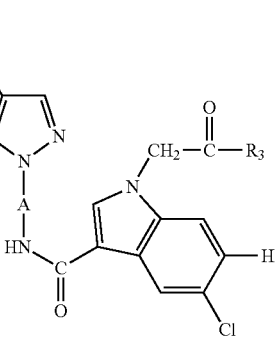

(I)

X = —CH—
R₁ = n-Pr
R₂ = Me
R₄ = 5-Cl
R₅ = H

| Compounds No. | R₃ | A | Salt m.p. °C. MH⁺; $t_R$ (Conditions) NMR | Inhibition of platelet aggregation in vitro (rat blood) in μM |
|---|---|---|---|---|
| 60 | (N-methylaminomethyl tetrahydropyran) | 3,6-pyridazinediyl | — <br> 578.23; 1.16 <br> (MJ) <br> — | 0.09 |
| 61 | Me—O—CH₂CH₂—N(Me)— | 3,6-pyridazinediyl | — <br> 552.21; 1.18 <br> (MJ) <br> — | 0.09 |
| 62 | (N-methylaminomethyl furan) | 3,6-pyridazinediyl | — <br> 574.2; 1.21 <br> (MJ) <br> — | 0.15 |
| 63 | (aminomethyl tetrahydrofuran) | 3,6-pyridazinediyl | TFA <br> 633.27; 1.01 <br> (MJ) <br> — | 0.12 |
| 64 | (4-methyl-2-oxopiperazinyl) | 3,6-pyridazinediyl | — <br> 563.19; 4.23 <br> (MJ) <br> — | 0.06 |

TABLE XII-continued (I)

X = —CH—
R₁ = n-Pr
R₂ = Me
R₄ = 5-Cl
R₅ = H

| Compounds No. | R₃ | A | Salt m.p. ° C. MH⁺; $t_R$ (Conditions) NMR | Inhibition of platelet aggregation in vitro (rat blood) in μM |
|---|---|---|---|---|
| 65 | morpholine-piperidine(N-Me) | pyridazine | TFA — 633.27; 0.99 (MJ) — | 0.12 |
| 66 | 3-hydroxy-azetidine(N-Me) | pyridazine | — — 536.18; 1.11 (MJ) — | 0.22 |
| 67 | octahydropyrido[1,2-a]pyrazine(N-Me) | pyridazine | TFA — 603.26; 1.01 (MJ) — | 0.09 |
| 68 | 4-hydroxy-piperidine(N-Me) | pyridazine | — — 564.21; 1.13 (MJ) — | 0.07 |
| 69 | 4-(N,N-dimethylcarbamoyl)-piperazine(N-Me) | pyridazine | — — 620.25; 1.15 (MJ) — | 0.10 |
| 70 | 5,6,7,8-tetrahydro-[1,2,4]triazolo[4,3-a]pyrazine(N-Me) | pyridazine | — — 587.2; 1.09 (MJ) — | 0.11 |

TABLE XII-continued

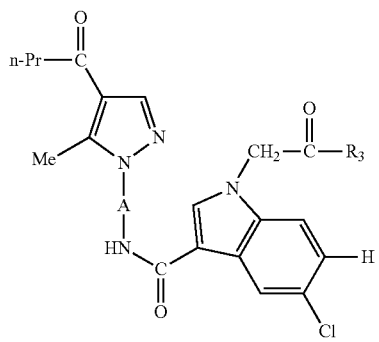

X = —CH—
R₁ = n-Pr
R₂ = Me
R₄ = 5-Cl
R₅ = H (I)

| Compounds No. | R₃ | A | Salt m.p. °C. MH⁺; $t_R$ (Conditions) NMR | Inhibition of platelet aggregation in vitro (rat blood) in μM |
|---|---|---|---|---|
| 71 | (4-methyl-1,1-dioxo-thiomorpholinyl) | pyridazine-3,6-diyl | — — 598.16; 1.14 (MJ) — | 0.12 |
| 72 | HO-(CH₂)₃-N(Me)- | pyridazine-3,6-diyl | — — 552.21; 1.13 (MJ) — | 0.06 |
| 73 | (4-methylpiperazinyl)-tetrahydrothiophene-1,1-dioxide | pyridazine-3,6-diyl | TFA — 667.22; 1.12 (MJ) — | 0.05 |
| 74 | (3-methyl-1H-1,2,4-triazol-5-yl)methyl-NH- | pyridazine-3,6-diyl | — — 575.2; 1.08 (MJ) — | 0.12 |
| 75 | 1-methyl-3-(trifluoromethyl)pyrrolidinyl | pyridazine-3,6-diyl | — — 602.19; 1.22 (MJ) — | 0.27 |
| 76 | 2-methyl-2,3-dihydro-1H-pyrrolo[3,4-c]pyridinyl | pyridazine-3,6-diyl | — — 583.2; 1.08 (MJ) — | 0.06 |

TABLE XII-continued (I)

X = —CH—
R₁ = n-Pr
R₂ = Me
R₄ = 5-Cl
R₅ = H

| Compounds No. | R₃ | A | Salt m.p. °C. MH⁺; $t_R$ (Conditions) NMR | Inhibition of platelet aggregation in vitro (rat blood) in μM |
|---|---|---|---|---|
| 77 | (1,4-dimethylpiperazin-2-yl, Me on ring C and N-Me) | pyridazine-3,6-diyl | TFA — 577.24; 1 (MJ) — | 0.09 |
| 78 | Me-CH(NHMe)-tetrazole (1H-tetrazol-5-yl) | pyridazine-3,6-diyl | — — 576.2; 1.12 (MJ) — | 0.28 |
| 79 | 4-cyclobutyl-piperazin-1-yl (N-methyl) | pyridazine-3,6-diyl | TFA — 603.26; 1.01 (MJ) — | 0.08 |
| 80 | Chiral (1-methyl-3-hydroxypiperidinyl) | pyridazine-3,6-diyl | — — 564.21; 1.14 (MJ) — | 0.09 |
| 81 | 4-methylpiperazin-1-yl-CH₂-C(O)NH-cyclopropyl | pyridazine-3,6-diyl | — — 646.27; 1.05 (MJ) — | 0.04 |

TABLE XII-continued

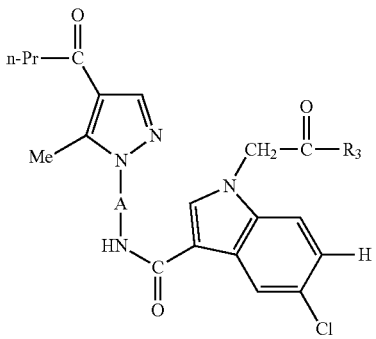

X = —CH—
R₁ = n-Pr
R₂ = Me
R₄ = 5-Cl
R₅ = H

| Compounds No. | R₃ | A | Salt m.p. °C. MH⁺; $t_R$ (Conditions) NMR | Inhibition of platelet aggregation in vitro (rat blood) in μM |
|---|---|---|---|---|
| 82 | Me-oxadiazole-CH₂-piperazine-N-Me | pyridazine | TFA — 645.25; 1.14 (MJ) — | 0.05 |
| 83 | Me₂N-C(Me)₂-CH₂-NHMe | pyridazine | TFA — 579.26; 1 (MJ) — | 0.33 |
| 84 | N-Me octahydropyrrolo[1,2-a]pyrazine with Me | pyridazine | TFA — 603.26; 1.01 (MJ) — | 0.09 |
| 85 | N-Me piperazine-CH₂-(3-F-4-OMe-phenyl) | pyridazine | TFA — 687.26; 1.06 (MJ) — | 0.10 |
| 86 | N-Me azetidine-piperidine | pyridazine | TFA — 603.26; 1 (MJ) — | 0.39 |

TABLE XII-continued (I)

X = —CH—
R₁ = n-Pr
R₂ = Me
R₄ = 5-Cl
R₅ = H

| Compounds No. | R₃ | A | Salt m.p. °C. MH⁺; $t_R$ (Conditions) NMR | Inhibition of platelet aggregation in vitro (rat blood) in μM |
|---|---|---|---|---|
| 87 | *methyl piperazinyl acetate (N-methylpiperazine-CH₂-C(O)-O-Me)* | pyridazine-3,6-diyl | TFA<br>—<br>621.23; 1.1<br>(MJ)<br>— | 0.04 |
| 88 | *3-methyl-octahydropyrrolo[1,2-a]pyrazin-2-yl* | pyridazine-3,6-diyl | TFA<br>—<br>603.26; 1.01<br>(MJ)<br>— | 0.09 |
| 89 | *3-methyl-2-methyl-octahydro-2H-pyrido[1,2-a]pyrazin-yl* | pyridazine-3,6-diyl | TFA<br>—<br>617.28; 1.02<br>(MJ)<br>— | 0.17 |
| 90 | *N-cyclopropyl-N-methyl* | pyridazine-3,6-diyl | —<br>—<br>534.2; 1.2<br>(MJ)<br>— | 0.06 |
| 91 | *N-methyl-N-((tetrahydrofuran-3-yl)methyl)* | pyridazine-3,6-diyl | —<br>—<br>578.23; 1.17<br>(MJ)<br>— | 0.12 |
| 92 | *4-(4-fluorobenzyl)-1-methylpiperazinyl* | pyridazine-3,6-diyl | TFA<br>—<br>657.25; 1.06<br>(MJ)<br>— | 0.20 |

TABLE XII-continued
X = —CH—
R₁ = n-Pr
R₂ = Me
R₄ = 5-Cl
R₅ = H
| Compounds No. | R₃ | A | Salt m.p. °C. MH⁺; $t_R$ (Conditions) NMR | Inhibition of platelet aggregation in vitro (rat blood) in μM |
|---|---|---|---|---|
| 93 | 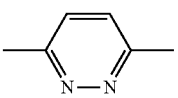 | 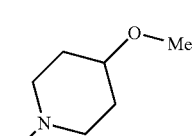 | TFA —— 621.27; 1.02 (MJ) —— | 0.15 |
| 94 | 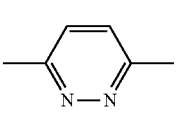 | 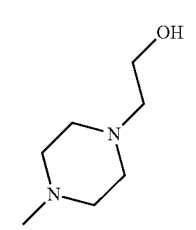 | —— 578.23; 1.18 (MJ) —— | 0.18 |
| 95 | 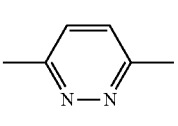 | 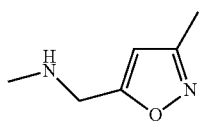 | —— 593.24; 1.13 (MJ) —— | 0.05 |
| 96 | 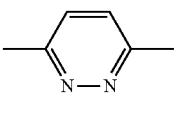 | 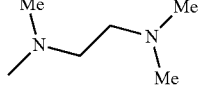 | —— 575.19; 1.17 (MJ) —— | 0.93 |
| 97 | 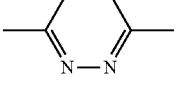 | | —— 565.24; 1.14 (MJ) —— | 0.09 |

TABLE XII-continued

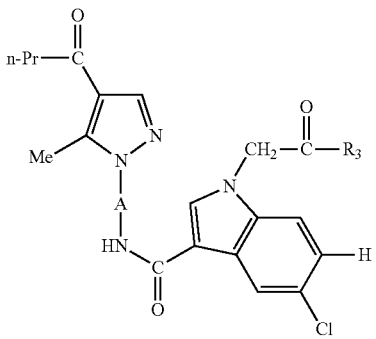

(I)

X = —CH—
R₁ = n-Pr
R₂ = Me
R₄ = 5-Cl
R₅ = H

| Compounds No. | R₃ | A | Salt m.p. °C. MH⁺; $t_R$ (Conditions) NMR | Inhibition of platelet aggregation in vitro (rat blood) in μM |
|---|---|---|---|---|
| 98 | Me-N(Me)-CH₂CH₂-N(piperazine-N-Me) | pyridazine-3,6-diyl | —<br>620.29; 1.14<br>(MJ)<br>— | 0.07 |
| 99 | N-Me-diazepane-N-Me | pyridazine-3,6-diyl | —<br>577.24; 1.02<br>(MJ)<br>— | 0.11 |
| 100 | Me-N(Me)-CH(Me)-CH₂-NH-Me | pyridazine-3,6-diyl | —<br>565.24; 1.03<br>(MJ)<br>— | 0.19 |
| 101 | Me-N(Me)-C(O)-CH₂-piperazine-N-Me | pyridazine-3,6-diyl | —<br>634.27; 1.03<br>(MJ)<br>— | 0.11 |
| 102 | N-Me-piperazine-CH₂-pyridin-4-yl | pyridazine-3,6-diyl | —<br>640.26; 1.05<br>(MJ)<br>— | 0.03 |

TABLE XII-continued

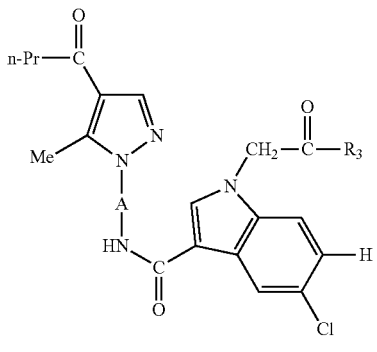

X = —CH—
R₁ = n-Pr
R₂ = Me
R₄ = 5-Cl
R₅ = H

| Compounds No. | R₃ | A | Salt m.p. °C. MH⁺; $t_R$ (Conditions) NMR | Inhibition of platelet aggregation in vitro (rat blood) in μM |
|---|---|---|---|---|
| 103 | methyl 3-methylcyclobutanecarboxylate group | 3,6-pyridazinediyl (Me-substituted) | — <br> 578.19; 1.16 <br> (MJ) <br> — | 0.09 |
| 104 | 1-methyl-3-(morpholin-4-yl)azetidine group | 3,6-pyridazinediyl (Me-substituted) | — <br> 605.24; 1.07 <br> (MJ) <br> — | 0.10 |

The NMR analyses for certain compounds are given below:

Compound 27

¹H NMR: DMSO-d₆ (400 MHz): δ (ppm): 0.94 (3H, t); 1.64 (2H, m); 2.70-4.50 (16H, m); 5.38 (2H, br); 7.29 (1H, d); 7.57 (1H, d); 8.25 (1H, s); 8.36 (1H, s); 8.57 (1H, s); 8.85 (1H, s); 9.42 (1H, d); 11.10 (1H, s); 11.15 (1H, br).

Compound 28

¹H NMR: DMSO-d₆ (400 MHz): δ (ppm): 0.95 (3H, t); 1.65 (2H, m); 2.80-2.89 (8H, m); 2.93-3.25 (3H, m); 3.41-4.08 (3H, m); 4.20 (1H, d); 4.39 (1H, d); 5.35 (1H, d); 5.50 (1H, d); 7.30 (1H, d); 7.59 (1H, d); 8.14 (1H, d); 8.24 (1H, s); 8.41 (1H, s); 8.58 (1H, s); 8.71 (1H, d); 10.97 (1H, br); 11.38 (1H, s).

Compound 29

¹H NMR: DMSO-d₆ (400 MHz): δ (ppm): 0.95 (3H, t); 1.65 (2H, m); 2.82 (3H, s); 2.87 (2H, t); 2.98-3.29 (3H, m); 3.35 (3H, s); 3.36-3.42 (2H, m); 3.50-3.88 (5H, m); 4.19 (1H, d); 4.37 (1H, d); 5.36 (1H, d); 5.50 (1H, d); 7.30 (1H, d); 7.58 (1H, d); 8.14 (1H, d); 8.24 (1H, s); 8.41 (1H, s); 8.58 (1H, s); 8.71 (1H, d); 10.56 (1H, br); 11.38 (1H, s),

Compound 30

¹H NMR: DMSO-d₆ (500 MHz): δ (ppm): 0.95 (3H, t); 1.65 (2H, m); 2.82 (3H, s); 2.86 (2H, t); 3.11-3.80 (9H, m); 3.95-4.80 (3H, m); 5.20-5.65 (2H, m); 7.30 (1H, d); 7.57 (1H, d); 8.13 (1H, d); 8.24 (1H, s); 8.41 (1H, s); 8.59 (1H, s); 8.70 (1H, d).

Compound 31

H NMR: DMSO-d₆ (400 MHz): δ (ppm): 0.95: t: 3H, 1.65: m: 2H; 2.82: s: 3H, 2.86: t: 2H, 3.00-3.90: m: 9H, 3.95-4.70: m: 3H, 5.25-5.55: m: 2H; 7.30: d: 1H, 7.57: d: 1H, 8.13: d: 1H; 8.24: s: 1H; 8.41: s: 1H, 8.59: s: 1H, 8.70: d: 1H.

Example 11

Compound No. 105

N-[4-(4-Butyryl-5-methyl-1H-pyrazol-1-yl)phenyl]-5-chloro-1-{2-[4-(2-methoxyethyl)piperazin-1-yl]-2-oxoethyl}-1H-indole-3-carboxamide hydrochloride 1.28 g of 1-(2-methoxyethyl)piperazine and 1.40 g of BOP-Cl are added successively to 1.70 g of compound No. 3 in 35 ml of DCM. It is stirred at RT for 20 hours. The reaction mixture is evaporated to dryness, a dilute solution of NaHCO₃ is added and it is extracted with EtOAc. The organic phase is washed with water, with brine, dried over Na₂SO₄ and evaporated to dryness. It is triturated in iso ether and than drained. The product is dissolved in 5 ml of DCM/acetone mixture (50/50; v/v) and then 5 ml of 1N HCl solution in ether is added. The hydrochloride is precipitated with 10 ml of ether and then drained, obtaining 1.96 g of a white powder.

¹H NMR: DMSO-d₆ (250 MHz): δ (ppm): 0.94 (3H, t); 1.63 (2H, m); 2.52 (3H, s); 2.82 (2H, t); 2.97-3.29 (3H, m); 3.35-3.41 (5H, m); 3.50-3.78 (5H, m); 4.18 (1H, d); 4.37 (1H, d); 5.36 (1H, d); 5.51 (1H, d); 7.27 (1H, d); 7.49 (2H, d); 7.57 (1H, d); 7.97 (2H, d); 8.22 (1H, s); 8.25 (1H, s); 8.34 (1H, s); 10.22 (1H, s); 10.81 (1H, br).

m.p.=218° C.

Following the procedure described in Example 11 and starting from the corresponding compounds of formula (IA), the compounds of formula (I) presented in TABLE XIII below are prepared:

In this table:

in the column "Salt", "Base" represents a compound in the form of free base, whereas "HCl" represents a compound in the form of hydrochloride, "TFA" represents a compound in the form of trifluoroacetate;

Me represents a methyl radical;

Et represents an ethyl radical;

nPr represents an n-propyl radical.

TABLE XIII

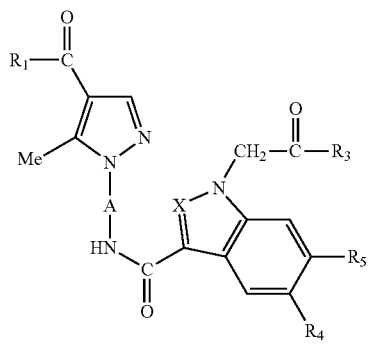

(I)

| Compounds No. | R₁ | A | R₃ | R₄ | R₅ | X | Salt, Hydrate m.p. ° C. MH+; t_R (min) Method | Inhibition of platelet aggregation in vitro (rat blood) in μM |
|---|---|---|---|---|---|---|---|---|
| 105 | nPr | p-phenylene | CH₂CH₂-N(piperazinyl-N-CH₂CH₂OMe) | Cl | H | CH | HCl, 0.7 H₂O 218 605; 6.07 G | 0.32 |
| 106 | nPr | p-phenylene | CH₂-N(Me)Me | Me | Me | CH | Base, H₂O 265 500; 8.48 G | 2.21 |
| 107 | nPr | p-phenylene | N-methylpiperazinyl | Me | Me | CH | HCl, 3 H₂O 201 555; 6.46 G | 0.30 |

TABLE XIII-continued
| Compounds No. | R₁ | A | R₃ | R₄ | R₅ | X | Salt, Hydrate m.p. °C. MH+; $t_R$ (min) Method | Inhibition of platelet aggregation in vitro (rat blood) in μM |
|---|---|---|---|---|---|---|---|---|
| 108 | nPr | 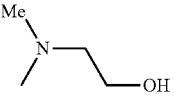 | 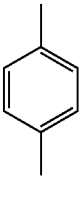 | Me | Me | CH | Base, 0.3 H₂O 177 530; 8.04 G | 0.98 |
| 109 | nPr |  | 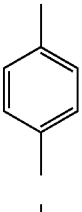 | Me | Me | CH | Base, 0.3 H₂O 300 486; 8.27 | 2.42 |
| 110 | nPr | 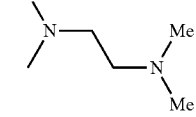 | 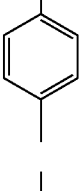 | Me | Me | CH | HCl, 2.5 H₂O 179 557; 6.50 G | 3.99 |
| 111 | nPr | 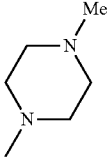 | 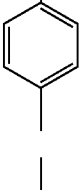 | Cl | Cl | CH | HCl, 2 H₂O 213 595, 6.83 G | 3.70 |
| 112 | nPr | 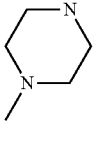 | 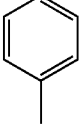 | Br | Me | CH | HCl, 2 H₂O 204 619; 6.78 G | 0.36 |
| 113 | nPr | 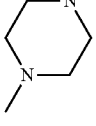 | | Cl | Me | CH | HCl, 2 H₂O 210 575; 13.09 H | 0.62 |

TABLE XIII-continued

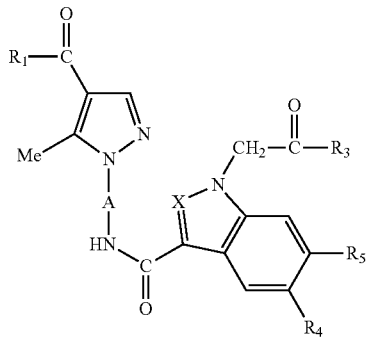

(I)

| Compounds No. | R₁ | A | R₃ | R₄ | R₅ | X | Salt, Hydrate m.p. °C. MH+; $t_R$ (min) Method | Inhibition of platelet aggregation in vitro (rat blood) in μM |
|---|---|---|---|---|---|---|---|---|
| 114 | nPr | 1,4-phenylene | 4-methylpiperazin-1-yl, Me | Me | H | CH | HCl, 1.7 H₂O 204 541; 6.31 G | 0.27 |
| 115 | nPr | 1,4-phenylene | 4-methylpiperazin-1-yl, Me | Cl | H | CH | HCl, 1.4 H₂O 243 561; 6.51 G | 0.32 |
| 116 | nPr | 1,4-phenylene | 4-methylpiperazin-1-yl, CH₂CH₂OH | Me | H | CH | HCl, 2.5 H₂O 184 571; 6.28 G | 0.26 |
| 117 | nPr | 1,4-phenylene | 4-methylpiperazin-1-yl, CH₂Me | Me | H | CH | HCl, 0.5 H₂O 212 555; 6.37 G | 0.50 |
| 118 | nPr | 1,4-phenylene | 4-methylpiperazin-1-yl, CH₂CHF₂ | Me | H | CH | HCl, 1 H₂O 281 591; 8.22 G | 0.29 |

TABLE XIII-continued

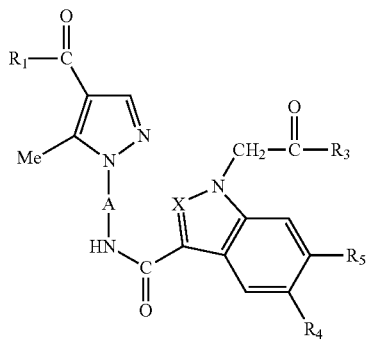

(I)

| Compounds No. | R₁ | A | R₃ | R₄ | R₅ | X | Salt, Hydrate m.p. ° C. MH+; t_R (min) Method | Inhibition of platelet aggregation in vitro (rat blood) in μM |
|---|---|---|---|---|---|---|---|---|
| 119 | nPr | *-C₆H₄-* (para) | 4-methylpiperazinyl-CH₂CH₂-O-Me | Me | H | CH | HCl, 2 H₂O 180 585; 6.41 G | 0.18 |
| 120 | nPr | *-C₆H₄-* (para) | 1-methyl-3-(dimethylamino)pyrrolidinyl | Me | H | CH | HCl, 1 H₂O 171 555; 6.3 G | 0.27 |
| 121 | nPr | *-C₆H₄-* (para) | 4-methylpiperazinyl-CH₂-cyclopropyl | Me | H | CH | HCl, 0.5 H₂O 296 581; 6.49 G | 1.06 |
| 122 | nPr | *-C₆H₄-* (para) | 1-cyclopropyl-4-methylpiperazinyl | Me | H | CH | HCl, 2.5 H₂O 199 567; 6.38 G | 0.45 |
| 123 | nPr | *-C₆H₄-* (para) | methyl-hexahydropyrrolo[1,2-a]pyrazinyl | Me | H | CH | HCl, 2.1 H₂O 140 567; 6.54 G | 0.35 |

TABLE XIII-continued
(I)
| Compounds No. | R₁ | A | R₃ | R₄ | R₅ | X | Salt, Hydrate m.p. °C. MH+; $t_R$ (min) Method | Inhibition of platelet aggregation in vitro (rat blood) in μM |
|---|---|---|---|---|---|---|---|---|
| 124 | nPr | 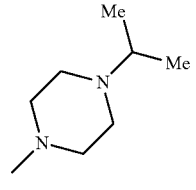 | 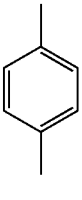 | Me | H | CH | HCl, H₂O 220 569; 6.42 G | 0.21 |
| 125 | nPr | 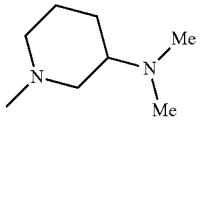 | 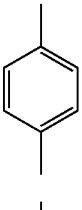 | Me | H | CH | HCl, 2 H₂O 164 569; 6.37 G | 0.58 |
| 126 | nPr | 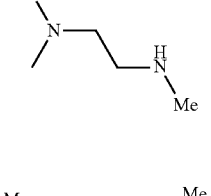 | 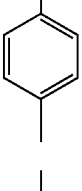 | Me | H | CH | HCl, 2.5 H₂O 164 529; 6.29 G | 0.76 |
| 127 | nPr | 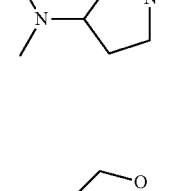 | 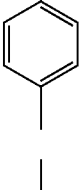 | Me | H | CH | HCl, H₂O 198 556; 6.37 G | 0.50 |
| 128 | nPr | 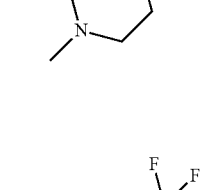 | 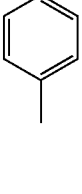 | Me | H | CH | HCl, 2.1 H₂O 189 528; 8.23 G | 0.29 |
| 129 | nPr | 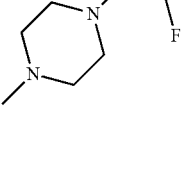 | | Me | H | CH | Base, 0.2 H₂O 143 609; 9.17 G | 0.65 |

TABLE XIII-continued

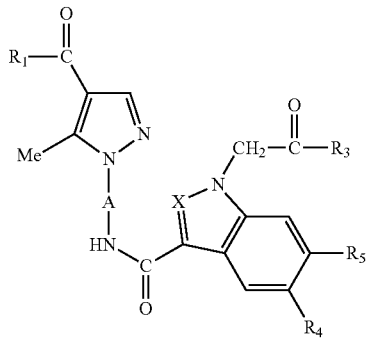

(I)

| Compounds No. | R₁ | A | R₃ | R₄ | R₅ | X | Salt, Hydrate m.p. °C. MH+; $t_R$ (min) Method | Inhibition of platelet aggregation in vitro (rat blood) in μM |
|---|---|---|---|---|---|---|---|---|
| 130 | nPr | p-phenylene | 4-methyl-1,4-diazepan-1-yl | Me | H | CH | HCl, 1.4 H₂O 200 555; 6.32 G | 0.47 |
| 131 | nPr | p-phenylene | NHMe-CH₂CH₂-NMe₂ | Me | H | CH | HCl, 1.3 H₂O 192 529; 6.27 G | 0.63 |
| 132 | nPr | p-phenylene | NHMe-CH(Me)-CH₂-NMe₂ | Me | H | CH | HCl, 2 H₂O 140 543; 6.33 G | 0.98 |
| 133 | nPr | p-phenylene | 4-(2-fluoroethyl)-1-methylpiperazinyl | Me | H | CH | HCl, 1.6 H₂O 192 573; 6.45 G | 0.32 |
| 134 | nPr | p-phenylene | NHMe-CH₂CH₂-imidazol-1-yl | Me | H | CH | HCl, H₂O 172 552; 6.22 G | 0.95 |

TABLE XIII-continued
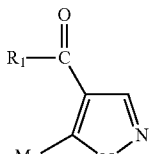
(I)
| Compounds No. | R₁ | A | R₃ | R₄ | R₅ | X | Salt, Hydrate m.p. °C. MH+; $t_R$ (min) Method | Inhibition of platelet aggregation in vitro (rat blood) in μM |
|---|---|---|---|---|---|---|---|---|
| 135 | nPr |  | 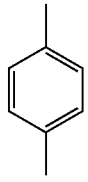 Chiral | Me | H | CH | Base, 0.5 H₂O 170 528; 7.26 G | 0.21 |
| 136 | nPr | 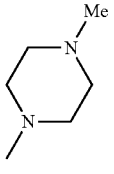 | 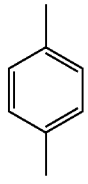 | OMe | H | CH | HCl, 1.6 H₂O 204 557; 5.53 G | 0.40 |
| 137 | nPr | 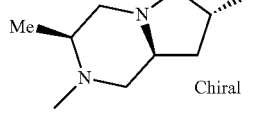 | 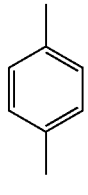 Chiral | Me | H | CH | HCl, 2.5 H₂O 215 597; 5.83 G | 0.39 |
| 138 | nPr | 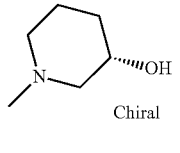 | 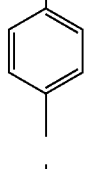 Chiral | Me | H | CH | Base, 0.3 H₂O 142 542; 8.00 G | 0.42 |
| 139 | nPr | 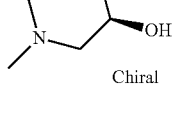 | 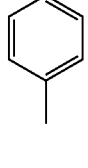 Chiral | Me | H | CH | Base, 0.65 H₂O 142 542; 7.99 G | 0.47 |
| 140 | nPr | 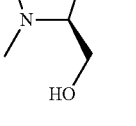 | Chiral | Me | H | CH | HCl, 0.3 H₂O 152 542; 8.10 G | 0.34 |

TABLE XIII-continued
(I)
| Compounds No. | R₁ | A | R₃ | R₄ | R₅ | X | Salt, Hydrate m.p. ° C. MH+; t$_R$ (min) Method | Inhibition of platelet aggregation in vitro (rat blood) in μM |
|---|---|---|---|---|---|---|---|---|
| 141 | nPr | 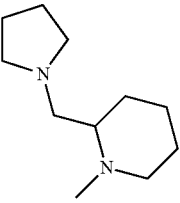 |  | Me | H | CH | HCl, 1.8 H₂O 202 609; 6.11 G | 0.64 |
| 142 | nPr | 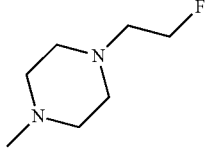 |  | Cl | H | CH | HCl, H₂O 192 593; 6.59 G | 0.13 |
| 143 | nPr | 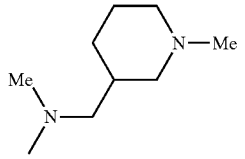 |  | Me | H | CH | HCl, 2.3 H₂O 202 583; 6.42 G | 0.53 |
| 144 | nPr | 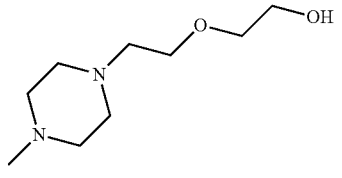 |  | Cl | H | CH | HCl, 3.3 H₂O 125 635; 6.51 G | 0.19 |
| 145 | nPr | | 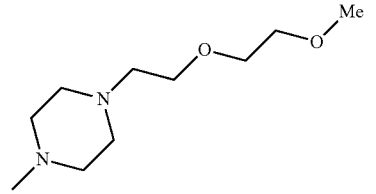 | Cl | H | CH | HCl, 1.4 H₂O 135 649; 6.69 G | 0.25 |

TABLE XIII-continued

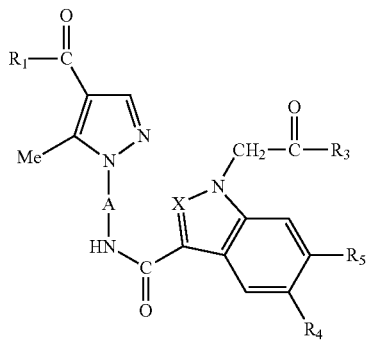

(I)

| Compounds No. | R₁ | A | R₃ | R₄ | R₅ | X | Salt, Hydrate m.p. ° C. MH+; $t_R$ (min) Method | Inhibition of platelet aggregation in vitro (rat blood) in μM |
|---|---|---|---|---|---|---|---|---|
| 146 | nPr | 1,4-phenylene | 4-(2-hydroxyethyl)piperazin-1-yl | Cl | H | CH | HCl, 2 H₂O 212 591; 6.50 G | 0.10 |
| 147 | nPr | 1,4-phenylene | 4-(4-fluorobenzyl)piperazin-1-yl | Me | H | CH | HCl, H₂O 251 635; 6.80 G | 0.19 |
| 148 | nPr | 1,4-phenylene | 4-(2-methylsulfonylethyl)piperazin-1-yl | Cl | H | CH | HCl, 0.8 H₂O 252 653; 6.78 G | 0.15 |
| 149 | nPr | 1,4-phenylene | 4-(4-morpholinyl)piperidin-1-yl | Cl | H | CH | HCl, 1.5 H₂O 217 631; 6.45 G | 0.41 |
| 150 | nPr | 1,4-phenylene | 4-(2-dimethylaminoethyl)piperazin-1-yl | Cl | H | CH | HCl, 1.25 H₂O 272 618; 6.42 G | 0.24 |

TABLE XIII-continued
(I)
| Compounds No. | R₁ | A | R₃ | R₄ | R₅ | X | Salt, Hydrate m.p. ° C. MH+; $t_R$ (min) Method | Inhibition of platelet aggregation in vitro (rat blood) in μM |
|---|---|---|---|---|---|---|---|---|
| 151 | nPr | 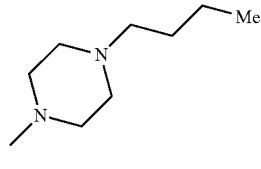 | 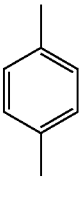 | Cl | H | CH | HCl, 0.4 H₂O 220 603; 6.67 G | 0.25 |
| 152 | nPr | 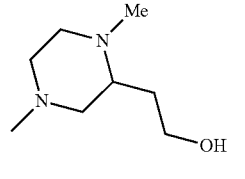 | 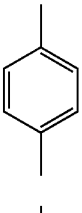 | Cl | H | CH | HCl, 2.5 H₂O 212 605; 6.15 G | 0.22 |
| 153 | nPr | 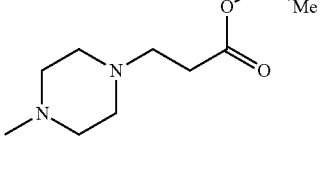 | 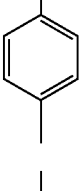 | Cl | H | CH | HCl, H₂O 190 647; 6.39 G | 0.29 |
| 154 | nPr | 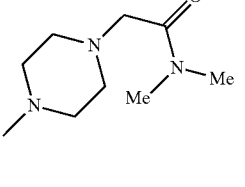 | 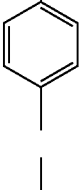 | Cl | H | CH | HCl, 1.5 H₂O 210 632; 6.12 G | 0.15 |
| 155 | nPr | 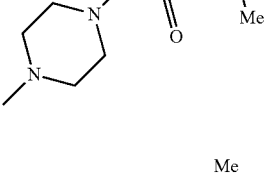 | 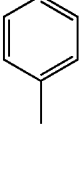 | Cl | H | CH | HCl, 0.15 H₂O 195 633; 7.53 G | 0.26 |
| 156 | nPr | 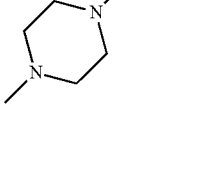 |  | Cl | H | CH | HCl, 0.9 H₂O 279 589; 6.14 G | 0.30 |

TABLE XIII-continued
(I)
| Compounds No. | R₁ | A | R₃ | R₄ | R₅ | X | Salt, Hydrate m.p. ° C. MH+; t$_R$ (min) Method | Inhibition of platelet aggregation in vitro (rat blood) in μM |
|---|---|---|---|---|---|---|---|---|
| 157 | nPr | 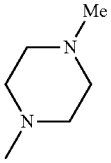 | 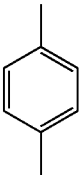 | Cl | F | CH | HCl, H₂O 222 579; 6.7 G | 0.18 |
| 158 | nPr | 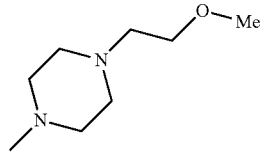 | 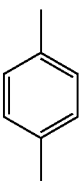 | Cl | F | CH | HCl, 0.15 H₂O 226 623; 6.76 G | 0.34 |
| 159 | nPr | 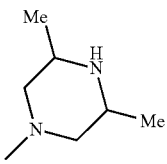 | 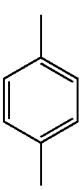 | Cl | H | CH | HCl, H₂O 230 575; 6.03 G | 0.41 |
| 160 | nPr | 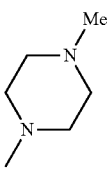 | 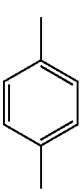 | CN | H | CH | HCl, 1.5 H₂O 209 552; 5.58 G | 1.38 |
| 161 | nPr | 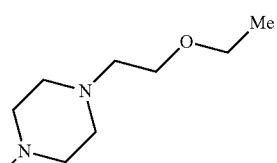 | | Cl | H | CH | HCl, H₂O 196 619; 6.8 G | 0.37 |

TABLE XIII-continued
(I)
| Compounds No. | R₁ | A | R₃ | R₄ | R₅ | X | Salt, Hydrate m.p. °C. MH+; $t_R$ (min) Method | Inhibition of platelet aggregation in vitro (rat blood) in μM |
|---|---|---|---|---|---|---|---|---|
| 162 | nPr | 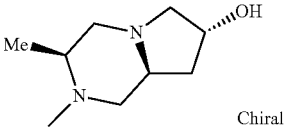 | 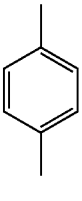 Chiral | Cl | H | CH | Base, H₂O 227 617; 6.53 G | 0.50 |
| 163 | nPr | 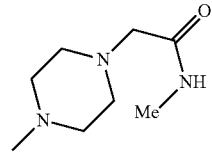 | 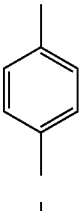 | Cl | H | CH | HCl, 0.8 H₂O 216 618; 6.43 G | 0.29 |
| 164 | nPr | 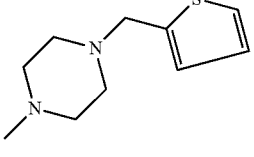 | 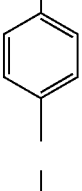 | Me | H | CH | HCl, 0.3 H₂O 240 623; 6.42 G | 1.01 |
| 165 | nPr | 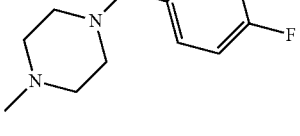 | 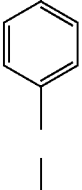 | Cl | H | CH | HCl, 1.2 H₂O 195 655; 7.14 G | 0.31 |
| 166 | nPr | 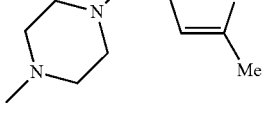 | 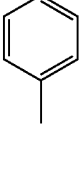 | Cl | H | CH | HCl, 0.6 H₂O 219 642; 7.52 G | 0.14 |
| 167 | nPr |  | | Cl | H | CH | — — 671; 3.74 A | 0.47 |

TABLE XIII-continued

| Compounds No. | R₁ | A | R₃ | R₄ | R₅ | X | Salt, Hydrate m.p. °C. MH+; t_R (min) Method | Inhibition of platelet aggregation in vitro (rat blood) in μM |
|---|---|---|---|---|---|---|---|---|
| 168 | nPr | 1,4-phenylene | 2-methoxybenzyl-4-methylpiperazine | Cl | H | CH | —<br>667; 3.44<br>A | 0.37 |
| 169 | nPr | 1,4-phenylene | 3-(N,N-dimethylamino)tetrahydrothiophene 1,1-dioxide | Cl | H | CH | —<br>610; 3.24<br>A | 0.40 |
| 170 | nPr | 1,4-phenylene | (S)-1-methyl-2-(trifluoromethyl)pyrrolidine (Chiral) | Cl | H | CH | —<br>600; 3.62<br>A | 0.12 |
| 171 | nPr | 1,4-phenylene | (2S,4R)-4-hydroxy-N-cyclobutyl-1-methylpyrrolidine-2-carboxamide (Chiral) | Cl | H | CH | —<br>645; 3.14<br>A | 0.57 |
| 172 | nPr | 1,4-phenylene | 7-methyl-5,6,7,8-tetrahydroimidazo[1,2-a]pyrazine | Cl | H | CH | —<br>584; 3.17<br>A | 0.33 |

TABLE XIII-continued

| Compounds No. | R₁ | A | R₃ | R₄ | R₅ | X | Salt, Hydrate m.p. °C. MH+; $t_R$ (min) Method | Inhibition of platelet aggregation in vitro (rat blood) in μM |
|---|---|---|---|---|---|---|---|---|
| 173 | nPr | p-phenylene | 5-methyl-4,5,6,7-tetrahydro-1H-pyrazolo[4,3-c]pyridine | Cl | H | CH | — — 584; 4.50 B | 0.17 |
| 174 | nPr | p-phenylene | 1,5-dimethyl-5,6-dihydro-4H-pyrrolo[3,4-c]pyrazole | Cl | H | CH | — — 584; 4.63 B | 0.49 |
| 175 | nPr | p-phenylene | 5-methyl-1,4,5,6-tetrahydropyrrolo[3,4-c]pyrazole | Cl | H | CH | — — 570; 4.49 B | 0.29 |
| 176 | nPr | p-phenylene | 3-hydroxy-1-methylazetidine | Cl | H | CH | — — 534; 3.05 B | 0.39 |
| 177 | nPr | p-phenylene | (S)-1,2,4-trimethylpiperazine (Chiral) | Cl | H | CH | HCl, H₂O 247 575; 6.66 G | 0.37 |
| 178 | nPr | p-phenylene | NMe₂ | NMe₂ | H | CH | HCl, 2 H₂O 185 515; 5.60 G | 0.50 |

TABLE XIII-continued
(I)
| Compounds No. | R₁ | A | R₃ | R₄ | R₅ | X | Salt, Hydrate m.p. °C. MH+; t_R (min) Method | Inhibition of platelet aggregation in vitro (rat blood) in μM |
|---|---|---|---|---|---|---|---|---|
| 179 | nPr | 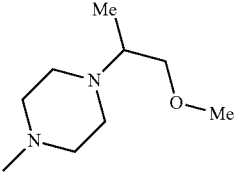 | 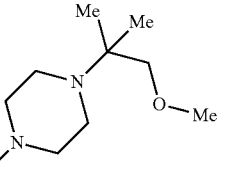 | Cl | H | CH | HCl, H₂O 198 619; 6.61 G | 0.17 |
| 180 | nPr | 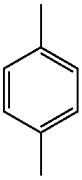 | 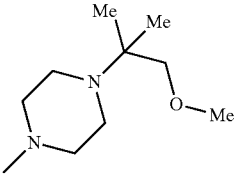 | Cl | H | CH | HCl, 1.5 H₂O 196 633; 6.66 G | 0.24 |
| 181 | nPr | 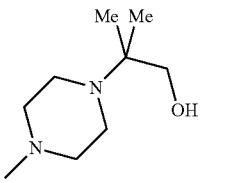 | 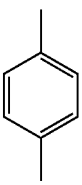 | Cl | H | CH | HCl, 2.2 H₂O 212 619; 6.51 G | 0.18 |
| 182 | nPr | 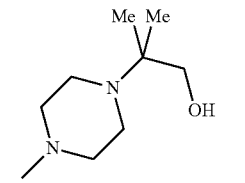 | 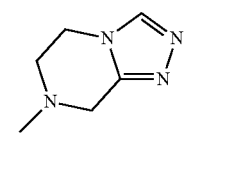 | Cl | H | CH | — — 585; 2.96 A | 0.27 |
| 183 | nPr | 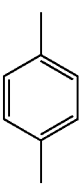 | 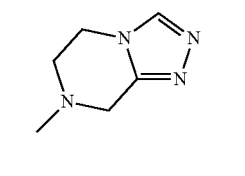 | Cl | H | CH | — — 601; 3.12 A | 0.23 |

TABLE XIII-continued

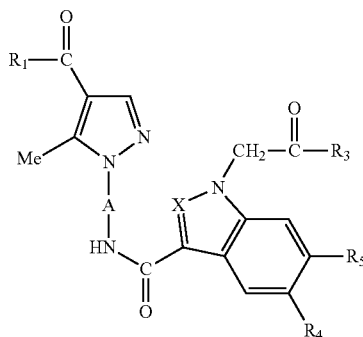

(I)

| Compounds No. | R₁ | A | R₃ | R₄ | R₅ | X | Salt, Hydrate m.p. °C. MH+; $t_R$ (min) Method | Inhibition of platelet aggregation in vitro (rat blood) in µM |
|---|---|---|---|---|---|---|---|---|
| 184 | nPr | 4-phenylene | 4-methyl-3-oxopiperazin-1-yl (Me-N, N-Me, C=O) | Cl | H | CH | —<br>—<br>575; 3.10<br>A | 0.17 |
| 185 | nPr | 4-phenylene | 4-(pyridin-2-yl)piperazin-1-yl | Cl | H | CH | HCl, 1.3 H₂O<br>232<br>624; 9.42<br>I | — |
| 186 | nPr | 4-phenylene | 3,3,4-trimethylpiperazin-1-yl | Cl | H | CH | —<br>—<br>589; 2.98<br>A | 0.25 |
| 187 | nPr | 4-phenylene | 6-methyl-5,7-dihydropyrrolo[3,4-b]pyridin-6-yl | Cl | H | CH | HCl, 0.3 H₂O<br>270<br>581; 8.79<br>I | 0.61 |
| 188 | nPr | 4-phenylene | (3S or 3R)-N-cyclopropyl-1-methylpyrrolidine-3-carboxamide (Chiral) | Cl | H | CH | —<br>—<br>615; 3.17<br>A | 0.55 |
| 189 | nPr | 4-phenylene | 3,3-difluoro-1-methylpyrrolidin-?-yl | Cl | H | CH | —<br>—<br>568; 4.70<br>E | 0.41 |

TABLE XIII-continued
(I)
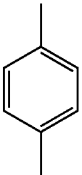
| Compounds No. | R₁ | A | R₃ | R₄ | R₅ | X | Salt, Hydrate m.p. °C. MH+; t_R (min) Method | Inhibition of platelet aggregation in vitro (rat blood) in μM |
|---|---|---|---|---|---|---|---|---|
| 190 | nPr | 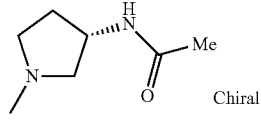 | 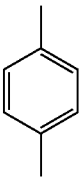 Chiral | Cl | H | CH | — — 589; 3.25 A | 0.36 |
| 191 | nPr | 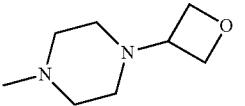 | 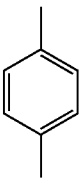 | Cl | H | CH | — — 603; 3.12 A | 0.16 |
| 192 | nPr | 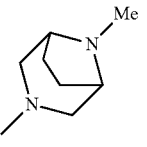 | 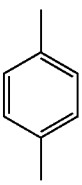 | Cl | H | CH | HCl 295 587; 6.54 G | 0.27 |
| 193 | nPr | 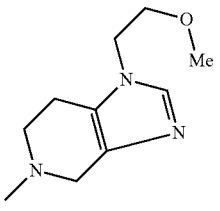 | 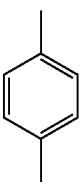 | Cl | H | CH | — — 642; 2.98 A | 0.12 |
| 194 | nPr | | 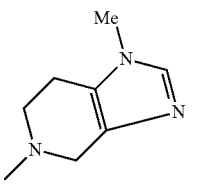 | Cl | H | CH | — — 598; 2.91 A | 0.20 |

TABLE XIII-continued (I)

| Compounds No. | R₁ | A | R₃ | R₄ | R₅ | X | Salt, Hydrate m.p. °C. MH+; t_R (min) Method | Inhibition of platelet aggregation in vitro (rat blood) in μM |
|---|---|---|---|---|---|---|---|---|
| 195 | nPr | *para-phenylene* | 5-methyl-4,5,6,7-tetrahydro-1-methyl-1H-pyrazolo[3,4-c]pyridine | Cl | H | CH | —<br>—<br>598; 3.27<br>A | 0.28 |
| 196 | nPr | *para-phenylene* | 2-methoxyethyl-(1,4-dimethylpiperazin-2-yl) | Cl | H | CH | —<br>—<br>619; 2.96<br>A | 0.23 |
| 197 | nPr | *para-phenylene* | N-[2-(4-methylpiperazin-1-yl)ethyl]acetamide | Cl | H | CH | —<br>—<br>632; 2.94<br>A | 0.25 |
| 198 | nPr | *para-phenylene* | 1-(4-methylpiperazin-1-yl)-2-(pyrrolidin-1-yl)ethanone | Cl | H | CH | —<br>—<br>658; 3.15<br>A | 0.41 |
| 199 | nPr | *para-phenylene* | 2-(4-methylpiperazin-1-yl)acetamide | Cl | H | CH | HCl, 3 H₂O<br>221<br>604; 6.71<br>G | 0.27 |
| 200 | nPr | *para-phenylene* | N-methyl-N-(2-methoxyethyl)methylamine | Cl | H | CH | Base<br>218<br>550; 8.79<br>G | 0.48 |

TABLE XIII-continued (I)

| Compounds No. | R₁ | A | R₃ | R₄ | R₅ | X | Salt, Hydrate m.p. ° C. MH+; tᴿ (min) Method | Inhibition of platelet aggregation in vitro (rat blood) in μM |
|---|---|---|---|---|---|---|---|---|
| 201 | nPr | *p-phenylene* | 4-cyclobutyl-piperazin-1-ylmethyl | Cl | H | CH | —<br>—<br>601; 3.25<br>A | 0.65 |
| 202 | nPr | *p-phenylene* | 1,4-dimethyl-3-(methoxymethyl)piperazin-2-yl | Cl | H | CH | —<br>—<br>605; 3.04<br>C | 0.43 |
| 203 | nPr | *p-phenylene* | 4-methylpiperazin-1-yl, Me | CF₃ | H | CH | HCl, H₂O<br>293<br>595; 6.75<br>G | 0.36 |
| 204 | nPr | *p-phenylene* | Chiral diazabicyclic-CH₂CH₂OMe | Cl | H | CH | —<br>—<br>631; 3.26<br>A | 0.44 |
| 205 | nPr | *p-phenylene* | Chiral diazabicyclic-CH₂CH₂OMe | Cl | H | CH | —<br>—<br>617; 3.22<br>A | 0.44 |

TABLE XIII-continued
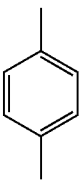
(I)
| Compounds No. | R₁ | A | R₃ | R₄ | R₅ | X | Salt, Hydrate m.p. ° C. MH+; t_R (min) Method | Inhibition of platelet aggregation in vitro (rat blood) in μM |
|---|---|---|---|---|---|---|---|---|
| 206 | nPr | 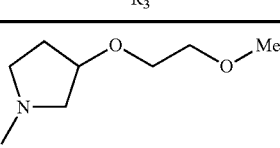 | 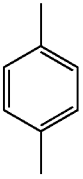 | Cl | H | CH | — <br> — <br> 606; 3.27 <br> A | 0.83 |
| 207 | nPr | 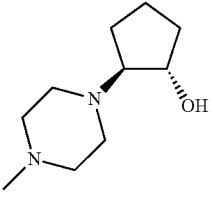 | 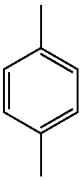 | Cl | H | CH | — <br> — <br> 631; 3.10 <br> A | 0.31 |
| 208 | nPr | 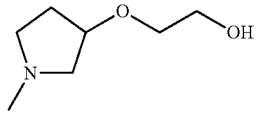 | 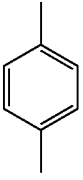 | Cl | H | CH | — <br> — <br> 592; 3.07 <br> A | 0.37 |
| 209 | nPr | 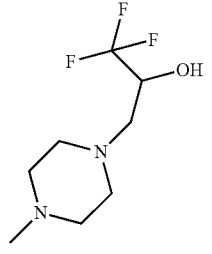 | 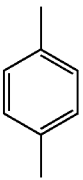 | Cl | H | CH | — <br> — <br> 659; 3.14 <br> A | 0.42 |
| 210 | nPr | | 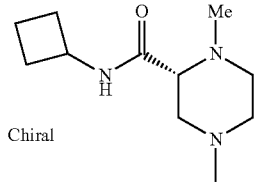 <br> Chiral | Cl | H | CH | — <br> — <br> 658; 3.19 <br> A | 0.70 |

TABLE XIII-continued (I)

| Compounds No. | R₁ | A | R₃ | R₄ | R₅ | X | Salt, Hydrate m.p. °C. MH+; t_R (min) Method | Inhibition of platelet aggregation in vitro (rat blood) in µM |
|---|---|---|---|---|---|---|---|---|
| 211 | nPr | *para-phenylene* | N-methylpiperazine-ethyl-N(Me)-C(O)Me | Cl | H | CH | —<br>646; 2.84;<br>A | 0.28 |
| 212 | nPr | *para-phenylene* | 1-methyl-piperazine-3-C(O)OMe | Cl | H | CH | NMR | / |
| 213 | nPr | *para-phenylene* | NH-S(O)₂Me (methylsulfonamide) | Me | H | CH | HCl, 1.6<br>H₂O<br>175<br>536; 9.02<br>G | 4.86 |
| 214 | nPr | *para-phenylene* | diazabicyclic-N-cyclobutyl, N-Me | Cl | H | CH | —<br>—<br>613; 3.33<br>A | 0.66 |
| 215 | nPr | *para-phenylene* | diazabicyclic-N-cyclobutyl, N-Me | Cl | H | CH | —<br>—<br>627; 3.44<br>A | 0.76 |

TABLE XIII-continued
(I)
| Compounds No. | R₁ | A | R₃ | R₄ | R₅ | X | Salt, Hydrate m.p. ° C. MH+; t$_R$ (min) Method | Inhibition of platelet aggregation in vitro (rat blood) in μM |
|---|---|---|---|---|---|---|---|---|
| 216 | Me | 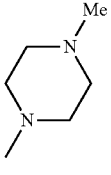 | 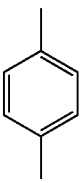 | Cl | H | CH | HCl, 1.9 H₂O 228 533; 5.89 J | 0.73 |
| 217 | Et | 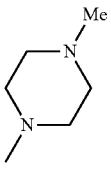 | 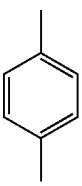 | Cl | H | CH | HCl, 0.3 H₂O 241 547; 6.23 G | 0.60 |
| 218 | EtO | 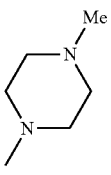 | 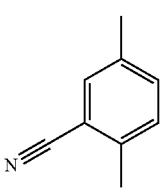 | Cl | H | CH | HCl, 1.2 H₂O 261 563; 11.81 H | 0.56 SAR196584 |
| 219 | nPr | 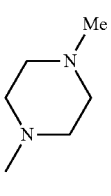 | 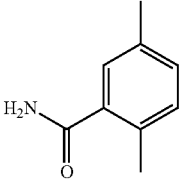 | Cl | H | CH | Base 126 586; 6.67 G | 0.54 |
| 220 | nPr | 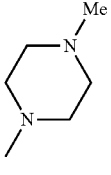 | | Cl | H | CH | HCl, 2 H₂O 250 604; 12.37 H | 0.22 |

TABLE XIII-continued

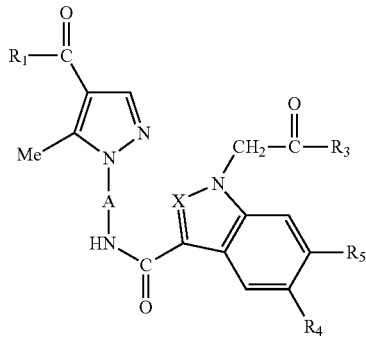
(I)

| Compounds No. | R₁ | A | R₃ | R₄ | R₅ | X | Salt, Hydrate m.p. °C. MH+; t_R (min) Method | Inhibition of platelet aggregation in vitro (rat blood) in μM |
|---|---|---|---|---|---|---|---|---|
| 221 | nPr | 2,5-dimethyl benzoate (methyl ester) | 4-methylpiperazin-1-yl | Cl | H | CH | —<br>—<br>619; 6.85<br>G | / |
| 222 | nPr | 2,5-dimethyl benzoate (methyl ester) | N,N-dimethylamino | Cl | H | CH | —<br>—<br>564; 9.38<br>G | / |
| 223 | nPr | 1,4-phenylene | 4-(tert-butoxycarbonyl)piperazin-1-yl | Me | H | CH | —<br>—<br>627; 9.26<br>G | / |
| 224 | nPr | 1,4-phenylene | 4-(tert-butoxycarbonyl)-3-methylpiperazin-1-yl | Me | H | CH | —<br>—<br>641; 9.45<br>G | / |
| 225 | nPr | 1,4-phenylene | 1-methyl-3-(tert-butoxycarbonylamino)piperidin-1-yl | Me | H | CH | —<br>—<br>641; 9.31<br>G | / |

TABLE XIII-continued

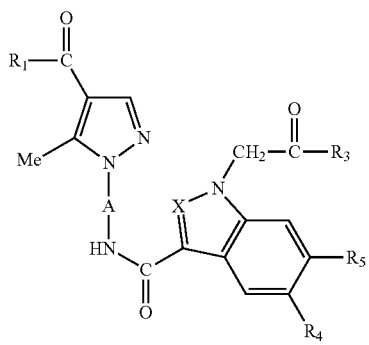

(I)

| Compounds No. | R₁ | A | R₃ | R₄ | R₅ | X | Salt, Hydrate m.p. °C. MH+; $t_R$ (min) Method | Inhibition of platelet aggregation in vitro (rat blood) in μM |
|---|---|---|---|---|---|---|---|---|
| 226 | nPr | *p-phenylene* | N-methyl-(S)-3-aminopyrrolidine-1-carboxylic acid tert-butyl ester | Me | H | CH | — — 627; 8.58 G | / |
| 227 | nPr | *p-phenylene* | 5-methyl-octahydropyrrolo[3,4-b]pyrrole-1-carboxylic acid tert-butyl ester | Me | H | CH | — ND — | / |
| 228 | nPr | *p-phenylene* | 2,5-dimethyl-4-methylpiperazine-1-carboxylic acid tert-butyl ester | Me | H | CH | — — 655; 9.26 G | / |
| 229 | nPr | *p-phenylene* | N-methyl-N-(1-methylpiperidin-4-yl)carbamic acid tert-butyl ester | Me | H | CH | — — 657; 9.09 G | / |

TABLE XIII-continued (I)

| Compounds No. | R₁ | A | R₃ | R₄ | R₅ | X | Salt, Hydrate m.p. °C. MH+; t_R (min) Method | Inhibition of platelet aggregation in vitro (rat blood) in μM |
|---|---|---|---|---|---|---|---|---|
| 230 | nPr | *p-phenylene* | N-methyl-2-(hydroxymethyl)piperazine-1-carboxylic acid tert-butyl ester | Me | H | CH | —<br>—<br>657; 8.25<br>G | / |
| 231 | nPr | *p-phenylene* | tert-butyl N-methyl-N-(1-methylpyrrolidin-3-yl)carbamate | Me | H | CH | —<br>—<br>ND<br>— | / |
| 232 | nPr | *p-phenylene* | tert-butyl N-methyl-N-(1-methylpiperidin-3-yl)carbamate | Me | H | CH | —<br>—<br>ND<br>— | / |
| 233 | nPr | *p-phenylene* | tert-butyl N-(1-methylpiperidin-4-yl)carbamate | Me | H | CH | —<br>—<br>ND<br>— | / |
| 234 | nPr | *p-phenylene* | tert-butyl 5-methyl-2,5-diazabicyclo[2.2.1]heptane-2-carboxylate (Chiral) | Me | H | CH | —<br>—<br>639; 9.11<br>G | / |

TABLE XIII-continued

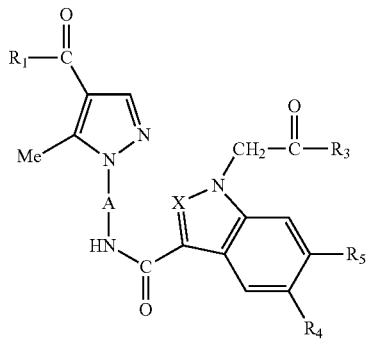

(I)

| Compounds No. | R₁ | A | R₃ | R₄ | R₅ | X | Salt, Hydrate m.p. °C. MH+; $t_R$ (min) Method | Inhibition of platelet aggregation in vitro (rat blood) in μM |
|---|---|---|---|---|---|---|---|---|
| 235 | nPr | *p-phenylene* | piperazine-N-Boc with 3-CH₂OH, N-Me | Me | H | CH | — <br> — <br> 657; 8.83 <br> G | / |
| 236 | nPr | *p-phenylene* | octahydropyrrolo[3,4-c]pyrrole-N-Boc, N'-Me | Me | H | CH | — <br> — <br> 653; 8.70 <br> G | / |
| 237 | nPr | *p-phenylene* | 3-(methylamino)piperidine-N-Boc | Me | H | CH | — <br> — <br> 641; 9.39 <br> G | / |
| 238 | nPr | *p-phenylene* | 4-methylpiperazine-N-Boc | Cl | H | CH | — <br> — <br> 647; 9.50 <br> G | / |
| 239 | nPr | *p-phenylene* | 2-methyl-4-methylpiperazine-N-Boc | Cl | H | CH | — <br> ND <br> — | / |

TABLE XIII-continued

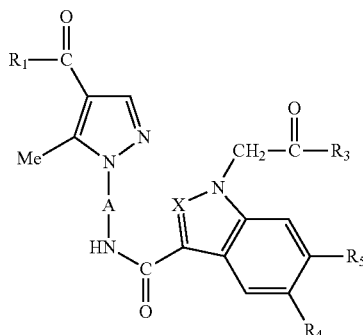

| Compounds No. | R₁ | A | R₃ | R₄ | R₅ | X | Salt, Hydrate m.p. °C. MH+; $t_R$ (min) Method | Inhibition of platelet aggregation in vitro (rat blood) in μM |
|---|---|---|---|---|---|---|---|---|
| 240 | nPr | (p-tolyl) | (5-methyl-4-(tert-butoxycarbonyl)piperazinyl with N-Me) | Cl | H | CH | — ND — | / |
| 241 | nPr | (p-tolyl) | (diazabicyclic tert-butoxycarbonyl with N-Me) | Cl | H | CH | — 673; 9.77 G | / |

Compounds Nos. 223 to 241 of formula (I) bearing a Pert-butyloxycarbonyl protective group on one of the nitrogen atoms do not display the required pharmacological activity. These are intermediates that can be used for preparing the compounds of formula (I) Nos. 242 to 260.

The NMR analyses for certain compounds are given below:

Compound 106

¹H NMR: DMSO-d₆ (250 MHz): δ (ppm): 0.94 (3H, t); 1.63 (2H, m); 2.33 (6H, s); 2.52 (3H, s); 2.81 (2H, t); 2.89 (3H, s); 3.14 (3H, s); 5.22 (2H, s); 7.25 (1H, s); 7.47 (2H, d); 7.93-7.99 (3H, m); 8.09 (1H, s); 8.24 (1H, s); 9.97 (1H, s).

Compound 107

¹H NMR: DMSO-d₆ (250 MHz): δ (ppm): 0.94 (3H, t); 1.63 (2H, m); 2.33 (6H, s); 2.52 (3H, s); 2.78-2.84 (5H, m); 2.91-3.24 (3H, m); 3.39-3.75 (3H, m); 4.11-4.45 (2H, m); 5.20-5.45 (2H, m); 7.27 (1H, s); 7.47 (2H, d); 7.95-8.01 (3H, m); 8.12 (1H, s); 8.25 (1H, s); 10.06 (1H, s); 11.18 (1H, br).

Compound 114

¹H NMR: DMSO-d₆ (250 MHz): δ (ppm): 0.94 (3H, t); 1.64 (2H, m); 2.43 (3H, s); 2.52 (3H, s); 2.78-2.81 (5H, m); 2.93-3.24 (3H, m); 3.41-3.64 (3H, m); 4.15-4.46 (2H, m); 5.29 (1H, d); 5.43 (1H, d); 7.06 (1H, d); 7.37 (1H, d); 7.48 (2H, d); 7.97 (2H, d); 8.02 (1H, s); 8.17 (1H, s); 8.24 (1H, s); 10.06 (1H, s); 10.60 (1H, br).

Compound 115

¹H NMR: DMSO-d₆ (250 MHz): δ (ppm): 0.94 (3H, t); 1.64 (2H, m); 2.52 (3H, s); 2.78-2.89 (5H, m); 2.93-3.24 (3H, m); 3.39-3.69 (3H, m); 4.20 (1H, s); 4.39 (1H, s); 5.35 (1H, d); 5.50 (1H, d); 7.28 (1H, d); 7.49 (2H, d); 7.56 (1H, d); 7.96 (2H, d); 8.22 (1H, s); 8.25 (1H, s); 8.31 (1H, s); 10.21 (1H, s); 10.95 (1H, br).

Compound 119

¹H NMR: DMSO-d₆ (250 MHz): δ (ppm): 0.94 (3H, t); 1.64 (2H, m); 2.43 (3H, s); 2.52 (3H, s); 2.82 (2H, t); 2.97-3.28 (3H, m); 3.34 (3H, s); 3.35-3.41 (2H, m); 3.50-3.77 (6H, m); 4.20 (1H, d); 4.38 (1H, d); 5.29 (1H, d); 5.42 (1H, d); 7.06 (1H, d); 7.39 (1H, d); 7.48 (2H, d); 7.98 (2H, d); 8.03 (1H, s); 8.20 (1H, s); 8.24 (1H, s); 10.08 (1H, s); 10.80 (1H, br).

Compound 128

¹H NMR: DMSO-d₆ (250 MHz): δ (ppm): 0.94 (3H, t); 1.64 (2H, m); 2.43 (3H, s); 2.52 (3H, s); 2.82 (2H, t); 3.48-

3.70 (8H, m); 5.31 (2H, s); 7.06 (1H, d); 7.37 (1H, d); 7.48 (2H, d); 7.97 (2H, d); 8.02 (1H, s); 8.20 (1H, s); 8.24 (1H, s); 10.01 (1H, s).

Compound 136

$^1$H NMR: DMSO-d$_6$ (250 MHz): δ (ppm): 0.94 (3H, t); 1.64 (2H, m); 2.52 (3H, s); 2.78-3.25 (8H, m); 3.40-3.68 (3H, m); 3.80 (3H, s); 4.13-4.49 (2H, m); 5.28 (1H, d); 5.43 (1H, d); 6.87 (1H, d); 7.40 (1H, d); 7.48 (2H, d); 7.74 (1H, s); 7.97 (2H, d); 8.20 (1H, s); 8.25 (1H, s); 10.07 (1H, s); 10.70 (1H, br).

Compound 137

$^1$H NMR: DMSO-d$_6$ (250 MHz): δ (ppm): 0.94 (3H, t); 1.11 (2H, d); 1.34 (1H, d); 1.63 (2H, m); 1.90-2.20 (2H, m); 2.44 (3H, s); 2.52 (3H, s); 2.82 (2H, t); 310-4.55 (10H, m); 5.15-5.60 (2H, m); 7.07 (1H, d); 7.37-7.48 (3H, m); 7.98-8.03 (3H, m); 8.18-8.25 (2H, m); 10.05 (1H, s); 10.30-11.50 (1H, m).

Compound 142

$^1$H NMR: DMSO-d$_6$ (250 MHz): δ (ppm): 0.94 (3H, t); 1.64 (2H, m); 2.52 (3H, s); 2.82 (2H, t); 3.01-3.77 (8H, m); 4.13-4.48 (2H, m); 4.81-5.03 (2H, m); 5.36 (1H, d); 5.51 (1H, d); 7.28 (1H, d); 7.50 (2H, d); 7.56 (1H, d); 7.96 (2H, d); 8.21 (1H, s); 8.25 (1H, s); 8.30 (1H, s); 10.20 (1H, s); 10.90 (1H, br).

Compound 145

$^1$H NMR: DMSO-d$_6$ (250 MHz): δ (ppm): 0.94 (3H, t); 1.64 (2H, m); 2.52 (3H, s); 2.82 (2H, t); 3.06 (1H, m); 3.10-3.78 (14H, m); 3.86 (2H, m); 4.19 (1H, d); 4.37 (1H, d); 5.36 (1H, d); 5.51 (1H, d); 7.27 (1H, d); 7.49 (2H, d); 7.58 (1H, d); 7.98 (2H, d); 8.22 (1H, s); 8.25 (1H, s); 8.36 (1H, s); 10.24 (1H, s); 11.03 (1H, br).

Compound 146

$^1$H NMR: DMSO-d$_6$ (250 MHz): δ (ppm): 0.94 (3H, t); 1.63 (2H, m); 2.52 (3H, s); 2.82 (2H, t); 2.98-3.31 (5H, m); 3.52-3.86 (5H, m); 4.15-4.42 (2H, m); 5.37 (1H, d); 5.50 (1H, d); 7.28 (1H, d); 7.49 (2H, d); 7.57 (1H, d); 7.97 (2H, d); 8.22 (1H, s); 8.25 (1H, s); 8.34 (1H, s); 10.22 (1H, s); 10.53 (1H, br).

Compound 147

$^1$H NMR: DMSO-d$_6$ (250 MHz): δ (ppm): 0.94 (3H, t); 1.64 (2H, m); 2.43 (3H, s); 2.52 (3H, s); 2.81 (2H, t); 2.90-3.70 (6H, m); 4.21 (2H, d); 4.40 (2H, d); 5.27 (1H, d); 5.41 (1H, d); 7.05 (1H, d); 7.31-7.39 (3H, m); 7.47 (2H, d); 7.66 (1H, d); 7.96 (2H, d); 8.02 (1H, s); 8.15 (1H, s); 8.24 (1H, s); 10.04 (1H, s); 10.90 (1H, br).

Compound 148

$^1$H NMR: DMSO-d$_6$ (250 MHz): δ (ppm): 0.94 (3H, t); 1.63 (2H, m); 2.52 (3H, s); 2.82 (2H, t); 2.88-4.70 (15H, m); 5.39 (1H, br); 5.49 (1H, br); 7.28 (1H, d); 7.49 (2H, d); 7.57 (1H, d); 7.97 (2H, d); 8.22 (1H, s); 8.25 (1H, s); 8.36 (1H, s); 10.20 (1H, s); 11.64 (1H, br).

Compound 154

$^1$H NMR: DMSO-d$_6$ (250 MHz): δ (ppm): 0.94 (3H, t); 1.64 (2H, m); 2.52 (3H, s); 2.82 (2H, t); 2.95 (6H, d); 3.01-3.29 (3H, m); 3.47-3.80 (3H, m); 4.10-4.46 (4H, m); 5.38 (1H, s); 5.49 (1H, s); 7.28 (1H, d); 7.50 (2H, d); 7.56 (1H, d); 7.96 (2H, d); 8.22 (1H, s); 8.25 (1H, s); 8.31 (1H, s); 10.09-10.24 (2H, m).

Compound 157

$^1$H NMR: DMSO-d$_6$ (250 MHz): δ (ppm): 0.94 (3H, t); 1.63 (2H, m); 2.52 (3H, s); 2.80-3.70 (11H, m); 4.15 (1H, br); 4.39 (1H, br); 5.33 (1H, br); 5.48 (1H, br); 7.50 (2H, d); 7.73 (1H, d); 7.96 (2H, d); 8.25 (1H, d); 8.30 (1H, d); 8.34 (1H, s); 10.25 (1H, s); 10.95 (1H, br).

Compound 158

$^1$H NMR: DMSO-d$_6$ (250 MHz): δ (ppm): 0.94 (3H, t); 1.63 (2H, m); 2.52 (3H, s); 2.82 (2H, t); 2.91-3.84 (13H, m); 4.15 (1H, d); 4.37 (1H, d); 5.33 (1H, d); 5.49 (1H, d); 7.49 (2H, d); 7.74 (1H, d); 7.98 (2H, d); 8.25 (1H, s); 8.31 (1H, d); 8.34 (1H, s); 10.29 (1H, s); 11.02 (1H, br).

Compound 159

$^1$H NMR: DMSO-d$_6$ (250 MHz): δ (ppm): 0.94 (3H, t); 1.29 (3H, d); 1.35 (3H, d); 1.64 (2H, m); 2.52 (3H, s); 2.69-2.85 (3H, m); 3.11-3.68 (3H, m); 4.15 (1H, d); 4.42 (1H, d); 5.35 (1H, d); 5.54 (1H, d); 7.27 (1H, d); 7.49 (2H, d); 7.58 (1H, d); 7.98 (2H, d); 8.21 (1H, s); 8.24 (1H, s); 8.34 (1H, s); 9.22-9.46 (1H, m); 9.60-9.79 (1H, m); 10.22 (1H, br).

Compound 165

$^1$H NMR: DMSO-d$_6$ (250 MHz): δ (ppm): 0.94 (3H, t); 1.64 (2H, m); 2.52 (3H, s); 2.82 (2H, t); 2.90-3.23 (3H, m); 3.44-3.73 (2H, m); 4.19 (1H, d); 4.41 (3H, s); 5.34 (1H, d); 5.49 (1H, d); 7.27 (1H, d); 7.36 (2H, t); 7.49 (2H, d); 7.55 (1H, d); 7.68 (2H, s); 7.96 (2H, d); 8.21 (1H, s); 8.25 (1H, s); 8.30 (1H, s); 10.19 (1H, s); 11.08 (1H, br).

Compound 166

$^1$H NMR: DMSO-d$_6$ (250 MHz): δ (ppm): 0.94 (3H, t); 1.64 (2H, m); 2.48 (3H, s); 2.52 (3H, s); 2.82 (2H, t); 2.88-3.35 (4H, m); 3.63-4.78 (6H, m); 5.39 (1H, s); 5.44 (1H, s); 6.61 (1H, s); 7.27 (1H, d); 7.49 (2H, d); 7.56 (1H, d); 7.97 (2H, d); 8.21 (1H, s); 10.20 (1H, s); 11.83 (1H, br).

Compound 177

$^1$H NMR: DMSO-d$_6$ (250 MHz): δ (ppm): 0.94 (3H, t); 1.34 (2H, d); 1.56 (1H, d); 1.63 (2H, m); 2.52 (3H, s); 2.77-2.87 (6H, m); 3.13 (1H, br); 3.35-3.74 (3H, m); 4.11 (0.6H, d); 4.41 (0.39H, d); 4.59 (0.39H, br); 4.74 (0.61 H, br); 5.22-5.65 (2H, m); 7.28 (1H, d); 7.45-7.58 (3H, m); 7.97 (2H, d); 8.20-8.35 (3H, m); 10.21 (1H, s); 10.68 (1H, br).

Compound 179

$^1$H NMR: DMSO-d$_6$ (250 MHz): δ (ppm): 0.94 (3H, t); 1.33 (3H, d); 1.64 (2H, m); 2.52 (3H, s); 2.82 (2H, t); 3.00-3.79 (12H, m); 4.18 (1H, d); 4.42 (1H, d); 5.36 (1H, d); 5.49 (1H, d); 7.28 (1H, d); 7.49 (2H, d); 7.58 (1H, d); 7.97 (2H, d); 8.21 (1H, s); 8.24 (1H, s); 8.38 (1H, s); 10.21 (1H, s); 10.62 (1H, br).

Compound 180

$^1$H NMR: DMSO-d$_6$ (250 MHz): δ (ppm): 0.94 (3H, t); 1.38 (6H, s); 1.63 (2H, m); 2.52 (3H, s); 2.81 (2H, t); 2.96-

3.09 (1H, m); 3.19-3.30 (2H, m); 3.37 (3H, s); 3.47-3.61 (4H, m); 3.72-3.84 (1H, m); 4.16 (1H, d); 4.42 (1H, d); 5.37 (1H, d); 5.47 (1H, d); 7.27 (1H, d); 7.49 (2H, d); 7.59 (1H, d); 7.98 (2H, d); 8.22 (1H, s); 8.24 (1H, s); 8.35 (1H, s); 10.22 (1H, s); 10.44 (1H, br).

Compound 181

$^1$H NMR: DMSO-$d_6$ (250 MHz): δ (ppm): 0.94 (3H, t); 1.33 (6H, s); 1.63 (2H, m); 2.52 (3H, s); 2.81 (2H, t); 2.97-3.10 (1H, m); 3.20-3.30 (2H, m); 3.50-3.64 (4H, m); 3.73-3.84 (1H, m); 4.18 (1H, d); 4.43 (1H, d); 5.38 (1H, d); 5.48 (1H, d); 5.80 (1H, br); 7.27 (1H, d); 7.49 (2H, d); 7.59 (1H, d); 7.98 (2H, d); 8.22 (1H, s); 8.24 (1H, s); 8.36 (1H, s); 10.13 (1H, br); 10.24 (1H, s).

Compound 192

$^1$H NMR: DMSO-$d_6$ (250 MHz): δ (ppm): 0.94 (3H, t); 1.64 (2H, m); 1.88-2.30 (4H, m); 2.52 (3H, s); 2.76-2.85 (5H, m); 3.08 (1H, t); 3.36-3.57 (3H, m); 4.65 (1H, s); 4.72 (1H, s); 5.31 (1H, d); 5.42 (1H, d); 7.29 (1H, d); 7.49 (2H, d); 7.60 (1H, d); 7.97 (2H, d); 8.22 (1H, s); 8.25 (1H, s); 8.36 (1H, s); 10.15 (1H, br); 10.19 (1H, s).

Compound 196

$^1$H NMR: DMSO-$d_6$ (250 MHz): δ (ppm): 0.95 (3H, t); 1.64 (2H, m); 1.76 (1H, m); 1.91 (1H, m); 2.24 (1H, m); 2.55 (3H, s); 2.85 (2H, t); 2.88 (1H, m); 2.95 (2H, m); 3.27 (3H, s); 3.42-3.72 (5H, m); 3.89-4.07 (1H, br); 4.23 (1H, br); 4.48 (1H, br); 5.50 (2H, br); 7.34 (1H, br); 7.56 (2H, d); 7.63 (1H, d); 8.02 (2H, d); 8.28 (1H, d); 8.32 (1H, s); 8.35 (1H, s); 10.23 (2H, s Br).

Compound 199

$^1$H NMR: DMSO-$d_6$ (250 MHz): δ (ppm): 0.94 (3H, t); 1.64 (2H, m); 2.52 (3H, s); 2.82 (2H, t); 2.98-4.48 (10H, m); 5.38 (1H, s); 5.46 (1H, s); 7.28 (1H, d); 7.49 (2H, d); 7.56 (1H, d); 7.74 (1H, s); 7.97 (2H, d); 8.02 (1H, s); 8.21 (1H, s); 8.24 (1H, s); 8.31 (1H, s); 10.20 (1H, s); 10.31 (1H, br).

Compound 200

$^1$H NMR: DMSO-$d_6$ (250 MHz): δ (ppm): 0.94 (3H, t); 1.64 (2H, m); 2.53 (3H, s); 2.82 (2H, t); 2.89 (1.65H, s); 3.18 (1.35H, s); 3.26 (1.35H, s); 3.41 (1.65H, s); 3.47 (2H, m); 3.64 (2H, m); 5.34 (2H, s); 7.27 (1H, d); 7.43 (0.55H, d); 7.49 (2H, d); 7.54 (0.45H, d); 7.96 (2H, d); 8.21 (1H, s); 8.24 (1H, s); 8.30 (1H, s); 10.11 (0.55H, s); 10.13 (0.45H, s).

Compound 203

$^1$H NMR: DMSO-$d_6$ (250 MHz); δ (ppm): 0.94 (3H, t); 1.64 (2H, m); 2.53 (3H, s); 2.79-3.25 (8H, m); 3.40-3.69 (3H, m); 4.10-4.50 (2H, m); 5.43 (1H, d); 5.58 (1H, d); 7.50 (2H, d); 7.57 (1H, d); 775 (1H, d); 7.98 (2H, d); 8.25 (1H, s); 8.41 (1H, s); 8.59 (1H, s); 10.29 (1H, s); 10.49 (1H, br).

Compound 209

$^1$H NMR: DMSO-$d_6$ (250 MHz): δ (ppm): 0.93 (3H, t); 1.63 (2H, m); 2.52 (3H, s); 2.82 (2H, t); 3.05-3.75 (11H, m); 4.32/1H, br); 4.83 (1H, br); 5.49 (2H, br); 7.33 (1H, d); 7.55 (2H, d); 7.61 (1H, d); 8.01 (2H, d); 8.27 (1H, d); 8.31 (1H, s); 8.36 (1H, s); 10.23 (1H, s); 10.68 (1H, br).

Compound 212: TLC $^1$H NMR: DMSO-$d_6$ (250 MHz): δ (ppm): 0.94 (3H, t); 1.64 (2H, m); 2.53 (3H, s); 2.55-4.20 (13H, m); 5.20-5.60 (2H, m); 7.26 (1H, d); 7.45-7.55 (3H, m); 7.96 (2H, d); 8.22 (1H, s); 8.24 (1H, s); 8.32 (1H, s); 10.15 (1H, s).

Compound 219

$^1$H NMR: DMSO-$d_6$ (250 MHz): δ (ppm): 0.94 (3H, t); 1.64 (2H, m); 2.23 (3H, s); 2.30 (2H, m); 2.44 (2H, m); 2.58 (3H, s); 2.84 (2H, t); 3.48 (2H, m); 3.59 (2H, m); 5.40 (2H, s); 7.28 (1H, d); 7.56 (1H, d); 7.81 (1H, d); 7.90 (1H, d); 8.11 (1H, s); 8.16 (1H, s); 8.28 (1H, s); 8.32 (1H, s); 10.37 (1H, s).

Compound 221

$^1$H NMR: DMSO-$d_6$ (250 MHz): δ (ppm): 0.95 (3H, t); 1.64 (2H, m); 2.24 (3H, s); 2.32 (2H, m); 2.45 (2H, m); 2.55 (3H, s); 2.83 (2H, t); 3.48 (2H, m); 3.58 (2H, m); 5.43 (2H, s); 7.30 (1H, d); 7.56 (1H, d); 7.85 (1H, d); 8.08 (1H, s); 8.12 (1H, s); 8.22 (1H, s); 8.29 (1H, s); 8.76 (1H, d); 11.25 (1H, s).

Example 12

Compound No. 242

N-[4-(4-Butyryl-5-methyl-1H-pyrazol-1-yl)phenyl]-5-methyl-1-[2-(3-methylpiperazin-1-yl)-2-oxoethyl]-1H-indole-3-carboxamide hydrochloride 8.19 ml of a solution of 4N HCl in dioxane is added to 1.05 g of compound No. 224 in 20 ml of EtOAc/MeOH mixture (50/50; v/v). After 20 hours at RT, the precipitate is filtered, triturated with acetone and then filtered, obtaining 0.77 g of the expected compound.

$^1$H NMR: DMSO-$d_6$ (250 MHz): δ (ppm): 0.94 (3H, t); 1.22-1.39 (3H, m); 1.64 (2H, m); 2.43 (3H, s); 2.52 (3H, s); 2.81 (2H, t); 2.85-3.75 (5H, m); 4.02-4.39 (2H, m); 5.22-5.50 (2H, m); 7.06 (1H, d); 7.40 (1H, d); 7.48 (2H, d); 7.99 (2H, d); 8.03 (1H, s); 8.22 (1H, s); 8.24 (1H, s); 9.44-9.74 (2H, m); 10.09 (1H, s).

MH$^+$=541; $t_R$=6.33 min (Method G).

m.p.=223° C.

Following the procedure described in Example 12 and starting from the N-protected compounds No. 224 to 241, the compounds of formula (I) presented in TABLE XIV below are prepared:

In this table:

in the column "Salt", "-" represents a compound in the form of free base, whereas "HCl" represents a compound in the form of hydrochloride, "TFA" represents a compound in the form of trifluoroacetate;

Me represents a methyl radical;

TABLE XIV (I)

[Structure: n-Pr-C(=O)- attached to pyrazole (with Me) - phenyl - NH-C(=O)- indole (with R4) - N-CH2-C(=O)-R3]

| Compounds No. | R4 | R3 | Salt, Hydrate m.p. °C. MH+; t_R (min) Method | Inhibition of platelet aggregation in vitro (rat blood) in μM |
|---|---|---|---|---|
| 242 | Me | (2-methyl-piperazinyl, NH) | HCl, 223 541; 6.33 G | 0.51 |
| 243 | Me | (4-methyl-piperazinyl, NH) | HCl, 1.7 H2O 195 527; 6.27 G | 0.54 |
| 244 | Me | (1-methyl-3-aminopiperidinyl) | HCl, 3.7 H2O 208 541; 5.85 G | 0.96 |
| 245 | Me | (1-methyl-3-(methylamino)pyrrolidinyl) Chiral | HCl, 1.3 H2O 180 527; 6.25 G | 0.53 |
| 246 | Me | (octahydropyrrolo[3,4-b]pyrrole) | HCl, 1.4 H2O 186 553; 6.27 G | 0.85 |
| 247 | Me | (2,5-dimethylpiperazinyl, N-Me) | HCl, 2.5 H2O 196 555; 6.41 G | 0.26 |

TABLE XIV-continued (I)

[Structure: n-Pr-C(=O)- attached to pyrazole (with Me) - phenyl - NH-C(=O)- indole (with R4) - N-CH2-C(=O)-R3]

| Compounds No. | R4 | R3 | Salt, Hydrate m.p. °C. MH+; t_R (min) Method | Inhibition of platelet aggregation in vitro (rat blood) in μM |
|---|---|---|---|---|
| 248 | Me | (1-methyl-4-(methylamino)piperidinyl) | HCl, 1 H2O 199 555; 6.30 G | 0.32 |
| 249 | Me | (1-methyl-2-(hydroxymethyl)piperazinyl) | HCl, 2 H2O 213 557; 6.27 G | 0.24 |
| 250 | Me | (1-methyl-3-(methylamino)pyrrolidinyl) | HCl 175 541; 6.27 G | 0.61 |
| 251 | Me | (1-methyl-3-(methylamino)hexahydropyrimidinyl) | HCl, H2O 196 555; 6.36 G | 0.54 |
| 252 | Me | (1-methyl-4-aminopiperidinyl) | HCl, 1.5 H2O 222 541; 6.28 G | 0.40 |
| 253 | Me | Chiral (2-methyl-2,5-diazabicyclo[2.2.1]heptanyl) | HCl, 2.3 H2O 223 549; 6.25 G | 0.33 |

TABLE XIV-continued (I)

| Compounds No. | R$_4$ | R$_3$ | Salt, Hydrate m.p. ° C. MH$^+$; t$_R$ (min) Method | Inhibition of platelet aggregation in vitro (rat blood) in μM |
|---|---|---|---|---|
| 254 | Me | (1-methylpiperazin-2-yl)methanol group | HCl, 3 H$_2$O 225 557; 6.23 G | 0.19 |
| 255 | Me | octahydropyrrolo[3,4-b]pyrrole (N-methyl) | HCl, 1.8 H$_2$O 230 553; 11.44 H | 0.18 |
| 256 | Cl | 4-methylpiperazine | HCl, 2.6 H$_2$O 258 547; 5.86 G | 0.23 |
| 257 | Cl | 3-methyl-1-methylpiperazine | — 561; 3.24 A | 0.46 |
| 258 | Cl | 2-methyl-1-methylpiperazine | — 561; 3.20 A | 0.30 |
| 259 | Cl | diazabicyclic amine | HCl, H$_2$O 219 573; 6.52 G | 0.45 |
| 260 | Me | N-methyl-3-aminopiperidine | — 541; 6.33 G | / |

The NMR analyses for certain compounds are given below:

Compound 256

$^1$H NMR: DMSO-d$_6$ (250 MHz): δ (ppm): 0.94 (3H, t); 1.63 (2H, m); 2.52 (3H, s); 2.82 (2H, t); 3.11 (2H, br); 3.27 (2H, br); 3.64-3.84 (4H, m); 5.42 (2H, s); 7.27 (1H, d); 7.49 (2H, d); 7.58 (1H, d); 7.97 (2H, d); 8.21 (1H, s); 8.25 (1H, s); 8.33 (1H, s); 9.32 (2H, br); 10.21 (1H, s).

Compound 259

$^1$H NMR: DMSO-d$_6$ (250 MHz): δ (ppm): 0.94 (3H, t); 1.64 (2H, m); 1.86-2.17 (4H, m); 2.52 (3H, s); 2.82 (2H, t); 3.10 (1H, d); 3.67 (1H, d) 3.92 (1H, d); 4.02-4.20 (3H, m); 5.30 (2H, d); 5.58 (2H, d); 7.28 (1H, d); 7.49 (2H, d); 7.56 (1H, d); 7.96 (2H, d); 8.21 (1H, s); 8.25 (1H, s); 8.33 (1H, s); 9.18 (2H, br); 10.16 (1H, s).

Example 13

Compound No. 261

N-[4-(4-Butyryl-5-methyl-1H-pyrazol-1-yl)phenyl]-5-chloro-1-{2-[4-(2-methoxyethyl)-3,5-dimethylpiperazin-1-yl]-2-oxoethyl}-1H-indole-3-carboxamide hydrochloride 0.12 g of potassium carbonate, 0.13 g of sodium iodide and then 0.080 ml of 1-bromo-2-methoxyethane are added to 0.4 g of compound No. 159 in 5 ml of DMF. The reaction mixture is placed in a microwave apparatus at 160° C. for 40 min (300 W). After it returns to RT, it is poured into 50 ml of water and extracted with EtOAc. The combined organic phases are washed with water, dried over $Na_2SO_4$ and evaporated to dryness. The solid residue is purified by silica gel chromatography, eluting with DCM/MeOH mixture (gradient from 3 to 5% of MeOH), obtaining 0.12 g of powder. The product is dissolved in 4 ml of DCM/MeOH mixture (1/1; v/v) and then 0.38 ml of 1M HCl solution in ether is added. The hydrochloride is precipitated with 10 ml of ether and then filtered, obtaining 0.103 g of a white powder.

$^1$H NMR: DMSO-$d_6$ (250 MHz): δ (ppm): 0.94 (3H, t); 1.36 (3H, d); 1.43 (3H, d); 1.63 (2H, m); 2.52 (3H, s); 2.81 (2H, t); 3.05 (1H, t); 3.35 (3H, s); 3.38-3.77 (7H, m); 4.19 (1H, d); 4.41 (1H, d); 5.33 (1H, d); 5.55 (1H, d); 7.28 (1H, d); 7.49 (2H, d); 7.58 (1H, d); 7.97 (2H, d); 8.22 (1H, s); 8.24 (1H, s); 8.34 (1H, s); 10.21 (1H, s); 10.97 (1H, br), $MH^+$=633; $t_R$=6.25 min (Method G).

m.p.=187° C.

Example 14

Compound No. 262

N-[4-(4-Butyryl-5-methyl-1H-pyrazol-1-yl)phenyl]-5-chloro-1-[2-oxo-2-(3,4,5-trimethylpiperazin-1-yl)ethyl]-1H-indole-3-carboxamide hydrochloride 0.12 g of potassium carbonate, and then 0.053 ml of iodomethane, are added to 0.4 g of compound No. 159 in 5 ml of DMF. After 20 h at RT, water is added and it is extracted with EtOAc. The organic phase is washed with water, dried over $Na_2SO_4$ and then evaporated to dryness. The solid residue is purified by silica gel chromatography, eluting with DCM/MeOH mixture (95/5; v/v), obtaining 0.17 g of powder, The product is dissolved in 5 ml of acetone, then 1 ml of 1M HCl solution in ether is added. The hydrochloride is precipitated with 10 ml of diethyl ether and then filtered, obtaining 0.095 g of a white powder.

$^1$H NMR: DMSO-$d_6$ (250 MHz): δ (ppm): 0.94 (3H, t); 1.38 (3H, d); 1.45 (3H, d); 1.63 (2H, m); 2.52 (3H, s); 2.79-2.85 (5H, m); 2.97 (1H, t); 3.22-3.52 (3H, m); 4.21 (1H, d); 4.41 (1H, d); 5.33 (1H, d); 5.55 (1H, d); 7.28 (1H, d); 7.49 (2H, d); 7.57 (1H, d); 7.97 (2H, d); 8.22 (1H, s); 8.25 (1H, s); 8.33 (1H, s); 10.21 (1H, s); 10.85 (1H, br), $MH^+$=589; $t_R$=6.12 min (Method G).

m.p.=217° C.

Following the procedure described in Example 14, the compounds of formula (I) presented in TABLE XV below are prepared:

In this table:

in the column "Salt", "Base" represents a compound in the form of free base, whereas "HCl" represents a compound in the form of hydrochloride, "TFA" represents a compound in the form of trifluoroacetate;

Me represents a methyl radical;

TABLE XV (I)

[Structure of formula (I): n-Pr-C(O)- attached to pyrazole with Me, linked via N to phenyl ring, attached to indole bearing R4, with CH2-C(O)-R3 on indole N and HN-C(O)- amide linkage]

| Compounds No. | R$_4$ | R$_3$ | Salt, Hydrate m.p. ° C. $MH^+$; $t_R$ (min) Method | Inhibition of platelet aggregation in vitro (rat blood) in μM |
|---|---|---|---|---|
| 263 | Me | [3,4,5-trimethylpiperazin-1-yl] | HCl, 2 H$_2$O 195 569; 6.44 G | 0.42 |
| 264 | Me | Chiral [2,5-diazabicyclo with Me, H stereochem] | HCl, 1.7 H$_2$O 217 553; 5.71 G | 0.56 |
| 265 | Me | [octahydropyrrolo[3,4-b]pyrrole N-Me, N-Me] | HCl, 1.1 H$_2$O 205 567; 6.29 G | 0.79 |
| 266 | Me | [octahydropyrrolo[3,4-c]pyrrole with Me groups] | HCl, 2.7 H$_2$O 260 567; 6.18 G | 0.40 |
| 267 | Me | [3-(methylamino)piperidine with Me] | HCl, 1.5 H$_2$O 197 555; 5.79 G | 0.45 |

TABLE XV-continued (I)

[Structure showing n-Pr-C(=O)- attached to pyrazole with Me, N-N, connected to phenyl-NH-C(=O)- indole with R4, and CH2-C(=O)-R3]

| Compounds No. | R4 | R3 | Salt, Hydrate m.p. ° C. MH⁺; t_R (min) Method | Inhibition of platelet aggregation in vitro (rat blood) in μM |
|---|---|---|---|---|
| 268 | Me | [N-Me piperazine with CH2OH substituent, N-Me] | HCl, 2 H₂O 234 571; 6.27 G | 0.24 |
| 269 | Me | [N-Me piperazine with Me substituent, N-Me] | HCl, 1.7 H₂O 198 555; 6.37 G | 0.35 |

The NMR analyses for certain compounds are given below:

Compound 263

$^1$H NMR: DMSO-d$_6$ (250 MHz): δ (ppm): 0.94 (3H, t); 1.36 (3H, d); 1.58-1.68 (5H, m); 2.43 (3H, s); 2.52 (3H, s); 2.82 (2H, t); 2.88 (3H, s); 3.06-3.30 (2H, m); 3.42-3.59 (2H, m); 4.56-4.75 (2H, m); 5.18 (1H, d); 5.56 (1H, d); 7.07 (1H, d); 7.31 (1H, d); 7.48 (2H, d); 7.98 (2H, d); 8.03 (1H, s); 8.25 (2H, s); 10.07 (1H, s); 10.56 (1H, br).

Compound 268

$^1$H NMR: DMSO-d$_6$ (250 MHz): δ (ppm): 0.94 (3H, t); 1.64 (2H, m); 2.43 (3H, s); 2.52 (3H, s); 2.82 (2H, t); 2.89 (3H, s); 3.00-4.50 (9H, m); 5.20-5.52 (2H, m); 5.70 (1H, br); 7.06 (1H, d); 7.38 (1H, d); 7.48 (2H, d); 7.97 (2H, d); 7.99 (1H, s); 8.03 (1H, s); 8.21 (1H, s); 10.00-10.30 (2H, m).

Compound 269

$^1$H NMR: DMSO-d$_6$ (250 MHz): δ (ppm): 0.94 (3H, t); 1.37 (3H, d); 1.63 (2H, m); 2.43 (3H, s); 2.52 (3H, s); 2.74-2.85 (5H, m); 2.89-4.46 (7H, m); 5.22-5.53 (2H, m); 7.06 (1H, d); 7.38 (1H, d); 7.48 (2H, d); 7.98 (2H, d); 8.03 (1H, s); 8.19 (1H, s); 8.25 (1H, s); 10.08 (1H, s); 11.01 (0.8H, br); 11.19 (0.2H, br).

Example 15

Compound No. 270

Methyl 4-[(3-{[4-(4-butyryl-5-methyl-1H-pyrazol-1-yl)phenyl]carbamoyl}-5-chloro-1H-indol-1-yl)acetyl]-1-methylpiperazine-2-carboxylate 0.62 ml of formaldehyde in solution at 37% in water is added to 0.5 g of compound No. 212 in 1 ml of formic acid at 50° C., and it is heated at 70° C. for 1.5 h. The reaction mixture is added to 15 ml of a saturated solution of sodium bicarbonate. The precipitate formed is filtered, it is washed with water and then dried in a vacuum stove at 50° C., obtaining 0.49 g of a white powder.

$^1$H NMR: DMSO-d$_6$ (250 MHz): δ (ppm): 0.94 (3H, t); 1.65 (2H, m); 2.20-345 (4H, m); 2.52 (3H, s); 2.82 (2H, t); 3.06-3.35 (2H, m); 3.40-3.85 (7H, m); 5.10-5.50 (2H, m); 7.27 (1H, d); 7.48-7.52 (3H, m); 7.95 (2H, d); 8.21 (1H, s); 8.24 (1M, s); 8.29 (1H, s); 10.15 (1H, s).

MH⁺=619; t$_R$=7.41 min (Method G)

Example 16

Compound No. 271

4-[(3-{[4-(4-Butyryl-5-methyl-1H-pyrazol-1-yl)phenyl]carbamoyl}-5-chloro-1H-indol-1-yl)acetyl]-1-methylpiperazine-2-carboxylic acid 0.89 ml of 1N soda solution is added to 0.49 g of compound No. 270 in 5 ml of methanol, and it is stirred for 18 h. It is evaporated to dryness, the solid residue is taken up in water and then 2 ml of 1N HCl is added dropwise. The precipitate formed is filtered, it is washed with water and then dried in a vacuum stove at 50° C., obtaining 0.40 g of a white powder.

$^1$H NMR: DMSO-d$_6$+trifluoroacetic acid (250 MHz): δ (ppm): 0.93 (3H, t); 1.64 (2H, m); 2.51 (3H, s); 2.80 (2H, t); 2.99 (3H, s); 3.10-4.60 (7H, m); 5.30-5.60 (2H, m); 7.26 (1H, d); 7.48 (2H, d); 7.52 (1H, d); 7.96 (2H, d); 8.21 (1H, s); 8.22 (1H, s); 8.27 (1H, s).

MH⁺=605; t$_R$=6.79 min (Method G)

Example 17

Compound No. 272

N-[4-(4-butyryl-5-methyl-1H-pyrazol-1-yl)phenyl]-5-chloro-1-{2-[4-methyl-3-(methylcarbamoyl)piperazin-1-yl]-2-oxoethyl}-1H-indole-3-carboxamide 29 μL of N-methylmorpholine and then 25 μL of ethyl chloroformate are added to 0.20 g of compound No. 271 in 2 ml of THF at −10° C., and it is stirred for 2 h, maintaining the temperature at −10° C. After adding 159 μL of 2M methylamine solution in THF, it is allowed to return slowly to RT and then it is stirred for 15 h. The reaction mixture is evaporated and then the solid residue is purified by silica gel chromatography, eluting with DCM/MeOH mixture (gradient from 0 to 10% of MeOH). The product is dissolved in 5 ml of acetone/MeOH mixture (1/1: v/v). Then 0.4 ml of 1M HCl solution in ether is added. It is evaporated to dryness, the solid residue is triturated with acetone, it is washed with MeOH and dried under vacuum, obtaining 0.090 g of a white powder.

$^1$H NMR: DMSO-d$_6$+trifluoroacetic acid (250 MHz): δ (ppm): 0.94 (3H, t); 1.64 (2H, m); 2.52 (3H, s); 2.69 (2H, s);

2.77-2.87 (6H, m); 2.89-4.70 (7H, m); 5.25-5.67 (2H, m); 7.28 (1H, d); 7.45-7.59 (3H, m); 7.96 (2H, d); 8.23 (2H, s); 8.30 (1H, d).

MH$^+$=618; $t_R$=6.63 min (Method G)

m.p.=274° C.

Inhibition of platelet aggregation in vitro (rat blood): 0.21 μM

Example 18

Compound No. 273

N-[4-(4-Butyryl-5-methyl-1H-pyrazol-1-yl)phenyl]-5-chloro-1-[2-oxo-2-(9-oxooctahydro-2H-pyrazino[1,2-a]pyrazin-2-yl)ethyl]-1H-indole-3-carboxamide hydrochloride 0.34 g of tert-butyl (2-oxoethyl)carbamate, 0.177 g of sodium cyanoborohydride and then 0.5 ml of acetic acid are added to 1 g of compound No. 212 in suspension in 15 ml of MeOH. After stirring at RT for 20 h, it is evaporated to dryness and then the raw reaction product is purified by silica gel chromatography, eluting with DCM/MeOH mixture (gradient from 0 to 5% of methanol). The powder obtained is dissolved in 2 ml of trifluoroacetic acid and then it is stirred at RT for 4 h. The reaction mixture is poured into 30 ml of 2N soda solution. The heterogeneous medium is stirred for 15 min and then extracted with EtOAc. The organic phase is washed with water, with brine and then evaporated to dryness. The solid residue is purified by silica gel chromatography, eluting with DCM/MeOH mixture (gradient from 2 to 10% of methanol). The product is dissolved in 5 ml of acetone/MeOH mixture (1/1: v/v) and then 1 ml of 2N HCl solution in ether is added. It is evaporated to dryness, recrystallized from acetone while hot and filtered, obtaining 0.38 g of a white powder.

$^1$H NMR: DMSO-d$_6$ (250 MHz): δ (ppm): 0.94 (3H, t); 1.64 (2H, m); 2.52 (3H, s); 2.80 (2H, t); 3.20-4.90 (11H, m); 5.20-5.65 (2H, m); 7.20-7.35 (1H, m); 7.49 (2H, d); 7.56 (1H, d); 7.96 (2H, d); 8.22 (1H, s); 8.23 (1H, s); 8.28 (1H, s).

MH$^+$=616; $t_R$=7.74 min (Method G)

m.p.=230° C.

Inhibition of platelet aggregation in vitro (rat blood): 0.29 μM

Example 19

Compound No. 274 SAR164737

N-[4-(4-Butyryl-5-methyl-1H-pyrazol-1-yl)phenyl]-5-chloro-1-[2-(8-methyl-9-oxooctahydro-2H-pyrazino[1,2-a]pyrazin-2-yl)-2-oxoethyl]-1H-indole-3-carboxamide hydrochloride 0.23 g of tert-butyl methyl(2-oxoethyl)carbamate, 0.082 g of sodium cyanoborohydride and than 0.4 ml of acetic acid are added to 0.79 g of compound No. 212 in suspension in 15 ml of MeOH. After stirring at RT for 20 h, it is evaporated to dryness and then the raw reaction product is purified by silica gel chromatography, eluting with DCM/MeOH mixture (gradient from 0 to 5% of methanol). The powder obtained is dissolved in 2 ml of trifluoroacetic acid and then it is stirred at RT for 4 h. The reaction mixture is poured into 30 ml of 2N soda solution. The heterogeneous medium is stirred for 15 min and then extracted with EtOAc. The organic phase is washed with water, with brine and then evaporated to dryness. The solid residue is purified by silica gel column chromatography, eluting with DCM/MeOH mixture (gradient from 2 to 10% of methanol). The product is triturated with iso ether and than filtered, obtaining 0.48 g of a white powder.

$^1$H NMR: DMSO-d$_6$ (250 MHz): δ (ppm): 0.94 (3H, t); 1.64 (2H, m); 2.07-3.54 (18H, m); 3.97 (0.5H, d); 4.16 (0.5H, d); 4.25 (0.5H, d); 4.72 (0.5H, d); 5.27-5.56 (2H, m); 7.22-7.29 (1H, m); 7.49 (2H, d); 7.52-7.61 (1H, m); 7.95 (2H, d); 8.19-8.22 (1H, m); 8.24 (1H, s); 8.27-8.31 (1H, m).

MH$^+$=630; $t_R$=7.96 min (Method G)

m.p.=220° C.

Inhibition of platelet aggregation in vitro (rat blood): 0.10 μM

Example 20

Compound No. 275

2-{4-[(3-{[4-(4-Butyryl-5-methyl-1H-pyrazol-1-yl)phenyl]carbamoyl}-5-chloro-1H-indol-1-yl)acetyl]piperazin-1-yl}ethyl acetate hydrochloride 0.27 ml of triethylamine and then 0.14 ml of acetyl chloride are added to 0.40 g of compound No. 146 in 5 ml of DCM at 0° C. After stirring at RT for 1 h, the reaction mixture is washed with water, with brine and then dried over Na$_2$SO$_4$ and evaporated to dryness. The solid residue is purified by silica gel column chromatography, eluting with DCM/MeOH mixture (gradient from 4 to 10% of MeOH). The product is dissolved in 2 ml of acetone/MeOH mixture (1/1: v/v), 1.5 ml of 1N HCl solution in ether is added and then it is poured into 15 ml of ether. The precipitate formed is filtered, obtaining 0.32 g of a white powder.

$^1$H NMR: DMSO-d$_6$ (250 MHz): δ (ppm): 0.94 (3H, t); 1.63 (2H, m); 2.10 (3H, s); 2.52 (3H, s); 2.82 (2H, t); 3.02-3.32 (3H, m); 3.45-3.75 (5H, m); 4.15-4.45 (4H, m); 5.36 (1H, d); 5.50 (1H, d); 7.28 (1H, d); 7.49 (2H, d); 7.57 (1H, d); 7.98 (2H, d); 8.22 (1H, s); 8.25 (1H, s); 8.32 (1H, s); 10.15 (1H, s); 11.10 (1H, br).

MH$^+$=633; $t_R$=6.26 min (Method G)

m.p.=160° C.

Inhibition of platelet aggregation in vitro (rat blood): 0.20 μM

Example 21

Compound No. 276

N-[4-(4-Butyryl-5-methyl-1H-pyrazol-1-yl)phenyl]-5-chloro-1-{2-oxo-2-[4-(2-oxopropyl)piperazin-1-yl]ethyl}-1H-indole-3-carboxamide hydrochloride 0.21 g of K$_2$CO$_3$ and then 0.057 ml of chloroacetone are added to 0.25 g of compound No. 256 in 11 ml of DMF. After stirring at RT for 48 h, 100 ml of EtOAc is added, it is washed with water, with brine, dried over Na$_2$SO$_4$ and then evaporated to dryness. The solid residue is purified by silica gel column chromatography, eluting with DCM/MeOH mixture (gradient from 0 to 5% of MeOH). The product is dissolved in 1 ml of DCM, 0.5 ml of 1N HCl solution in ether is added and then it is poured into 15 ml of ether. The precipitate formed is filtered, obtaining 0.073 g of a beige powder.

$^1$H NMR: DMSO-d$_6$ (250 MHz): δ (ppm): 0.94 (3H, t); 1.63 (2H, m); 2.23 (3H, s); 2.52 (3H, s); 2.82 (2H, t); 2.93-4.64 (10H, m); 5.38 (1H, br); 5.47 (1H, br); 7.28 (1H, d); 7.50 (2H, d); 7.57 (1H, d); 7.97 (2H, d); 8.22 (1H, s); 8.25 (1H, s); 8.33 (1H, s); 10.21 (1H, s); 10.50 (1H, br).

MH$^+$=603; $t_R$=6.11 min (Method G)

m.p.=248° C.

Inhibition of platelet aggregation in vitro (rat blood): 0.22 µM

The compounds according to the invention were submitted to pharmacological tests.

Inhibition of Platelet Aggregation In Vitro (Human Blood)

The blood is taken from healthy volunteers, using 20-ml syringes containing 2 ml of buffered sodium citrate. The blood is transferred to polypropylene tubes, and centrifuged for 5 minutes (100 g) at room temperature (without using the brake of the centrifuge). The supernatant platelet-rich plasma (PRP) is then removed, diluted, and the platelets are counted before it is used in aggregation measurements.

The measurements of platelet aggregation are performed at 37° C. in glass tubes (Chrono-Log—Kordia aggregometer). 4 µl of the test compound (solution 100 times more concentrated than the required final concentration, in DMSO) is mixed with 392 µl of fresh PRP, and incubated for 1 minute with stirring, Then 4 µl of a solution of ADP at 250 µM is added to the mixture. The measurements of aggregation are monitored for 6 to 8 minutes, stirring continuously, by recording the variations of optical density according to the method of G.V.R. BORN (Born *Nature* (1962) 194, 927).

The results are calculated using the aggregation amplitude expressed as height, and are expressed as percentage inhibition.

The compounds according to the invention have $CI_{50}$ (of inhibition of platelet aggregation) between 0.1 and 2 µM.

Inhibition of Platelet Aggregation In Vitro (Rat Blood)

The blood is taken from male rats of the Sprague-Dawley strain, weighing 250-300 g. The sample is taken on sodium citrate at 3.8% (1 volume to 9 volumes of blood) by puncture of the abdominal aorta after anesthetizing the animal with pentobarbital sodium.

The platelet-rich plasma (PRP) is obtained by centrifugation of the blood at 300 g for 5 minutes, and the measurements of platelet aggregation are performed as described above.

The results are calculated using the area under the curve of absorbance measured for 6 minutes, and expressed as percentage inhibition.

The compounds according to the invention for which R3=NR7R8 have CI50 values (of inhibition of platelet aggregation) between 0.02 and 1.5 µM.

The compounds according to the invention for which R3=OH have CI50 values (of inhibition of platelet aggregation)>1.5 µM.

The results obtained for each compound are shown in tables X to XV

Inhibition of Platelet Aggregation Ex Vivo (Rat Blood)

Male rats of the Sprague-Dawley strain, weighing 250-300 g, are used at a rate of 6 animals per batch. Each test compound is diluted in a solution of glucose-containing water (glucose 5%) containing 5% of cremophore and 3% of glycofurol.

The compounds according to the invention are administered by stomach tube (10 ml/kg at 1 mg/ml) two hours before taking the sample or by infusion (1 ml/kg at 10 mg/ml) two hours before taking the sample.

The sample is taken on sodium citrate at 3.8% (1 volume to 9 volumes of blood) by puncture of the abdominal aorta after anesthetizing the animal with pentobarbital sodium.

The platelet-rich plasma (PRP) is obtained by centrifugation of the blood at 300 g for 5 minutes, and the measurements of platelet aggregation are performed as described above.

The results are calculated using the area under the curve of absorbance measured for 6 minutes, and expressed as percentage (%) of inhibition.

TABLE XVI below shows the results obtained for compounds 11, 28, 29, 105, 107, 115, 119, 133, 142, 145, 147, 166, 170, 177, 179, 180, 219, 262, 274 and 276:

TABLE XVI

| Compounds No. | Inhibition of platelet aggregation ex vivo (rat blood) in % | |
|---|---|---|
| | Infusion (Intravenous) 10 mg/kg | Gavage (oral) 10 mg/kg |
| 11 | 40.7 | / |
| 28 | 79.0 (3 mg/kg) | 73.5 |
| 29 | 76.0 (1 mg/kg) | 86.3 |
| 105 | / | 67.9 |
| 107 | 57.8 | 36.8 |
| 115 | 78.2 | 50.6 |
| 119 | / | 61.1 |
| 133 | / | 74.2 |
| 142 | / | 76.5 |
| 145 | / | 53.7 |
| 147 | / | 74.9 |
| 166 | / | 72.0 |
| 170 | / | 71.5 |
| 177 | / | 63.9 |
| 179 | / | 76.1 |
| 180 | / | 65.1 |
| 219 | / | 65.1 |
| 262 | / | 58.8 |
| 274 | / | 82.7 |
| 276 | / | 49.9 |

The compounds of the present invention are notably active principles compatible with their use as medicinal products and/or pharmaceutical compositions.

According to one of these aspects, the present invention relates to the use of a compound of formula (I) or a pharmaceutically acceptable salt thereof for preparing medicinal products intended for preventing or treating any human pathology and/or for veterinary use. Thus, the compounds according to the invention can be used in humans or in animals (notably in mammals including but not limited to dogs, cats, horses, cattle, sheep) for the prevention or treatment of diseases involving the P2Y12 receptor.

They are therefore indicated as inhibitors of platelet activation, aggregation and degranulation, as promoters of platelet disaggregation, and as antithrombotic agents. They are also indicated in the treatment or prevention of unstable angina, of percutaneous transluminal coronary angioplasty (PTCA), of myocardial infarction, of peri-thrombolysis, of thrombotic arterial complications of atherosclerosis such as embolic or thrombotic cerebrovascular accidents, transient ischemic attacks, peripheral vascular disease, myocardial infarction with or without thrombolysis, arterial complications of atherosclerosis due to surgical interventions such as angioplasty, endarterectomy, placement of stents, coronary vascular and other grafts, thrombotic complications of surgery or mechanical damage such as recovery of tissues after accidental or surgical trauma, reconstructive surgery (including skin and muscle flaps), disseminated intravascular coagulation, thrombotic thrombocytopenic purpura, hemolytic and uremic syndrome, thrombotic complications of septicemia, respiratory distress syndrome, antiphospholipid syndrome, heparin-induced thrombocytopenia and pre-eclampsia/eclampsia; or venous thromboses such as deep vein thrombosis, venoocclusive disease, hematological conditions such as myelo-proliferative disease (including thrombocythemia), sickle-cell anemia; or in the prevention of platelet activation induced mechanically in vivo, such as during cardiopulmonary bypass and extracorporeal oxygenation (prevention of micro-thromboembolisms), in the prevention of platelet activation induced mechanically in vitro (use in the storage of blood products—for example, platelet concentrates—use during shunts such as renal dialysis and plasmapheresis), thrombosis secondary to vascular lesion/inflammation such as angiitis, arteritis, glomerulonephritis, inflammatory bowel disease, and organ graft rejection, conditions such as migraine. Raynaud phenomenon, conditions in which platelets can contribute to the underlying inflammatory disease process in the vessel wall such as formation/progression of atheromatous plaques, stenosis/restenosis, and in other inflammatory diseases such as asthma, in which platelets and platelet-derived factors are involved in the immunological disease process.

The use of the compounds according to the invention for the prevention and/or treatment of the aforementioned diseases, as well as for preparing medicinal products intended for treating these diseases, forms an integral part of the invention.

The compounds of formula (I) above, or a pharmaceutically acceptable salt thereof, can be used at daily doses from 0.01 to 100 mg per kilogram of body weight of the mammal to be treated, preferably at daily doses from 0.1 to 50 mg/kg. In humans, the dose can vary preferably from 0.1 to 4000 mg per day, more particularly from 0.5 to 1000 mg depending on the age of the subject to be treated or the type of treatment: prophylactic or curative.

Thus, according to another of its aspects, the present invention relates to pharmaceutical compositions containing, as active principle, a compound of formula (I), or a pharmaceutically acceptable salt thereof, as well as one or more pharmaceutically acceptable excipients.

In the pharmaceutical compositions of the present invention for administration by the oral, sublingual, inhaled, subcutaneous, intramuscular, intravenous, topical, local, intratracheal, intranasal, transdermal, local or rectal route, the active principles can be administered in unit dosage forms, mixed with conventional pharmaceutical carriers, to animals and to human beings.

The appropriate unit dosage forms comprise oral dosage forms such as tablets, soft or hard capsules, powders, granules, oral solutions or suspensions, forms for administration by the sublingual, buccal, intratracheal, intraocular, intranasal route, by inhalation, aerosols, topical and transdermal dosage forms, implants, forms for subcutaneous, intramuscular, and intravenous administration and forms for rectal administration.

For topical administration, the compounds according to the invention can be used in creams, ointments, gels, or lotions.

As an example, a unit dosage form of a compound according to the invention in tablet form can comprise the following components:

| | |
|---|---:|
| Compound according to the invention | 50.0 mg |
| Mannitol | 223.75 mg |
| Croscarmellose sodium | 6.0 mg |
| Maize starch | 15.0 mg |
| Hydroxypropyl-methylcellulose | 2.25 mg |
| Magnesium stearate | 3.0 mg |

By the oral route, the dose of active principle administered per day can reach 0.01 to 100 mg/kg, in one or more individual doses, preferably 0.02 to 50 mg/kg.

There may be special cases in which higher or lower dosages are appropriate; such dosages fall within the scope of the invention. According to the usual practice, the appropriate dosage for each patient is determined by the doctor depending on the method of administration, and the weight and response of said patient.

The present invention, according to another of its aspects, also relates to a method of treatment of the aforementioned disorders that comprises the administration, to a patient, of an effective dose of a compound according to the invention, or of a pharmaceutically acceptable salt thereof.

The compounds according to the invention can also be used for preparing compositions for veterinary use.

The invention claimed is:
1. A compound corresponding to formula (I):

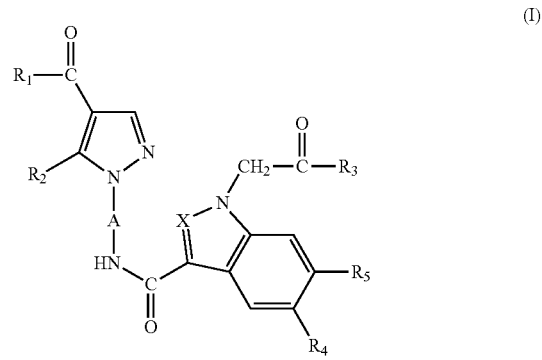

in which:
A represents a divalent aromatic radical selected from:

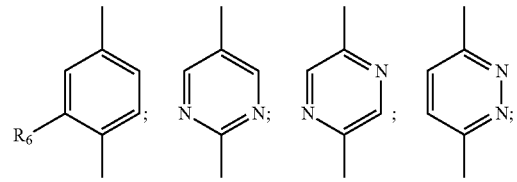

X represents a —CH— group or a nitrogen atom;
$R_1$ represents a $(C_1-C_4)$alkyl or a $(C_1-C_4)$alkoxy;
$R_2$ represents a group Alk;
$R_3$ represents a hydroxyl or a group —$NR_7R_8$;
$R_4$ represents a hydrogen atom, a halogen atom, a cyano, a phenyl, a group Alk, a group OAlk or a group —$NR_9R_{10}$;
$R_5$ represents a hydrogen atom, a halogen atom or a group Alk;
$R_6$ represents a hydrogen atom, a halogen atom, a cyano, a group
—COOAlk or a —$CONH_2$ group;
$R_7$ represents a hydrogen atom or a $(C_1-C_4)$alkyl;
$R_8$ represents:
a) a hydrogen atom;
b) a $(C_1-C_4)$alkyl, unsubstituted or substituted with:
  (i) a hydroxyl;
  (ii) a group OAlk;
  (iii) a group —$NR_9R_{10}$;
  (iv) a $(C_3-C_6)$heterocycloalkyl, unsubstituted or substituted with a $(C_1-C_4)$alkyl or with a group —COOAlk;
  (v) a heteroaryl, unsubstituted or substituted with a $(C_1-C_4)$alkyl;
c) a $(C_3-C_7)$cycloalkyl;

d) a (C$_3$-C$_6$)heterocycloalkyl, unsubstituted or substituted with a (C$_1$-C$_4$)alkyl, a group —COOAlk or with one or two oxo groups;
e) a group —SO$_2$Alk;
or else R$_7$ and R$_8$, together with the nitrogen atom to which they are attached, constitute a heterocyclic, saturated or unsaturated, mono- or polycyclic, condensed or bridged group, comprising 4 to 10 ring members and that can contain one, two or three other nitrogen atoms or another heteroatom selected from an oxygen atom or a sulfur atom; said heterocyclic group being unsubstituted or substituted once, twice or three times with substituents selected independently from:
a) a halogen atom;
b) a hydroxyl;
c) a group —OR$_{11}$;
d) an oxo;
e) a group —NR$_9$R$_{10}$;
f) a group —NR$_{12}$COR$_{13}$;
g) a group —NR$_{12}$COOR$_{13}$;
h) a group —COR$_{13}$;
i) a group —COOR$_{13}$;
j) a group —CONR$_{14}$R$_{15}$;
k) a (C$_3$-C$_7$)cycloalkyl, unsubstituted or substituted with a hydroxyl or with a (C$_1$-C$_4$)alkyl;
l) a (C$_3$-C$_6$)heterocycloalkyl, unsubstituted or substituted with one or two oxo groups;
m) a phenyl, unsubstituted or substituted one or more times with substituents selected independently from a halogen atom, a group Alk or a group OAlk;
n) a pyridinyl;
o) a (C$_1$-C$_4$)alkyl, unsubstituted or substituted one or more times with substituents selected independently from:
(i) a halogen atom;
(ii) a hydroxyl;
(iii) a group —OR$_{11}$;
(iv) a group —NR$_9$R$_{10}$;
(v) a group —NR$_{12}$COR$_{13}$;
(vi) a group —COOR$_{13}$;
(vii) a group —CONR$_{14}$R$_{15}$;
(viii) a group —SO$_2$Alk;
(ix) a (C$_3$-C$_7$)cycloalkyl;
(x) a (C$_3$-C$_6$)heterocycloalkyl;
(xi) a phenyl, unsubstituted or substituted one or more times with substituents selected independently from a halogen atom, a group Alk or a group OAlk;
(xii) a heteroaryl, unsubstituted or substituted with a (C$_1$-C$_4$)alkyl;
R$_9$ and R$_{10}$ represent, each independently, a hydrogen atom or a (C$_1$-C$_4$)alkyl;
R$_{11}$ represents a group Alk, a —(C$_1$-C$_4$)alkylene-OH or a —(C$_1$-C$_4$)alkylene-OAlk;
R$_{12}$ represents a hydrogen atom or a (C$_1$-C$_4$)alkyl;
R$_{13}$ represents a (C$_1$-C$_4$)alkyl;
R$_{14}$ and R$_{15}$ represent, each independently, a hydrogen atom, a (C$_1$-C$_4$)alkyl or a (C$_3$-C$_7$)cycloalkyl;
or else R$_{14}$ and R$_{15}$, together with the nitrogen atom to which they are attached, constitute a heterocyclic radical selected from: azetidin-1-yl, pyrrolidin-1-yl, piperidin-1-yl, morpholin-4-yl or piperazin-1-yl;
Alk represents a (C$_1$-C$_4$)alkyl, unsubstituted or substituted one or more times with a fluorine atom;
in the form of a base or salt of addition with a pharmaceutically acceptable acid or base.

2. A compound of formula (I) according to claim 1, wherein R$_3$ represents a group —NR$_7$R$_8$ (reference IB) and the other substituents A, X, R$_1$, R$_2$, R$_4$, R$_5$, R$_7$ and R$_8$ are as defined in claim 1.

3. A compound of formula (I) according to claim 1, wherein:
A represents a divalent aromatic radical selected from:

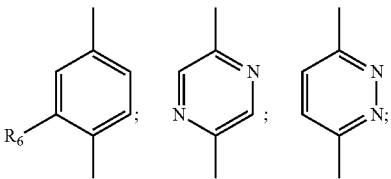

X represents a —CH— group or a nitrogen atom;
R$_1$ represents a methyl, ethyl, n-propyl radical or an ethoxy radical;
R$_2$ represents a methyl radical;
R$_3$ represents a hydroxyl or a group —NR$_7$R$_8$;
R$_4$ represents a hydrogen atom, a bromine, chlorine or fluorine atom, a cyano, a phenyl, a methyl radical, a trifluoromethyl radical, a methoxy radical or a dimethylamino group;
R$_5$ represents a hydrogen atom, a bromine, chlorine or fluorine atom or a methyl radical;
R$_6$ represents a hydrogen atom, a bromine atom, a cyano, a methoxycarbonyl group or a —CONH$_2$ group;
R$_7$ represents a hydrogen atom or a methyl radical;
R$_8$ represents:
a) a hydrogen atom;
b) a methyl radical, a 2-hydroxyethyl, a 3-hydroxypropyl, a 2-methoxyethyl, a 2-(methylamino)ethyl, a 2-(dimethylamino)ethyl, a 2-(dimethylamino)propyl, a 2-(dimethylamino)-1-methylethyl, a 2-(dimethylamino)-2-methylpropyl, a 3-(dimethylamino)propyl, a (1-methylpiperidin-3-yl)methyl, a tetrahydrofuran-3-ylmethyl, a tetrahydro-2H-pyran-4-ylmethyl, a 2-furylmethyl, a (3-methyl-1H-1,2,4-triazol-5-yl)methyl, 1-(1H-tetrazol-5-yl)ethyl, a 2-(1H-pyrrol-1-yl)ethyl, a 2-(1H-imidazol-1-yl)ethyl;
c) a cyclopropyl;
d) a 1,1-dioxidotetrahydro-3-thienyl, a pyrrolidin-3-yl, a 1-methylpyrrolidin-3-yl, a 1-(tert-butoxycarbonyl)pyrrolidin-3-yl, a piperidin-3-yl, a 1-methylpiperidin-3-yl, a 1-(tert-butoxycarbonyl)piperidin-3-yl, a 1-methylpiperidin-4-yl;
e) a methylsulfonyl group;
or else R$_7$ and R$_8$, together with the nitrogen atom to which they are attached, constitute a heterocyclic group selected from: an azetidinyl, a pyrrolidinyl, a piperidinyl, a piperazinyl, a morpholinyl, a thiomorpholinyl, an octahydro-2H-pyrido[1,2-a]pyrazinyl, a 5,6,7,8-tetrahydro[1,2,4]triazolo[4,3-a]pyrazinyl, a 2,3-dihydro-1H-pyrrolo[3,4-c]pyridinyl, an octahydropyrrolo[1,2-a]pyrazinyl, a 1,4-diazepanyl, a 5,6,7,8-tetrahydroimidazo[1,2-a]pyrazinyl, a 4,5,6,7-tetrahydro-1H-pyrazolo[4,3-c]pyridinyl, a 1,4,5,6-tetrahydropyrrolo[3,4-c]pyrazolyl, a 6,7-dihydro-5H-pyrrolo[3,4-b]pyridinyl, a 3,8-diazabicyclo[3.2.1]octanyl, a 4,5,6,7-tetrahydro-1H-imidazo[4,5-c]pyridinyl, a 4,5,6,7-tetrahydro-1H-pyrazolo[3,4-c]pyridinyl, a 2,5-diazabicyclo[2.2.2]octanyl, a 2,5-diazabicyclo[2.2.1]heptanyl, an octahydropyrrolo[3,4-b]pyrrolyl, an octahydropyrrolo[3,4-c]pyrrolyl, and an octahydro-2H-pyrazino[1,2-a]pyrazinyl; said heterocyclic group being unsubstituted or substituted once, twice or three times with substituents selected independently from:
a) a fluorine atom;
b) a hydroxyl;
c) a methoxy radical, a 2-hydroxyethoxy, a 2-methoxyethoxy;
d) an oxo;
e) an amino group, a methylamino, a dimethylamino;
f) an acetamido group;
g) a (tert-butoxycarbonyl)amino group, a (tent-butoxycarbonyl)(methy)amino group;
h) an acetyl group;
i) a methoxycarbonyl group, a tert-butoxycarbonyl group;
j) a dimethylcarbamoyl group, a cyclopropylcarbamoyl, a cyclobutylcarbamoyl;
k) a cyclopropyl, a cyclobutyl, a 2-hydroxycyclopentyl radical;
l) an oxetan-3-yl, a 1,1-dioxidotetrahydro-3-thienyl, a piperidin-1-yl, a morpholin-4-yl;
m) a 4-fluorophenyl;
n) a pyridin-2-yl; and
o) groups selected from a methyl, an ethyl, an n-propyl, an isopropyl, an n-butyl, a trifluoromethyl, a 2-fluoroethyl, a 2,2-difluoroethyl, a 2,2,2-trifluoroethyl, a 3,3,3-trifluoropropyl, a 3,3,3-trifluoro-2-hydroxypropyl, a hydroxymethyl, a 2-hydroxyethyl, a 2-hydroxy-1,1-dimethylethyl, a methoxymethyl, a 2-methoxyethyl, a 2-methoxy-1-methylethyl, a 2-methoxy-1,1-dimethylethyl, a 2-ethoxyethyl, a 2-(trifluoromethoxy)ethyl, a 2-(2-hydroxyethoxy)ethyl, a 2-(2-methoxyethoxy)ethyl, a 2-(dimethylamino)ethyl, a 2-acetamidoethyl, a 2-[acetyl(methyl)amino]ethyl, a 2-methoxy-2-oxoethyl, a 2-ethoxy-2-oxoethyl, a 3-ethoxy-3-oxopropyl, a 2-amino-2-oxoethyl, a 2-(methylamino)-2-oxoethyl, a 2-(isopropylamino)-2-oxoethyl, a 2-(dimethylamino)-2-oxoethyl, a 2-(cyclopropylamino)-2-oxoethyl, a 2-oxo-2-pyrrolidin-1-ylethyl, a 2-(methylsulfonyl)ethyl, a cyclopropylmethyl, a pyrrolidin-1-ylmethyl, a tetrahydrofuran-2-ylmethyl, a 2-thienylmethyl, a 4-chlorobenzyl, a 4-fluorobenzyl, a 2-methoxybenzyl, a 3-fluoro-4-methoxybenzyl, a pyridin-4-ylmethyl, a (5-methyl-1,2,4-oxadiazol-3-yl)methyl, and a (5-methylisoxazol-3-yl)methyl radical.

4. A compound of formula (I) according to claim 1, wherein:
A represents a divalent aromatic radical selected from:

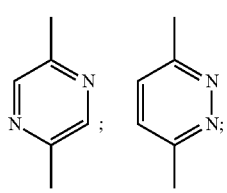

X represents a —CH— group;
$R_1$ represents an n-propyl radical;
$R_2$ represents a methyl radical;
$R_3$ represents a hydroxyl or a group —$NR_7R_8$;
$R_4$ represents a chlorine atom;
$R_5$ represents a hydrogen atom;
$R_7$ represents a hydrogen atom or a methyl radical;
$R_8$ represents:

b) a methyl radical, a 2-hydroxyethyl, a 3-hydroxypropyl, a 2-methoxyethyl, a 2-(dimethylamino)ethyl, a 2-(dimethylamino)propyl, a 2-(dimethylamino)-2-methylpropyl, a 3-(dimethylamino)propyl, a tetrahydrofuran-3-ylmethyl, a tetrahydro-2H-pyran-4-ylmethyl, a 2-furylmethyl, a (3-methyl-1H-1,2,4-triazol-5-yl)methyl, 1-(1H-tetrazol-5-yl)ethyl, a 2-(1H-pyrrol-1-yl)ethyl;
c) a cyclopropyl;
d) a 1-methylpyrrolidin-3-yl, a 1-(tert-butoxycarbonyl)piperidin-3-yl, a 1-methylpiperidin-4-yl;
or else $R_7$ and $R_8$, together with the nitrogen atom to which they are attached, constitute a heterocyclic group selected from: an azetidinyl, a pyrrolidinyl, a piperidinyl, a piperazinyl, a morpholinyl, a thiomorpholinyl, an octahydro-2H-pyrido[1,2-a]pyrazinyl, a 5,6,7,8-tetrahydro[1,2,4]triazolo[4,3-a]pyrazinyl, a 2,3-dihydro-1H-pyrrolo[3,4-c]pyridinyl, an octahydropyrrolo[1,2-a]pyrazinyl, and a 1,4-diazepanyl radical; said heterocyclic group being unsubstituted or substituted once, twice or three times with substituents selected independently from:
b) a hydroxyl;
c) a methoxy radical;
d) an oxo;
h) an acetyl group;
i) a methoxycarbonyl group;
j) a dimethylcarbamoyl group;
k) a cyclobutyl radical;
l) a 1,1-dioxidotetrahydro-3-thienyl, a piperidin-1-yl, a morpholin-4-yl;
m) a 4-fluorophenyl; and
o) groups selected from a methyl radical, an ethyl, an n-propyl, an isopropyl, an n-butyl, a trifluoromethyl, a 3,3,3-trifluoropropyl, a hydroxymethyl, a 2-hydroxyethyl, a methoxymethyl, a 2-methoxyethyl, a 2-ethoxyethyl, a 2-(trifluoromethoxy)ethyl, a 2-(dimethylamino)ethyl, a 2-methoxy-2-oxoethyl, a 2-ethoxy-2-oxoethyl, a 2-(isopropylamino)-2-oxoethyl, a 2-(dimethylamino)-2-oxoethyl, a 2-(cyclopropylamino)-2-oxoethyl, a 2-oxo-2-pyrrolidin-1-ylethyl, a tetrahydrofuran-2-ylmethyl, a 4-fluorobenzyl, a 3-fluoro-4-methoxybenzyl, pyridin-4-ylmethyl, and a (5-methyl-1,2,4-oxadiazol-3-yl)methy.

5. A compound of formula (I) according to claim 1, wherein:
A represents a divalent aromatic radical selected from:

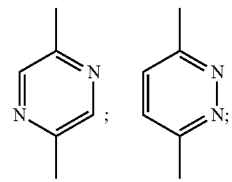

X represents a —CH— group;
$R_1$ represents an n-propyl radical;
$R_2$ represents a methyl radical;
$R_3$ represents a hydroxyl or a group —$NR_7R_8$ selected from:

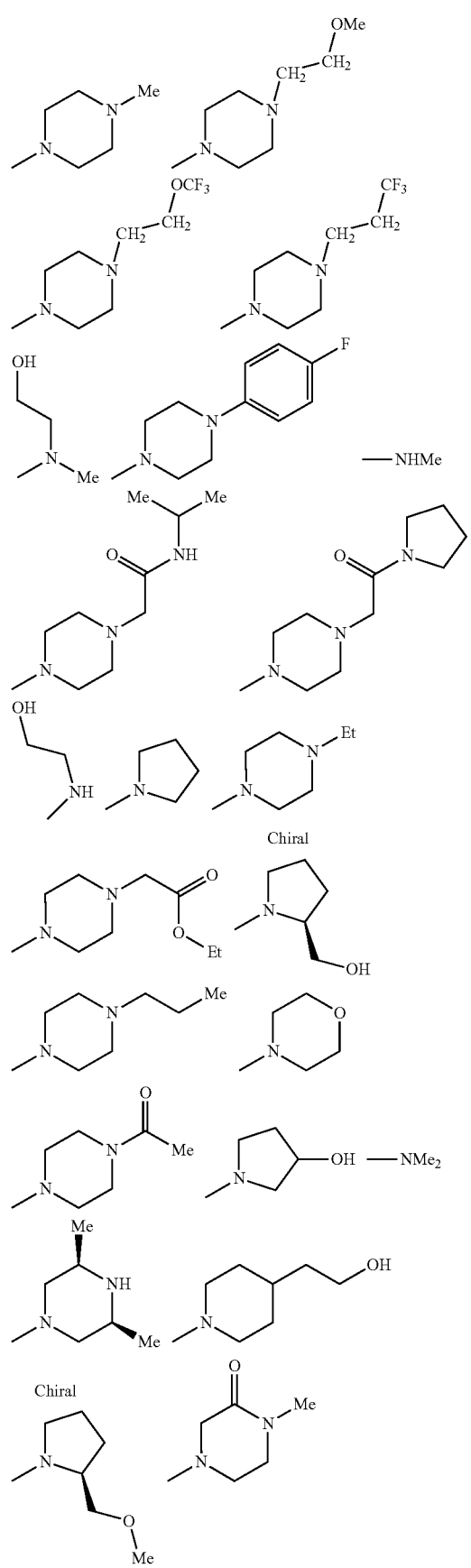
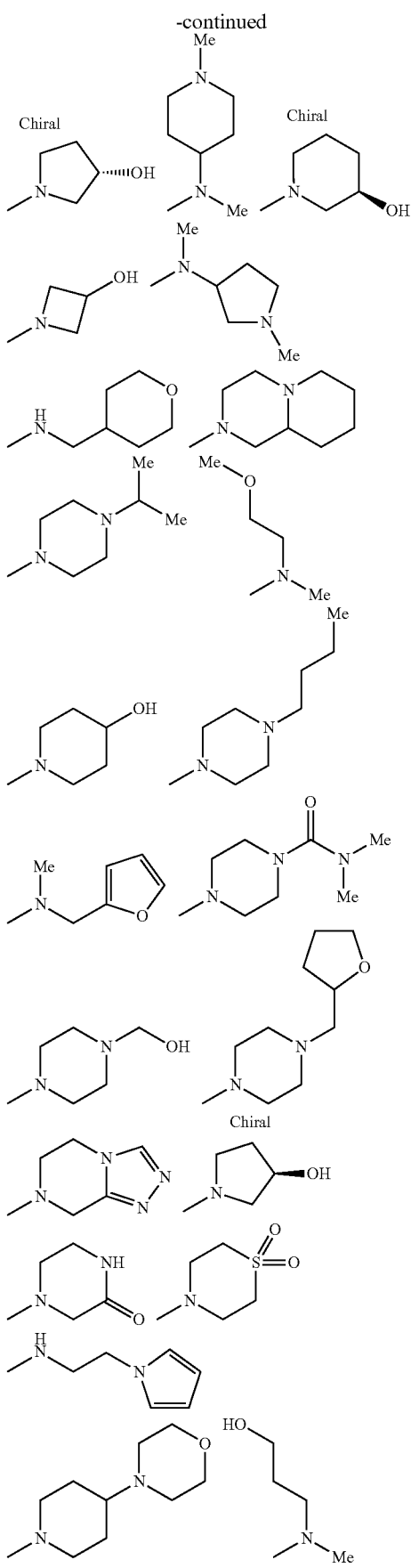
-continued

197
-continued
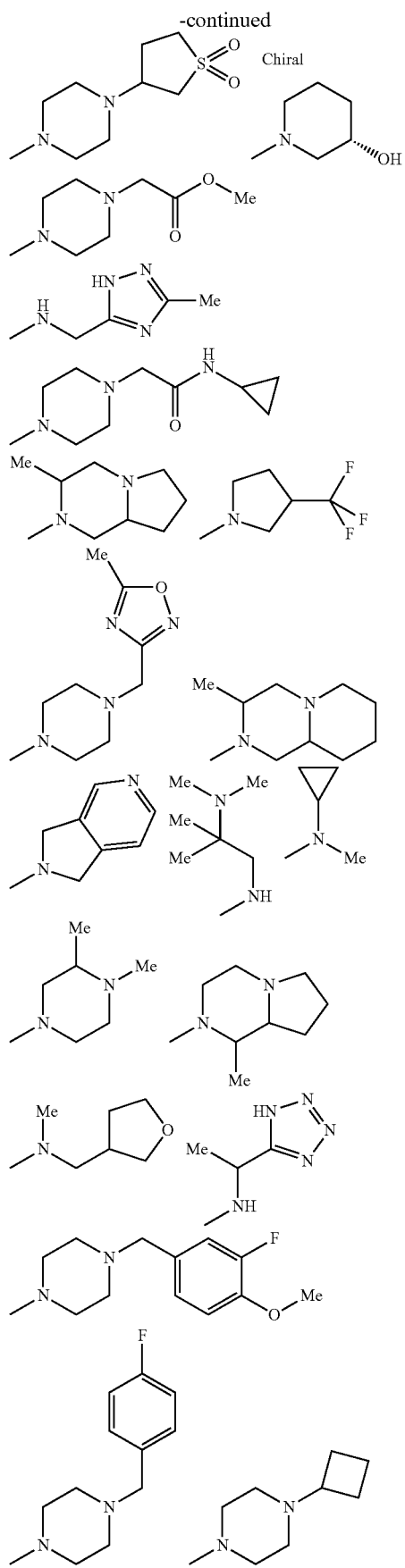
198
-continued
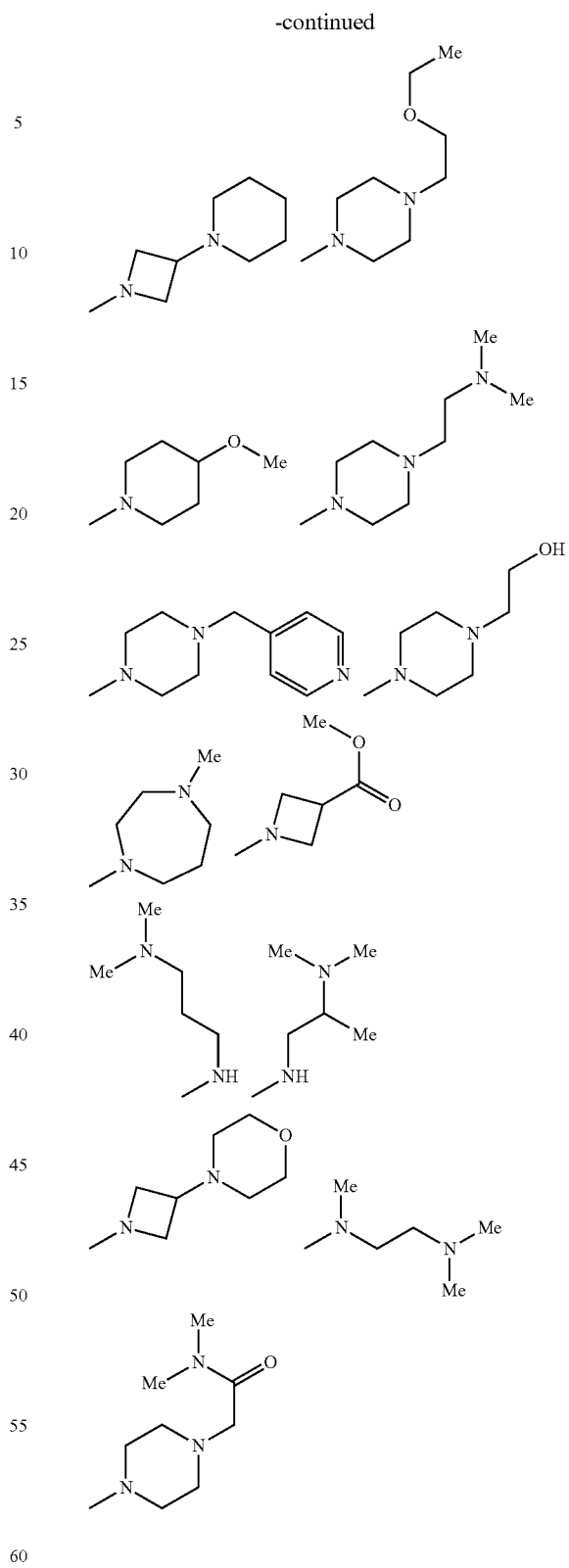
$R_4$ represents a chlorine atom; and
$R_5$ represents a hydrogen atom.
6. A compound of formula (I) according to claim 1, wherein:

A represents a divalent aromatic radical selected from:

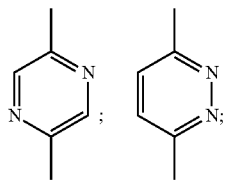

X represents a —CH— group;

R$_1$ represents an n-propyl radical;

R$_2$ represents a methyl radical;

R$_3$ represents a hydroxyl or a group —NR$_7$R$_8$ selected from:

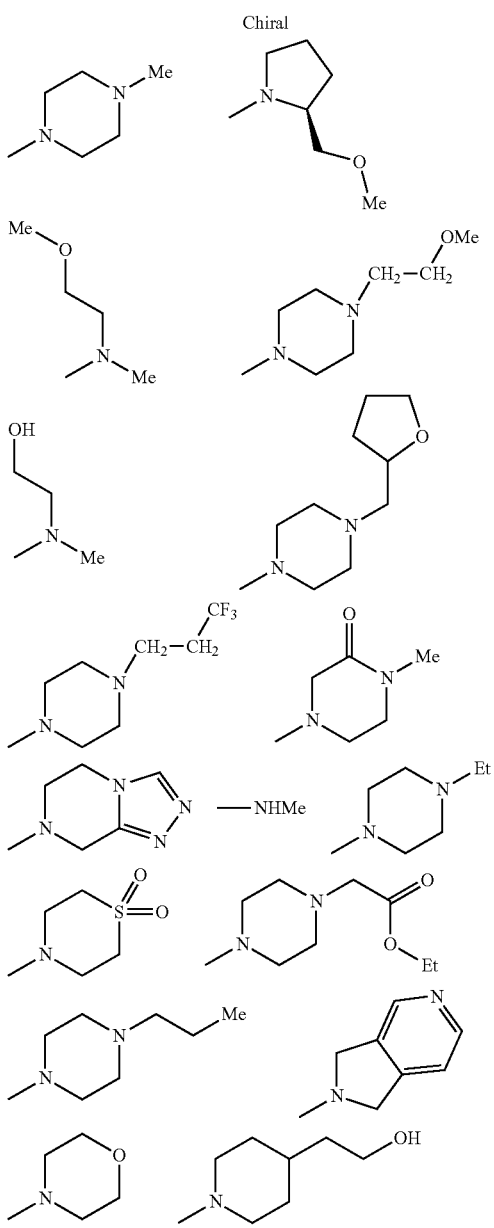

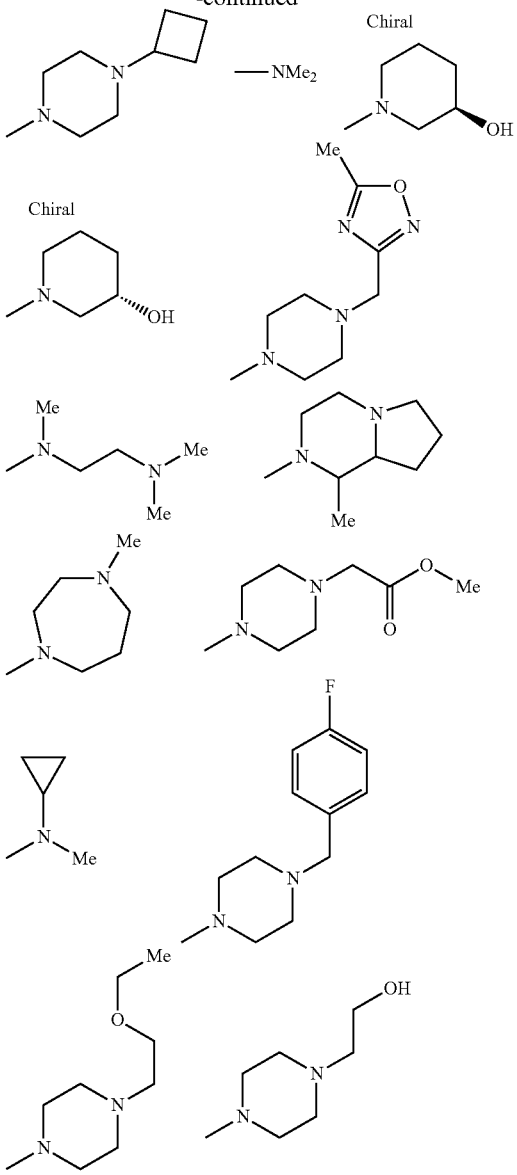

R$_4$ represents a chlorine atom; and

R$_5$ represents a hydrogen atom.

7. Compound A compound of formula (I) according to claim 1 selected from:

(3-{[4-(4-butyryl-5-methyl-1H-pyrazol-1-yl)phenyl]carbamoyl}-5-methyl-1H-indol-1-yl)acetic acid;

(3-{[4-(4-butyryl-5-methyl-1H-pyrazol-1-yl)phenyl]carbamoyl}-5,6-dimethyl-1H-indol-1-yl)acetic acid;

(3-{[6-(4-butyryl-5-methyl-1H-pyrazol-1-yl)pyridazin-3-yl]carbamoyl}-5-chloro-1H-indol-1-yl)acetic acid;

N-[5-(4-butyryl-5-methyl-1H-pyrazol-1-yl)pyrazin-2-yl]-5-chloro-1-[2-(4-methylpiperazin-1-yl)-2-oxoethyl]-1H-indole-3-carboxamide;

N-[6-(4-butyryl-5-methyl-1H-pyrazol-1-yl)pyridazin-3-yl]-5-chloro-1-[2-(4-methylpiperazin-1-yl)-2-oxoethyl]-1H-indole-3-carboxamide;

N-[6-(4-butyryl-5-methyl-1H-pyrazol-1-yl)pyridazin-3-yl]-5-chloro-1-{2-[4-(2-methoxyethyl)piperazin-1-yl]-2-oxoethyl}-1H-indole-3-carboxamide;

N-[6-(4-butyryl-5-methyl-1H-pyrazol-1-yl)pyridazin-3-yl]-5-chloro-1-{2-oxo-2-[4-(3,3,3-trifluoropropyl)piperazin-1-yl]ethyl}-1H-indole-3-carboxamide;

N-[6-(4-butyryl-5-methyl-1H-pyrazol-1-yl)pyridazin-3-yl]-5-chloro-1-[2-(methylamino)-2-oxoethyl]-1H-indole-3-carboxamide;

N-[6-(4-butyryl-5-methyl-1H-pyrazol-1-yl)pyridazin-3-yl]-5-chloro-1-(2-morpholin-4-yl-2-oxoethyl)-1H-indole-3-carboxamide;

N-[6-(4-butyryl-5-methyl-1H-pyrazol-1-yl)pyridazin-3-yl]-5-chloro-1-[2-(dimethylamino)-2-oxoethyl]-1H-indole-3-carboxamide;

N-[6-(4-butyryl-5-methyl-1H-pyrazol-1-yl)pyridazin-3-yl]-5-chloro-1-{2-[(2S)-2-(methoxymethyl)pyrrolidin-1-yl]-2-oxoethyl}-1H-indole-3-carboxamide;

N-[6-(4-butyryl-5-methyl-1H-pyrazol-1-yl)pyridazin-3-yl]-5-chloro-1-[2-(4-ethylpiperazin-1-yl)-2-oxoethyl]-1H-indole-3-carboxamide;

N-[6-(4-butyryl-5-methyl-1H-pyrazol-1-yl)pyridazin-3-yl]-5-chloro-1-[2-(4-propylpiperazin-1-yl)-2-oxoethyl]-1H-indole-3-carboxamide;

N-[6-(4-butyryl-5-methyl-1H-pyrazol-1-yl)pyridazin-3-yl]-5-chloro-1-{2-[(2-methoxyethyl)(methyl)amino]-2-oxoethyl}-1H-indole-3-carboxamide;

N-[6-(4-butyryl-5-methyl-1H-pyrazol-1-yl)pyridazin-3-yl]-5-chloro-1-{2-oxo-2-[4-(tetrahydrofuran-2-ylmethyl)piperazin-1-yl]ethyl}-1H-indole-3-carboxamide;

N-[6-(4-butyryl-5-methyl-1H-pyrazol-1-yl)pyridazin-3-yl]-5-chloro-1-[2-(5,6-dihydro [1,2,4]triazolo[4,3-a]pyrazin-7(8H)-yl)-2-oxoethyl]-1H-indole-3-carboxamide;

N-[6-(4-butyryl-5-methyl-1H-pyrazol-1-yl)pyridazin-3-yl]-5-chloro-1-[2-(4-cyclobutylpiperazin-1-yl)-2-oxoethyl]-1H-indole-3-carboxamide;

N-[6-(4-butyryl-5-methyl-1H-pyrazol-1-yl)pyridazin-3-yl]-5-chloro-1-(2-{4-[(5-methyl-1,2,4-oxadiazol-3-yl)methyl]piperazin-1-yl}-2-oxoethyl)-1H-indole-3-carboxamide;

{4-[(3-{[6-(4-butyryl-5-methyl-1H-pyrazol-1-yl)pyridazin-3-yl]carbamoyl}-5-chloro-1H-indol-1-yl)acetyl]piperazin-1-yl}methyl acetate;

N-[6-(4-butyryl-5-methyl-1H-pyrazol-1-yl)pyridazin-3-yl]-5-chloro-1-{2-[cyclopropyl(methy)amino]-2-oxoethyl}-1H-indole-3-carboxamide;

N-[6-(4-butyryl-5-methyl-1H-pyrazol-1-yl)pyridazin-3-yl]-5-chloro-1-{2-[4-(4-fluorobenzyl)piperazin-1-yl]-2-oxoethyl}-1H-indole-3-carboxamide;

N-[6-(4-butyryl-5-methyl-1H-pyrazol-1-yl)pyridazin-3-yl]-5-chloro-1-{2-[4-(2-ethoxyethyl)piperazin-1-yl]-2-oxoethyl}-1H-indole-3-carboxamide;

N-[6-(4-butyryl-5-methyl-1H-pyrazol-1-yl)pyridazin-3-yl]-5-chloro-1-{2-[4-(2-hydroxyethyl)piperazin-1-yl]-2-oxoethyl}-1H-indole-3-carboxamide;

N-[6-(4-butyryl-5-methyl-1H-pyrazol-1-yl)pyridazin-3-yl]-5-chloro-1-(2-{[2-(dimethylamino)ethyl](methyl)amino}-2-oxoethyl)-1H-indole-3-carboxamide;

N-[6-(4-butyryl-5-methyl-1H-pyrazol-1-yl)pyridazin-3-yl]-5-chloro-1-[2-(4-methyl-1,4-diazepan-1-yl)-2-oxoethyl]-1H-indole-3-carboxamide;

N-[4-(4-butyryl-5-methyl-1H-pyrazol-1-yl)phenyl]-5-chloro-1-[2-(8-methyl-9-oxooctahydro-2H-pyrazino[1,2-a]pyrazin-2-yl)-2-oxoethyl]-1H-indole-3-carboxamide;

N-[4-(4-butyryl-5-methyl-1H-pyrazol-1-yl)-2-cyanophenyl]-5-chloro-1-[2-(4-methylpiperazin-1-yl)-2-oxoethyl]-1H-indole-3-carboxamide;

N-[4-(4-butyryl-5-methyl-1H-pyrazol-1-yl)phenyl]-5-chloro-1-{2-[4-(4-fluorobenzyl)piperazin-1-yl]-2-oxoethyl}-1H-indole-3-carboxamide;

N-[4-(4-butyryl-5-methyl-1H-pyrazol-1-yl)phenyl]-5-chloro-1-{2-[4-(2-methoxyethyl)piperazin-1-yl]-2-oxoethyl}-1H-indole-3-carboxamide;

N-[4-(4-butyryl-5-methyl-1H-pyrazol-1-yl)phenyl]-1-{2-[4-(2-methoxyethyDpiperazin-1-yl]-2-oxoethyl}-5-methyl-1H-indole-3-carboxamide;

N-[4-(4-butyryl-5-methyl-1H-pyrazol-1-yl)phenyl]-5-chloro-1-[2-(4-methylpiperazin-1-yl)-2-oxoethyl]-1H-indole-3-carboxamide;

N-[4-(4-butyryl-5-methyl-1H-pyrazol-1-yl)phenyl]-5-chloro-1-{2-[4-(2-methoxy-1-methylethyl)piperazin-1-yl]-2-oxoethyl}-1H-indole-3-carboxamide;

N-[4-(4-butyryl-5-methyl-1H-pyrazol-1-yl)phenyl]-5-methyl-1-[2-(4-methylpiperazin-1-yl)-2-oxoethyl]-1H-indole-3-carboxamide;

N-[4-(4-butyryl-5-methyl-1H-pyrazol-1-yl)phenyl]-5-chloro-6-fluoro-1-{2-[4-(2-Methoxyethyl)piperazin-1-yl]-2-oxoethyl}-1H-indole-3-carboxamide;

N-[4-(4-butyryl-5-methyl-1H-pyrazol-1-yl)phenyl]-5-methoxy-1-[2-(4-methylpiperazin-1-yl)-2-oxoethyl]-1H-indole-3-carboxamide;

N-[4-(4-butyryl-5-methyl-1H-pyrazol-1-yl)phenyl]-5-chloro-1-{2-[4-methyl-3-(methylcarbamoyl)piperazin-1-yl]-2-oxoethyl}-1H-indole-3-carboxamide;

N-[4-(4-butyryl-5-methyl-1H-pyrazol-1-yl)phenyl]-5,6-dimethyl-1-[2-(4-methylpiperazin-1-yl)-2-oxoethyl]-1H-indole-3-carboxamide;

N-[4-(4-butyryl-5-methyl-1H-pyrazol-1-yl)phenyl]-5-methyl-1-[2-(4-methylpiperazin-1-yl)-2-oxoethyl]-1H-indazole-3-carboxamide;

N-[4-(4-butyryl-5-methyl-1H-pyrazol-1-yl)phenyl]-5-methyl-1-(2-oxo-2-piperazin-1-ylethyl)-1H-indole-3-carboxamide;

N-[4-(4-butyryl-5-methyl-1H-pyrazol-1-yl)phenyl]-5-chloro-6-fluoro-1-[2-(4-methylpiperazin-1-yl)-2-oxoethyl]-1H-indole-3-carboxamide;

N-[4-(4-butyryl-5-methyl-1H-pyrazol-1-yl)phenyl]-5-chloro-1-(2-{4-[(5-methylisoxazol-3-yl)methyl]piperazin-1-yl}-2-oxoethyl)-1H-indole-3-carboxamide;

N-[4-(4-butyryl-5-methyl-1H-pyrazol-1-yl)phenyl]-5-methyl-1-(2-morpholin-4-yl-2-oxoethyl)-1H-indole-3-carboxamide;

N-[4-(4-butyryl-5-methyl-1-pyrazol-1-yl)phenyl]-5-chloro-1-(2-oxo-2-piperazin-1-ylethyl)-1H-indole-3-carboxamide;

N-[4-(4-butyryl-5-methyl-1H-pyrazol-1-yl)phenyl]-5-chloro-1-{2-[4-(2-methoxy-1,1-dimethylethyl)piperazin-1-yl]-2-oxoethyl}-1H-indole-3-carboxamide;

N-[4-(4-butyryl-5-methyl-1H-pyrazol-1-yl)phenyl]-5-chloro-1-{2-[4-(2-hydroxy-1,1-dimethylethyl)piperazin-1-yl]-2-oxoethyl}-1H-indole-3-carboxamide;

N-[4-(4-butyryl-5-methyl-1H-pyrazol-1-yl)phenyl]-5-chloro-1-[2-(8-methyl-3,8-diazabicyclo[3.2.1]oct-3-yl)-2-oxoethyl]-1H-indole-3-carboxamide;

N-[4-(4-butyryl-5-methyl-1H-pyrazol-1-yl)phenyl]-1-[2-(4-methylpiperazin-1-yl)-2-oxoethyl]-5-(trifluoromethyl)-1H-indole-3-carboxamide; and N-[4-(4-butyryl-5-methyl-1H-pyrazol-1-yl)phenyl]-5-chloro-1-[2-oxo-2-(9-oxooctahydro-2H-pyrazino[1,2-a]pyrazin-2-yl)ethyl]-1H-indole-3-carboxamide;

in the form of a base or salt of addition with a pharmaceutically acceptable acid or base.

8. A pharmaceutical composition comprising a compound of formula (I) according to claim 1 or a pharmaceutically acceptable salt of said compound, and at least one pharmaceutically acceptable excipient.

* * * * *